(12) United States Patent
Liu

(10) Patent No.: US 12,145,926 B2
(45) Date of Patent: Nov. 19, 2024

(54) COMPOUNDS AND RADIOLIGANDS FOR TARGETING NEUROTENSIN RECEPTOR AND USES THEREOF

(71) Applicant: Full-Life Technologies HK Limited, Hong Kong (CN)

(72) Inventor: Fa Liu, Watchung, NJ (US)

(73) Assignee: Full-Life Technologies HK Limited, Admiralty (CN)

( * ) Notice: Subject to any disclaimer, the term of this patent is extended or adjusted under 35 U.S.C. 154(b) by 0 days.

(21) Appl. No.: 18/604,397

(22) Filed: Mar. 13, 2024

(65) Prior Publication Data

US 2024/0287046 A1 Aug. 29, 2024

Related U.S. Application Data

(63) Continuation of application No. PCT/US2023/013314, filed on Feb. 17, 2023.

(60) Provisional application No. 63/311,621, filed on Feb. 18, 2022.

(51) Int. Cl.
| | |
|---|---|
| *C07D 403/12* | (2006.01) |
| *A61K 31/41* | (2006.01) |
| *A61K 31/4155* | (2006.01) |
| *A61K 51/04* | (2006.01) |
| *A61P 35/00* | (2006.01) |

(52) U.S. Cl.
CPC ........ *C07D 403/12* (2013.01); *A61K 31/4155* (2013.01); *A61K 51/0482* (2013.01); *A61P 35/00* (2018.01)

(58) Field of Classification Search
CPC .............. C07D 403/12; A61K 31/4155; A61K 51/0482
See application file for complete search history.

(56) References Cited

U.S. PATENT DOCUMENTS

| | | | |
|---|---|---|---|
| 5,021,556 A | | 6/1991 | Srinivasan |
| 5,075,099 A | | 12/1991 | Srinivasan |
| 5,364,613 A | | 11/1994 | Sieving |
| 5,367,080 A | | 11/1994 | Toner |
| 5,723,482 A | | 3/1998 | Degwert |
| 5,723,483 A | * | 3/1998 | Labeeuw ............ C07D 453/02 548/375.1 |

(Continued)

FOREIGN PATENT DOCUMENTS

| | | | |
|---|---|---|---|
| WO | 199632382 A1 | 10/1996 | |
| WO | WO-2014086499 A1 * | 6/2014 | ........... A61K 31/415 |
| WO | 2015188934 A1 | 12/2015 | |

(Continued)

OTHER PUBLICATIONS

Faisal Alshoukr et al., Novel DOTA-Neurotensin Analogues for 111In Scintigraphy and 68Ga PET Imaging of Neurotensin Receptor-Positive Tumors, Bio conjugate Chem,22, 1374-1385. (Year: 2011).*

(Continued)

*Primary Examiner* — Jagadishwar R Samala
(74) *Attorney, Agent, or Firm* — Harness, Dickey & Pierce, P.L.C.

(57) ABSTRACT

The present application relates to a compound of Formula (I) or a pharmaceutically acceptable salt and/or solvate thereof, or a radionuclide complex comprising a compound of Formula (I) or a pharmaceutically acceptable salt and/or solvate thereof, and one or more radionuclides, and to compositions thereof. The present application also includes methods of using the compounds, complexes and compositions for targeting neurotensin receptors, and further to their use in the imaging, diagnosis and treatment of diseases, disorders or conditions such as cancer. The present application relates to a compound of Formula (II) or a pharmaceutically acceptable salt and/or solvate thereof, and to compositions and uses thereof, for example, in the treatment of diseases, disorders or conditions such as cancer.

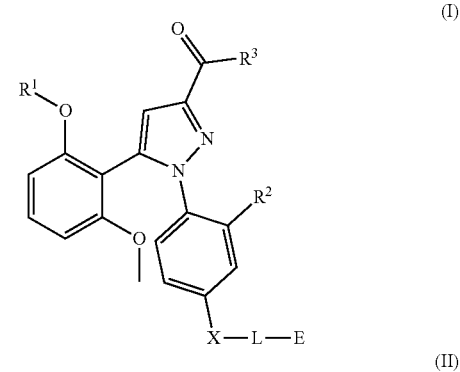

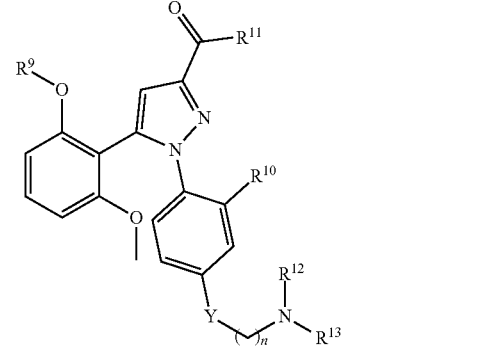

27 Claims, 24 Drawing Sheets

(56) References Cited

U.S. PATENT DOCUMENTS

| | | | |
|---|---|---|---|
| 5,886,142 | A | 3/1999 | Thakur |
| 10,961,199 | B2 | 3/2021 | Osterkamp |

FOREIGN PATENT DOCUMENTS

| | | |
|---|---|---|
| WO | 2018024789 A1 | 2/2018 |
| WO | 2023158802 A1 | 8/2023 |

OTHER PUBLICATIONS

Banerjee, S.R. et al. (2005). "New Directions in the Coordination Chemistry of 99mTc: A Reflection on Technetium Core Structures and a Strategy for New Chelate Design," Nuclear Medicine and Biology 32(1):1-20.

Baum, R.P. et al. (May 2018, e-pub. Oct. 12, 2017). "177Lu-3BP-227 for Neurotensin Receptor 1-Targeted Therapy of Metastatic Pancreatic Adenocarcinoma: First Clinical Results," Journal of Nuclear Medicine 59(5):809-814.

Dubois, M.A. et al. (Oct. 2021). "Investigating 3, 3-Diaryloxetanes as Potential Bioisosteres Through Matched Molecular Pair Analysis," RSC Medicinal Chemistry 12(12):2045-2052.

Dupouy, S. et al. (Jan. 19, 2009). "The Neurotensin Receptor-1 Pathway Contributes to Human Ductal Breast Cancer Progression," PLoS One 4(1):e4223, 1-7.

Ehlers, R.A. et al. (Jun. 2000). "Gut Peptide Receptor Expression In Human Pancreatic Cancers," Annals of Surgery 231(6):838-848.

Fields, G.B. et al. (1990). "Solid Phase Peptide Synthesis Utilizing 9-Fluorenylmethoxycarbonyl Amino Acids," Int. J. Peptide Protein Res. 35(3):161-214.

Geysen, H.M. et al. (1987). "Strategies for Epitope Analysis Using Peptide Synthesis," J. Immunol. Meth. 102:259-274.

Gui, X. et al. (2008, e-pub. May 2, 2008). "Increased Neurotensin Receptor-1 Expression During Progression of Colonic Adenocarcinoma," Peptides 29(9):1609-1615.

Gully, D. et al. (1997). "Biochemical And Pharmacological Activities of SR 142948A, A New Potent Neurotensin Receptor Antagonist," Journal of Pharmacology and Experimental Therapeutics 280(2):802-812.

International Search Report and Written Opinion from the International Searching Authority mailed Jul. 7, 2023, for International Patent Application No. PCT/US2023/013314 filed on Feb. 17, 2023, 11 pages.

Lee, S.L. et al. (Sep. 22, 2011). "Identification and Characterization of a Novel Integrin-Linked Kinase Inhibitor," Journal of Medicinal Chemistry 54(18):6364-6374, 23 pages.

Narayanan, S. et al. (Aug. 15, 2016). "Discovery of a Novel Small Molecule Agonist Scaffold for the APJ Receptor," Bioorganic & Medicinal Chemistry 24(16):3758-3770, 32 pages.

Renard, E. et al. (2021). "Positron Emission Tomography Imaging of Neurotensin Receptor-Positive Tumors With 68Ga-Labeled Antagonists: The Chelate Makes the Difference Again," Journal of Medicinal Chemistry 64 (12):8564-8578, 21 pages.

Schulz, J. et al. (Jul. 2016, e-pub. Mar. 3, 2016). "Comparative Evaluation of the Biodistribution Profiles of a Series of Nonpeptidic Neurotensin Receptor-1 Antagonists Reveals a Promising Candidate for Theranostic Applications," J Nucl Med 57(7):1120-1123.

Schulz, J. et al. (Jun. 2017, e-pub. Mar. 2, 2017). "Proof of Therapeutic Efficacy of a 177Lu-Labeled Neurotensin Receptor 1 Antagonist in a Colon Carcinoma Xenograft Model," J Nucl Med 58(6):936-941.

Souazé, F. et al. (Jun. 15, 2006). "Expression of Neurotensin and NT1 Receptor in Human Breast Cancer: A Potential Role in Tumor Progression," Cancer Research 66(12):6243-6249.

Thomas, J.B. et al. (May 23, 2014). "Identification of 1-({[1-(4-Fluorophenyl)-5-(2-methoxyphenyl)-1 H-pyrazol-3-yl]carbonyl}amino)cyclohexane Carboxylic Acid as a Selective Nonpeptide Neurotensin Receptor Type 2 Compound," Journal of Medicinal Chemistry 57(12):5318-5332.

Mncent, J.P. (1995). "Neurotensin Receptors: Binding Properties, Transduction Pathways, and Structure," Cellular and Molecular Neurobiology 15(5): 501-512.

Mncent, J.P. et al. (Jul. 1999). "Neurotensin And Neurotensin Receptors," TiPS 20(7):302-309.

Wadas, T.J. et al. (2010, e-pub. Apr. 23, 2010). "Coordinating Radiometals of Copper, Gallium, Indium, Yttrium, and Zirconium for PET and SPECT Imaging of Disease," Chemical Reviews 110(5):2858-2902.

\* cited by examiner pH7.4 PBS pH7.4 PBS+3mg/mL Ascorbate acid pH7.4 PBS pH7.4 PBS pH7.4 PBS+3mg/mL Ascorbate acid pH7.4 PBS pH7.4 PBS+3mg/mL Ascorbate acid

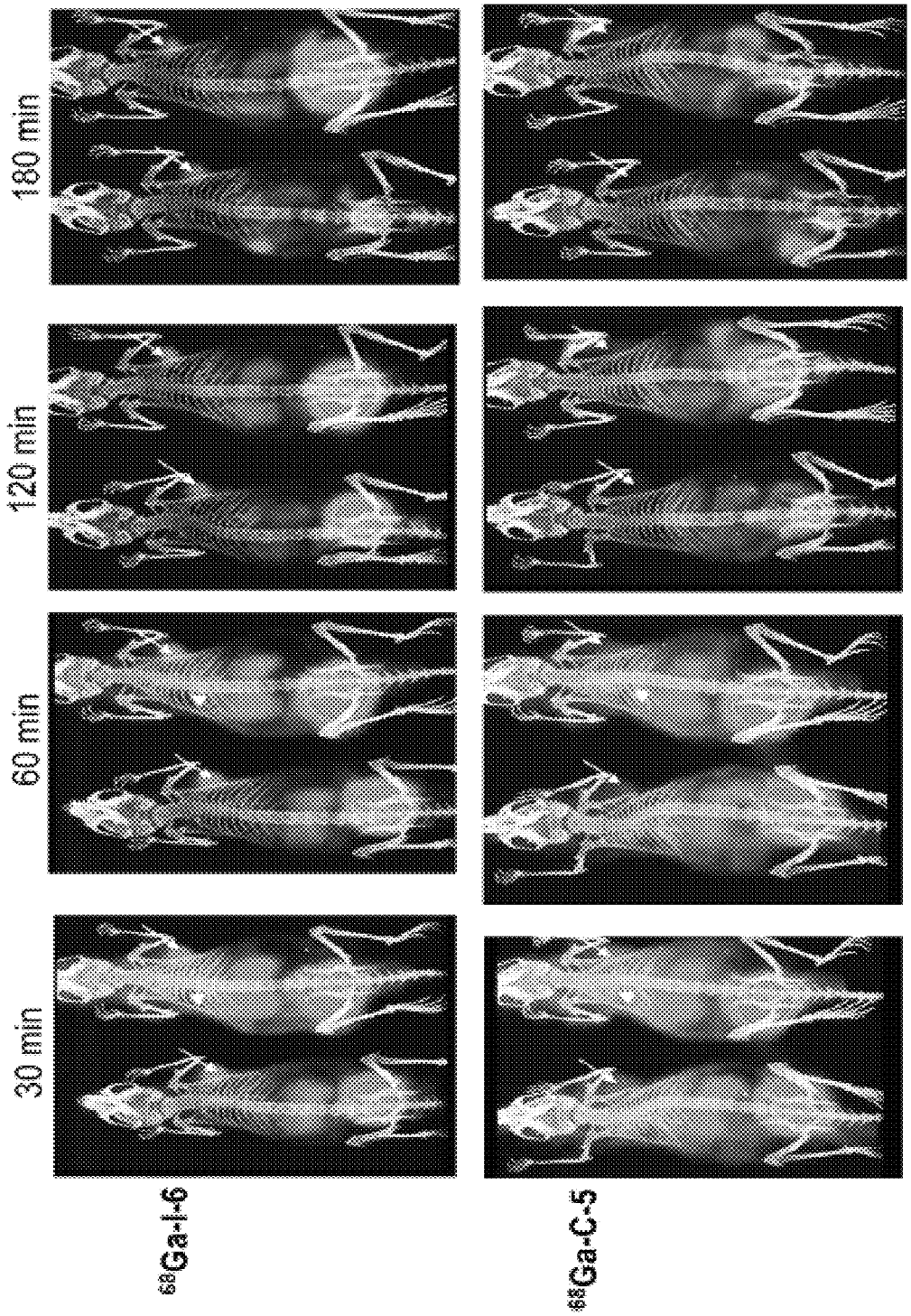

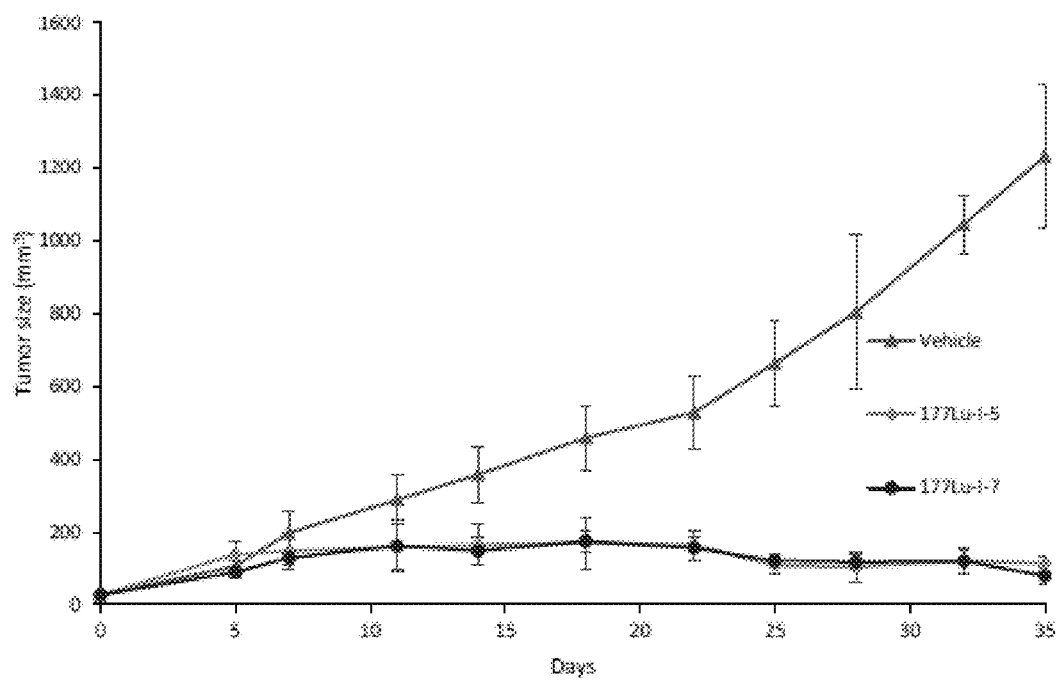
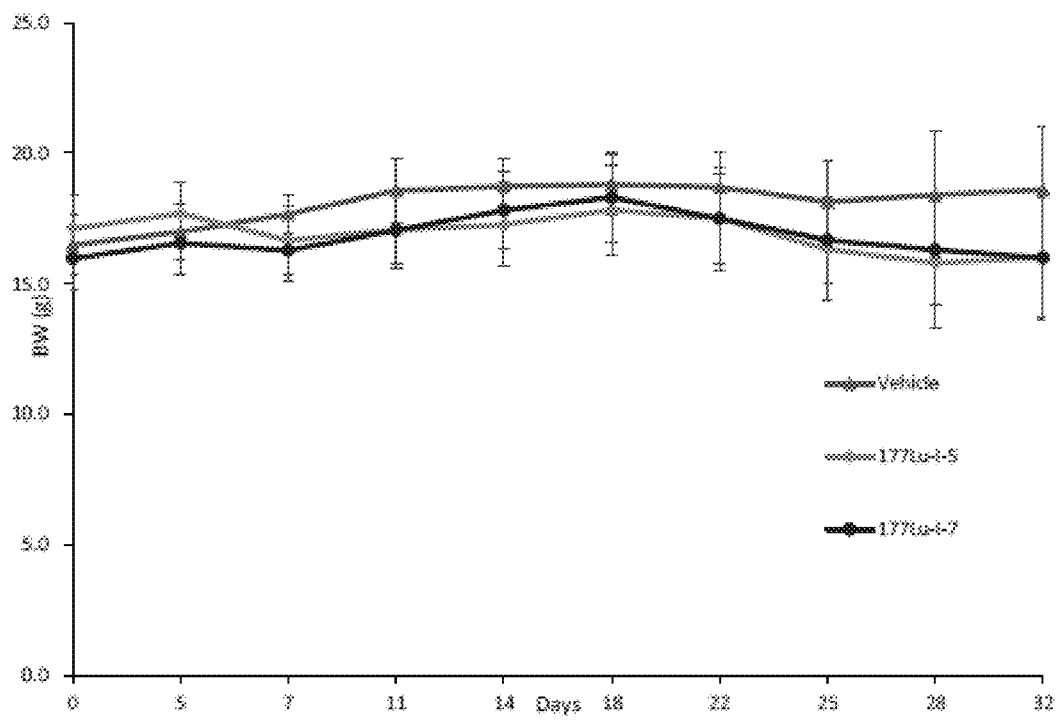

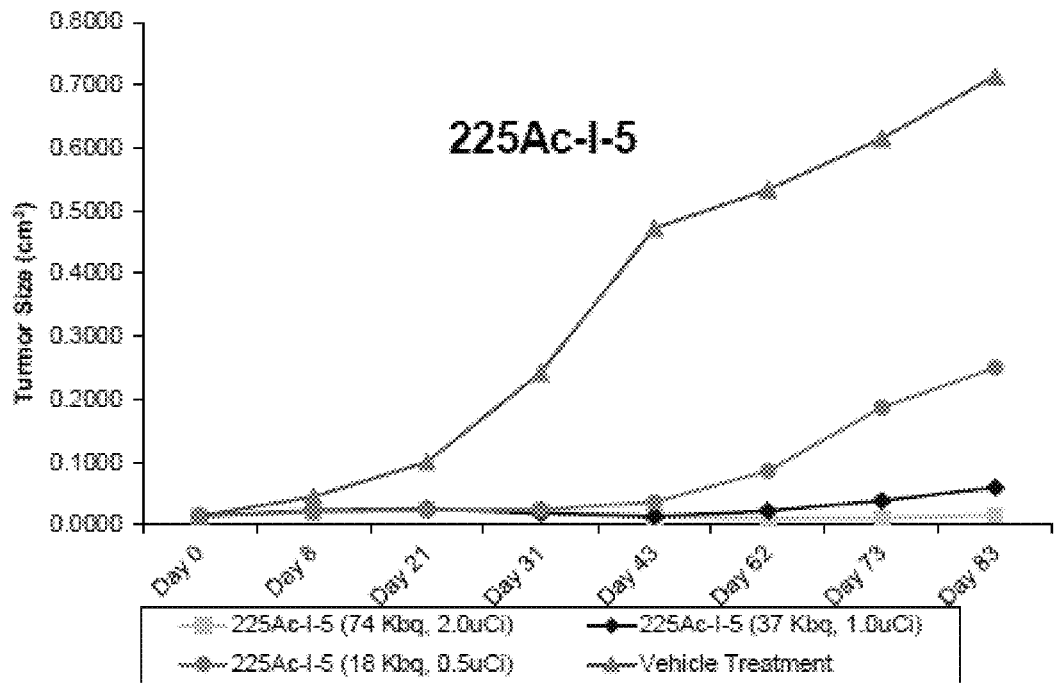
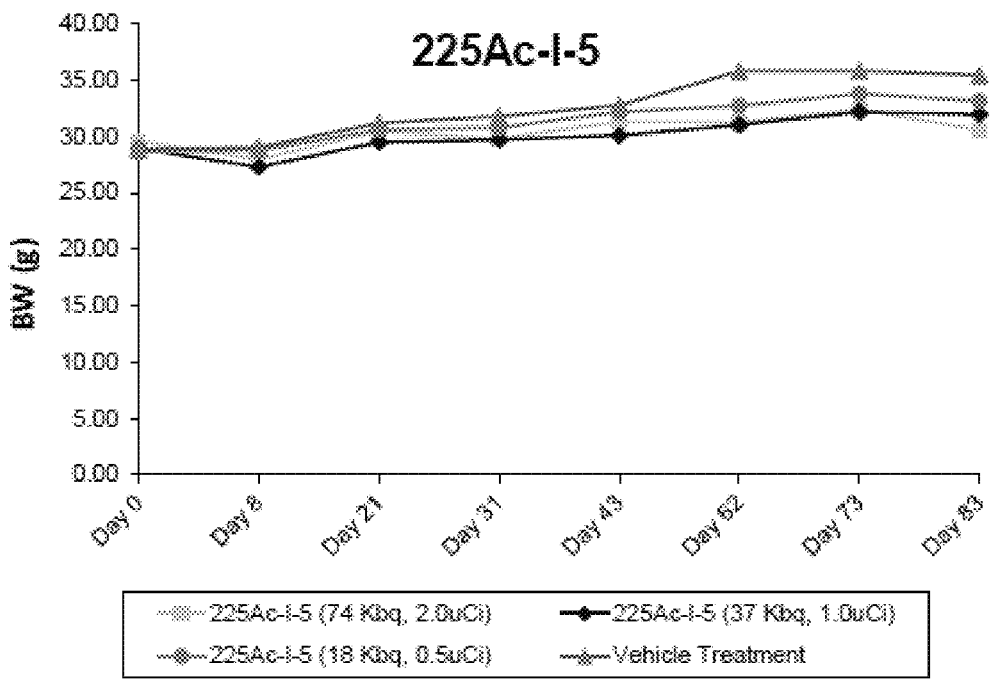

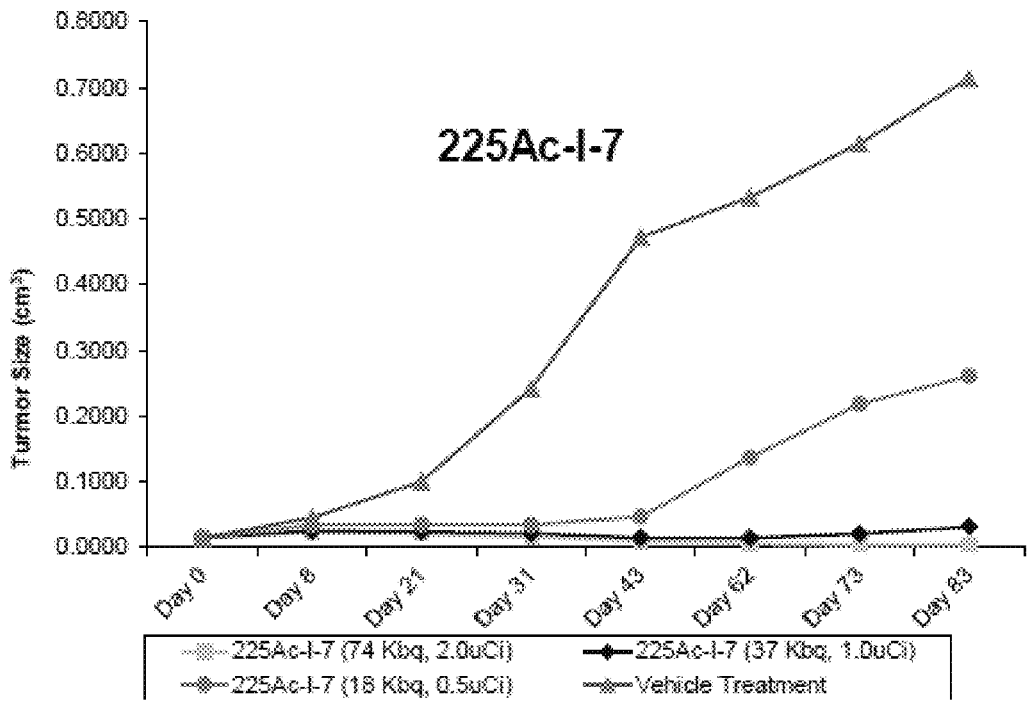
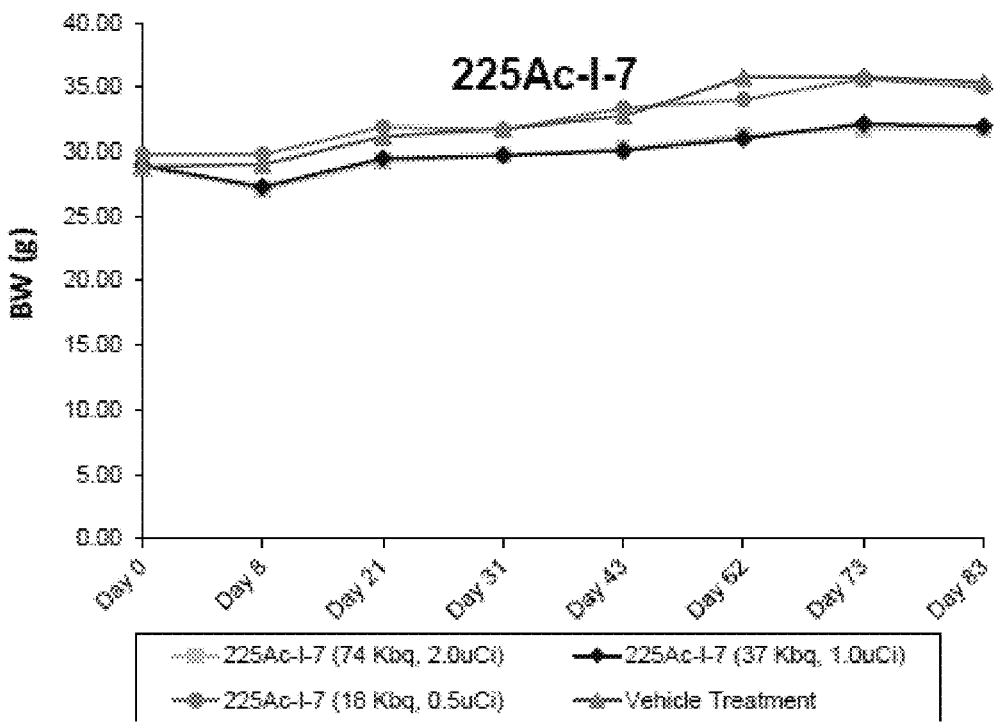

COMPOUNDS AND RADIOLIGANDS FOR TARGETING NEUROTENSIN RECEPTOR AND USES THEREOF

CROSS REFERENCE TO RELATED APPLICATIONS

The present application is a continuation of PCT Application No. PCT/US2023/013314, filed on Feb. 17, 2023, which claims the benefit of priority of U.S. provisional patent application No. 63/311,621 filed on Feb. 18, 2022, the contents of both of which are incorporated herein by reference in their entirety.

FIELD

The present application relates generally to the field of radioligands that target neurotensin receptors. In particular, it relates to compounds and complexes of the compounds comprising radionuclides. The application also relates to methods of using the compounds and complexes for targeting and/or killing target cells.

BACKGROUND

Neurotensin is a 13-mer peptide that functions as a neurotransmitter and hormone. It acts through neurotensin receptor family which consists of 3 receptor subtypes: neurotensin receptor 1 (NTR1 or NTSR1), NTSR2 and NTSR3 (sortilin). NTSR1 and NTSR2 are G-protein coupled receptors (GPCRs) while sortilin is a sorting receptor with a single transmembrane domain [1,2].

High expression of NTR1 has been identified in a number of tumors including colorectal and pancreatic cancers, and breast, prostate, small and non-small cell lung cancers [3-5]. Studies have also shown a tight association between NTR1 expression level and disease progression [6]. Such disease-related over-expression has suggested NTR1 as a viable target for targeted cancer therapies. In the case of pancreatic cancer, NTR1 is found to be present in 75%-90% of pancreatic ductal adenocarcinoma (PDAC), while the normal pancreas does not express NTRs.

Small molecule antagonists of NTR1 have been disclosed. For example, compound SR142948 (C-3) is one of the structures described in U.S. Pat. No. 5,723,483 that demonstrated high binding affinity to NTR1 as an antagonist [7]. Radioligand compounds that derived from SR142948 have been reported. For example, radioligand compounds derived from SR142948 have been disclosed in WO2014086499A1 and WO2018024789A1. Further, their abilities of detecting NTR1-positive tumors and inhibiting its growth have been confirmed in animals [8,9]. One of the leading compounds, 3BP-227 (C-2), has also been tested in a small number of pancreatic cancer patients in its $^{177}$Lu-chelated form where the tumor uptake of the radioligand has been clearly observed [10].

High binding affinity is an important factor to achieve high tumor uptake of the radioligand in vivo. Relatedly, high binding affinity is also important to realize an ideal ratio of tumor uptake vs normal tissue accumulation of the radioligand. However, the methods of derivatizing SR142948 towards a radioligand disclosed in the prior arts are not aimed to improve its binding affinity, in fact, such derivatization are often detrimental to its interactions with the receptor, NTR1. For example, 3BP-227 is about 40% potent as SR142948 in the competitive radioligand binding assay using HT-29 cells. In the human study of $^{177}$Lu-3BP-227, the kidney was identified as the dose limiting organ [10]. In addition, the requirement of a high tumor to kidney, and tumor to other normal organ ratio is even more stringent for alpha-emitters ($^{225}$Ac, $^{212}$Pb etc.) than for beta-emitters ($^{177}$Lu, $^{90}$Y etc.), as the former is significantly more powerful than the latter in breaking down DNA and killing cell. Collectively, further optimization of the tumor uptake and tumor to kidney ratio, and tumor to other normal organs ratio are still warranted in order to establish a NTR1-based radioligand therapy with a wide therapeutic window in the clinical use.

SUMMARY

Given the aforementioned limitations, derivatives of SR142948 and new radioligands that target neurotensin receptors derived therefrom are described herein.

Accordingly, the present application includes a compound or a pharmaceutically acceptable salt and/or solvate thereof,

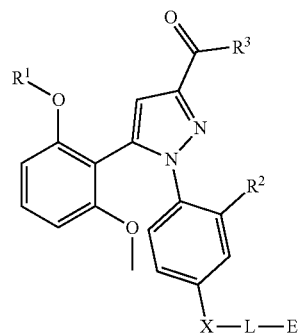

(I)

wherein $R^1$ is selected from H, $C_{1-6}$alkyl, $C_{3-6}$cycloalkyl and $C_{1-3}$alkyleneC$_{3-6}$cycloalkyl, the latter three groups being optionally substituted with one or more halo;

$R^2$ is selected from H, halo, NO$_2$, $C_{1-6}$alkyl, $C_{3-8}$cycloalkyl and $C_{1-3}$alkyleneC$_{3-8}$cycloalkyl, the latter three groups being optionally substituted with one or more halo;

$R^3$ is selected from 2-amino-2-adamantane carboxylic acid, cyclohexylglycine and 9-amino-bicyclo[3.3.1]nonane-9-carboxylic acid;

X is selected from CH$_2$, O, NR$^4$, S, S(O), SO$_2$NR$^4$ and NR$^4$C(O);

L is a linker;

E is a chelating group;

$R^4$ is selected from H, $C_{1-6}$alkyl, $C_{1-6}$alkenyl, $C_{1-6}$alkynyl, C(O)$_{1-6}$alkyl, $C_{1-10}$alkyleneNR$^5$R$^6$, $C_{1-10}$alkenyleneNR$^5$R$^6$, and $C_{1-10}$alkynyleneNR$^5$R$^6$; and $R^5$ and $R^6$ are independently selected from H and $C_{1-6}$alkyl.

The present application further includes a radionuclide complex or a pharmaceutically acceptable salt and/or solvate thereof, comprising a compound of Formula I or a pharmaceutically acceptable salt and/or solvate thereof, and one or more radionuclides.

The present application also includes a compound of Formula II or a pharmaceutically acceptable salt and/or solvate thereof

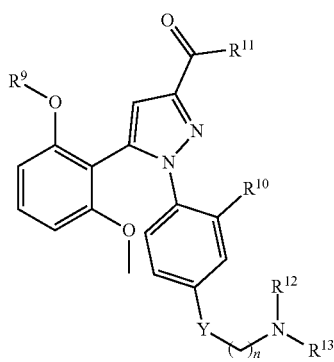

(II)

wherein
$R^9$ is selected from H, $C_{1-6}$alkyl, $C_{3-6}$cycloalkyl and $C_{1-3}$alkylene$C_{3-8}$cycloalkyl, the latter three groups being optionally substituted with one or more halo;

$R^{10}$ is selected from H, halo, $NO_2$, $C_{1-6}$alkyl, $C_{3-8}$cycloalkyl and $C_{1-3}$alkylene$C_{3-8}$cycloalkyl), the latter three groups being optionally substituted with one or more halo;

$R^{11}$ is selected from 2-amino-2-adamantane carboxylic acid, cyclohexylglycine and 9-amino-bicyclo[3.3.1]nonane-9-carboxylic acid;

Y is selected from $CH_2$, O, $NR^{14}$, S, S(O), $SO_2NR^{14}$ and $NR^{14}C(O)$;

$R^{12}$ and $R^{13}$ are independently selected from H and $C_{1-6}$alkyl and $R^{14}$ is selected from H and $C_{1-6}$alkyl; and n is an integer selected from 1 to 10.

The application includes a composition comprising one or more compounds as described above or a pharmaceutically acceptable salt and/or solvate thereof, or one or more radionuclide complexes as described above or a pharmaceutically acceptable salt and/or solvate thereof and a carrier.

The application includes a composition comprising one or more compounds as described above or a pharmaceutically acceptable salt and/or solvate thereof, or one or more radionuclide complexes as described above or a pharmaceutically acceptable salt and/or solvate thereof and a pharmaceutically acceptable carrier.

Further included is a method of treating a disease or disorder comprising administering a therapeutically effective amount of one or more compounds as described above or one or more radionuclide complexes as described above or a pharmaceutically acceptable salt and/or solvate thereof to a subject in need thereof.

In some embodiments, the disease or disorder is cancer. In some embodiments, the cancer is a neurotensin receptor positive cancer, optionally wherein the neurotensin receptor is neurotensin receptor 1 (NTR1).

The application also includes a method of inhibiting proliferative activity in a cell, comprising administering an effective amount of one or more compounds of as described above or one or more radionuclide complexes as described above or a pharmaceutically acceptable salt and/or solvate thereof to the cell.

The application also includes a method of imaging a tissue in a subject by administering a therapeutically effective amount of one or more compounds as described above or one or more radionuclide complexes for use in imaging as described above or a pharmaceutically acceptable salt and/or solvate thereof and applying an imaging technique to detect emitted gamma rays.

The application also includes a method of diagnosing cancer in subject by administering a therapeutically effective amount of one or more compounds of as described above or one or more radionuclide complexes for use in imaging as described above or a pharmaceutically acceptable salt and/or solvate thereof and applying an imaging technique to detect emitted gamma rays.

The present application also includes a method of theranostic treatment comprising administering an effective amount of one or more complexes of the application to a subject in need thereof and performing a medical diagnostic method on the subject.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

BRIEF DESCRIPTION OF THE DRAWINGS

Certain embodiments of the application will now be described in greater detail with reference to the attached drawings in which:

FIG. 6 illustrates mice PET/CT imaging results after administration of the exemplary $^{68}$Ga labeled comparative and exemplary complexes, $^{68}$Ga—C-5 and $^{68}$Ga—I-8 respectively of the present application over 180 minutes.

FIGS. 7A-7B illustrate in vivo efficacy of the $^{177}$Lu therapy with exemplary complexes $^{177}$Lu—I-5, and $^{177}$Lu—I-7 in ASPC-1 tumor-bearing mice.

FIGS. 8A-8D illustrate in vivo efficacy of the $^{225}$Ac therapy with exemplary complexes $^{225}$Ac—I-5, and $^{225}$Ac—I-7 in ASPC-1 tumor-bearing mice.

DETAILED DESCRIPTION

I. Definitions

Figure 1:
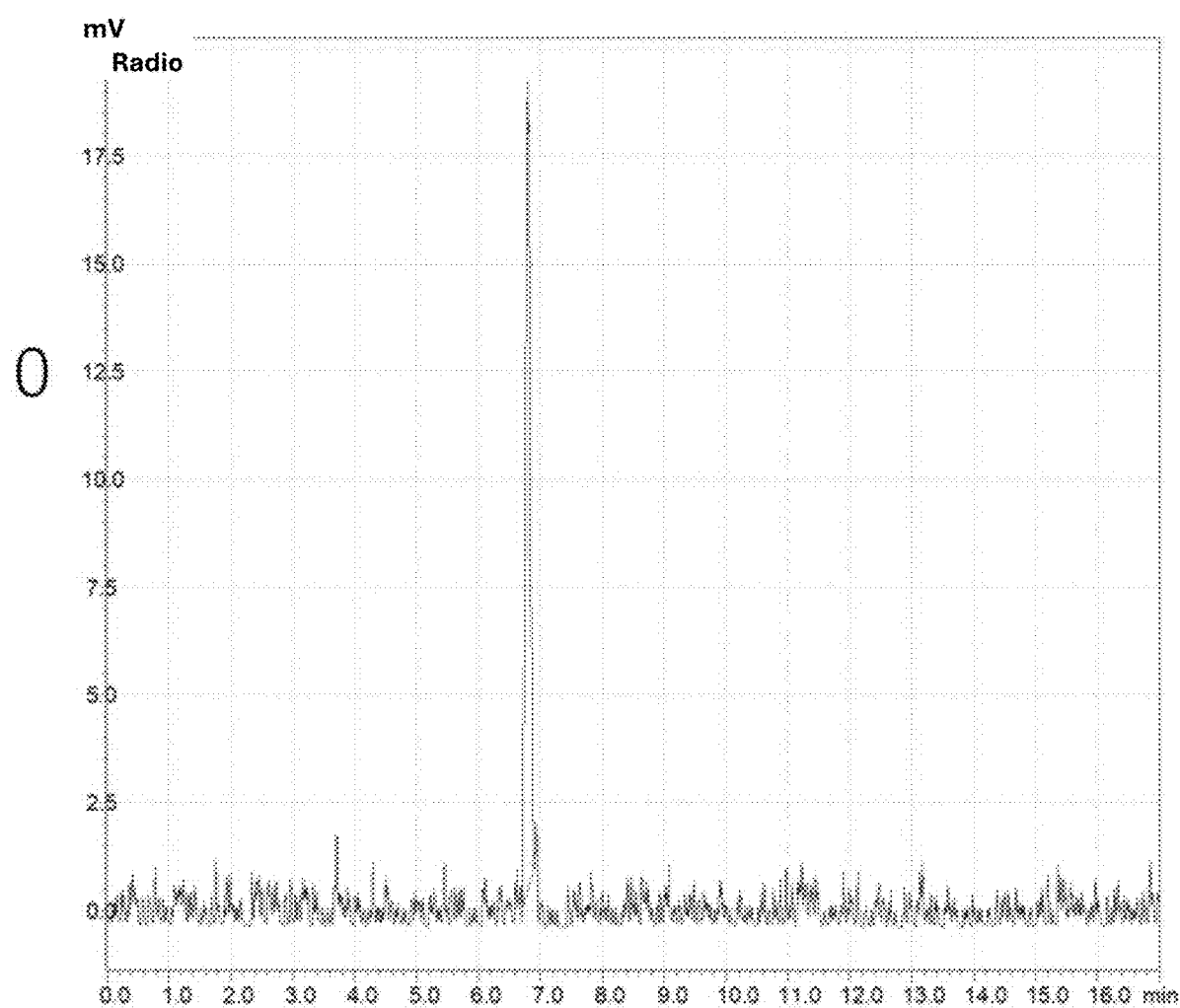
FIG. 1 illustrates the stability of the exemplary $^{177}$Lu labeled compounds.
Figure 1:
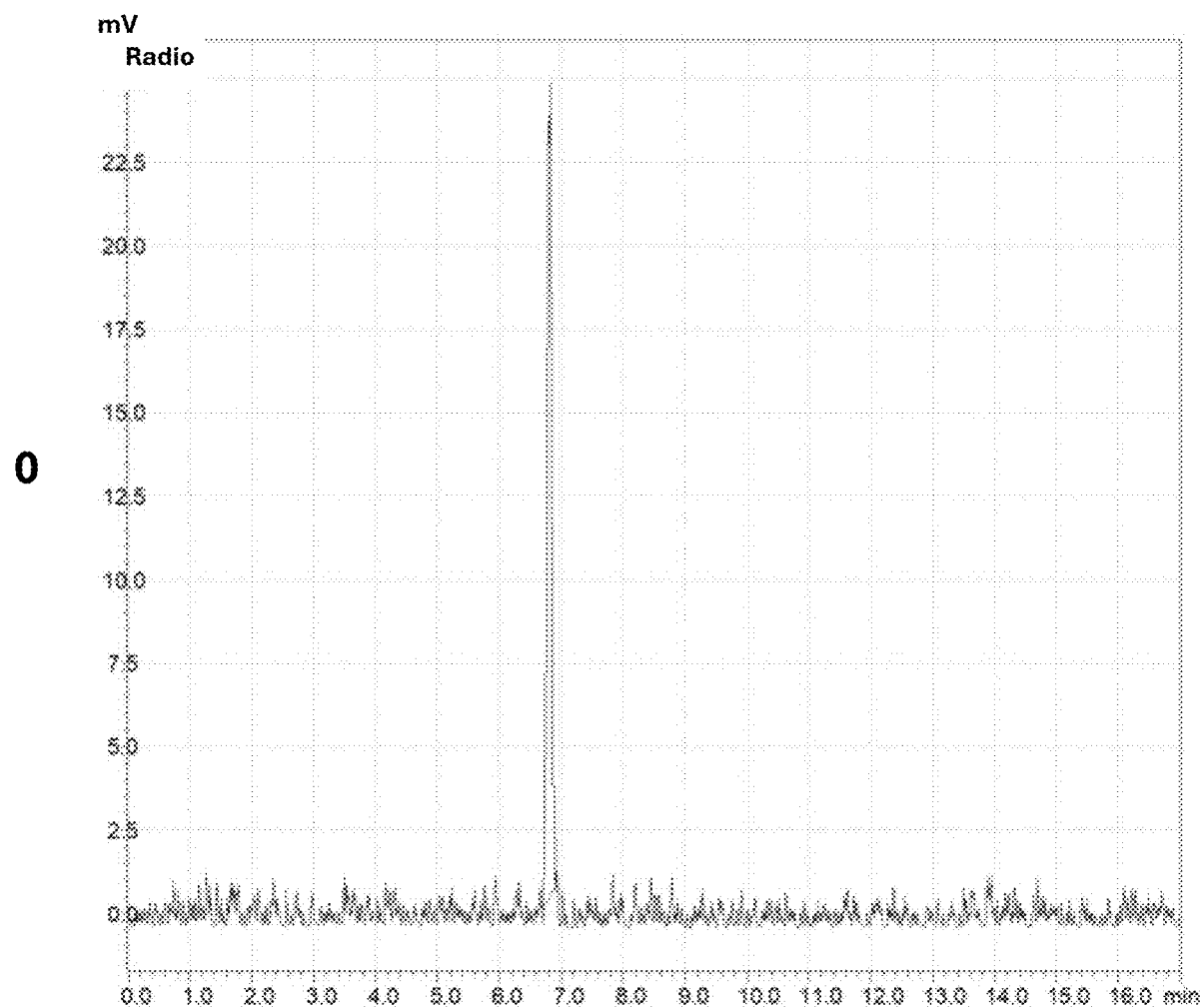
Figure 1:
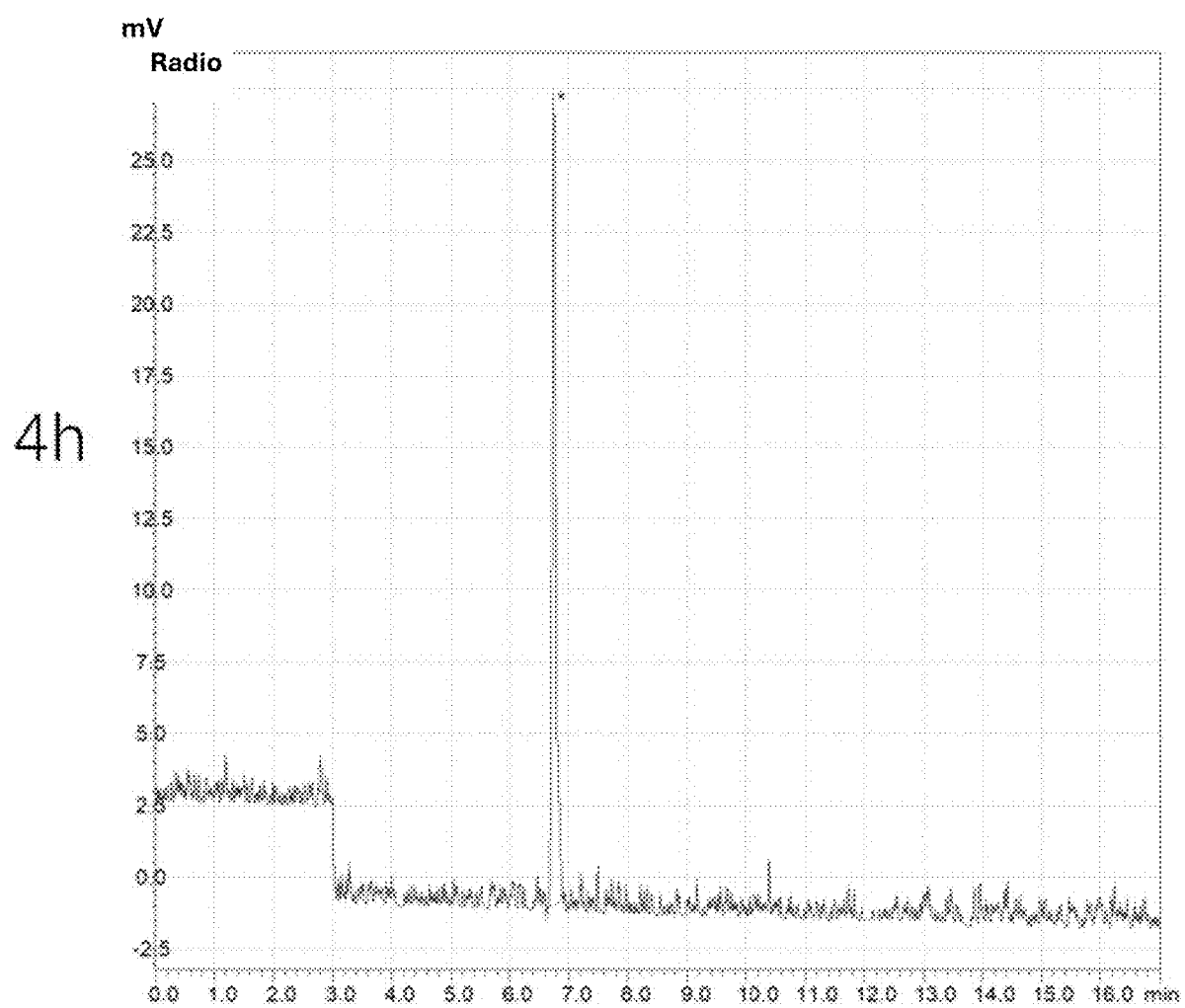
Figure 1:
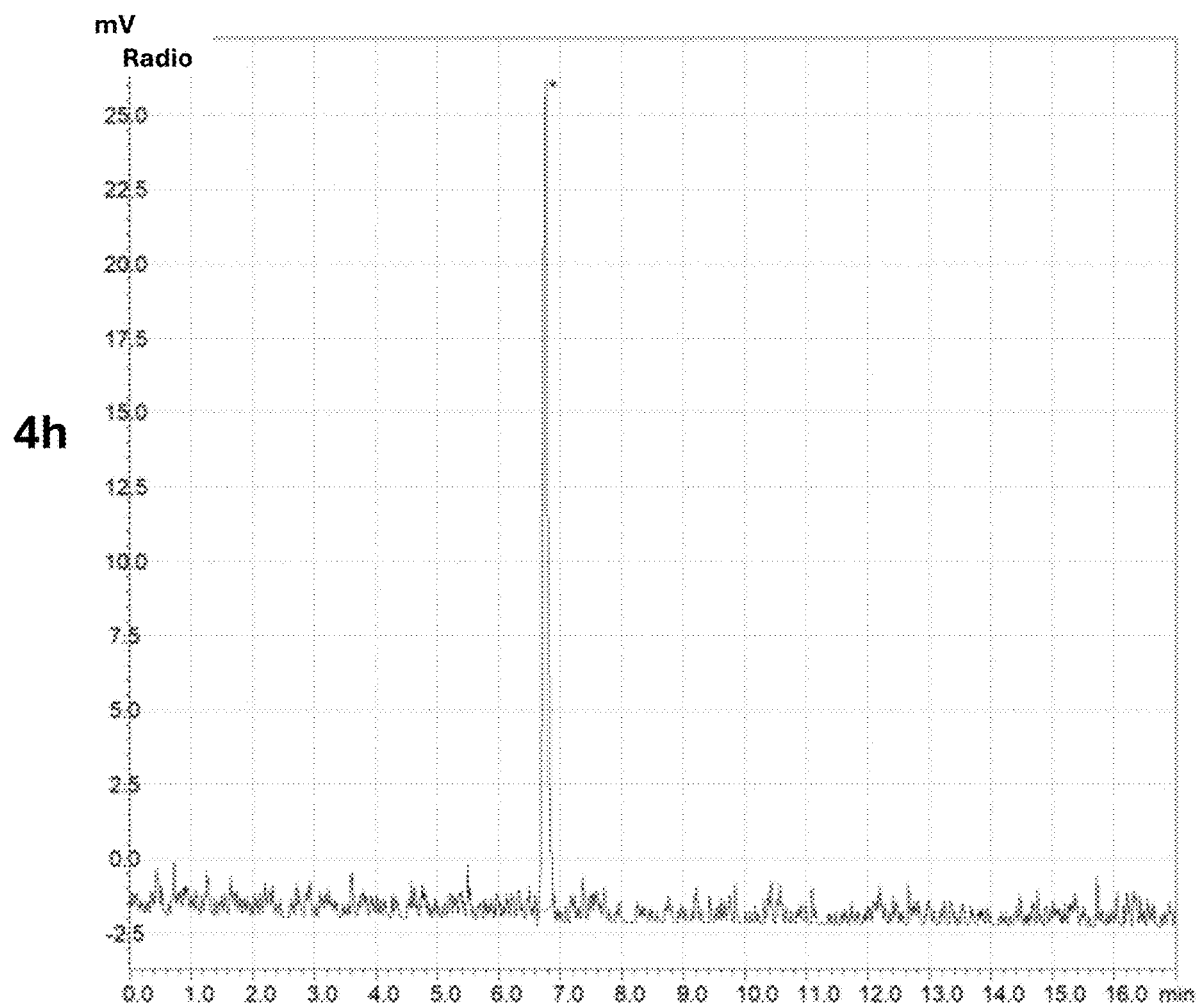
Figure 1:
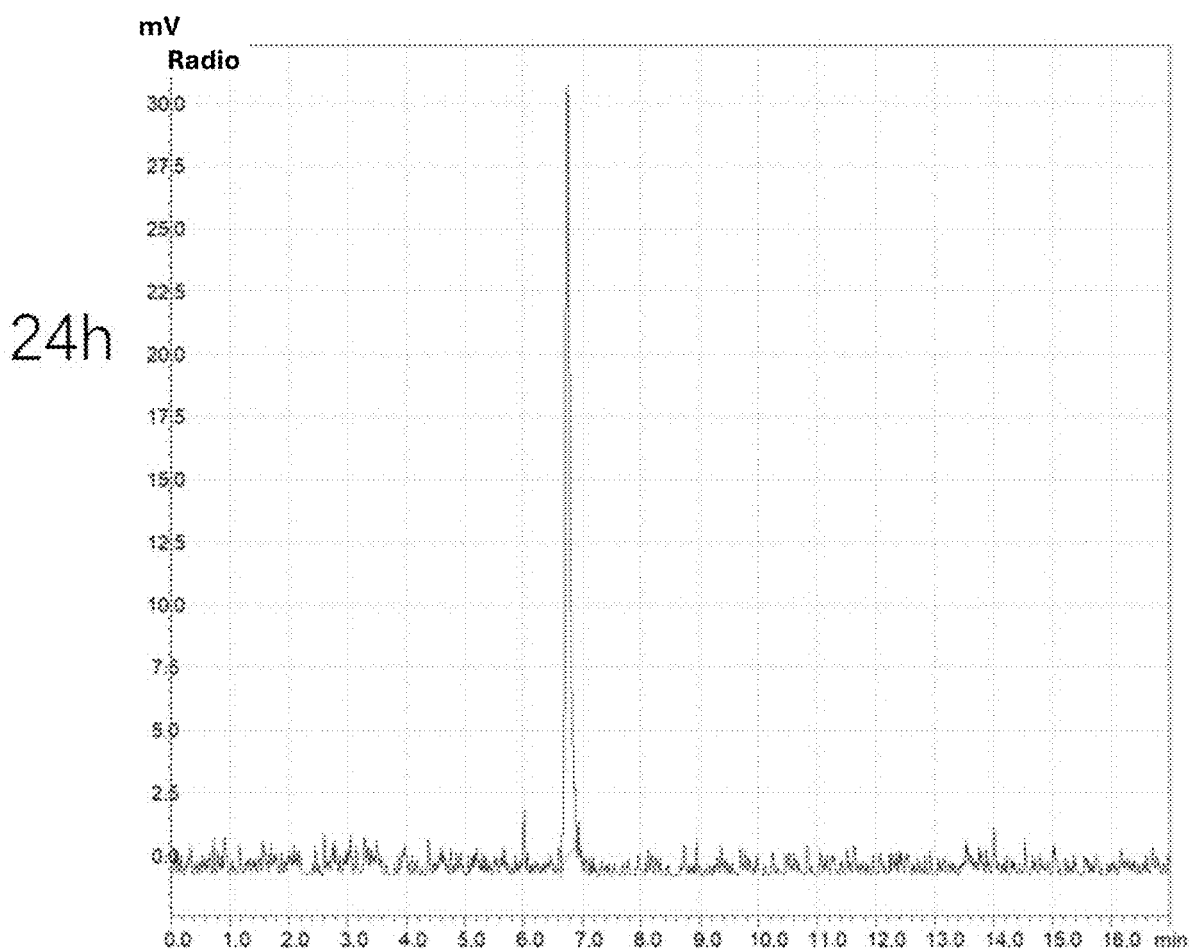
Figure 1:
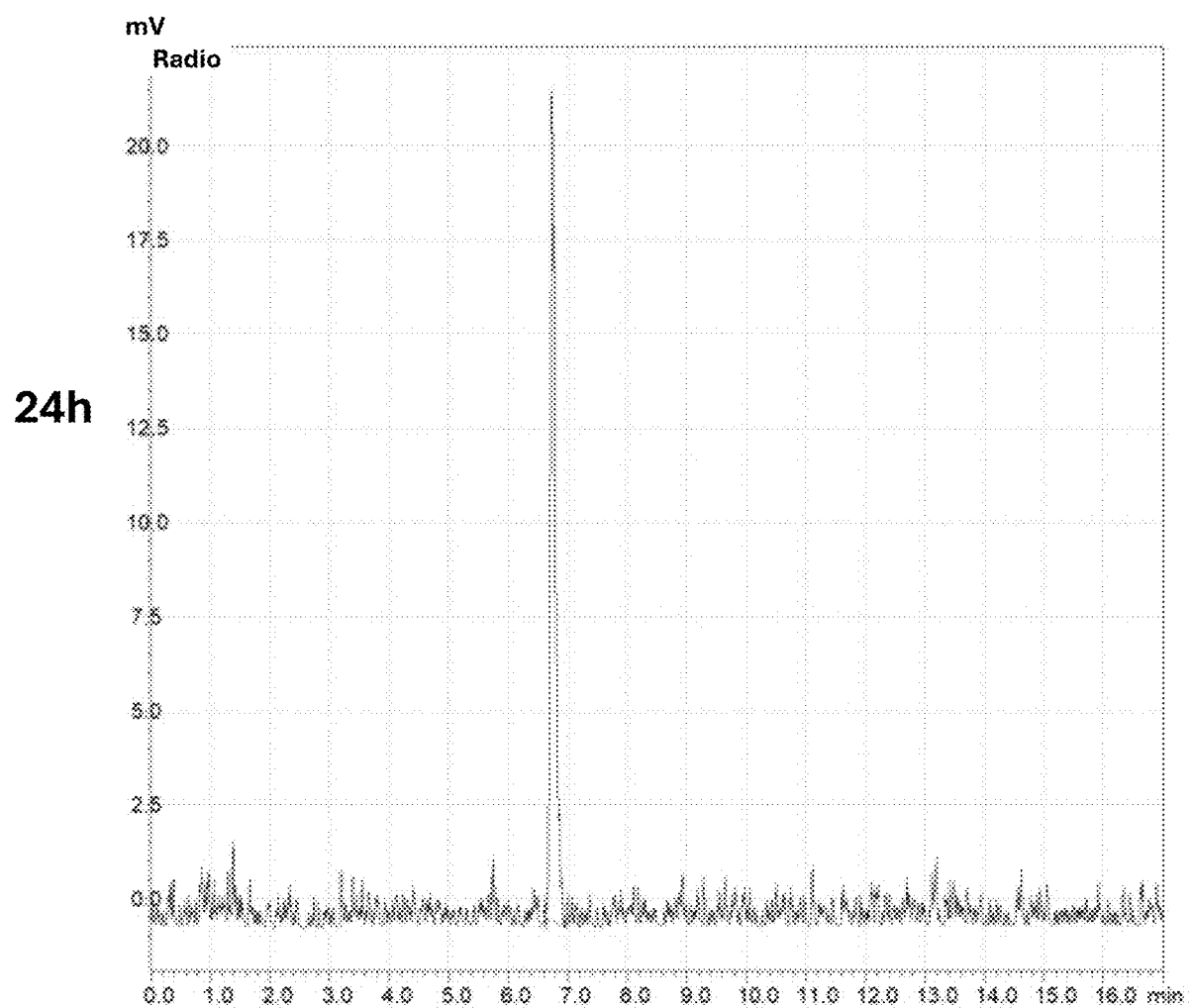
Figure 1:
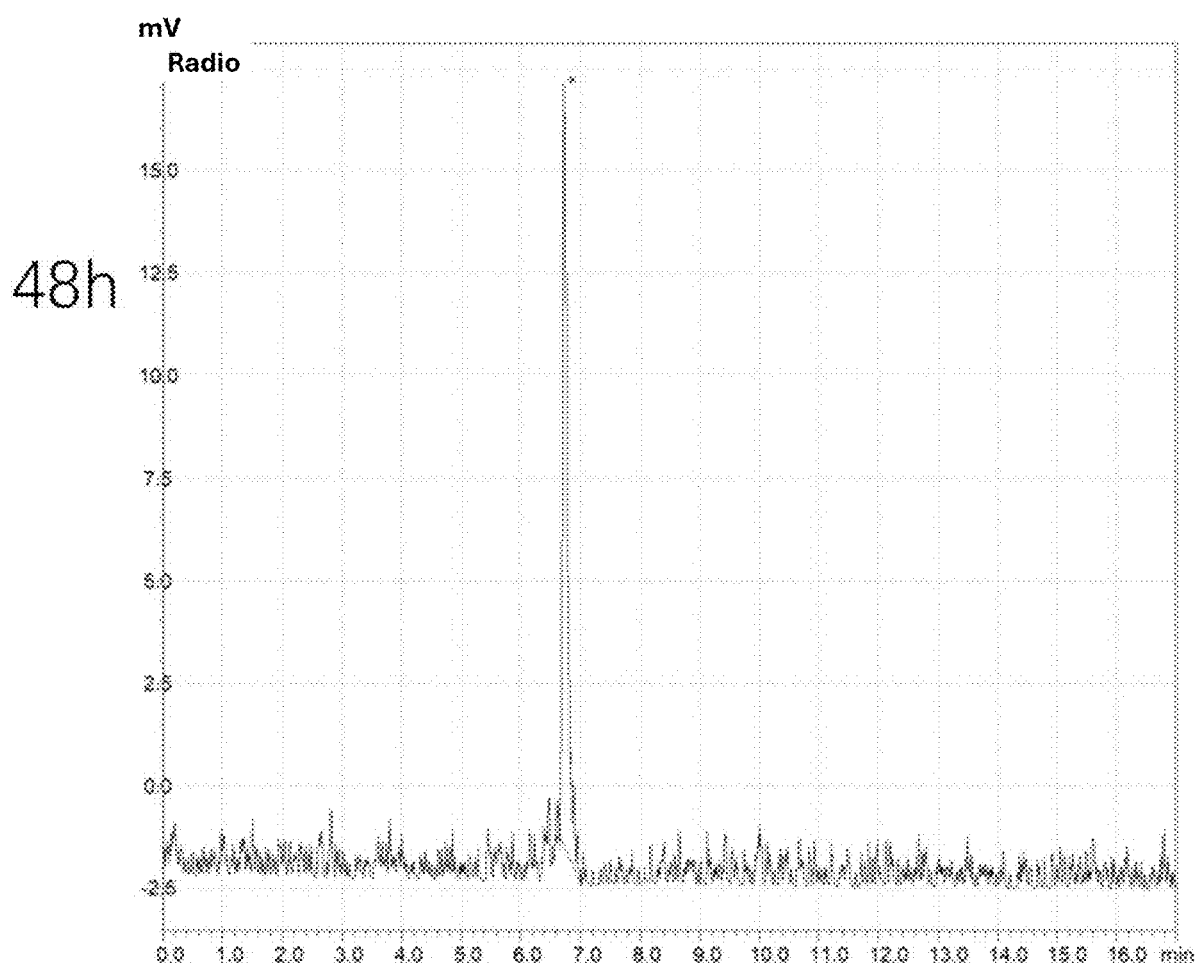
Figure 1:
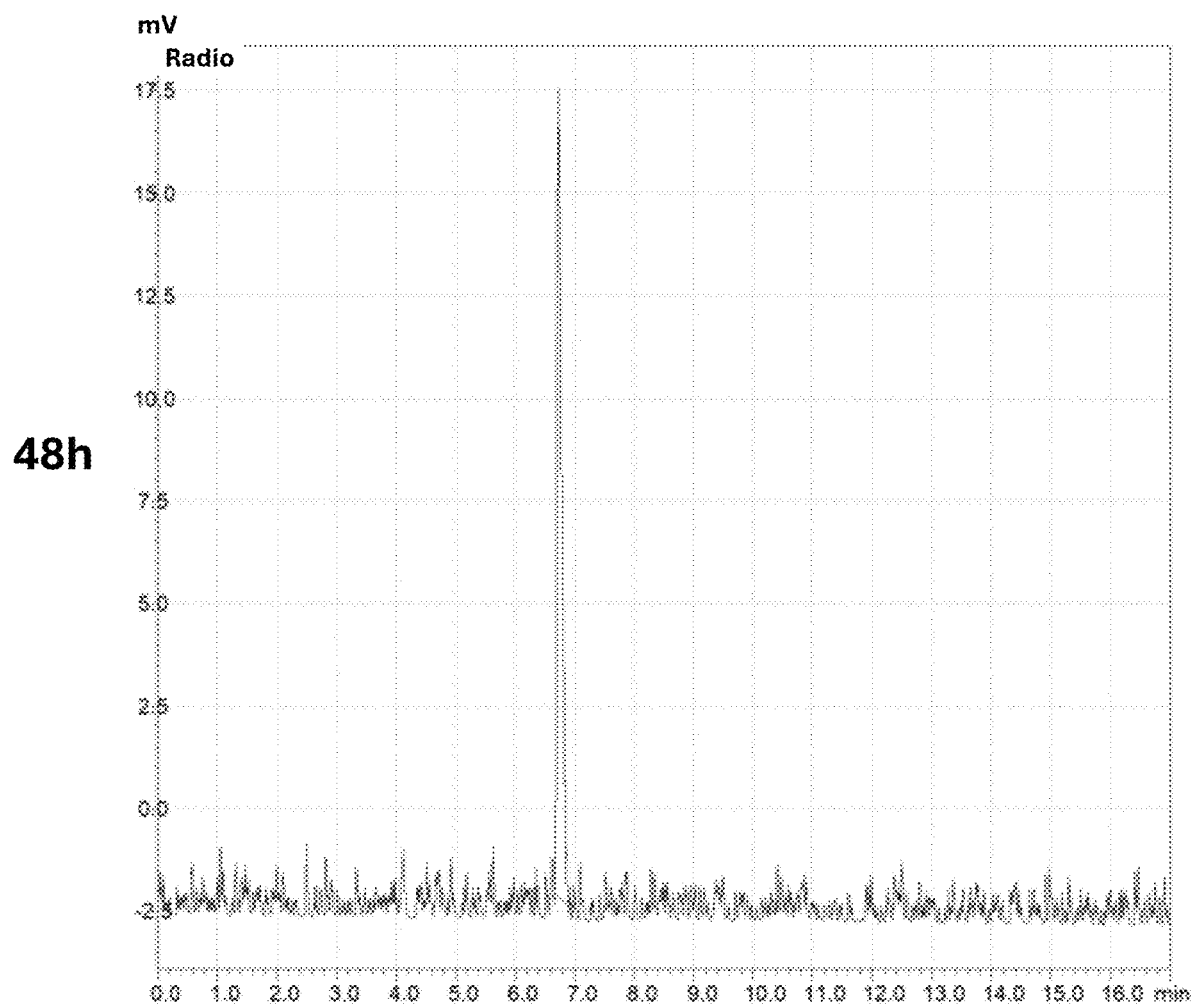
Figure 1:
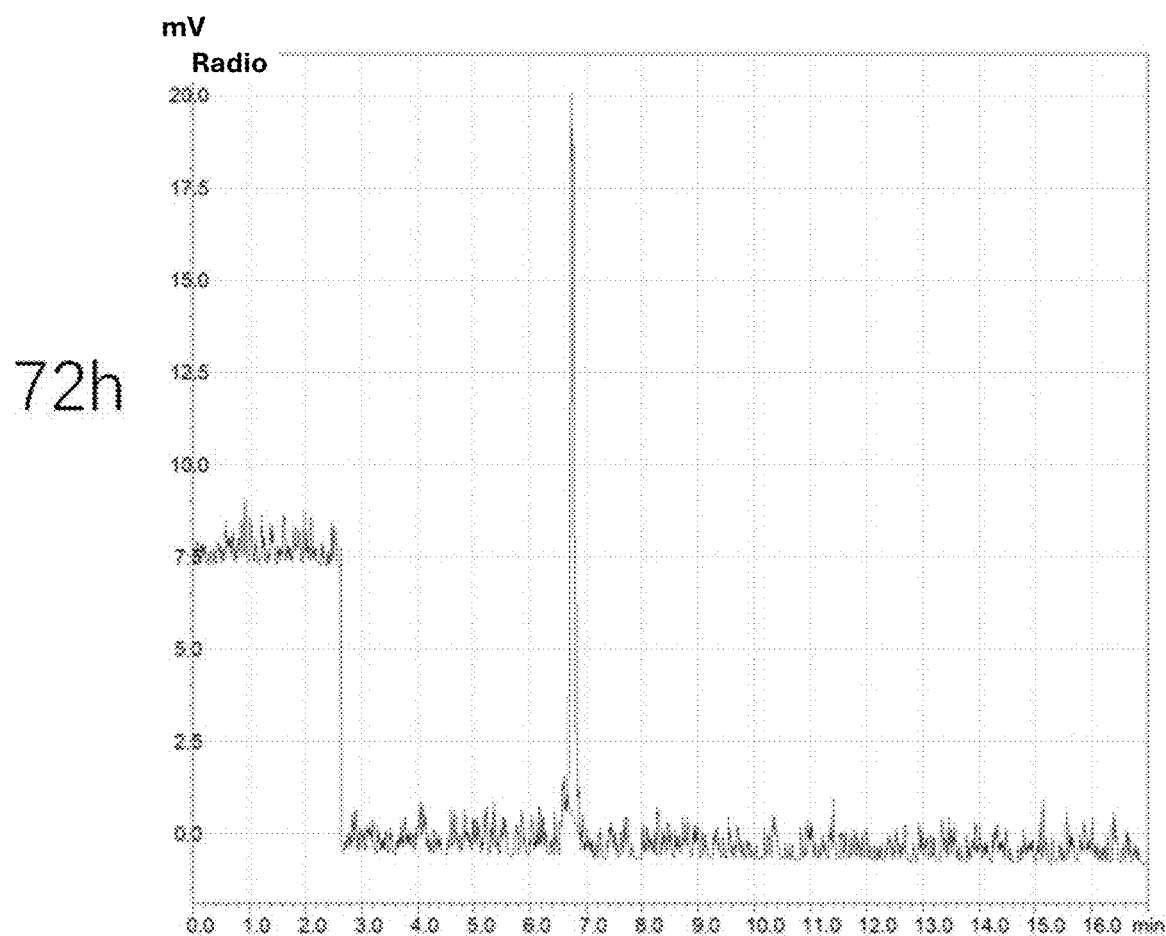
Figure 1:
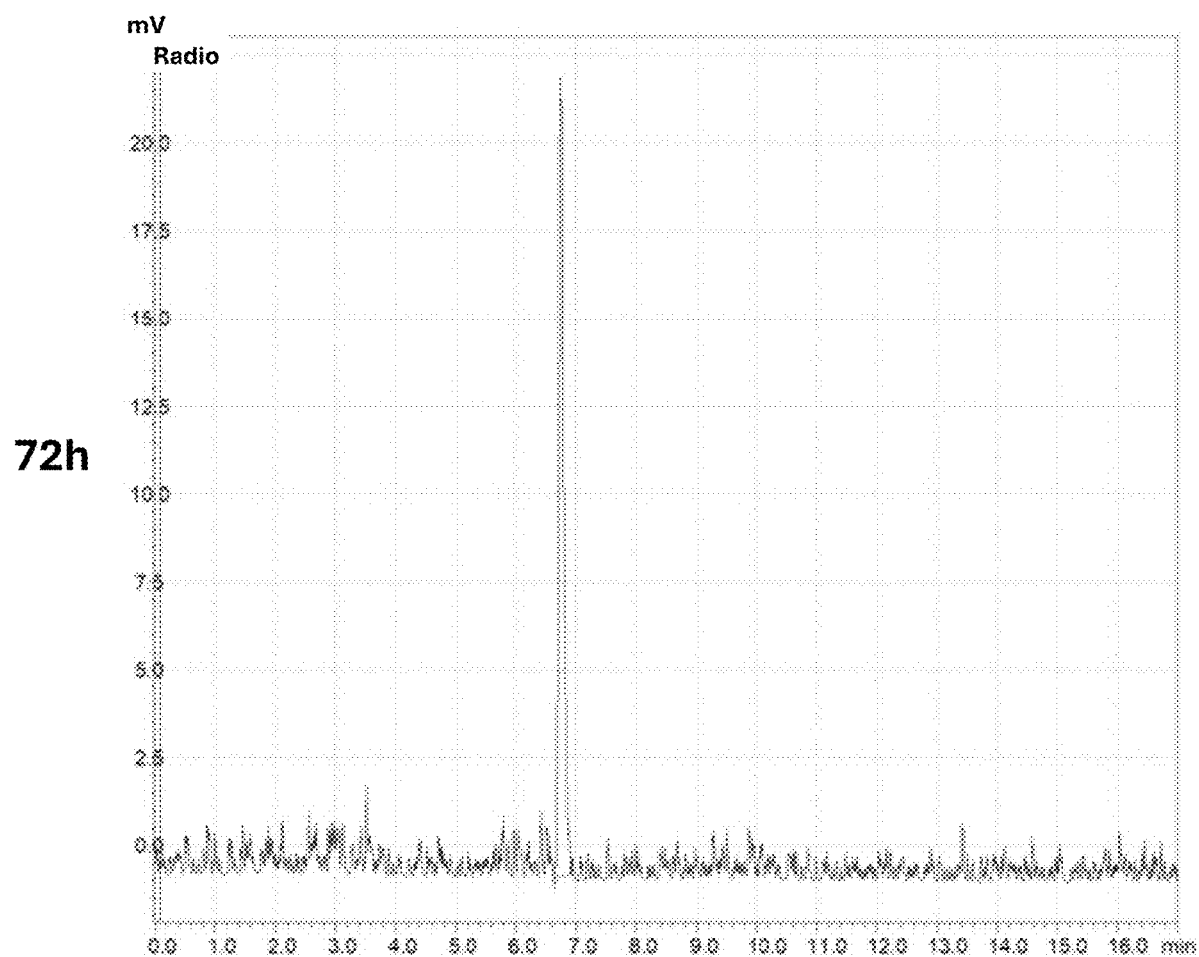
Figure 1:
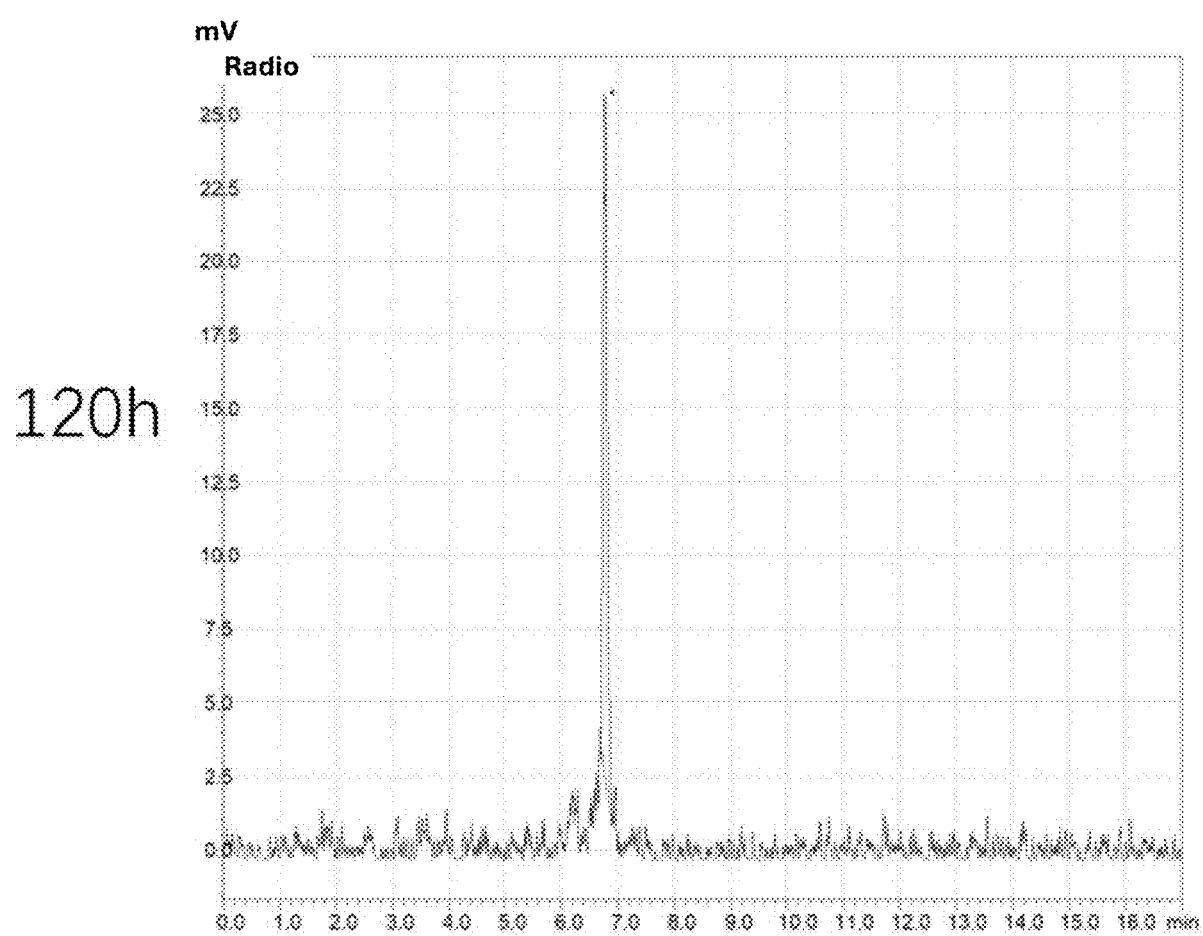
Figure 1:
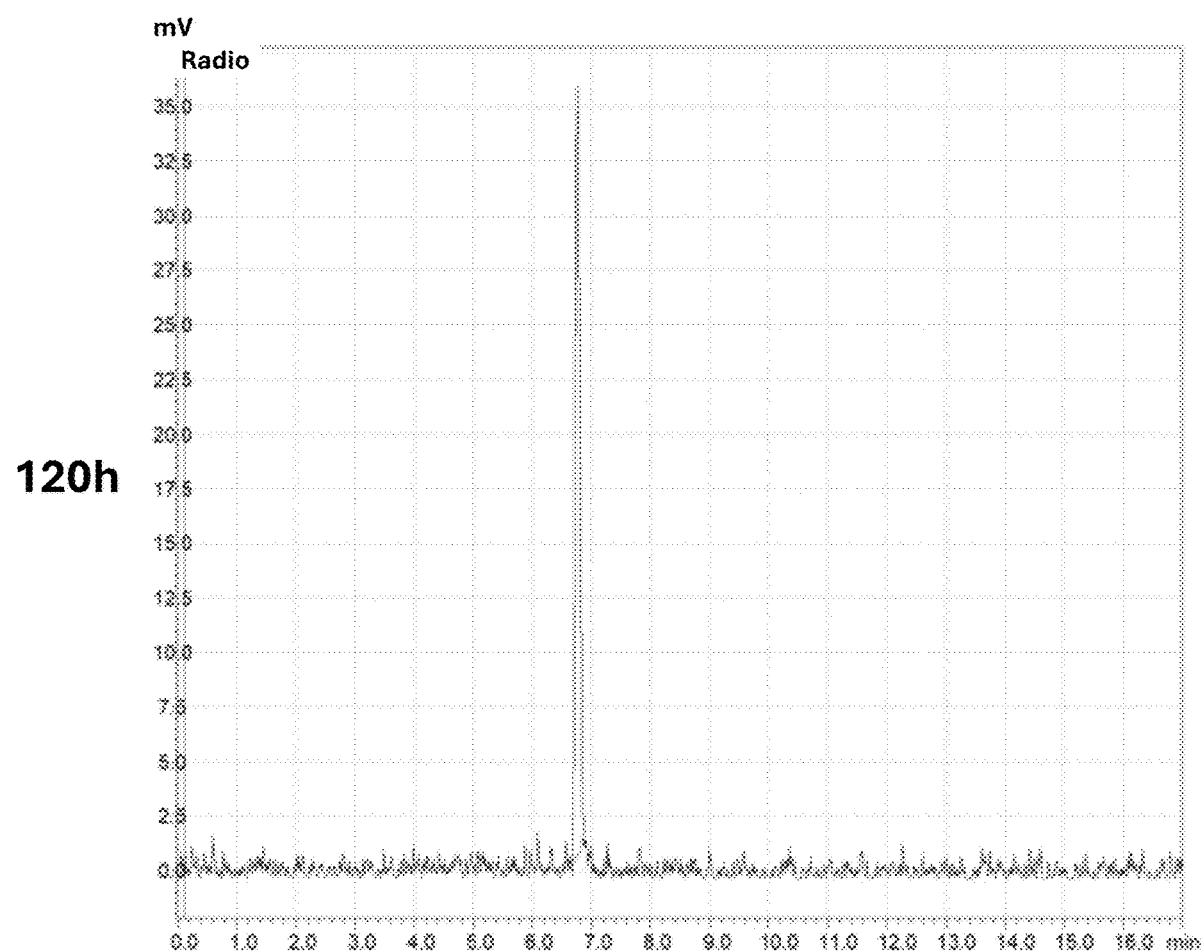

Unless otherwise indicated, the definitions and embodiments described in this and other sections are intended to be applicable to all embodiments and aspects of the present application herein described for which they are suitable as would be understood by a person skilled in the art.

All features disclosed in the specification, including the claims, abstract, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent, or similar purpose, unless expressly stated otherwise.

As used in this application and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "consisting" and its derivatives as used herein are intended to be closed terms that specify the presence of the stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies or unless the context suggests otherwise to a person skilled in the art.

As used in the present application, the singular forms "a", "an" and "the" include plural references unless the content clearly dictates otherwise. For example, an embodiment including "a compound" should be understood to present certain aspects with one compound, or two or more additional compounds.

In embodiments comprising an "additional" or "second" component or effect, such as an additional or second compound, the second compound as used herein is different from the other compounds or first compound. A "third" compound is different from the other, first, and second compounds, and further enumerated or "additional" compounds are similarly different.

The term "and/or" as used herein means that the listed items are present, or used, individually or in combination. In effect, this term means that "at least one of" or "one or more" of the listed items is used or present. The term "and/or" with respect to enantiomers, prodrugs, salts and/or solvates thereof means that the compounds of the application exist as individual enantiomers, prodrugs, salts and hydrates, as well as a combination of, for example, a salt of a solvate of a compound of the application.

The term "compound(s) of the application" or "compound(s) of the present application" and the like as used herein refers to a compound of Formula I, I-A, Formula II, II-A and II-B or pharmaceutically acceptable salts and/or solvates thereof.

The term "complex of the application" or "complexes of the application" and the like as used herein refers to a complex comprising one or more compounds of Formula I or pharmaceutically acceptable salts and/or solvates thereof and one or more radionuclides.

The term "composition of the application" or "composition of the present application" and the like as used herein refers to a composition comprising one or more compounds or complexes of the application.

The term "radioligand" as used herein refers to compound comprising a neurotensin receptor binding moiety and a radionuclide. The complexes of the application are examples of radioligands.

The term "radionuclide" as used herein refers to any atom capable of undergoing radioactive decay. The term radionuclide is used synonymously herein with radioactive nuclide, radioisotope, and radioactive isotope. Radionuclides occur naturally, or can be produced artificially.

The term "suitable" as used herein means that the selection of the particular compound or conditions would depend on the specific synthetic manipulation to be performed, the identity of the molecule(s) to be transformed and/or the specific use for the compound, but the selection would be well within the skill of a person trained in the art.

The present description refers to a number of chemical terms and abbreviations used by those skilled in the art. Nevertheless, definitions of selected terms are provided for clarity and consistency.

The term "protecting group" or "PG" and the like as used herein refers to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOrrie, J. F. W. Ed., Plenum Press, 1973, in Greene, T. W. and Wuts, P. G. M., "Protective Groups in Organic Synthesis", John Wiley & Sons, $3^{rd}$ Edition, 1999 and in Kocienski, P. Protecting Groups, 3rd Edition, 2003, Georg Thieme Verlag (The Americas).

The term "alkyl" as used herein, whether it is used alone or as part of another group, means straight or branched chain, saturated alkyl groups. The number of carbon atoms that are possible in the referenced alkyl group are indicated by the prefix "$C_{n1-n2}$". For example, the term $C_{1-10}$alkyl means an alkyl group having 1, 2, 3, 4, 5, 6, 7, 8, 9 or 10 carbon atoms. All alkyl groups are optionally fluoro-substituted unless otherwise indicated.

The term "alkylene", whether it is used alone or as part of another group, means straight or branched chain, saturated alkylene group, that is, a saturated carbon chain that contains substituents on two of its ends. The number of carbon atoms that are possible in the referenced alkylene group are indicated by the prefix "$C_{n1-n2}$". For example, the term $C_{2-6}$alkylene means an alkylene group having 2, 3, 4, 5 or 6 carbon atoms. All alkylene groups are optionally fluoro-substituted unless otherwise indicated.

The term "alkenyl" as used herein, whether it is used alone or as part of another group, means straight or branched chain, unsaturated alkyl groups containing at least one double bond. The number of carbon atoms that are possible in the referenced alkylene group are indicated by the prefix "$C_{n1-n2}$". For example, the term $C_{2-6}$-alkenyl means an alkenyl group having 2, 3, 4, 5 or 6 carbon atoms and at least one double bond. All alkenyl groups are optionally fluoro-substituted unless otherwise indicated.

The term "alkenylene", whether it is used alone or as part of another group, means straight or branched chain, unsaturated alkyl groups containing at least one double bond that contains substituents on two of its ends. The number of carbon atoms that are possible in the referenced alkylene group are indicated by the prefix "$C_{n1-n2}$". For example, the term $C_{2-6}$alkenylene means an alkenylene group having 2, 3, 4, 5 or 8 carbon atoms. All alkenylene groups are optionally fluoro-substituted unless otherwise indicated.

The term "aryl" as used herein, whether it is used alone or as part of another group, refers to carbocylic groups containing at least one aromatic ring and contains 6 to 20 carbon atoms.

The term "cycloalkyl," as used herein, whether it is used alone or as part of another group, means a saturated carbocyclic group containing from 3 to 20 carbon atoms and one or more rings. The number of carbon atoms that are possible in the referenced cycloalkyl group are indicated by the numerical prefix "$C_{n1-n2}$". For example, the term $C_{3-10}$cycloalkyl means a cycloalkyl group having 3, 4, 5, 6, 7, 8, 9 or 10 carbon atoms.

The term "heterocycloalkyl" as used herein, whether it is used alone or as part of another group, refers to cyclic groups containing at least one non-aromatic ring containing from 3 to 20 atoms in which one or more of the atoms are a heteroatom selected from O, S, SO, $SO_2$, N, NH, and $NCH_3$ and the remaining atoms are C. Heterocycloalkyl groups are either saturated or unsaturated (i.e. contain one or more double bonds). When a heterocycloalkyl group contains the prefix $C_{n1-n2}$ this prefix indicates the number of carbon atoms in the corresponding carbocyclic group, in which one or more, suitably 1 to 5, of the ring atoms is replaced with a heteroatom as selected from O, S, SO, $SO_2$, N, NH, and $NCH_3$ and the remaining atoms are C. Heterocycloalkyl groups are optionally benzofused. When part of another group, "heterocycloalkyl" also refers to cyclic groups containing at least one heterocycloalkyl group fused to one or more cyclic groups (e.g. heterocycloalkyl groups are optionally fused to aryl, heteroaryl, heterocycloalkyl and cycloalkyl groups as defined herein).

The term "heteroaryl" as used herein, whether it is used alone or as part of another group, refers to cyclic groups containing at least one heteroaromatic ring containing 5-20 atoms in which one or more of the atoms are a heteroatom selected from O, S, N, NH, and $NCH_3$ and the remaining atoms are C. When a heteroaryl group contains the prefix $C_{n1-n2}$ this prefix indicates the number of carbon atoms in the corresponding carbocyclic group, in which one or more, suitably 1 to 5, of the ring atoms is replaced with a heteroatom as defined above. Heteroaryl groups are optionally benzofused.

All cyclic groups, including aryl, heteroaryl, heterocycloalkyl and cycloalkyl groups, contain one or more than one ring (i.e. are polycyclic). When a cyclic group contains more than one ring, the rings may be fused, bridged, spirofused or linked by a bond.

The term "benzofused" as used herein refers to a polycyclic group in which a benzene ring is fused with another ring.

A first ring being "fused" with a second ring means the first ring and the second ring share two adjacent atoms there between.

A first ring being "bridged" with a second ring means the first ring and the second ring share two non-adjacent atoms there between.

A first ring being "spirofused" with a second ring means the first ring and the second ring share one atom there between.

The term "optionally substituted" refers to groups, structures, or molecules that are either unsubstituted or are substituted with one or more substituents.

The term "halo" or "halogen" as used herein, whether it is used along or as part of another group, refers to a halogen atom and includes fluoro, chloro, bromo and iodo.

The term "neurotensin receptor binding group" as used herein refers to a moiety that is recognized by a neurotensin receptor to which it binds.

The term "neurotensin receptors" as used herein refers to a transmembrane receptor that binds neurotensin.

The term "NTR1" (also referred to as NTR-1, NTSR1, NTSR-1 or Neurotensin receptor 1) as used herein refers to a neurotensin receptor encoded by the NTSR1 gene. NTR1 belongs to the large superfamily of G-protein coupled receptors and mediates multiple functions of neurotensin. NTR1 may be a native sequence NTR1 or an amino acid sequence variant thereof. In one embodiment, NTR1 is native sequence human NTR1.

The term "chelating group" as used herein is chelator capable of binding with and/or complexing a radionuclide.

The term "linker" as used herein refers to any molecular structure that connects two or more other molecular structures together.

The term "reacts with" as used herein generally means that there is a flow of electrons or a transfer of electrostatic charge resulting in the formation of a chemical interaction.

The term "theranostic" as used herein refers to an agent that can be used for both diagnosis and therapy.

The term "theranostic application" as used herein means using one radioactive drug to diagnose and treat a condition of choice.

The term "therapeutic treatment" as used herein can include a treatment administered to a subject in need of imaging. The subject can be in need of imaging to aid in diagnosis; to locate a position for a therapeutic intervention; to assess the functioning of a body part; and/or to assess the presence or absence of a condition. The effectiveness of a therapeutic imaging treatment can be confirmed based on the capture of an image sufficient for its intended purpose.

The term "disease, disorder or condition associated with a neurotensin receptor" as used herein refers to any disease, disorder or condition is affected by, modulated by and/or has some biological basis, either direct or indirect, that includes neurotensin receptor activity, in particular, increased neurotensin receptor activity. These diseases respond favourably when neurotensin receptor, for example, NTR1, activity associated with the disease, disorder or condition is inhibited by one or more of the compounds or compositions of the application.

The term "Positron Emission Tomography (PET)" as used herein means a functional imaging technique applied in nuclear medicine, whereby a three-dimensional image (e.g. of functional processes) in the body is produced. The system detects pairs of gamma rays emitted indirectly by a positron-emitting radionuclide, which is introduced into the body in form of a pharmaceutical compound.

The term "Single-Photon Emission Computed Tomography (SPECT)" as used herein means a three-dimensional diagnostic imaging technique using gamma rays emitted by radioisotopes. In contrast with PET, the tracer used in SPECT emits gamma radiation that is measured directly, whereas a PET tracer emits positrons that annihilate with near-by electrons, which are a few millimeters away, causing two gamma photons to be emitted in opposite directions.

The term "treating" or "treatment" as used herein and as is well understood in the art, means an approach for obtaining beneficial or desired results, including clinical results. Beneficial or desired clinical results include, but are not limited to alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. A subject with early cancer can be treated to prevent progression for example, or alternatively a subject in remission can be treated with a compound or composition of the application to prevent recurrence. Treatment methods comprise administering to a subject a therapeutically effective amount of one or more of the compounds of the application and optionally consist of a single administration, or alternatively comprise a series of administrations.

"Palliating" a disease, disorder or condition means that the extent and/or undesirable clinical manifestations of a disease, disorder or condition are lessened and/or time course of the progression is slowed or lengthened, as compared to not treating the disorder.

The terms "preventing", "prevention" or "prophylaxis", or synonyms thereto, as used herein refers to a reduction in the risk or probability of a patient becoming afflicted with a disease, disorder or condition or manifesting a symptom associated with a disease, disorder or condition.

As used herein, the term "effective amount" or "therapeutically effective amount" means an amount of a compound, or one or more compounds, of the application that is effective, at dosages and for periods of time necessary to achieve the desired result.

The term "imaging effective amount" when used in connection with a one or more complexes of the application, is an amount of the complex that is sufficient to produce a visible image when the complex is administered to a subject and the radiation emitted by the complex is detected using positron-emission tomography ("PET") or single photon emission tomography (SPECT) or autoradiography or ex vivo or in vitro binding assays.

As used herein, the term "diagnostic effective amount" means an amount of a compound, or one or more compounds, of the application or complex, or one or more complexes of the application, that is effective, at dosages and for periods of time necessary to achieve the desired diagnostic effect including, for example, diagnosing a particular condition being assessed.

The term "administered" as used herein means administration of a therapeutically effective amount of one or more compounds, complexes or compositions of the application to a cell, tissue, organ or subject.

The term "cancer" as used herein refers to cellular-proliferative disease states.

The term "subject" as used herein includes all members of the animal kingdom including mammals, and suitably refers to humans. Thus, the methods and uses of the present application are applicable to both human therapy and veterinary applications.

The term "cell" as used herein refers to a single cell or a plurality of cells and includes a cell either in a cell culture or in a subject.

The term "pharmaceutically acceptable" means compatible with the treatment of subjects, for example humans.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to a subject.

The term "pharmaceutically acceptable salt" means either an acid addition salt or a base addition salt which is suitable for, or compatible with the treatment of subjects.

An acid addition salt suitable for, or compatible with, the treatment of subjects is any non-toxic organic or inorganic acid addition salt of any basic compound.

A base addition salt suitable for, or compatible with, the treatment of subjects is any non-toxic organic or inorganic base addition salt of any acidic compound.

The term "solvate" as used herein means a compound, or a salt and/or prodrug of a compound, wherein molecules of a suitable solvent are incorporated in the crystal lattice. A suitable solvent is physiologically tolerable at the dosage administered.

When used, for example, with respect to the methods of treatment, uses, compositions of the application, a subject, for example a subject "in need thereof" is a subject that would benefit from administration of one or more compounds or complexes of the application, or a pharmaceutically acceptable salt and/or solvate thereof.

II. Compounds and Complexes of the Application

The Applicant has developed novel radioligands which exhibit advantageous properties such as high binding affinity to the neurotensin receptor, high uptake by the tumor and low accumulation in normal organs.

The Applicant has unexpectedly found that modifying the amide group, for example, the removal of the carbonyl group from the amide group, that directly connects adi-amine moiety to the remainder of the structure of a known neurotensin antagonist compound SR142948 (C-3) improves the potency by about 10 fold or more (see, for example, II-1 vs SR142948 (C-3), Table 1 & Table 2). Such compounds have been further derivatized to provide a set of novel compounds comprising a neurotensin receptor binding group and a chelating group coupled by a linker. The compounds of the application when complexed to a radionuclide to form radioligands that possess higher binding affinity, for example, about 20 fold enhanced binding affinity when compared to 3BP-227 (C-2) (Table 2). Furthermore, with such derivatization, the removal of the tertiary amine motif in the linker region was found to not compromise the binding affinity (see, for example, I-10 vs 3BP-227 (C-2), Table 2). In animal studies, radioligands of the application have demonstrated, for example, high uptake by NTR1-positive tumors, and an improved overall biodistribution profile including high ratio of tumor uptake vs normal organ accumulation including kidney, live and lung.

Accordingly, the present application Includes a compound of Formula I or a pharmaceutically acceptable salt and/or solvate thereof

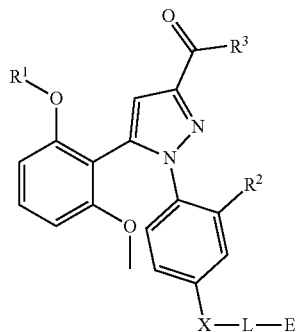

(I)

wherein
- $R^1$ is selected from H, $C_{1-6}$alkyl, $C_{3-6}$cycloalkyl and $C_{1-3}$alkylene$C_{3-6}$cycloalkyl, the latter three groups being optionally substituted with one or more halo;
- $R^2$ is selected from H, halo, $NO_2$, $C_{1-6}$alkyl, $C_{3-8}$cycloalkyl and $C_{1-3}$alkylene$C_{3-8}$cycloalkyl), the latter three groups being optionally substituted with one or more halo;
- $R^3$ is selected from 2-amino-2-adamantane carboxylic acid, cyclohexylglycine and 9-amino-bicyclo[3.3.1]nonane-9-carboxylic acid;
- X is selected from $CH_2$, O, $NR^4$, S, S(O), $SO_2NR^4$ and $NR^4C(O)$;
- L is a linker;
- E is a chelating group;
- $R^4$ is selected from H, $C_{1-6}$alkyl, $C_{1-6}$alkenyl, $C_{1-6}$alkynyl, $C(O)C_{1-6}$alkyl, $C_{1-10}$alkyleneNR$^5$R$^6$, $C_{1-10}$alkenyleneNR$^5$R$^6$, and $C_{1-10}$alkynyleneNR$^5$R$^6$; and
- $R^5$ and $R^6$ are independently selected from H and $C_{1-6}$alkyl.

In some embodiments, $R^1$ is selected from H, $C_{1-4}$alkyl, $C_{3-6}$cycloalkyl and $C_{1-3}$alkylene$C_{3-6}$cycloalkyl, the latter three groups being optionally substituted with one or more halo. In some embodiments, $R^1$ is selected from H, $C_{1-3}$alkyl, cyclopropyl, cyclobutyl, and $CH_2$cyclopropyl and $CH_2$cyclobutyl, the latter five groups being optionally substituted with one or more halo. In some embodiments, $R^1$ is selected from $CH_3$, $CH_2CH_3$, $CH_2CH_2CH_3$, $CH(CH_3)_2$, cyclopropyl, cyclobutyl. $CH_2$cyclopropyl, and $CH_2$cyclobutyl, each of which is optionally substituted with one or more halo. In some embodiments, halo is selected from fluoro and chloro. In some embodiments, $R^1$ is selected from $CH_3$, $CH_2CH_3$, $CH_2CH_2CH_3$, $CH(CH_3)_2$, cyclopropyl, and $CH_2$cyclopropyl, each of which is optionally substituted with one or more fluoro. In some embodiments, $R^1$ is selected from $CH_3$, $CH_2CH_3$, $CH_2CH_2CH_3$, $CH(CH_3)_2$, cyclopropyl, and $CH_2$cyclopropyl, each of which is optionally substituted with one to three fluoro. In some embodiments, $R^1$ is selected from $CH_3$, $CH_2CH_3$, $CH_2CH_2CH_3$, and $CH(CH_3)_2$. In some embodiments, $R^1$ is $CH_3$.

In some embodiments, $R^2$ is selected from H, halo, $NO_2$, $C_{1-6}$alkyl, $C_{3-6}$cycloalkyl and $C_{1-3}$alkylene$C_{3-6}$cycloalkyl, latter three groups being optionally substituted with one or more halo. In some embodiments, $R^2$ is selected from halo, $NO_2$, $C_{1-6}$alkyl, $C_{3-6}$cycloalkyl and $CH_2C_{3-6}$cycloalkyl, the latter three groups being optionally substituted with one or more halo. In some embodiments, $R^2$ is selected from halo, $NO_2$, and $C_{1-6}$alkyl, the latter group being optionally substituted with one or more halo. In some embodiments, $R^2$ is $C_{1-6}$alkyl, optionally substituted with one or more halo. In some embodiments, halo is selected from fluoro and chloro. In some embodiments, $R^2$ is selected from $CH_3$, $CH_2CH_3$. $CH_2CH_2CH_3$, $CH(CH_2)_2$, optionally substituted with one or more fluoro. In some embodiments, $R^2$ is selected from $CH_3$, $CH_2CH_3$, $CH_2CH_2CH_3$, $CH(CH_3)_2$, optionally substituted with one to three fluoro. In some embodiments, $R^2$ is selected from $CH_3$, $CH_2CH_3$, $CH_2CH_2CH_3$, $CH(CH_3)_2$. In some embodiments, $R^2$ is $CH(CH_3)_2$.

In some embodiments, $R^3$ is 2-amino-2-adamantane carboxylic acid. In some embodiments, $R^3$ is cyclohexylglycine. In some embodiments, $R^3$ is 9-amino-bicyclo[3.3.1]nonane-9-carboxylic acid. In some embodiments, $R^3$ is a group having the following formula

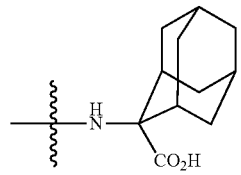 [SMILES: *NC1(C(=O)O)C2CC3CC(C2)CC1C3]

In some embodiments, the compound of Formula I is a compound of Formula I-A or a pharmaceutically acceptable salt and/or solvate thereof

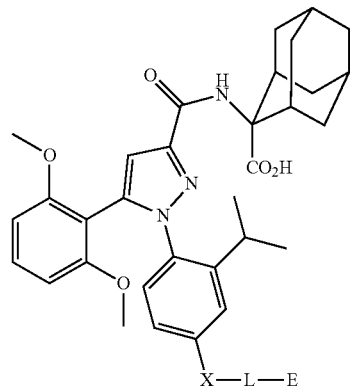

(I-A)

wherein X, L and E are as defined in Formula I.

In some embodiments, X is selected from $CH_2$, O, S, $NR^4$ and $NR^4C(O)$. In some embodiments, X is $CH_2$. In some embodiments, X is O. In some embodiments, X is S. In some embodiments, X is $NR^4$. In some embodiments, X is $NR^4C(O)$.

In some embodiments. $R^4$ is selected from H, $C_{1-4}$alkyl, $C_{1-4}$alkenyl, $C_{1-4}$alkynyl, $C(O)C_{1-5}$alkyl, $C_{1-8}$alkyleneNR$^5$R$^6$, $C_{1-8}$ alkenyleneNR$^5$R$^6$, and $C_{1-8}$alkynyleneNR$^5$R$^6$. In some embodiments, $R^4$ is selected from H, $C_{1-4}$-alkyl, $C_{1-4}$alkenyl, $C_{1-4}$alkynyl, $C(O)C_{1-4}$alkyl, $C_{1-6}$alkyleneNR$^5$R$^6$, $C_{1-6}$alkenyleneNR$^5$R$^6$ and $C_{1-4}$alkynyleneNR$^5$R$^6$.

In some embodiments, $R^4$ is $C(O)C_{1-3}$alkyl. In some embodiments, $R^4$ is $C(O)CH_3$.

In some embodiments, $R^4$ is selected from H, $C_{1-4}$alkyl, $C(O)C_{1-4}$alkyl, and $C_{1-8}$alkyleneNR$^5$R$^6$. In some embodiments, $R^4$ is selected from H, $C_{1-4}$alkyl and $C_{1-6}$alkyleneNR$^5$R$^6$.

In some embodiments, $R^4$ is selected from H and $C_{1-4}$alkyl. In some embodiments, $R^4$ is selected from H, $CH_3$, $CH_2CH_3$, $CH_2CH_2CH_3$, $CH(CH_3)_2$, $CH(CH_3)CH_2CH_3$, and $CH(CH_3)_3$. In some embodiments, $R^4$ is selected from H and $CH_3$.

In some embodiments. $R^4$ is $C_{1-8}$alkyleneNR$^5$R$^6$. In some embodiments, $R^4$ is $C_{1-6}$alkyleneNR$^5$R$^6$. In some embodiments, $R^4$ is $C_{1-4}$alkyleneNR$^5$R$^6$. In some embodiments, $R^4$ is $C_{2-6}$alkyleneNR$^5$R$^6$. In some embodiments, $R^4$ is $C_{2-4}$alkyleneNR$^5$R$^6$. In some embodiments, $R^4$ is $CH_2CH_2CH_2$alkyleneNR$^5$R$^6$ (e.g., $C_3$alkyleneNR$^5$R$^6$)

In some embodiments, $R^5$ and $R^6$ are independently selected from H and $C_{1-4}$alkyl. In some embodiments, $R^5$ and $R^6$ are independently selected from H, $CH_3$, $CH_2CH_3$, $CH_2CH_2CH_3$, $CH(CH_3)_2$, $CH(CH_3)CH_2CH_3$, and $CH(CH_3)_3$. In some embodiments, $R^5$ and $R^6$ are independently selected from H and $CH_3$.

In some embodiments, X is NR$^4$ and $R^4$ is selected from H and $C_{1-4}$alkyl. In some embodiments, X is NR$^4$ and $R^4$ is selected from H and $CH_3$.

In some embodiments, X is NR$^4$C(O) and $R^4$ is $C_{1-6}$alkyleneNR$^5$R$^6$. In some embodiments, X is NR$^4$C(O) and $R^4$ is $C_{2-6}$-alkyleneNR$^5$R$^6$. In some embodiments, X is NR$^4$C(O) and $R^4$ is $CH_2CH_2CH_2$alkyleneNR$^5$R$^6$.

In some embodiments, X is NR$^4$ and $R^4$ is $C_{1-6}$alkyleneNR$^5$R$^5$. In some embodiments, X is NR$^4$ and $R^4$ is $C_{2-6}$alkyleneNR$^5$R$^6$. In some embodiments, X is NR$^4$ and $R^4$ is $C_{2-4}$alkyleneNR$^5$R$^6$. In some embodiments, X is NR$^4$C and $R^4$ is $CH_2CH_2CH_2$alkyleneNR$^5$R$^6$.

It would be appreciated by a person skilled in the art that the linker forms covalent bonds with both X and E. Therefore, in some embodiments, L is any chemical moiety capable of forming covalent bond with both X and E. In some embodiments, L comprises linker moieties selected from amines, ethers, thioethers, carbonyl, thiocarbonyl, sulfones, sulfoxides, urea, thiourea, and amides. In some embodiments, L comprises a group on an end terminus capable of forming covalent bond with E. For example, in some embodiments, L comprises an amine on an end terminus that reacts with a carboxylic acid group of the chelating group.

In some embodiments, L comprises one or more of $C_{1-20}$alkylene, $C_{1-20}$alkenylene, and $C_{1-20}$alkynylene. In some embodiments, the one or more of $C_{1-20}$alkylene, $C_{1-20}$alkenylene, and $C_{1-6}$alkynylene are optionally interrupted by one or more linker moieties selected from amines, ethers, thioethers, carbonyl, thiocarbonyl, sulfones, sulfoxides, urea, thiourea, amides, $C_{4-10}$cycloalkylene, $C_{4-10}$heterocycloalkylene, $C_{6-10}$arylene and $C_{5-10}$heteroarylene. In some embodiments, the one or more $C_{1-20}$alkylene, $C_{1-20}$alkenylene, $C_{1-6}$alkynylene groups, $C_{4-10}$cycloalkylene, $C_{4-10}$heterocycloalkylene, $C_{6-10}$arylene and $C_{5-10}$heteroarylene are optionally substituted with one or more of hydroxy, halogen, alkyl and alkyl substituted with one or more of hydroxy, halogen and amino.

Accordingly, in some embodiments, L comprises 1 to 20 groups independently selected from $R^a$—$W^a$, $W^b$—$R^b$, $R^a$—$W^a$—$R^b$ and $W^a$—$R^b$—$W^b$;

wherein $W^a$ and $W^b$ are independently selected from O, S, S(O), S(O)$_2$, NR$^7$, C(Q), C(Q)N, NR$^7$C(Q), NR$^7$C(Q')NR$^8$;

$R^a$ and $R^b$ are independently selected from $C_{1-20}$alkylene, $C_{1-20}$alkenylene, and $C_{1-20}$alkynylene;

each Q is independently selected from O and S;

each Q' is independently selected from O, S, NH and N($C_{1-6}$alkyl);

$R^7$ and $R^8$ are independently selected from H and $C_{1-6}$alkyl, and each alkylene, alkenylene, alkynylene in $R^a$ and $R^b$ are optionally interrupted by one or more $C_{3-10}$cycloalkylene, $C_{4-10}$heterocycloalkylene, $C_{1-10}$arylene and $C_{5-10}$heteroarylene, and each alkylene, alkenylene, alkynylene, cycloalkylene, heterocycloalkylene, arylene and heteroarylene is independently and optionally substituted with one or more substituents selected from halo, $CO_2H$, OH, SH, $NH_2$, NHC$_{1-4}$alkyl, N($C_{1-4}$alkyl)($C_{1-4}$alkyl), $C_{1-6}$alkyl, OC$_{1-6}$alkyl and SC$_{1-6}$alkyl, wherein all alkyl groups are optionally further substituted one or more substituents selected from halo, $CO_2H$, OH $NH_2$, NHC$_{1-4}$alkyl and N($C_{1-4}$alkyl)($C_{1-4}$alkyl).

A person skilled in the art would appreciate that two adjacent groups in L should be chosen so as to avoid a direct bond between two groups which would result in a partial structure that is not stable, for example, in an aqueous medium at room temperature such as about 18° C. to about 25° C.

In some embodiments, $R^a$ and $R^b$ are independently selected from $C_{1-15}$alkylene, $C_{1-15}$alkenylene, and $C_{1-15}$alkynylene, each alkylene, and each alkenylene, alkynylene in $R^a$ and $R^b$ are independently and optionally interrupted by one or more of $C_{3-10}$cycloalkylene, $C_{4-10}$heterocycloalkylene, $C_{6-10}$arylene and $C_{5-10}$heteroarylene, and each alkylene, alkenylene, alkynylene, cycloalkylene, heterocycloalkylene, arylene and heteroarylene is independently and optionally substituted with one or more substituents selected from halo, $CO_2H$, OH, $NH_2$, NHC$_{1-4}$alkyl, N($C_{1-4}$alkyl)($C_{1-4}$alkyl), $C_{1-6}$alkyl and OC$_{1-6}$alkyl, wherein all alkyl groups are optionally further substituted one or more substituents selected from halo, $CO_2H$, OH, $NH_2$, NHC$_{1-4}$alkyl, and N($C_{1-4}$alkyl)($C_{1-4}$alkyl). In some embodiments, $R^a$ and $R^b$ are independently and optionally selected from $C_{1-10}$alkylene, $C_{1-10}$alkenylene and $C_{1-10}$alkynylene, and each alkylene, alkenylene and alkynylene in $R^a$ and $R^b$ are independently and optionally interrupted by one or more of $C_{3-10}$cycloalkylene, $C_{4-10}$heterocycloalkylene, $C_{6-10}$arylene and $C_{5-10}$heteroarylene, and each alkylene, alkenylene, alkynylene, cycloalkylene, heterocycloalkylene, arylene and heteroarylene is independently and optionally substituted with one or more substituents selected from halo, $CO_2H$, OH, $C_{1-6}$alkyl and OC$_{1-6}$alkyl, wherein all alkyl groups are optionally further substituted one or more substituents selected from halo, $CO_2H$, OH, $NH_2$, NHC$_{1-4}$alkyl and N($C_{1-4}$alkyl)($C_{1-4}$alkyl). In some embodiments. $R^a$ and $R^b$ are independently and optionally selected from $C_{1-10}$alkylene, $C_{1-10}$alkenylene, and $C_{1-10}$alkynylene, each alkylene, alkenylene and alkynylene in $R^a$ and $R^b$ are independently and optionally interrupted by one or two of $C_{3-10}$cycloalkylene, $C_{4-10}$heterocycloalkylene, $C_{6-10}$arylene and $C_{5-10}$heteroarylene, and each alkylene, alkenylene, alkynylene, cycloalkylene, heterocycloalkylene, arylene and heteroarylene is independently and optionally substituted with one to three substituents selected from halo, $CO_2H$, OH, $C_{1-8}$alkyl and OC$_{1-6}$alkyl, wherein all alkyl groups are optionally further substituted one or more substituents selected from halo, $CO_2H$, OH, $NH_2$, NHC$_{1-4}$alkyl, and N($C_{1-4}$alkyl)($C_{1-4}$alkyl). In some embodiments, $R^a$ and $R^b$ are independently selected from $C_{1-10}$alkylene, $C_{1-10}$alkenylene, and $C_{1-10}$alkynylene. In some embodiments, $R^a$ and $R^b$ are independently $C_{1-10}$alkylene. In some embodiments, $R^a$ and $R^b$ are independently $C_{1-6}$alkylene.

In some embodiments, $C_{3-10}$cycloalkyl is selected from cyclopropyl, cyclobutyl, cyclopentyl, cyclohexyl and cycloheptyl.

In some embodiments, $C_{4-10}$heterocycloalkyl is selected from azetidinyl, oxetanyl, tetrohydrofuranyl, tetrahydrothiophenyl, pyrrolidinyl, dihydropyrrolyl, imidazolidinyl, pyrazolidinyl, thiazolidinyl, isothiazolidinyl, dioxolanyl, dithiolanyl, 3,4,5,6-tetrahydro-1,2,4-triazinyl, dioxidothiomorpholino, tetrahydropyridinyl, dihydropyridinyl, dihydropyranyl, thianyl, piperidinyl, piperazinyl, tetrahydropyranyl, thiomorpholinyl, morpholinyl, dioxanyl, azepanyl, diazepanyl, oxepanyl and thiepanyl.

In some embodiments, $C_{6-10}$aryl is selected from phenyl, indanyl or naphthyl.

In some embodiments, $C_{5-10}$heteroaryl is selected from triazolyl, pyrrolyl, imidazolyl, oxazolyl, pyrazolyl, thiazolyl, pyridinyl, pyrazinyl, pyridazinyl and pyrimidinyl.

In some embodiments, each Q is independently S. In some embodiments, each Q is independently O.

In some embodiments, each Q' is independently selected from O, S, NH and $N(C_{1-4}alkyl)$.

In some embodiments, each Q is independently selected from O and S and $W^a$ and $W^b$ are independently selected from O, S, S(O), S(O)$_2$, NR$^7$, C(O), C(O)NR$^7$, NR$^7$C(O), NR$^7$C(O)NR$^8$ and NR$^7$C(S)NR$^8$. In some embodiments, $W^a$ and $W^b$ are independently selected from O, S, S(O), S(O)$_2$, NR$^7$, C(O), C(O)NR$^7$, NR$^7$C(O), NR$^7$C(O)NR$^8$ and NR$^7$C(S)NR$^8$. In some embodiments, $W^a$ and $W^b$ are independently selected from O, S, S(O), S(O)$_2$ and NR$^7$. In some embodiments, $W^a$ and $W^b$ are independently selected from O, NR$^7$ and C(O).

In some embodiments, $W^a$ and $W^b$ are independently selected from O, S, S(O), S(O)$_2$, NR$^7$, C(O), C(O)NR$^7$, NR$^7$C(O), NR$^7$C(O)NR$^8$ and NR$^7$C(S)NR$^8$, and R$^a$ and R$^b$ are independently $C_{1-10}$alkylene. In some embodiments, L comprises 1 to 20 groups independently selected from $C_{1-10}$alkyleneO, $C_{1-10}$alkyleneNR$^7$, OC$_{1-10}$alkylene, NR$^7$C$_{1-10}$alkylene, $C_{1-10}$alkyleneNR$^7$C(S)NR$^8$. NR$^7$C(S)NR$^8$C$_{1-10}$alkylene, C(O)C$_{1-10}$alkyleneO, C(O)C$_{1-10}$alkyleneNR$^7$, OC$_{1-10}$alkyleneC(O) and NR$^7$C$_{1-10}$alkyleneC(O) and each alkylene, alkenylene and alkynylene is independently and optionally interrupted by one or more of $C_{3-10}$cycloalkylene, $C_{4-10}$heterocycloalkylene, $C_{6-10}$arylene and $C_{5-10}$heteroarylene, and each alkylene, alkenylene, alkynylene, cycloalkylene, heterocycloalkylene, arylene and heteroarylene is independently and optionally substituted with one or more substituents selected from halo, CO$_2$H, OH, NH$_2$, NHC$_{1-4}$alkyl, N(C$_{1-4}$alkyl)(C$_{1-4}$alkyl), C$_{1-6}$alkyl, and OC$_{1-6}$alkyl, wherein all alkyl groups are optionally further substituted one or more substituents selected from halo, CO$_2$H, OH NH$_2$, NHC$_{1-4}$alkyl, and N(C$_{1-4}$alkyl)(C$_{1-4}$alkyl). In some embodiments, $W^a$ and $W^b$ are independently selected from O, NR$^7$ and C(O), and R$^a$ and R$^b$ are independently $C_{1-10}$alkylene. In some embodiments, L comprises 1 to 20 groups independently selected from $C_{1-10}$alkyleneO, $C_{1-10}$alkyleneNR$^7$, OC$_{1-6}$alkylene, NR$^7$C$_{1-10}$alkylene, C(O)C$_{1-10}$alkyleneO, C(O)C$_{1-10}$alkyleneNR$^7$, OC$_{1-10}$alkyleneC(O) and NR$^7$C$_{1-10}$alkyleneC(O), and each alkylene, alkenylene and alkynylene is independently and optionally interrupted by one or two of $C_{3-10}$cycloalkylene, $C_{4-10}$heterocycloalkylene, $C_{6-10}$arylene and $C_{5-10}$heteroarylene, and each alkylene, alkenylene, alkynylene, cycloalkylene, heterocycloalkylene, arylene and heteroarylene is independently and optionally substituted with one to four substituents selected from halo, CO$_2$H, OH, $C_{1-6}$alkyl and OC$_{1-6}$alkyl, wherein all alkyl groups are optionally further substituted one to four substituents selected from halo, CO$_2$H, OH NH$_2$, NHC$_{1-4}$alkyl, and N(C$_{1-4}$alkyl)(C$_{1-4}$alkyl). In some embodiments, L comprises 1 to 20 groups independently selected from $C_{1-10}$alkyleneO, $C_{1-10}$alkyleneNR$^7$, OC$_{1-6}$alkylene, NR$^7$C$_{1-10}$alkylene, C(O) C$_{1-10}$alkyleneO, C(O)C$_{1-10}$alkyleneNR$^7$, OC$_{1-10}$alkyleneC (O) and NR$^7$C$_{1-10}$alkyleneC(O), and each alkylene, alkenylene and alkynylene is independently and optionally interrupted by one or two of $C_{3-10}$cycloalkylene, $C_{4-10}$heterocycloalkylene, $C_{6-10}$arylene and $C_{5-10}$heteroarylene, and each alkylene, alkenylene, alkynylene, cycloalkylene, heterocycloalkylene, arylene and heteroarylene is independently and optionally substituted with one to four substituents selected from halo, CO$_2$H, OH, $C_{1-4}$alkyl and OC$_{1-4}$alkyl, wherein all alkyl groups are optionally further substituted one to four substituents selected from halo, CO$_2$H, OH NH$_2$, NHC$_{1-4}$alkyl, and N(C$_{1-4}$alkyl)(C$_{1-4}$alkyl). In some embodiments, L comprises 1 to 20 groups independently selected from $C_{1-10}$alkyleneO, $C_{1-10}$alkyleneNR$^7$, OC$_{1-10}$alkylene, NR$^7$C$_{1-10}$alkylene, C(O)C$_{1-10}$alkyleneO. C(O)C$_{1-10}$alkyleneNR$^7$, OC$_{1-10}$alkyleneC(O) and NR$^7$C$_{1-10}$alkyleneC(O), and each alkylene, alkenylene and alkynylene is independently and optionally interrupted by one or two of $C_{3-10}$cycloalkylene and $C_{4-10}$heterocycloalkylene, and each alkylene, alkenylene, alkynylene, cycloalkylene and heterocycloalkylene is independently and optionally substituted with one to four substituents selected from F, Cl, CO$_2$H, OH, C$_{1-4}$alkyl and OC$_{1-4}$alkyl, wherein all alkyl groups are optionally further substituted one to four substituents selected from halo, CO$_2$H, OH NH$_2$, NHC$_{1-4}$alkyl, and N(C$_{1-4}$alkyl)(C$_{1-4}$alkyl). In some embodiments, L comprises 1 to 20 groups independently selected from $C_{1-10}$alkyleneO, $C_{1-10}$alkyleneNR$^7$, OC$_{1-10}$alkylene, NR$^7$C$_{1-10}$alkylene, C(O)C$_{1-10}$alkyleneO, C(O)C$_{1-10}$alkyleneNR$^7$, OC$_{1-10}$alkyleneC(O) and NR$^7$C$_{1-10}$alkyleneC(O). In some embodiments, L comprises 1 to 20 groups independently selected from $C_{1-10}$alkyleneO, $C_{1-10}$alkyleneNR$^7$, C(O)C$_{1-10}$alkyleneO and C(O)C$_{1-10}$alkyleneNR$^7$. In some embodiments, L comprises 1 to 20 groups independently selected from $C_{1-4}$alkyleneO, $C_{1-6}$alkyleneNR$^7$, C(O)C$_{1-6}$alkyleneO and C(O)C$_{1-6}$alkyleneNR$^7$. In some embodiments, L comprises 1 to 15 groups independently selected from $C_{1-7}$alkyleneO, $C_{1-6}$alkyleneNR$^7$, C(O)C$_{1-6}$alkyleneO and C(O)C$_{1-6}$alkyleneNR$^7$. In some embodiments, L comprises 1 to 10 groups independently selected from $C_{1-6}$alkyleneO, $C_{1-6}$alkyleneNR$^7$, C(O)C$_{1-6}$alkyleneO and C(O)C$_{1-6}$alkyleneNR$^7$. In some embodiments, L comprises 2 to 10 groups independently selected from $C_{1-6}$alkyleneO, $C_{1-6}$alkyleneNR$^7$, C(O)C$_{1-6}$alkyleneO and C(O)C$_{1-6}$alkyleneNR$^7$. In some embodiments, L comprises 2 to 7 groups independently selected from $C_{1-6}$alkyleneO, $C_{1-6}$alkyleneNR$^7$, C(O)C$_{1-6}$alkyleneO and C(O)C$_{1-6}$alkyleneNR$^7$. In some embodiments, L comprises 2 to 5 groups independently selected from $C_{1-6}$alkyleneO, $C_{1-6}$alkyleneNR$^7$, C(O)C$_{1-6}$alkyleneO and C(O)C$_{1-6}$alkyleneNR$^7$.

In some embodiments, L comprises 1 to 18 groups, 1 to 15 groups, 1 to 10 groups, 1 to 8 groups, 1 to 6 groups, 1 to 5 groups, 1 to 4 groups, 1 to 3 groups, 2 to 10 groups, 2 to 7 groups, 2 to 5 groups, 2 to 4 groups or 2 to 3 groups. In some embodiments, L comprises 1 to 18 groups, 1 to 15 groups, 1 to 10 groups, 1 to 8 groups, 1 to 6 groups, 1 to 5 groups, 1 to 4 groups or 1 to 3 groups. In some embodiments, L comprises 1 to 10 groups, 1 to 8 groups, 1 to 6 groups, 1 to 5 groups, 1 to 4 groups or 1 to 3 groups. In some embodiments, L comprises 1 to 8 groups, 1 to 7 groups, 1 to 6 groups 1 to 5 groups, 1 to 4 groups, 1 to 3 groups, 2 to 8 groups, 2 to 7 groups, 2 to 5 groups, 2 to 4 groups or 2 to 3 groups. In some embodiments, L comprises 2 to 7 groups or 2 to 5 groups.

In some embodiments, L comprises 1 to 6 $C_{1-6}$alkyleneNR$^7$ groups and each $C_{1-6}$alkyleneNR$^7$ group is the same or different. In some embodiments, L comprises 1 to 6 $C_{2-6}$alkyleneNR$^7$ groups and each $C_{2-6}$alkyleneNR$^7$ group is the same or different. In some embodiments, L is $C_{2-6}$alkyleneNR$^7$—$C_{2-6}$alkyleneNR$^7$. In some embodiments, L comprises 2 to 6 groups $C_{2-5}$alkyleneNR$^7$ groups and each $C_{2-5}$alkyleneNR$^7$ group is the same or different. In some embodiments, L comprises 2 to 4 $C_{2-5}$alkyleneNR$^7$ groups and each $C_{2-5}$alkyleneNR$^7$ group is the same or different. In some embodiments, L is $C_{2-5}$alkyleneNR$^7$—$C_{2-5}$alkyleneNR$^7$. In some embodiments, L comprises 2 to 4 $C_3$alkyleneNR$^7$ groups and each $C_3$alkyleneNR$^7$ group is the same or different. In some embodiments, L comprises 2 $C_3$alkyleneNR$^7$ groups and each $C_3$alkyleneNR$^7$ group is the same or different. In some embodiments, L is $C_3$alkyleneNR$^7$—$C_3$alkyleneNR$^7$.

In some embodiments, X is selected from $CH_2$, O, S, NR$^4$ and NR$^4$C(O), R$^4$ is selected from H and $C_{1-4}$alkyl and L is $(C_3alkyleneNR^7)_n$ and n is an integer selected from 2 to 4. In some embodiments, X is selected from $CH_2$, O, S, NR$^4$ and NR$^4$C(O), R$^4$ is selected from H and $CH_3$ and L comprises 2 to 4 $C_3$alkyleneNR$^7$ groups and each $C_3$alkyleneNR$^7$ group is the same or different. In some embodiments, X is selected from $CH_2$, O, S, NR$^4$ and NR$^4$C(O), R$^4$ is selected from H and $CH_3$ and L is $C_3$alkyleneNR$^7$—$C_3$alkyleneNR$^7$. In some embodiments, X is selected from $CH_2$, O, S, NR$^4$ and NR$^4$C(O), and L is $C_3$alkyleneNR$^7$—$C_3$alkyleneNR$^7$.

In some embodiments, L comprises 3 to 10 groups independently selected from $C_{1-6}$alkyleneNR$^7$, C(O)$C_{1-6}$alkyleneO and $C_{1-6}$alkyleneO. In some embodiments, L comprises 1 to 4 $C_{1-6}$alkyleneNR$^7$ groups and each $C_{1-6}$alkyleneNR$^7$ group is the same or different, 1 or 2 C(O)$C_{1-6}$alkyleneO groups and each C(O)$C_{1-6}$alkylene group is the same or different, and 1 to 4 $C_{1-6}$alkyleneO and each $C_{1-6}$alkyleneO group is the same or different. In some embodiments, L comprises 3 $C_{1-6}$alkyleneNR$^7$ groups and each $C_{1-6}$alkyleneNR$^7$ group is the same or different, 1 C(O)$C_{1-6}$alkyleneO group and 1 $C_{1-6}$alkyleneO group. In some embodiments, L is $(C_{1-6}alkyleneNR^7)_2$—C(O)$C_{1-6}$alkyleneO—$C_{1-6}$alkyleneO—$C_{1-6}$alkyleneNR$^7$. In some embodiments, L is $(C_3alkyleneNR^7)$—C(O)$C_1$alkyleneO—$C_2$alkyleneO—$C_2$alkyleneNR$^7$.

In some embodiments, X is selected from $CH_2$, O, S, NR$^4$ and NR$^4$C(O), and L comprises 1 to 4 $C_{1-6}$alkyleneNR$^7$ groups and each $C_{1-6}$alkyleneNR$^7$ group is the same or different, 1 or 2 C(O)$C_{1-6}$alkyleneO groups and each C(O) $C_{1-6}$alkylene group is the same or different, and 1 to 4 $C_{1-6}$alkyleneO and each $C_{1-6}$alkyleneO group is the same or different. In some embodiments, X is selected from $CH_2$, O, S, NR$^4$ and NR$^4$C(O), R$^4$ is selected from H and $C_{1-4}$alkyl, and L is $C_{1-6}$alkyleneNR$^7$—$C_{1-6}$alkyleneNR$^7$—C(O)$C_{1-6}$alkyleneO—$C_{1-6}$alkyleneO—$C_{1-6}$alkyleneNR$^7$. In some embodiments, X is selected from $CH_2$, O, S and NR$^4$, R$^4$ is selected from H and $CH_3$, and L is $C_{1-6}$alkyleneNR$^7$—$C_{1-6}$alkyleneNR$^7$—C(O)$C_{1-6}$alkyleneO—$C_{1-6}$alkyleneO—$C_{1-6}$alkyleneNR$^7$. In some embodiments, X is NR$^4$, R$^4$ is selected from H and $CH_3$, and L is $(C_3alkyleneNR^7)_2$—C(O)$C_1$alkyleneO—$C_2$alkyleneO—$C_2$alkyleneNR$^7$.

In some embodiments. L comprises 3 to 8 groups independently selected from C(O)$C_{1-6}$alkyleneO, $C_{1-6}$alkyleneO and $C_{1-6}$alkyleneNR$^7$. In some embodiments. L comprises 1 or 2 C(O)$C_{1-6}$alkyleneO groups and each C(O)$C_{1-6}$alkyleneO group is the same or different, 1 or 2 $C_{1-6}$alkyleneO groups and each $C_{1-6}$alkyleneO group is the same or different and 1 or 2 $C_{1-6}$alkyleneNR$^7$ groups and each $C_{1-6}$alkyleneNR$^7$ group is the same or different. In some embodiments, L comprises 1 of C(O)$C_{1-6}$alkyleneO, 1 of $C_{1-8}$alkyleneO and 1 of $C_{1-6}$alkyleneNR$^7$. In some embodiments, L is C(O)$C_{1-6}$alkyleneO—$C_{1-6}$alkyleneO—$C_{1-6}$alkyleneNR$^7$.

In some embodiments, X is NR$^4$C(O), R$^4$ is $C_{1-6}$alkyleneNR$^5$R$^6$ and L is C(O)$C_{1-6}$alkyleneO—$C_{1-6}$alkyleneO—$C_{1-6}$alkyleneNR$^7$. In some embodiments. X is NR$^4$, R$^4$ is $C_{1-6}$alkyleneNR$^5$R$^6$ and L is C(O)$C_{1-6}$alkyleneO—$C_{1-6}$alkyleneO—$C_{1-6}$alkyleneNR$^7$.

In some embodiments, L comprises 3 to 10 groups independently selected from $C_{1-6}$alkyleneO and $C_{1-6}$alkyleneNR$^7$. In some embodiments, L comprises 1 to 8 $C_{1-6}$alkyleneO groups and each $C_{1-6}$alkyleneO group is the same or different and 1 or 2 $C_{1-6}$alkyleneNR$^7$ groups and each $C_{1-6}$alkyleneNR$^7$ group is the same or different. In some embodiments, L comprises 2 to 6 $C_{1-6}$alkyleneO groups and each $C_{1-6}$alkyleneO group is the same or different and 1 or 2 $C_{1-6}$alkyleneNR$^7$ groups and each $C_{1-6}$alkyleneNR$^7$ group is the same or different. In some embodiments, L is $C_{1-6}$alkyleneO—$C_{1-6}$alkyleneO—$C_{1-6}$alkyleneO—$C_{1-6}$alkyleneO—$C_{1-6}$alkyleneO—$C_{1-6}$alkyleneNR$^7$. In some embodiments, L is $C_{1-6}$alkyleneO—$C_{1-6}$alkyleneO—$C_{1-6}$alkyleneNR$^7$. In some embodiments, L is $C_2$alkyleneO—$C_2$alkyleneO—$C_2$alkyleneNR$^7$. In some embodiments, L is $C_1$alkyleneO—$C_2$alkyleneO—$C_2$alkyleneNR$^7$.

In some embodiments, X is selected from $CH_2$, O, S, NR$^4$ and NR$^4$C(O). R$^4$ is selected from H, $C_{1-4}$alkyl and $C_{1-6}$alkyleneNR$^5$R$^6$ and L comprises 2 to 6 $C_{1-6}$alkyleneO groups and each $C_{1-6}$alkyleneO group is the same or different and 1 or 2 $C_{1-6}$alkyleneNR$^7$ groups and each $C_{1-6}$alkyleneNR$^7$ group is the same or different.

In some embodiments, X is selected from $CH_2$, O, S, NR$^4$ and NR$^4$C(O), R$^4$ is selected from H and $C_{1-4}$alkyl, and L is $C_{1-6}$alkyleneO—$C_{1-6}$alkyleneO—$C_{1-6}$alkyleneO—$C_{1-6}$alkyleneO—$C_{1-6}$alkyleneO—$C_{1-6}$alkyleneNR$^7$. In some embodiments, X is NR$^4$, R$^4$ is selected from H and $C_{1-4}$alkyl, and L is $C_{1-6}$alkyleneO—$C_{1-6}$alkyleneO—$C_{1-6}$alkyleneO—$C_{1-6}$alkyleneO—$C_{1-6}$alkyleneO—$C_{1-6}$alkyleneNR$^7$. In some embodiments, X is NR$^4$ or NR$^4$C(O), R$^4$ is selected from H and $CH_3$, and L is $C_{1-6}$alkyleneO—$C_{1-6}$alkyleneO—$C_{1-6}$alkyleneO—$C_{1-6}$alkyleneO—$C_{1-6}$alkyleneO—$C_{1-6}$alkyleneNR$^7$ or $C_{1-6}$alkyleneO—$C_{1-6}$alkyleneO—$C_{1-6}$alkyleneNR$^7$. In some embodiments, X is NR$^4$ or NR$^4$C(O), R$^4$ is selected from H and $CH_3$, and L is $C_{1-6}$alkyleneO—$C_{1-6}$alkyleneO—$C_{1-6}$alkyleneNR$^7$. In some embodiments, X is NR$^4$, R$^4$ is selected from H and $CH_3$, and L is $C_2$alkyleneO—$C_2$alkyleneO—$C_2$alkyleneNR$^7$. In some embodiments, X is NR$^4$C(O), R$^4$ is selected from H and $CH_3$, and L is $C_1$alkyleneO—$C_2$alkyleneO—$C_2$alkyleneNR$^7$.

In some embodiments, X is selected from NR$^4$ and NR$^4$C(O), R$^4$ is $C_{1-6}$alkyleneNR$^5$R$^6$, and L is $C_{1-6}$alkyleneO—$C_{1-6}$alkyleneO—$C_{1-6}$alkyleneNR$^7$. In some embodiments. X is NR$^4$, R$^4$ is $C_{1-6}$alkyleneNR$^5$R$^6$, and L is $C_2$alkyleneO—$C_2$alkyleneO—$C_2$alkyleneNR$^7$. In some embodiments, X is NR$^4$C(O), R$^4$ is $C_{1-6}$alkyleneNR$^5$R$^6$, and L is $C_1$alkyleneO—$C_2$alkyleneO—$C_2$alkyleneNR$^7$.

In some embodiments, R$^7$ and R$^8$ are independently selected from H and $C_{1-4}$alkyl. In some embodiments, R$^7$ and R$^8$ are independently selected from H and $CH_3$, $CH_2CH_3$, $CH_2CH_2CH_3$ and $CH(CH_3)_2$. In some embodiments, R$^7$ and R$^8$ are independently selected from H and $CH_3$.

In some embodiment, the E is any chelating group that is capable of binding with and/or complexing a metal ion. In some embodiment, the E is any chelating group that is capable of binding with and/or complexing a metal ion to form a heterocyclic ring including the metal ion. In some embodiments, the E is any chelating group derived from a chelating agent known in the art, for example, as disclosed in Banerjee et al., Nucl. Med. Biol., 2005, 32. 1-20, Wadas et al., Chem. Rev., 2010, 110, 2858-2902, U.S. Pat. Nos. 5,367,080, 5,364,613, 5,021,556, 5,075,099, and 5,886,142, Therefore, in some embodiments. E is a chelating group derived from a chelating agent. In some embodiments, the chelating agent is selected from a cyclic or an acyclic bifunctional chelating agent capable of binding with and/or complexing one or more radionuclides. In some embodiments, the chelating agent is selected from 1,4,7-Triazacyclononane (TACN); 1,4,7-triazacyclononane-triacetic acid (NOTA); 1,4,7-triazacyclononane-N-succinic acid-N',N'-diacetic acid (NOTASA); 1,4,7-triazacyclononane-N-glutamic acid-N',N'-diacetic acid (NODAGA); 1,4,7-triazacyclononane-N,N',N"-tris (methylenephosphonic) acid (NOTP); 1,4,7,10-tetraazacyclododecane ([12]aneN4) (cyclen); 1,4,7,10-tetraazacyclotridecane ([13]aneN4); 1,4,7,11-tetraazacyclotetradecane (iso-cyclam); 1,4,7,10-tetraazacyclododecane-1,4,7,10-tetraacetic acid (DOTA); 2-(1,4,7,10-tetraazacyclododecan-1-yl)acetate (DO1A); 2,2'-(1,4,7,10-tetraazacyclododecane-1,7-diyl) diacetic acid (DO2A); 2,2',2"-(1,4,7,10-tetraazacyclododecane-1,4,7-triyl) triacetic acid (DO3A); 1,4,7,10-tetraazacyclododecane-1,4,7,10-tetra (methanephosphonic acid) (DOTP); 1,4,7,10-tetraazacyclododecane-1,7-di(methanephosphonic acid) (DO2P); 1,4,7,10-tetraazacyclododecane-1,4,7-tri(methanephosphonic acid) (DO3P); 1,4,7,10-tetraazacyclo-decane-1-glutamic acid-4,7,10-triacetic acid (DOTAGA); 1,4,7,10-tetraazacyclodecane-1-succinic acid-4,7,10-triacetic acid (DOTASA); 1,4,8,11-tetraazacyclotetradecane ([14]aneN4) (cyclam); 1,4,8,12-tetraazacyclopentadecane ([15]aneN4); 1,5,9,13-tetraazacyclohexadecane ([16]aneN4); 1,4-ethano-1,4,8,11-tetraazacyclo-tetradecane (et-cyclam); 1,4,8,11-tetraazacyclotetradecane-1,4,8,1 1-tetraacetic acid (TETA); 2-(1,4,8,11-tetraazacyclotetradecane-1-yl) acetic acid (TE1A); 2,2'-(1,4,8,11-tetraazacyclotetradecane-1,8-diyl) diacetic acid (TE2A); 4,11-bis(carboxy methyl)-1,4,8,11-tetraazabicyclo [6.6.2]-hexadecane (CB-TE2A); 3,6,10,13,16,19-hexaazabicyclo[6.6.6]icosane (Sar); 1,4,7,10-tetra-(2-carbamoyl-methyl)-cyclododecane (TCMC); N,N'-bis[(6-carboxy-2-pyridil)methyl]-4,13-diaza-18-crown-6 (macropa), phthalocyanines and derivatives thereof; porphyrins and derivatives thereof. In some embodiments, the chelating agent is selected from DOTA, DOTAGA and NOTA. In some embodiments, the chelating agent is NOTA. In some embodiments, the chelating agent is selected from DOTA and DOTAGA. In some embodiments, the chelating agent is DOTA.

A person skilled in the art would appreciate that "a chelating group derived from a chelating agent" as used herein refers to a chelating agent derivative formed after the chelating agent is connected to the compound of Formula I or a pharmaceutically acceptable salt, solvate and/or prodrug thereof, e.g., to connected to L For example, "a chelating group derived from a chelating agent" may be a chelating agent without the "—OH" (or ester thereof) of an available carboxyl group (or ester thereof) on the chelating agent, without the "H" portion of an available amino group on the chelating agent, without the "NCS" portion of an available isothiocyanate on the chelating agent, without the "H" portion of an available maleimide group on the chelating agent, a chelating agent after an available acetylene group on the chelating agent has been reacted to connect to the compound of Formula I or a pharmaceutically acceptable salt, solvate and/or prodrug thereof, or a chelating agent after an available tetrazole group on the chelating agent has been reacted to connect to the compound of Formula I or a pharmaceutically acceptable salt, solvate and/or prodrug thereof. For example, a person skilled in the art would appreciate that when E is a chelating group derived from a DOTA, one "—OH" from one of the four available carboxyl groups on DOTA is removed to form the connection, such as an amide bond, to L in the compound of Formula I or a pharmaceutically acceptable salt, solvate and/or prodrug thereof leaving three available carboxyl groups.

In some embodiments, the one or more radionuclides is a radioactive isotope of C, N, F, S, Br, Ru, Pd, Tc, Ga, In, Zn, Gd, Bi, At, Cu, Pb, Fe, Ti, F, I, Y, Sr, Ra, P, Re, Sc, Zr, Rh, Pt, Rb, Au, Sn, Tl, Co, Pm, a lanthanide, or an actinide.

In some embodiments, the lanthanide is Lu, Sm, Pm, Ho, or Tb.

In some embodiments, the actinide is Ac or Th.

In some embodiments, the one or more radionuclides are selected from $^{14}$C, $^{15}$N, $^{18}$F, $^{75}$Br, $^{76}$Br, $^{77}$Br, $^{123}$I, $^{124}$I, $^{125}$I, $^{131}$I, $^{35}$S, $^{99}$Tc, $^{99m}$Tc, $^{188}$Re, $^{186}$Re, $^{153}$Sm, $^{67}$Ga, $^{68}$Ga, $^{111}$In, $^{59}$Fe, $^{63}$Zn, $^{52}$Fe, $^{45}$Ti, $^{60}$Cu, $^{61}$Cu, $^{87}$Cu, $^{84}$Cu, $^{62}$Cu, $^{82}$Rb, $^{195m}$Pt, $^{191m}$Pt, $^{193m}$Pt, $^{117m}$Sn, $^{89}$Zr, $^{177}$Lu, $^{18}$F, $^{123}$I, $^{188}$Re, $^{186}$Re, $^{153}$Sm, $^{68}$Ho, $^{86}$Y, $^{87}$Y, $^{90}$Y, $^{89}$Sr, $^{111}$In, $^{153}$Gd, $^{225}$Ac, $^{212}$Bi, $^{213}$Bi, $^{211}$At, $^{198}$Au, $^{199}$Au, $^{193m}$Pt, $^{197}$Pt, $^{103}$Pd, $^{109}$Pd, $^{105}$Rh, $^{103m}$Rh, $^{223}$Ra, $^{224}$Ra, $^{97}$Ru, $^{227}$Th, $^{229}$Th, $^{32}$P, $^{161}$Tb, $^{33}$P, $^{149}$Tb, $^{125}$I, $^{203}$Pb, $^{212}$Pb, $^{201}$Tl, $^{119}$Sb, $^{58m}$Co, $^{55}$Co, $^{47}$Sc, $^{149}$Pm and $^{161}$Ho.

In some embodiments, the one or more radionuclides are for use in imaging or for use in therapy.

In some embodiments, the one or more radionuclides for use in imaging are selected from $^{99m}$Tc, $^{188}$Re, $^{186}$Re, $^{153}$Sm, $^{67}$Ga, $^{88}$Ga, $^{111}$In, $^{59}$Fe, $^{63}$Zn, $^{52}$Fe, $^{45}$Ti, $^{60}$Cu, $^{61}$Cu, $^{67}$Cu, $^{54}$Cu, $^{62}$Cu, $^{82}$Rb, $^{198}$Au, $^{199}$Au, $^{195m}$Pt, $^{191m}$Pt, $^{193m}$Pt, $^{117m}$Sn, $^{89}$Zr, $^{177}$Lu, $^{18}$F and $^{123}$I.

In some embodiments, the one or more radionuclides for use in therapy are selected from $^{188}$Re, $^{186}$Re, $^{153}$Sm, $^{65}$Ho, $^{90}$Y, $^{89}$Sr, $^{111}$In, $^{153}$Gd, $^{225}$Ac, $^{212}$Bi, $^{213}$Bi, $^{211}$At, $^{60}$Cu, $^{81}$Cu, $^{67}$Cu, $^{64}$Cu, $^{62}$Cu, $^{198}$Au, $^{99}$Au, $^{195}$Pt, $^{193m}$Pt, $^{197}$Pt $^{117m}$Sn, $^{103}$Pd, $^{105}$Rh, $^{103m}$Rh, $^{177}$Lu, $^{223}$Ra, $^{224}$Ra, $^{227}$Th, $^{229}$Th, $^{149}$Tb, $^{161}$Tb, $^{32}$P, $^{33}$P, $^{125}$I, $^{203}$Pb, $^{212}$Pb, $^{201}$Tl, $^{119}$Sb, $^{58m}$Co, $^{47}$Sc, $^{149}$Pm and $^{161}$Ho.

In some embodiments, the one or more radionuclides for use in therapy are selected from $^{177}$Lu, $^{212}$Pb, and $^{225}$Ac. In some embodiments, the one or more radionuclides for use in therapy is $^{177}$Lu.

In some embodiments, the compound of Formula I is selected from the following list of compounds:
| Compound I.D | Structure |
|---|---|
| I-1 | 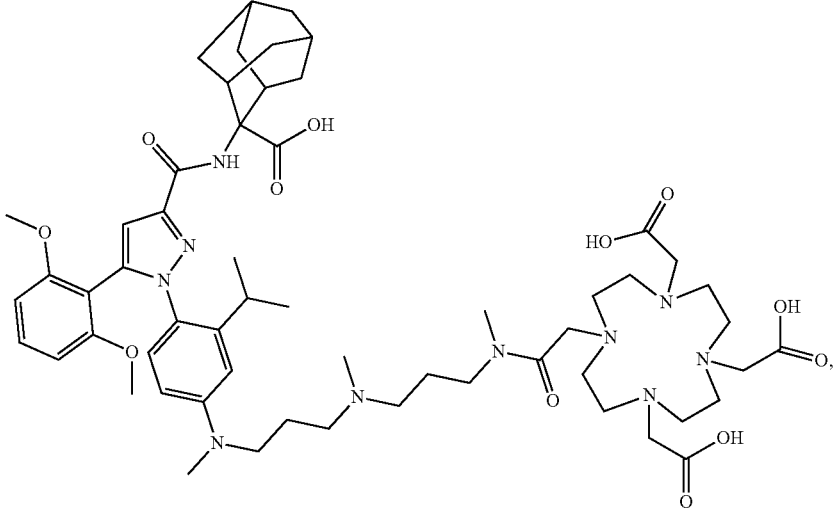 [SMILES: COc1cccc(OC)c1-c1cc(C(=O)NC2(C(=O)O)C3CC4CC(C3)CC2C4)nn1-c1ccc(N(C)CCCN(C)CCCN(C)C(=O)CN2CCN(CC(=O)O)CCN(CC(=O)O)CCN(CC(=O)O)CC2)cc1C(C)C] |
| I-2 | 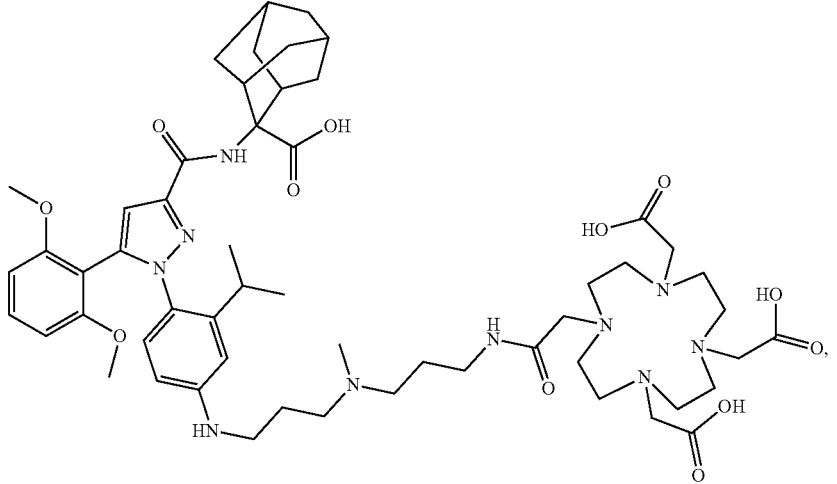 [SMILES: COc1cccc(OC)c1-c1cc(C(=O)NC2(C(=O)O)C3CC4CC(C3)CC2C4)nn1-c1ccc(NCCCN(C)CCCNC(=O)CN2CCN(CC(=O)O)CCN(CC(=O)O)CCN(CC(=O)O)CC2)cc1C(C)C] |

| Compound I.D | Structure |
|---|---|
| I-3 | 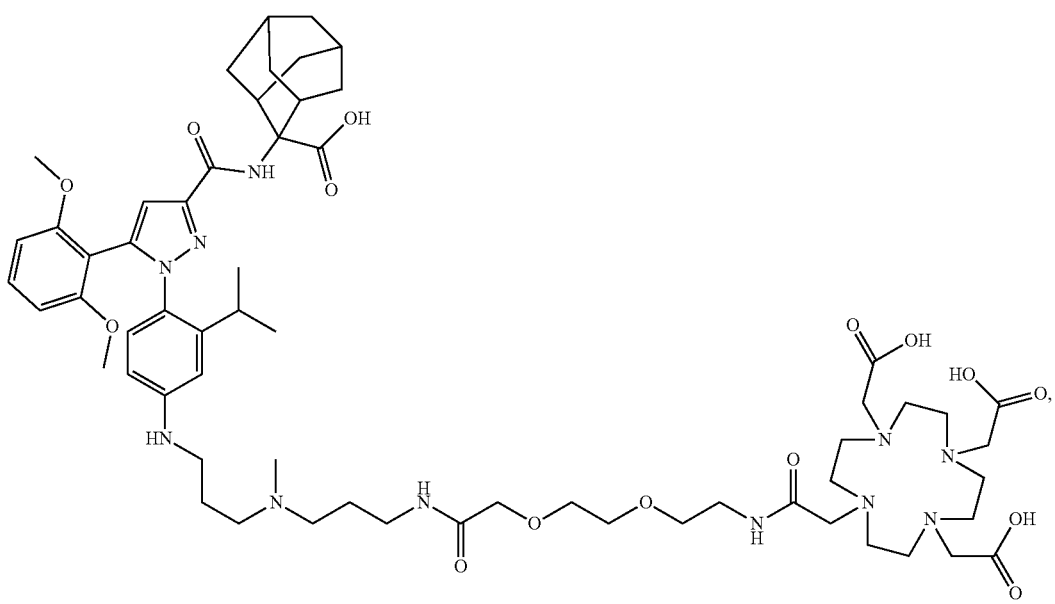 [SMILES: COc1cccc(OC)c1-c1cc(C(=O)NC2(C(=O)O)C3CC4CC(C3)CC2C4)nn1-c1ccc(NCCCN(C)CCCNC(=O)COCCOCCNC(=O)CN2CCN(CC(=O)O)CCN(CC(=O)O)CCN(CC(=O)O)CC2)cc1C(C)C] |
| I-4 | 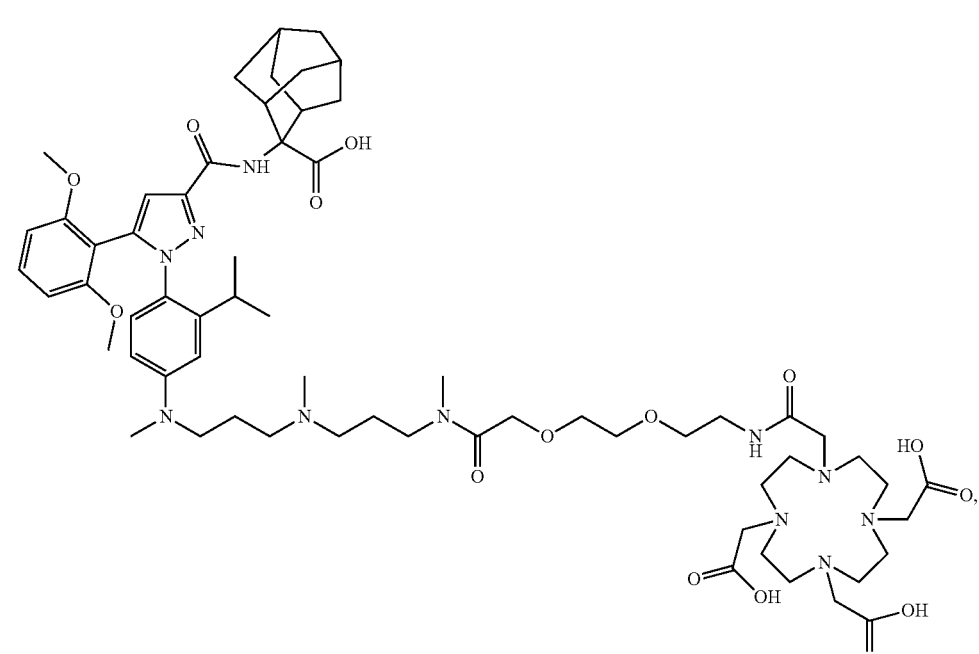 |

| Compound I.D | Structure |
|---|---|
| I-5 | 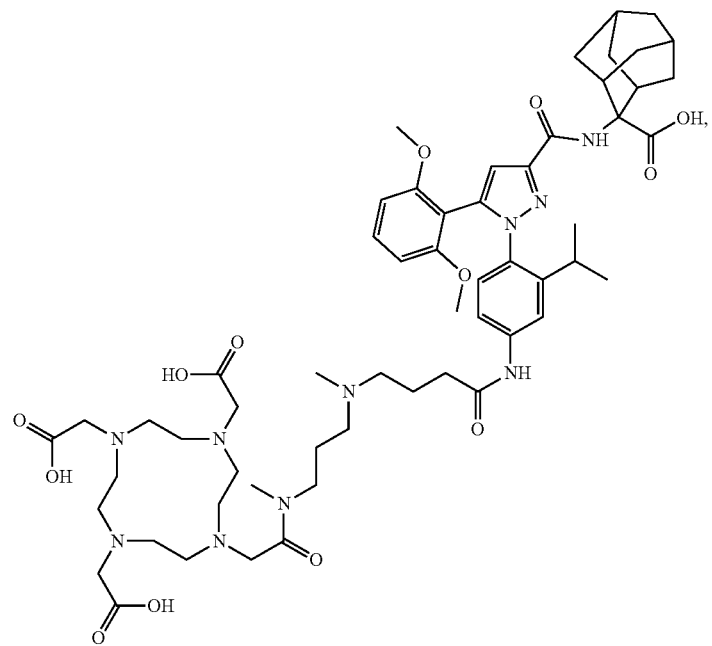 [SMILES: COc1cccc(OC)c1-c1cc(C(=O)NC2(C(=O)O)C3CC4CC(C3)CC2C4)nn1-c1ccc(NC(=O)CCCN(C)CCCN(C)C(=O)CN2CCN(CC(=O)O)CCN(CC(=O)O)CCN(CC(=O)O)CC2)cc1C(C)C] |
| I-6 | 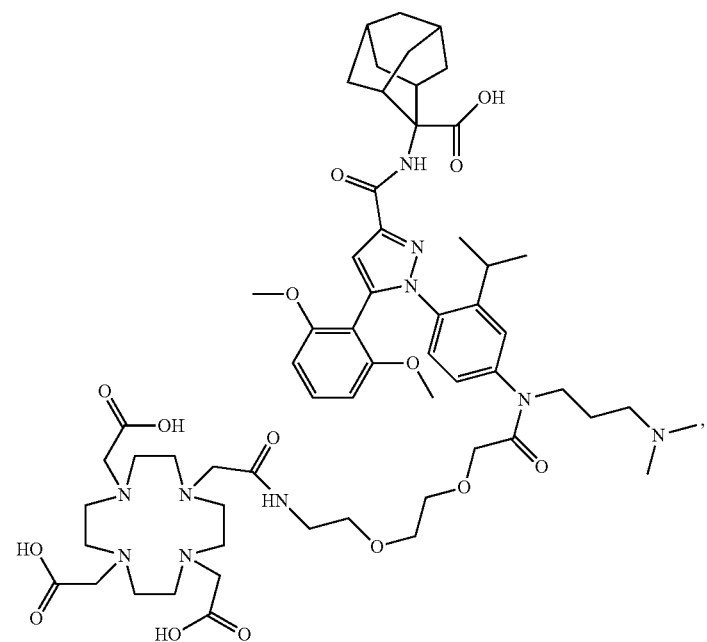 [SMILES: COc1cccc(OC)c1-c1cc(C(=O)NC2(C(=O)O)C3CC4CC(C3)CC2C4)nn1-c1ccc(N(CCCN(C)C)C(=O)COCCOCCNC(=O)CN2CCN(CC(=O)O)CCN(CC(=O)O)CCN(CC(=O)O)CC2)cc1C(C)C] |

-continued
| Compound I.D | Structure |
|---|---|
| I-7 | 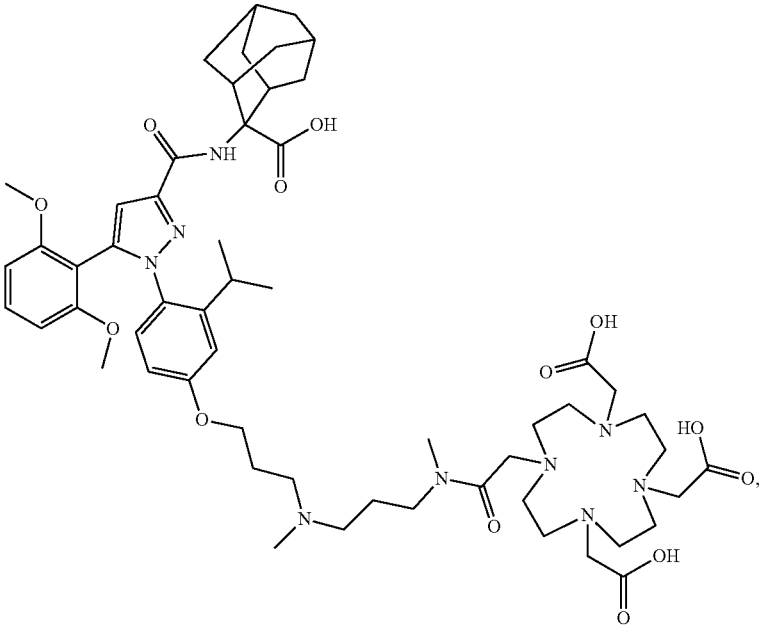 [SMILES: COc1cccc(OC)c1-c1cc(C(=O)NC2(C(=O)O)C3CC4CC(C3)CC2C4)nn1-c1ccc(OCCCN(C)CCCN(C)C(=O)CN2CCN(CC(=O)O)CCN(CC(=O)O)CCN(CC(=O)O)CC2)cc1C(C)C] |
| I-8 | 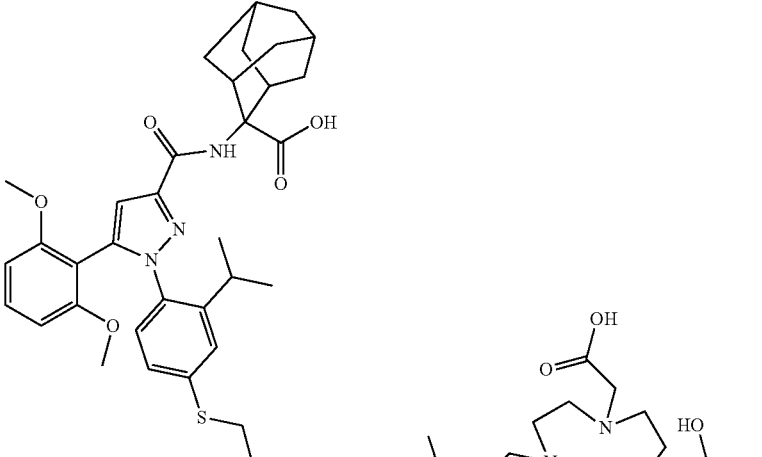 |

-continued
| Compound I.D | Structure |
|---|---|
| I-9 | 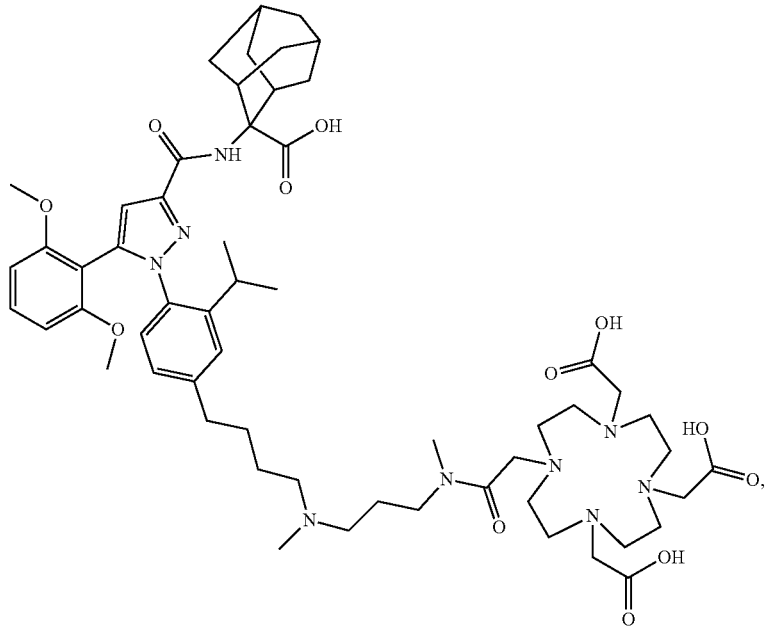 [SMILES: COc1cccc(OC)c1-c1cc(C(=O)NC2(C(=O)O)C3CC4CC(C3)CC2C4)nn1-c1ccc(CCCCN(C)CCCN(C)C(=O)CN2CCN(CC(=O)O)CCN(CC(=O)O)CCN(CC(=O)O)CC2)cc1C(C)C] |
| I-10 | 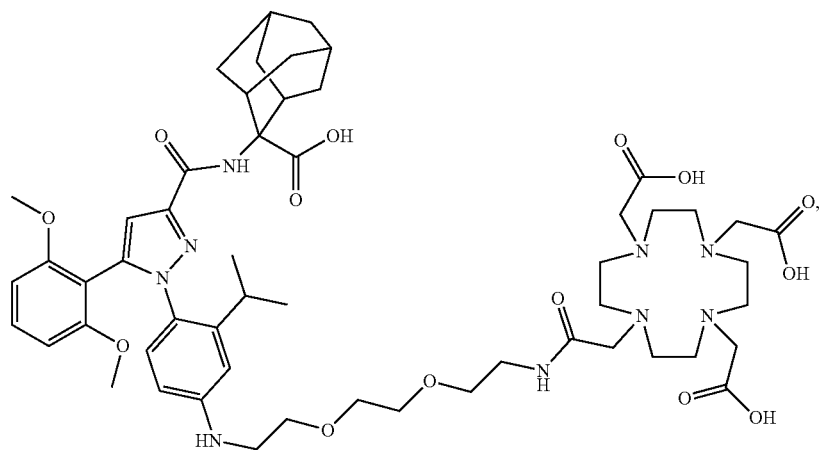 [SMILES: COc1cccc(OC)c1-c1cc(C(=O)NC2(C(=O)O)C3CC4CC(C3)CC2C4)nn1-c1ccc(NCCOCCOCCNC(=O)CN2CCN(CC(=O)O)CCN(CC(=O)O)CCN(CC(=O)O)CC2)cc1C(C)C] |
| I-11 | 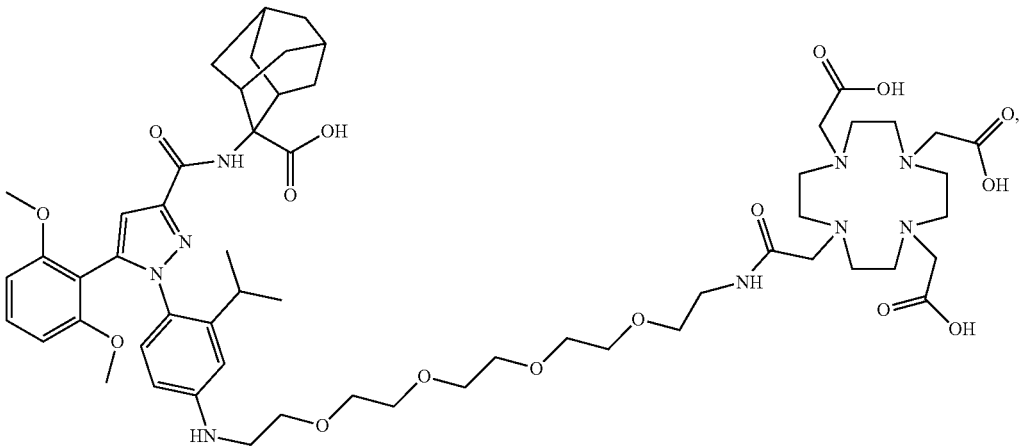 [SMILES: COc1cccc(OC)c1-c1cc(C(=O)NC2(C(=O)O)C3CC4CC(C3)CC2C4)nn1-c1ccc(NCCOCCOCCOCCOCCNC(=O)CN2CCN(CC(=O)O)CCN(CC(=O)O)CCN(CC(=O)O)CC2)cc1C(C)C] |

-continued
| Compound I.D | Structure |
|---|---|
| I-12 | 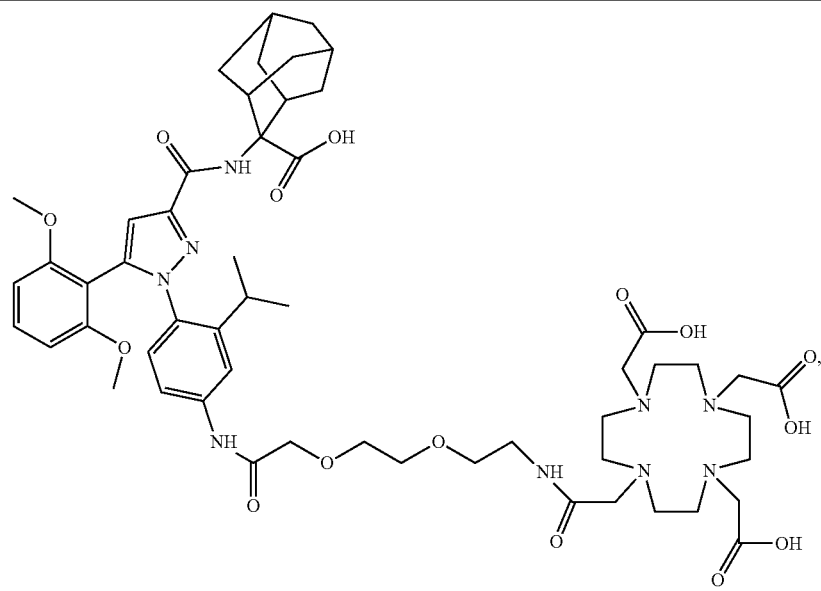 |
| I-13 | 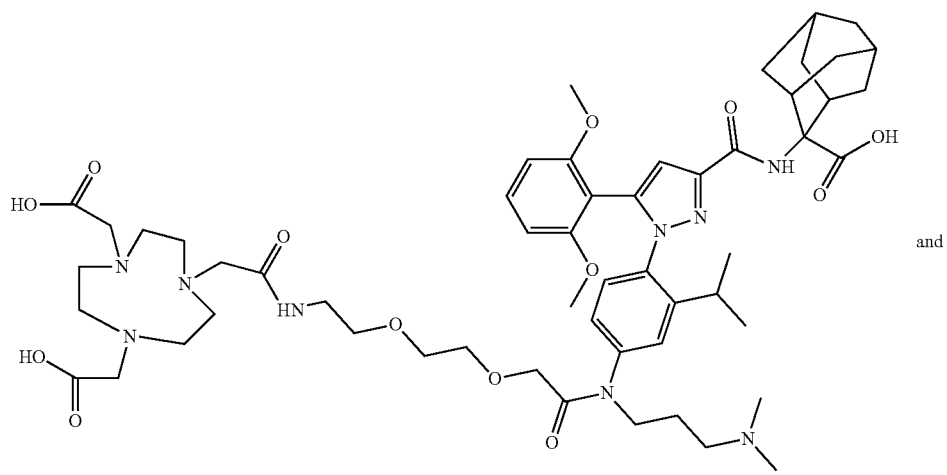 [SMILES: COc1cccc(OC)c1-c1cc(C(=O)NC2(C(=O)O)C3CC4CC(C3)CC2C4)nn1-c1ccc(N(CCCN(C)C)C(=O)COCCOCCNC(=O)CN2CCN(CC(=O)O)CCN(CC(=O)O)CC2)cc1C(C)C] and |
| 14 | 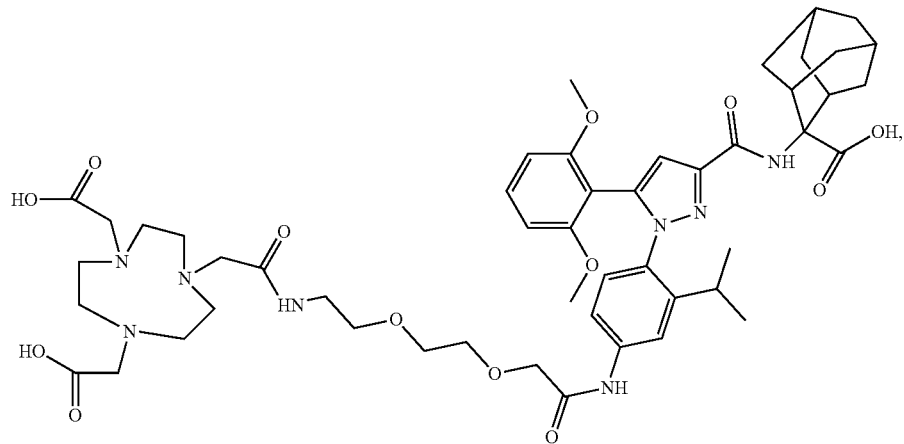 [SMILES: COc1cccc(OC)c1-c1cc(C(=O)NC2(C(=O)O)C3CC4CC(C3)CC2C4)nn1-c1ccc(NC(=O)COCCOCCNC(=O)CN2CCN(CC(=O)O)CCN(CC(=O)O)CC2)cc1C(C)C] |
or a pharmaceutically acceptable salt and/or solvate thereof.

The chelating binding group is capable of binding with and/or complexing a radionuclide. Therefore, in some embodiments, the compound of Formula I further comprises a radionuclide complexed to the chelating binding group.

Accordingly, the present application also includes a radionuclide complex (radioligand) or a pharmaceutically acceptable salt and/or solvate thereof, comprising a compound of the application or a pharmaceutically acceptable salt and/or solvate thereof, and one or more radionuclides.

In some embodiments, the radionuclide is selected from a transition metal, rare-earth metal, lanthanide, actinide and metalloid.

In some embodiments, the one or more radionuclides is a radioactive isotope of C, N, F, S, Br, Ru, Tc, Ga, In, Zn, Gd, Bi, At, Cu, Pb, Fe, Ti, F, I, Y, Sr, Ra, P, Re, Sc, Zr, Rh, Pt, Rb, Au, Sn, Tl, Co, Pm, a lanthanide, or an actinide.

In some embodiments, the lanthanide Lu, Sm, Ho, or Tb.

In some embodiments, the actinide is Ac or Th.

In some embodiments, the radionuclide is selected from $^{225}$Ac, $^{226}$Ac, $^{228}$Ac, $^{105}$Ag, $^{106}$mAg, $^{110}$mAg, $^{111}$Ag, $^{112}$Ag, $^{113}$Ag, $^{239}$Am, $^{240}$Am, $^{242}$Am, $^{244}$Am, $^{37}$Ar, $^{71}$As, $^{72}$As, $^{73}$As, $^{74}$As, $^{76}$As, $^{77}$As, $^{209}$At, $^{210}$At, $^{191}$Au, $^{192}$Au, $^{193}$Au, $^{194}$Au, $^{195}$Au, $^{196}$Au, $^{196m2}$Au, $^{198}$Au, $^{198m}$Au, $^{199}$Au $^{200m}$Au, $^{128}$Ba, $^{131}$Ba, $^{133m}$Ba, $^{135m}$Ba, $^{140}$Ba, $^{7}$Be, $^{203}$Bi, $^{204}$Bi, $^{205}$Bi, $^{206}$Bi, $^{210}$Bi, $^{212}$Bi, $^{243}$Bk, $^{244}$Bk $^{245}$Bk, $^{246}$Bk, $^{248m}$Bk, $^{250}$Bk, $^{76}$Br, $^{77}$Br, $^{80m}$Br, $^{82}$Br, $^{11}$C, $^{14}$C, $^{45}$Ca, $^{47}$Ca, $^{107}$Cd, $^{115}$Cd, $^{115m}$Cd $^{117mr}$Cd, $^{132}$Ce, $^{133}$Ce, $^{134}$Ce, $^{135}$Ce, $^{137}$Ce, $^{137m}$Ce, $^{139}$Ce, $^{141}$Ce, $^{143}$Ce, $^{144}$Ce, $^{246}$Cf, $^{247}$Cf, $^{253}$Cf $^{254}$Cf, $^{240}$Cm, $^{241}$Cm, $^{242}$Cm, $^{252}$Cm, $^{55}$Co, $^{56}$Co, $^{57}$Co, $^{58}$Co, $^{58m}$Co, $^{60}$Co, $^{48}$Cr, $^{51}$Cr, $^{127}$Cs, $^{129}$Cs, $^{131}$Cs, $^{132}$Cs, $^{136}$Cs, $^{137}$Cs, $^{61}$Cu, $^{62}$Cu, $^{84}$Cu, $^{87}$Cu, $^{153}$Dy, $^{155}$Dy, $^{157}$Dy, $^{159}$Dy, $^{165}$Dy, $^{166}$Dy, $^{160}$Er $^{161}$Er, $^{185}$Er, $^{169}$Er, $^{171}$Er, $^{172}$Er, $^{250}$Es, $^{251}$Es, $^{253}$Es, $^{254}$Es, $^{254m}$Es, $^{255}$Es, $^{256m}$Es, $^{145}$Eu, $^{146}$Eu, $^{147}$Eu $^{148}$Eu, $^{149}$Eu, $^{150m}$Eu, $^{152m}$Eu, $^{156}$Eu, $^{157}$Eu, $^{52}$Fe, $^{59}$Fe, $^{251}$Fm, $^{252}$Fm, $^{253}$Fm, $^{254}$Fm, $^{255}$Fm, $^{257}$Fm $^{86}$Ga, $^{87}$Ga, $^{68}$Ga, $^{72}$Ga, $^{73}$Ga, $^{146}$Gd, $^{147}$Gd, $^{149}$Gd, $^{151}$Gd, $^{153}$Gd, $^{159}$Gd, $^{68}$Ge, $^{69}$Ge, $^{71}$Ge, $^{77}$Ge $^{170}$Hf, $^{171}$Hf, $^{173}$Hf, $^{175}$Hf, $^{179m2}$Hf, $^{180m}$Hf, $^{181}$Hf, $^{184}$Hf, $^{192}$Hg, $^{193}$Hg, $^{193m}$Hg, $^{195}$Hg, $^{195m}$Hg, $^{197}$Hg $^{197m}$Hg, $^{203}$Hg, $^{160m}$Ho, $^{166}$Ho, $^{167}$Ho, $^{123}$I, $^{124}$I, $^{128}$I, $^{130}$I, $^{132}$I, $^{133}$I, $^{135}$I, $^{109}$In, $^{110}$In, $^{111}$In, $^{114}$In, $^{115}$In, $^{184}$Ir, $^{185}$Ir, $^{186}$Ir, $^{187}$Ir, $^{188}$Ir, $^{189}$Ir, $^{191}$Ir, $^{190m2}$Ir, $^{192}$Ir, $^{193m}$Ir, $^{194}$Ir, $^{194m2}$Ir, $^{195m}$Ir, $^{42}$K, $^{43}$K, $^{76}$Kr, $^{79}$Kr, $^{81m}$Kr, $^{85m}$Kr, $^{132}$La, $^{133}$La, $^{135}$La, $^{140}$La, $^{141}$La, $^{262}$Lr, $^{189}$Lu, $^{170}$Lu, $^{171}$Lu, $^{172}$Lu, $^{174m}$Lu, $^{176m}$Lu, $^{177}$Lu, $^{177m}$Lu, $^{179}$Lu, $^{257}$Md, $^{258}$Md, $^{260}$Md, $^{28}$Mg, $^{52}$Mn, $^{90}$Mo, $^{93m}$Mo, Mo, $^{13}$N, $^{24}$Na, $^{90}$Nb, $^{91m}$Nb, $^{92m}$Nb, $^{95}$Nb, $^{95m}$Nb, $^{96}$Nb, $^{138}$Nd, $^{139m}$Nd, $^{140}$Nd, $^{147}$Nd, $^{58}$Ni, $^{57}$Ni, $^{66}$Ni, $^{234}$Np, $^{238m}$Np, $^{238}$Np $^{239}$Np, $^{15}$O, $^{182}$Os, $^{183}$Os $^{183m}$Os, $^{185}$Os, $^{189m}$Os $^{191}$Os, $^{191m}$OS, $^{193}$Os, $^{32}$P, $^{33}$P, $^{228}$Pa, $^{229}$Pa, $^{230}$Pa, $^{232}$Pa, $^{233}$Pa, $^{234}$Pa, $^{200}$Pb, $^{201}$Pb, $^{202m}$Pb, $^{203}$Pb, $^{209}$Pb, $^{212}$Pb, $^{100}$Pd, $^{101}$Pd, $^{103}$Pd, $^{109}$Pd, $^{111m}$Pd, $^{112}$Pd, $^{143}$Pm, $^{148}$Pm, $^{148m}$Pm, $^{149}$Pm, $^{151}$Pm, $^{204}$Po, $^{206}$Po, $^{207}$Po, $^{210}$Po, $^{139}$Pr, $^{142}$Pr, $^{143}$Pr, $^{145}$Pr, $^{188}$Pt, $^{189}$Pt, $^{191}$Pt, $^{193m}$Pt, $^{195m}$Pt, $^{197}$Pt, $^{200}$Pt, $^{202}$Pt, $^{234}$Pu, $^{237}$Pu, $^{243}$Pu, $^{245}$Pu, $^{246}$Pu, $^{247}$Pu, $^{223}$Ra, $^{224}$Ra, $^{225}$Ra, $^{81}$Rb, $^{82}$Rb, $^{82m}$Rb, $^{83}$Rb, $^{84}$Rb, $^{88}$Rb, $^{181}$Re, $^{182}$Re, $^{182m}$Re, $^{183}$Re, $^{184}$Re $^{184m}$Re $^{186}$Re, $^{188}$Re, $^{189}$Re, $^{190m}$Re, $^{99}$Rh, $^{99m}$Rh, $^{100}$Rh, $^{101m}$Rh, $^{102}$Rh, $^{103m}$Rh, $^{105}$Rh, $^{211}$Rn $^{222}$Rn, $^{97}$Ru $^{103}$Ru, $^{105}$Ru, $^{35}$S, $^{118m}$Sb, $^{119}$Sb, $^{120}$Sb, $^{120m}$Sb, $^{122}$Sb, $^{124}$Sb, $^{126}$Sb, $^{127}$Sb, $^{128}$Sb $^{129}$Sb, $^{43}$Sc, $^{44}$Sc, $^{44m}$Sc, $^{46}$Sc, $^{47}$Sc, $^{48}$Sc, $^{72}$Se, $^{73}$Se, $^{75}$Se, $^{153}$Sm, $^{158}$Sm, $^{110}$Sn, $^{113}$Sn, $^{117m}$Sn, $^{119m}$Sn, $^{121}$Sn, $^{123}$Sn, $^{125}$Sn, $^{82}$Sr, $^{83}$Sr, $^{85}$Sr, $^{89}$Sr, $^{91}$Sr, $^{173}$Ta, $^{175}$Ta, $^{176}$Ta, $^{177}$Ta, $^{180}$Ta, $^{182}$Ta $^{183}$Ta, $^{184}$Ta, $^{149}$Tb, $^{150}$Tb, $^{151}$Tb, $^{152}$Tb, $^{153}$Tb, $^{154}$Tb, $^{154m}$Tb, $^{154m2}$Tb, $^{155}$Tb, $^{156}$Tb, $^{156m}$Tb $^{156m2}$Tb, $^{160}$Tb, $^{161}$Tb, $^{94}$Tc, $^{95}$Tc, $^{95m}$Tc, $^{96}$Tc, $^{97m}$Tc, $^{99m}$Tc, $^{118}$Te, $^{119}$Te, $^{119m}$Te, $^{121}$Te, $^{121m}$Te $^{123m}$Te, $^{125m}$Te, $^{127}$Te, $^{127m}$Te, $^{129m}$Te, $^{131m}$Te, $^{132}$Te, $^{227}$Th, $^{231}$Th, $^{234}$Th, $^{45}$Ti, $^{198}$Tl, $^{199}$Tl, $^{200}$Tl $^{201}$Tl, $^{202}$Tl, $^{204}$Tl, $^{165}$Tm, $^{166}$Tm, $^{167}$Tm, $^{168}$Tm, $^{170}$Tm, $^{172}$Tm, $^{173}$Tm, $^{230}$U, $^{231}$U, $^{237}$U, $^{240}$U, $^{48}$V, $^{178}$W $^{181}$W, $^{185}$W, $^{187}$W, $^{188}$W, $^{122}$Xe, $^{125}$Xe, $^{127}$Xe, $^{129m}$Xe, $^{131m}$Xe, $^{133}$Xe, $^{133m}$Xe, $^{135}$Xe, $^{85m}$Y, $^{85}$Y, $^{87}$Y $^{87m}$Y, $^{88}$Y, $^{90}$Y, $^{90m}$Y, $^{91}$Y, $^{92}$Y, $^{93}$Y, $^{188}$Yb, $^{189}$Yb, $^{175}$Yb, $^{62}$Zn, $^{85}$Zn, $^{89m}$Zn, $^{71m}$Zn, $^{72}$Zn, $^{86}$Zr, $^{88}$Zr $^{89}$Zr, $^{96}$Zr, and $^{97}$Zr.

In some embodiments, the one or more radionuclides are selected from $^{14}$C, $^{15}$N, $^{18}$F, $^{75}$Br, $^{76}$Br, $^{77}$Br, $^{123}$I, $^{124}$I, $^{125}$I, $^{131}$I, $^{35}$S, $^{99}$Tc, $^{99m}$Tc, $^{188}$Re, $^{186}$Re, $^{153}$Sm, $^{67}$Ga, $^{68}$Ga, $^{111}$In, $^{59}$Fe, $^{63}$Zn, $^{52}$Fe, $^{45}$Ti, $^{60}$Cu, $^{61}$Cu, $^{67}$Cu, $^{64}$Cu, $^{82}$Cu, $^{82}$Rb, $^{195m}$Pt, $^{191m}$Pt, $^{193m}$Pt, $^{117m}$Sn, $^{89}$Zr, $^{177}$Lu, $^{18}$F, $^{123}$I, $^{188}$Re, $^{186}$Re, $^{153}$Sm, $^{66}$Ho, $^{86}$Y, $^{87}$Y, $^{90}$Y, $^{89}$Sr, $^{111}$In, $^{153}$Gd, $^{225}$Ac, $^{212}$Bi, $^{213}$Bi, $^{211}$At, $^{198}$Au, $^{199}$Au, $^{193m}$Pt, $^{197}$Pt, $^{103}$Pd, $^{109}$Pd, $^{105}$Rh, $^{103m}$Rh, $^{223}$Ra, $^{224}$Ra, $^{97}$Ru, $^{227}$Th, $^{229}$Th, $^{32}$P, $^{161}$Tb, $^{33}$P, $^{149}$T, $^{125}$I, $^{203}$Pb, $^{212}$Pb, $^{201}$Tl, $^{119}$Sb, $^{58m}$Co, $^{55}$Co, $^{47}$Sc, $^{149}$Pm and $^{161}$Ho.

In some embodiments, the one or more radionuclide are for use in imaging or diagnosing, or for use in therapy.

In some embodiments, the one or more radionuclide for use in imaging or diagnosing is selected from $^{99m}$Tc, $^{188}$Re, $^{186}$Re, $^{153}$Sm, $^{67}$Ga, $^{68}$Ga, $^{111}$In, $^{59}$Fe, $^{63}$Zn, $^{52}$Fe, $^{45}$Tl, $^{60}$Cu, $^{81}$Cu, $^{67}$Cu, $^{64}$Cu, $^{82}$Cu, $^{82}$Rb, $^{198}$Au, $^{199}$Au, $^{195m}$Pt, $^{191m}$Pt, $^{193m}$Pt, $^{117m}$Sn, $^{89}$Zr, $^{177}$Lu, $^{18}$F, $^{203}$Pb and $^{123}$I.

In some embodiments, the one or more radionuclide for use in imaging or diagnosing is selected from $^{68}$Ga, $^{111}$In, and $^{89}$Zr.

In some embodiments, one or more radionuclides for use in therapy are selected from $^{185}$Re, $^{186}$Re, $^{153}$Sm, $^{68}$Ho, $^{90}$Y, $^{89}$Sr, $^{111}$In, $^{153}$Gd, $^{225}$Ac, $^{212}$Bi, $^{213}$Bi, $^{211}$At, $^{60}$Cu, $^{51}$Cu, $^{67}$Cu, $^{67}$Cu, $^{62}$Cu, $^{198}$Au, $^{99}$Au, $^{195m}$Pt, $^{193m}$Pt, $^{197}$Pt, $^{117m}$Sn, $^{103}$Pd, $^{105}$Rh, $^{103m}$Rh, $^{177}$Lu, $^{223}$Ra, $^{224}$Ra, $^{227}$Th, $^{229}$Th, $^{149}$Tb, $^{161}$Tb, $^{32}$P, $^{33}$P, $^{125}$I, $^{203}$Pb, $^{212}$Pb, $^{201}$Tl, $^{119}$Sb, $^{58m}$Co, $^{47}$Sc, $^{149}$Pm and $^{151}$Ho.

In some embodiments, the radionuclides for use in therapy are selected from $^{177}$Lu, $^{177}$Sm, $^{212}$Pb, $^{90}$Y, and $^{225}$Ac. In some embodiments, the one or more radionuclides for use in therapy is $^{177}$Lu. In some embodiments, the one or more radionuclides for use in therapy is $^{225}$Ac.

The Applicant has unexpectedly found that modifying the amido group, for example, the removal of the carbonyl group from the amide group that directly connects a di-amine moiety to the remainder of the structure of a known neurotensin antagonist compound SR142948 (C-3) improves the potency of the antagonist. For example, the applicants have shown that a very structurally similar derivative of SR142948 having an amino linkage rather than an amido linkage, e.g., having no carbonyl group, shows more than a 10× improvement in activity, see Table 1. Therefore, derivatives of compound SR142948 not comprising the directly linked carbonyl group as useful are neurotensin receptor antagonists having improved inhibition of neurotensin receptors, e.g. NTR1 compared to SR142948. Such derivatives of compound SR142948 are also useful as intermediates in the process of preparing the compounds of Formula I.

Accordingly, the present application further includes a compound of Formula II or a pharmaceutically acceptable salt and/or solvate thereof

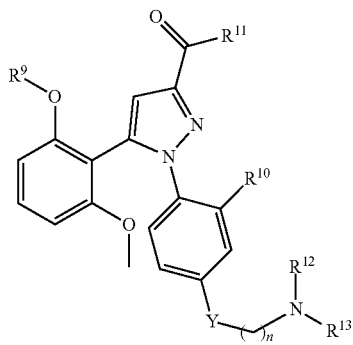

(II)

wherein
- $R^9$ is selected from H, $C_{1-6}$alkyl, $C_{3-6}$cycloalkyl and $C_{1-3}$alkylene$C_{3-8}$cycloalkyl, the latter three groups being optionally substituted with one or more halo;
- $R^{10}$ is selected from H, halo, $NO_2$, $C_{1-6}$alkyl, $C_{3-8}$cycloalkyl and $C_{1-3}$alkylene$C_{3-8}$cycloalkyl), the latter three groups being optionally substituted with one or more halo;
- $R^{11}$ is selected from 2-amino-2-adamantane carboxylic acid, cyclohexylglycine and 9-amino-bicyclo[3.3.1]nonane-9-carboxylic acid;
- Y is selected from $CH_2$, O, $NR^{14}$, S, S(O), $SO_2NR^{14}$ and $NR^{14}C(O)$;
- $R^{12}$ and $R^{13}$ are independently selected from H and $C_{1-6}$alkyl;
- $R^{14}$ is selected from H and $C_{1-6}$alkyl; and
- n is an integer selected from 1 to 10.

In some embodiments, $R^9$ is selected from H, $C_{1-4}$alkyl, $C_{3-6}$cycloalkyl and $C_{1-3}$alkylene$C_{3-6}$cycloalkyl, the latter three groups being optionally substituted with one or more halo. In some embodiments, $R^9$ is selected from H, $C_{1-3}$alkyl, cyclopropyl, cyclobutyl, and $CH_2$cyclopropyl and $CH_2$cyclobutyl, the latter five groups being optionally substituted with one or more halo. In some embodiments, $R^1$ is selected from $CH_3$, $CH_2CH_3$, $CH_2CH_2CH_3$, $CH(CH_3)_2$, cyclopropyl, cyclobutyl, $CH_2$cyclopropyl, and $CH_2$cyclobutyl, each of which is optionally substituted with one or more halo. In some embodiments, $R^9$ is selected from $CH_3$, $CH_2CH_3$, $CH_2CH_2CH_3$, $CH(CH_3)_2$, cyclopropyl, and $CH_2$cyclopropyl, each of which is optionally substituted with one or more fluoro. In some embodiments, $R^9$ is selected from $CH_3$, $CH_2CH_3$, $CH_2CH_2CH_3$, and $CH(CH_3)_2$. In some embodiments, $R^1$ is $CH_3$.

In some embodiments, $R^{10}$ is selected from H, halo. $NO_2$, $C_{1-6}$alkyl, $C_{3-8}$cycloalkyl and $C_{1-3}$alkylene$C_{3-6}$cycloalkyl, latter three groups being optionally substituted with one or more halo. In some embodiments, $R^{10}$ is selected from halo, $NO_2$, $C_{1-6}$alkyl, $C_{3-6}$cycloalkyl and $CH_2C_{3-8}$cycloalkyl, the latter three groups being optionally substituted with one or more halo. In some embodiments, $R^{10}$ is selected from halo, $NO_2$, and $C_{1-6}$alkyl, the latter group being optionally substituted with one or more halo. In some embodiments, $R^{10}$ is $C_{1-6}$alkyl, optionally substituted with one or more halo. In some embodiments, $R^{10}$ is selected from $CH_3$, $CH_2CH_3$, $CH_2CH_2CH_3$. $CH(CH_3)_2$, optionally substituted with one or more fluoro. In some embodiments. $R^{10}$ is selected from $CH_3$, $CH_2CH_3$, $CH_2CH_2CH_3$, $CH(CH_3)_2$. In some embodiments, $R^{10}$ is $CH(CH_3)_2$.

In some embodiments. $R^{11}$ is 2-amino-2-adamantane carboxylic acid. In some embodiments, $R^{11}$ is cyclohexylglycine. In some embodiments, $R^{11}$ is 9-amino-bicyclo[3.3.1]nonane-9-carboxylic acid. In some embodiments, $R^{11}$ is a group having the following formula

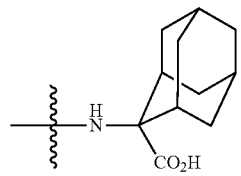

In some embodiments, the compound of Formula II is a compound of Formula II-A or a pharmaceutically acceptable salt and/or solvate thereof

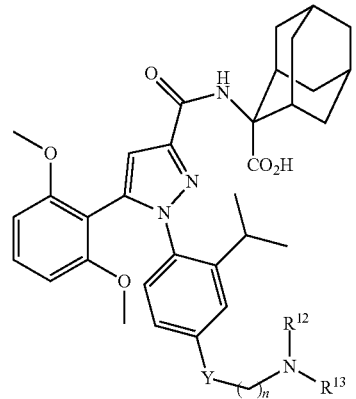

(II-A)

wherein Y, $R^{12}$, $R^{13}$ and n are as defined in Formula II.

In some embodiments, Y is selected from $CH_2$, O, S, $NR^{14}$ and $NR^{14}C(O)$. In some embodiments, Y is $CH_2$. In some embodiments, Y is O. In some embodiments, Y is S. In some embodiments, Y is $NR^{14}$. In some embodiments, Y is $NR^{14}C(O)$. In some embodiments, $R^{14}$ is selected from H and $C_{1-4}$alkyl. In some embodiments, $R^{14}$ is selected from H and $CH_3$.

In some embodiments, Y is S and the compound of Formula II is a compound of Formula II-B or a pharmaceutically acceptable salt and/or solvate thereof

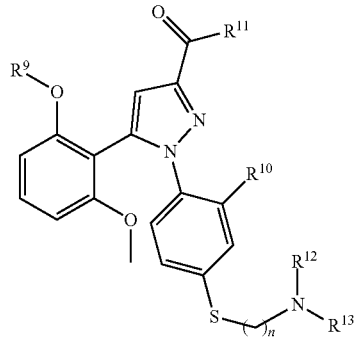

(II-B)

wherein $R^9$, $R^{10}$, $R^{11}$, $R^{12}$, $R^{13}$ and n are as defined in Formula I.

In some embodiments, $R^{12}$ and $R^{13}$ are independently selected from H and $C_{1-4}$alkyl. In some embodiments, $R^{12}$ and $R^{13}$ are selected from H and $CH_3$. In some embodiments. $R^{12}$ and $R^{13}$ are both H. In some embodiments, one of $R^{12}$ and $R^{13}$ is H and the other is and $CH_3$. In some embodiments, $R^{12}$ and $R^{13}$ are both $CH_3$.

In some embodiments, n is an integer selected from 2 to 10. In some embodiments, n is an integer selected from 2 to 9. In some embodiments, n is an integer selected from 2 to 8. In some embodiments, n is an integer selected from 2 to 7. In some embodiments, n is an integer selected from 2 to 6. In some embodiments, n is an integer selected from 2 to 5. In some embodiments, n is an integer selected from 2 to 4. In some embodiments, n is an integer selected from 2 to 3. In some embodiments, n is an integer selected from 1 to 5. In some embodiments, n is an integer selected from 2 to 5. In some embodiments, n is an integer selected from 1 to 4. In some embodiments, n is 3. In some embodiments, n is 4.

In some embodiments, the compound of Formula II is selected from the following list of compounds:

| Compound I.D | Structure |
| --- | --- |
| II-1 | |
| II-2 | |
| II-3 | 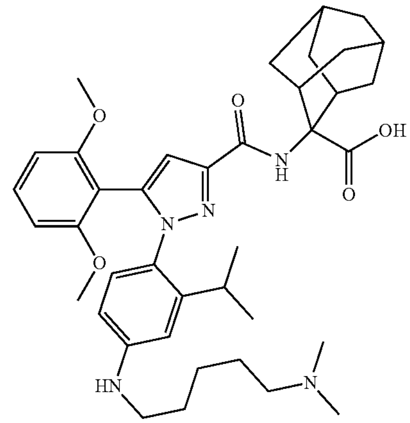 [SMILES: COc1cccc(OC)c1-c1cc(C(=O)NC2(C(=O)O)C3CC4CC(C3)CC2C4)nn1-c1ccc(NCCCCCN(C)C)cc1C(C)C] |
| II-4 | 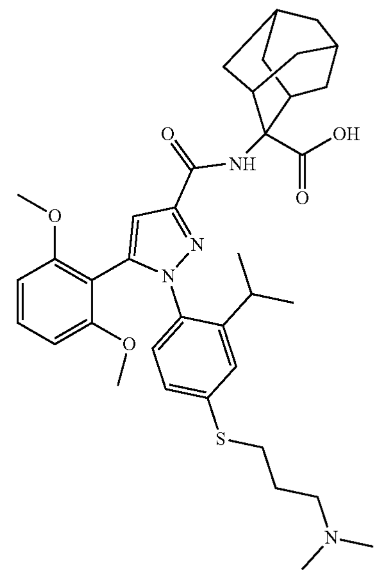 [SMILES: COc1cccc(OC)c1-c1cc(C(=O)NC2(C(=O)O)C3CC4CC(C3)CC2C4)nn1-c1ccc(SCCCN(C)C)cc1C(C)C] |
| II-5 | and |

| Compound I.D | Structure |
|---|---|
| II-6 | (structure shown) | or a pharmaceutically acceptable salt and/or solvate thereof.

In an embodiment the pharmaceutically acceptable salt is an acid addition salt or a base addition salt. The selection of a suitable salt may be made by a person skilled in the art (see, for example, S. M. Berge, et al., "Pharmaceutical Salts," J. Pharm. Sci. 1977, 68, 1-19).

III. Methods and Uses of the Application

The present application also includes a method of treating a disease, disorder or condition comprising administering a therapeutically effective amount of one or more compounds or complexes of the application to a subject in need thereof. The present application also includes a use of one or more compounds or complexes of the application for treatment of a disease, disorder or condition as well as a use of one or more compounds or complexes of the application for the preparation of a medicament for treatment of a disease, disorder or condition. The application further includes one or more compounds or complexes of the application for use in treating a disease disorder or condition.

The Applicant has shown that the compounds of the application have high binding affinity to neurotensin receptors, for example neurotensin receptor 1 (NTR1). Therefore, the compounds of the application which interacts with neurotensin receptors are useful as a neurotensin receptor targeting compound. NTR1 has been found to be highly expressed in several neoplastic cells and tumour indications.

Accordingly, the application includes a method of treating a disease, disorder or condition associated with a neurotensin receptor in a cell, comprising administering an effective amount of one or more compounds or complexes of the application or a pharmaceutically acceptable salt and/or solvate thereof, to the cell.

The present application also includes a use of one or more compounds or complexes of the application or a pharmaceutically acceptable salt and/or solvate thereof for treating a disease, disorder or condition associated with a neurotensin receptor in a cell as well as a use of one or more compounds one or more compounds or complexes of the application or a pharmaceutically acceptable salt and/or solvate thereof for the preparation of a medicament treating a disease, disorder or condition associated with a neurotensin receptor in a cell. The application further includes one or more compounds one or more compounds or complexes of the application or a pharmaceutically acceptable salt and/or solvate thereof for use in treating a disease, disorder or condition associated with a neurotensin receptor in a cell.

In some embodiments, the neurotensin receptor is neurotensin receptor-1 (NTR1).

In one embodiment, a neurotensin receptor target of the neurotensin receptor binding group of the compound or complex is present on disease cells. Indeed, the presence and/or overexpression of neurotensin receptors on the cell surface is a hallmark of many disease associated cells including cancer cells. According, in another embodiment, a neurotensin receptor target of the neurotensin receptor binding group is present on cancer cells and disease or disorder is cancer.

In one embodiment, the disease, disorder or condition associated with a neurotensin receptor is cancer.

In an embodiment, the cancer is selected from, but not limited to: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer, Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor. Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer, Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer, Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor, Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer, Rectal Cancer; Renal Cell (Kidney) Cancer, Renal Cell Cancer, Childhood; Renal Pelvis and Ureter, Transitional Cell Cancer; Retinoblastoma; Rhabdomyosarcoma, Childhood; Salivary Gland Cancer, Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; Wilms' Tumor and a neuroendocrine tumor. Metastases of the aforementioned cancers can also be treated in accordance with the methods described herein.

In some embodiments, the cancer is a cancer associated with a neurotensin receptor. In some embodiments, the cancer is a neurotensin receptor positive cancer. A "neurotensin receptor positive cancer" comprises cancer cells which have higher expression of a neurotensin receptor protein or gene compared to non-cancerous cells of the same tissue type. In some embodiments, the neurotensin receptor is neurotensin receptor 1 (NTR1).

In some embodiments, the cancer optionally the neurotensin receptor positive cancer, is selected from colorectal cancers, pancreatic cancers, breast cancers, prostate cancers, meningioma, Ewing's sarcoma, head and neck cancer, pleural mesothelioma, gastrointestinal stromal tumours, uterine leiomyoma, cutaneous T-cell lymphoma, small cell lung cancer and non-small cell lung cancer.

In some embodiments, the cancer is colorectal cancer.

In some embodiments, the cancer is pancreatic cancer.

As used herein, "treating a cancer" includes, but is not limited to, reversing, alleviating or inhibiting the progression of the cancer or symptoms or conditions associated with the cancer. "Treating the cancer" also includes extending survival in a subject. Survival is optionally extended by at least 1, 2, 3, 6 or 12 months, or at least 2, 3, 4, 5 or 10 years over the survival that would be expected without treatment with a compound, complex or composition as described herein. "Treating the cancer" also includes reducing tumour mass and/or reducing tumour. Optionally, tumour mass and/or tumour burden is reduced by at least 5, 10, 25, 50, 75 or 100% following treatment with a compound, complex or composition as described herein. "Treating the cancer" also includes reducing the aggressiveness, grade and/or invasiveness of a tumour.

The application also includes a method of inhibiting proliferative activity in a cell, comprising administering an effective amount of one or more compounds or complexes of the application to the cell. The present application also includes a use of one or more compounds or complexes of the application for inhibition of proliferative activity in a cell as well as a use of one or more compounds one or more compounds or complexes of the application for the preparation of a medicament for inhibition of proliferative activity in a cell. The application further includes one or more compounds one or more compounds or complexes of the application for use in inhibiting proliferative activity in a cell. In one embodiment, the one or more compounds or complexes comprises a radionuclide for use in therapy, optionally $^{188}$Re, $^{186}$Re, $^{153}$Sm, $^{66}$Ho, $^{90}$Y, $^{89}$Sr, $^{111}$In, $^{153}$Gd, $^{225}$Ac, $^{212}$Bi, $^{213}$Bi, $^{211}$At, $^{60}$Cu, $^{61}$Cu, $^{67}$Cu, $^{64}$Cu, $^{62}$Cu, $^{198}$Au, $^{99}$Au, $^{195m}$Pt, $^{193m}$Pt, $^{197}$Pt $^{117m}$Sn, $^{103}$Pd, $^{103m}$Rh, $^{177}$Lu, $^{223}$Ra, $^{224}$Ra, $^{227}$Th, $^{32}$P, $^{147}$Tb, $^{161}$Tb, $^{33}$P, $^{125}$I, $^{203}$Pb, $^{212}$Pb, $^{201}$Tl, $^{119}$Sb, $^{58m}$Co, or $^{161}$Ho.

The present application also includes a method of imaging a tissue in a subject by administering an imaging effective amount of one or more compounds or complexes of the application for use in imaging to a subject in need thereof and applying an imaging technique to detect emitted gamma rays. The present application also includes a use of one or more compounds or complexes of the application for use in imaging a tissue well as a use of one or more compounds or complexes of the application comprising a radionuclide for use in imaging for the preparation of a medicament for imaging a tissue. The application further includes one or more compounds or complexes of the application comprising a radionuclide for use in imaging for use in imaging a tissue. The present application also includes a method of imaging a tissue in a subject by administering a therapeutically effective amount of one or more compounds or complexes of the application for use in imaging to a subject in need thereof and applying an imaging technique to detect emitted gamma rays. The present application also includes a use of one or more compounds or complexes of the application for use in imaging a tissue well as a use of one or more compounds or complexes of the application comprising a radionuclide for use in imaging for the preparation of a medicament for imaging a tissue. The application further includes one or more compounds or complexes of the application comprising a radionuclide for use in imaging for use in imaging a tissue. In some embodiments, the use further includes applying an imaging technique to detect emitted gamma rays. In one embodiment, the one or more compounds or complexes comprises a radionuclide for use in imaging, optionally $^{99m}$Tc, $^{188}$Re, $^{186}$Re, $^{153}$Sm, $^{67}$Ga, $^{68}$Ga, $^{111}$In, $^{59}$Fe, $^{63}$Zn, $^{52}$Fe, $^{45}$Ti, $^{60}$Cu, $^{61}$Cu, $^{87}$Cu, $^{64}$Cu, $^{62}$Cu, $^{198}$Au, $^{199}$Au, $^{195m}$Pt, $^{191m}$Pt, $^{193m}$Pt, $^{117m}$Sn, $^{89}$Zr, $^{177}$Lu, $^{18}$F, $^{203}$Pb or $^{123}$I.

The present application also includes a method of diagnosing cancer in subject by administering a diagnostic effective amount of one or more compounds or complexes of the application to a subject in need thereof and applying an imaging technique to detect emitted gamma rays. The present application also includes a method of diagnosing cancer in subject by administering a therapeutically effective amount of one or more compounds or complexes of the application to a subject in need thereof and applying an imaging technique to detect emitted gamma rays. The present application also includes a use of one or more compounds or complexes of the application for diagnosing cancer in well as a use of one or more compounds or complexes of the application for diagnosing cancer. The application further includes one or more compounds or complexes of the application comprising a radionuclide for use in imaging for use in diagnosing cancer. In some embodiments, the use further includes applying an imaging technique to detect emitted gamma rays. In one embodiment, the one or more compounds or complexes comprises a radionuclide for use in imaging, optionally $^{99m}$Tc, $^{188}$Re, $^{186}$Re, $^{153}$Sm, $^{67}$Ga, $^{68}$Ga, $^{111}$In, $^{59}$Fe, $^{63}$Zn, $^{52}$Fe, $^{45}$Ti, $^{60}$Cu, $^{61}$Cu, $^{67}$Cu, $^{64}$Cu, $^{62}$Cu, $^{198}$Au, $^{199}$Au, $^{195m}$Pt, $^{191m}$Pt, $^{193m}$Pt, $^{117m}$Sn, $^{89}$Zr, $^{177}$Lu, $^{18}$F, or $^{123}$I.

In some embodiments, diagnosing cancer comprises identifying and localizing a primary tumour mass as well as potential local and distant metatheses. In some embodiments, diagnosing cancer comprises determining tumour volume.

The present application also includes a method of radionuclide treatment comprising administering an effective amount of one or more complexes of the application to a subject in need thereof.

The present application also includes a use of one or more complexes of the application for radionuclide treatment or a use of one or more complexes of the application for preparation of a medicament for radionuclide treatment.

The present application also includes a method of theranostic treatment comprising administering an effective amount of one or more complexes of the application to a subject in need thereof and performing a medical diagnostic method on the subject.

The present application also includes a use of one or more complexes of the application for theranostic treatment or a use of one or more complexes of the application for preparation of a medicament for theranostic treatment. For theranostic treatment, the same compound of the application binds to both an imaging radionuclide and a therapy radionuclide, meaning the compound effectively and stably binds both different radiometals.

In an embodiment, the subject is a mammal. In another embodiment, the subject is human. In an embodiment, the subject is a non-human animal. In an embodiment, the subject is canine. In an embodiment, the subject is feline. Accordingly, the compounds, methods and uses of the present application are directed to both human and veterinary diseases, disorders and conditions.

In some embodiments, the subject in need is a subject in need of imaging. In some embodiments, the subject in need of imaging is a subject in need of diagnosis, in need of locating a position for a therapeutic intervention, in need of assessment of the functioning of a body part, and/or in need of assessment of the presence of absence of a condition.

In some embodiments, the type of imaging that is used in the methods of the application are positron emission tomography (PET), single photon emission computerized tomography (SPECT), radioisotope renography and scintigraphy. Methods of performing such imaging techniques are well known to those skilled in the art.

In some embodiments, for use in diagnostic or therapeutic methods, the one or more compounds and/or complexes are comprised in a pharmaceutical composition as described above.

IV. Methods of Preparing the Compounds of the Application

Compounds and/or complexes of the present application or comparator compounds can be prepared by various synthetic processes. The choice of particular structural features and/or substituents may influence the selection of one process over another. The selection of a particular process to prepare a given compound and/or complexes of the present application or comparator compounds is within the purview of the person of skill in the art. Some starting materials for preparing compounds of the present application are available from commercial chemical sources. Other starting materials, for example as described below, are readily prepared from available precursors using straightforward transformations that are well known in the art.

In an embodiment, the compounds of Formula I wherein X is O, S or NR$^4$ and L comprises a terminal W$^8$ wherein W$^8$ is NR$^7$ for connecting with E are prepared as shown in Scheme 1. Therefore, a compound of Formula A is coupled with a compound of Formula B wherein PG is a protecting group under conditions, for example, under palladium-catalyzed coupling conditions such as Buchwald-Hartwig amination conditions, in the presence of a palladium catalyst such as tris(dibenzylideneacetone)dipalladium(0) (Pd$_2$(dba)$_3$) with cicyclohexyl[2',4',6'-tris(propan-2-yl)[1,1'-biphenyl]-2-yl]phosphane (X-Phos®), to provide a compound of Formula C which is subsequently deprotected to provide the compound of Formula D. The compound of Formula D is then coupled with a compound of Formula E wherein FG is a functional group (e.g., CO$_2$H) attached to the chelating group E under amide forming conditions such as in the presence of a coupling reagent (e.g. (2-(1H-benzotriazol-1-yl)-1,1,3,3-tetramethyluronium hexafluorophosphate (HBTU)) and a base such as an organic base (e.g. diethyl amine (DIEA)) to provide the compound of Formula I.

It would be appreciated by a person skilled in the art, that in some embodiments, the compound of Formula D is a compound of Formula II and therefore, the compound of Formula II can be prepared shown in Scheme I for compounds of Formula D.

In an embodiment, the compounds of Formula I wherein X is $NR^4C(O)$ and L comprises at least one terminal W wherein one W is independently $NR^7$ for connecting with E are prepared as shown in Scheme 2. Therefore, a compound of Formula A is coupled with a compound of Formula F wherein $PG^1$ is a protecting group under amination conditions, for example, such as palladium-catalyzed amination conditions such as Buchwald-Hartwig amination conditions, in the presence of a palladium catalyst such as tris(dibenzylideneacetone)dipalladium(0) ($Pd_2(dba)_3$) with cyclohexyl[2',4',6'-tris(propan-2-yl)[1,1'-biphenyl]-2-yl]phosphane (X-Phos®), to provide a compound of Formula G which is subsequently deprotected to provide the compound of Formula H. The compound of Formula H is then reacted with a compound of Formula J wherein LG is a leaving group and L' is a fragment of L in the presence of a base such as an organic amine base to provide the compound of Formula K. The compound of Formula K then undergoes a substitution reaction with a compound of Formula L wherein $PG^2$ is a protecting group and L'' is a fragment of L to provide the compound of Formula M wherein which is then deprotected to provide the compound of Formula N. The compound of Formula N is then coupled with a compound of Formula O wherein $FG^1$ is a functional group (e.g., $CO_2H$) attached to the chelating group E under amide forming conditions such as in the presence of a coupling reagent (e.g. 2-(1H-Benzotriazole-1-yl)-1,1,3,3-tetramethylaminium tetrafluoroborate (TBTU) and a base such as an organic base (e.g. diethyl amine (DIEA)) to provide the compound of Formula I.

Scheme 1

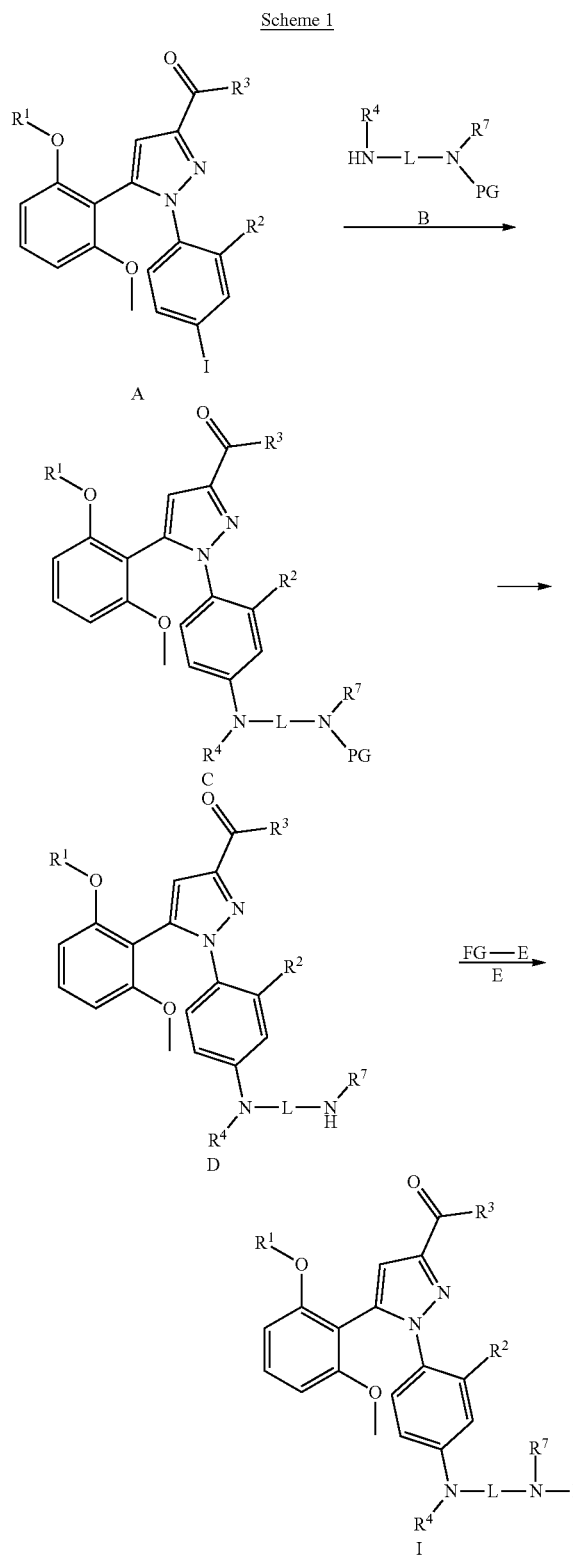

Scheme 2

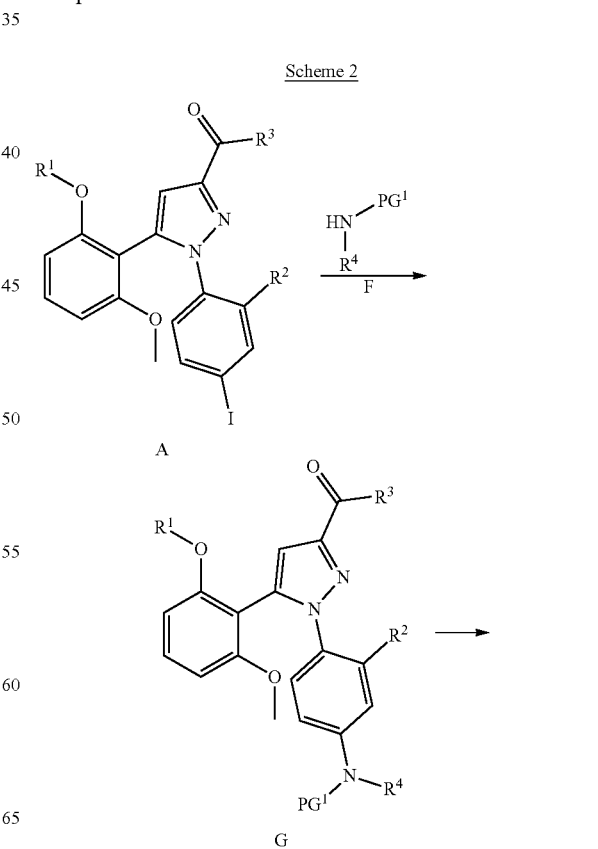

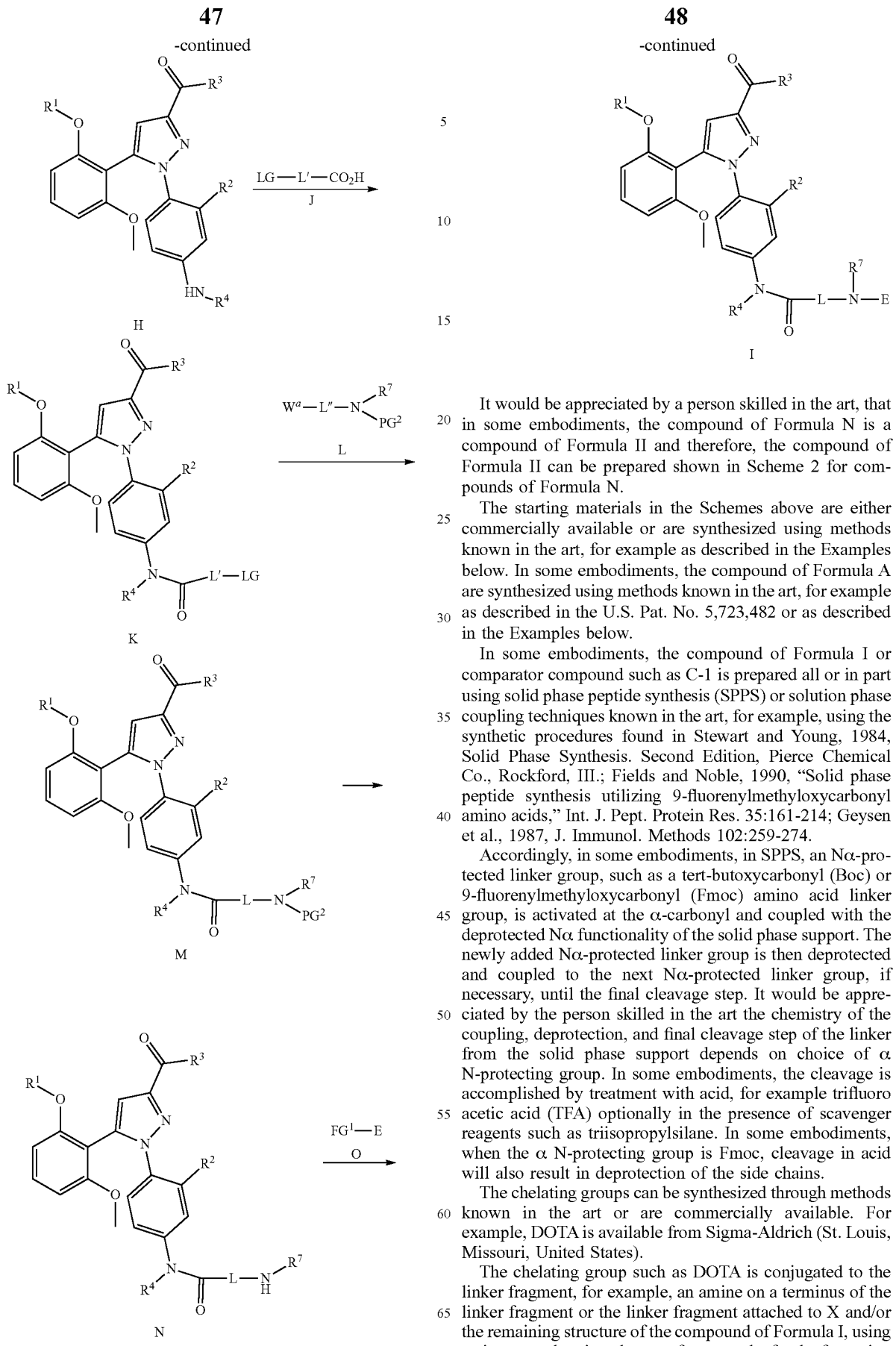

It would be appreciated by a person skilled in the art, that in some embodiments, the compound of Formula N is a compound of Formula II and therefore, the compound of Formula II can be prepared shown in Scheme 2 for compounds of Formula N.

The starting materials in the Schemes above are either commercially available or are synthesized using methods known in the art, for example as described in the Examples below. In some embodiments, the compound of Formula A are synthesized using methods known in the art, for example as described in the U.S. Pat. No. 5,723,482 or as described in the Examples below.

In some embodiments, the compound of Formula I or comparator compound such as C-1 is prepared all or in part using solid phase peptide synthesis (SPPS) or solution phase coupling techniques known in the art, for example, using the synthetic procedures found in Stewart and Young, 1984, Solid Phase Synthesis. Second Edition, Pierce Chemical Co., Rockford, Ill.; Fields and Noble, 1990, "Solid phase peptide synthesis utilizing 9-fluorenylmethyloxycarbonyl amino acids," Int. J. Pept. Protein Res. 35:161-214; Geysen et al., 1987, J. Immunol. Methods 102:259-274.

Accordingly, in some embodiments, in SPPS, an Nα-protected linker group, such as a tert-butoxycarbonyl (Boc) or 9-fluorenylmethyloxycarbonyl (Fmoc) amino acid linker group, is activated at the α-carbonyl and coupled with the deprotected Nα functionality of the solid phase support. The newly added Nα-protected linker group is then deprotected and coupled to the next Nα-protected linker group, if necessary, until the final cleavage step. It would be appreciated by the person skilled in the art the chemistry of the coupling, deprotection, and final cleavage step of the linker from the solid phase support depends on choice of α N-protecting group. In some embodiments, the cleavage is accomplished by treatment with acid, for example trifluoro acetic acid (TFA) optionally in the presence of scavenger reagents such as triisopropylsilane. In some embodiments, when the α N-protecting group is Fmoc, cleavage in acid will also result in deprotection of the side chains.

The chelating groups can be synthesized through methods known in the art or are commercially available. For example, DOTA is available from Sigma-Aldrich (St. Louis, Missouri, United States).

The chelating group such as DOTA is conjugated to the linker fragment, for example, an amine on a terminus of the linker fragment or the linker fragment attached to X and/or the remaining structure of the compound of Formula I, using active ester chemistry known, for example, for the formation of an amide known in the art. For example, DOTA is combined with the linker fragment comprising amine on one terminus in the presence of a base such as an organic amine Amide bond forming conditions comprise any known method for the coupling of carboxylic acids and amines that is compatible with the intermediates and products shown in the above Schemes or that may be used to prepare a compound of the application. Known methods to prepare amides by the coupling of carboxylic acids and amines comprise use of either a coupling reagent or by prior conversion of the carboxylic acid into an activated derivative. Coupling reagents include, but are not limited to, any of the known peptide coupling reagents, such as 1-[bis (dimethylamino)methylene]-1H-1,2,3-triazolo[4,5-b]pyridinium 3-oxid hexafluorophosphate (HATU), 1-ethyl-3-(3-dimethylaminopropyl)carbodiimide (EDC), dicyclohexylcarbodiimide (DCC) diisopropylcarbodiimide (DIC), hexafluorophosphate benzotriazole tetramethyl uronium (HBTU), 2-(1H-benzotriazole-1-yl)-1,1,3,3-tetramethylaminium tetrafluoroborate (TBTU), O-(1H-6-chlorobenzotriazole-1-yl)-1,1,3,3-tetramethyluronium hexafluorophosphate (HCTU), benzotriazol-1-yloxytripyrrolidinophosphonium hexafluorophosphate (PyBOP), (7-azabenzotriazol-1-yloxy)tripyrrolidinophosphonium hexafluorophosphate (PyAOP) and propanephosphonic acid anhydride.

In some embodiments, racemization of an enantiomer of a carboxylic acid occurs during amide bond formation using coupling reagents. In some embodiments, racemization is circumvented with 'racemization suppressing' additives such as the triazoles 1-hydroxy-benzotriazole (HOBt), 1-hydroxy-7-aza-benzotriazole (HOAt) and ethyl cyanohydroxyiminoacetate (Oxyma).

Nucleophilic displacement reaction conditions comprise any known method for the reaction of a nucleophile to displace a leaving group to form a bond that is compatible with the intermediates and products shown in the above Schemes or that may be used to prepare a compound of the application. In some embodiments, such conditions comprise combining reactants in the presence of a base in a suitable solvent.

Throughout the processes described herein it is to be understood that, where appropriate, suitable protecting groups will be added to, and subsequently removed from, the various reactants and intermediates in a manner that will be readily understood by one skilled in the art. Conventional procedures for using such protecting groups as well as examples of suitable protecting groups are described, for example, in "*Protective Groups in Organic Synthesis*", T. W. Green, P. G. M. Wuts, Wiley-Interscience, New York, (1999).

It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to one skilled in the art. Examples of transformations are given herein, and it is to be understood that the described transformations are not limited only to the generic groups or substituents for which the transformations are exemplified. References and descriptions of other suitable transformations are also given in "Comprehensive Organic Transformations—A Guide to Functional Group Preparations" R. C. Larock, VHC Publishers, Inc. (1989), "*Advanced Organic Chemistry*" March, 4th ed. McGraw Hill (1992) or, "*Organic Synthesis*", Smith. McGraw Hill, (1994).

Techniques for purification of intermediates and final products include, for example, straight and reversed phase chromatography on column or rotating plate, recrystallisation, distillation and liquid-liquid or solid-liquid extraction, which will be readily understood by one skilled in the art.

The products of the processes of the application may be isolated according to known methods, for example, the compounds may be isolated by evaporation of the solvent, by filtration, centrifugation, chromatography or other suitable method.

Generally, the reactions described above are performed in a suitable inert organic solvent and at temperatures and for times that will optimize the yield of the desired compounds. Examples of suitable inert organic solvents include, but are not limited to, 2-propanol, dimethylformamide (DMF), 1,4-dioxane, methylene chloride, chloroform, tetrahydrofuran (THF), toluene, and the like.

The formation of a desired compound salt is achieved using standard techniques. For example, the neutral compound is treated with an acid or base in a suitable solvent and the formed salt is isolated by filtration, extraction or any other suitable method.

The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art. Examples of suitable solvents are ethanol, water and the like. When water is the solvent, the molecule is referred to as a "hydrate". The formation of solvates of the compounds of the application will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art.

Prodrugs of the compounds of the present application may be, for example, conventional esters formed with available hydroxy, thiol, amino or carboxyl groups. For example, available hydroxy or amino groups may be acylated using an activated acid in the presence of a base, and optionally, in inert solvent (e.g. an acid chloride in pyridine).

Specific enantiomers or diastereomers of the compounds of the application are available by using corresponding single enantiomers or diastereomers of the corresponding starting materials.

In some embodiments, a compound of the application is reacted with one or more radionuclides under conditions for complexes to form. In some embodiments, the compound of the application is reacted with one radionuclide. In some embodiments, the compound of the application is reacted with two radionuclides. In some embodiments, the conditions to form complexes comprise dissolving a compound of the application in a suitable solvent, such as polar solvent or mixture of polar solvents that is miscible with aqueous solutions and combining the resulting solution with an aqueous solution of a salt of the desired radionuclide(s). In some embodiments, heat is used to facilitate dissolution of the compounds of the application and/or the reaction with the radionuclide salt. In some embodiments, the resulting radionuclide-containing complex solution is used within one day after preparation.

The following non-limiting examples are illustrative of the present application.

EXAMPLES

A. Synthesis of Exemplary Compounds

General Methods

Preparatory HPLC Condition.

The crude compound in DMF solution was purified by a reverse phase preparative HPLC (Waters Delta Prep 4000) using a C18-reverse phase column. Mobile phases: A: 0.1% TFA H2O; B: 0.1% TFA acetonitrile (ACN). Relevant fractions were analyzed by analytical UPLC. The pure fractions were pooled and freeze-dried.

LC-MS Conditions
  Instrument: Agilent prime-6125B_2LCMS
  Column: Boltimate EXT C18 CoreShell 4.6×50 mm, 2.7 μm
  Detection: UV (254 nm 214 nm 280 nm) and MS (ESI, 100 to 1000 amu)
  Mobile Phase: A: H2O (0.05% formic acid); B: ACN (0.05% formic acid)
  Flow Rate: 2.0 mL/min
  Column Temperature: 45° C.
  Gradient: 10% to 95% B within 1.5 min, followed by 95% B for 1.0 min Analytical HPLC Condition
  Instrument: WATERS ARC UPLC
  Column: XBridge BEH peptide BEH C18, 3.5 μm, 2.1 mm×150 mm
  Detection: UV 254 nm, 214 nm, 280 nm
  Mobile Phase: A: H2O (0.1% TFA); B: ACN (0.1% TFA)
  Column Temperature: 40° C.
  Flow Rate: 0.6 mL/min
  Gradient:

| Time (min) | 0  | 1  | 11 | 13 | 13.5 | 15 |
|------------|----|----|----|----|------|----|
| A %        | 90 | 90 | 5  | 5  | 90   | 90 |
| B %        | 10 | 10 | 95 | 95 | 10   | 10 |

Vendors of the key intermediates: tert-butyl 2-aminoadamantane-2-carboxylate was purchased from JiangSu Aikon; DOTA-Tris(t-Bu ester) and 1,8-Diamino-3,6-dioxaoctane was purchased from Bidepharmatech: 3,3'-Diamino-N-methyldipropylamine was purchased from Adamas-beta; and N,N-Bis[3-(methylamino)propyl]methylamine was purchased from Aladdin Bio-Chem.

Synthesis of Exemplary Compounds of Formula I of the Application

Example 1: Synthesis of I-1

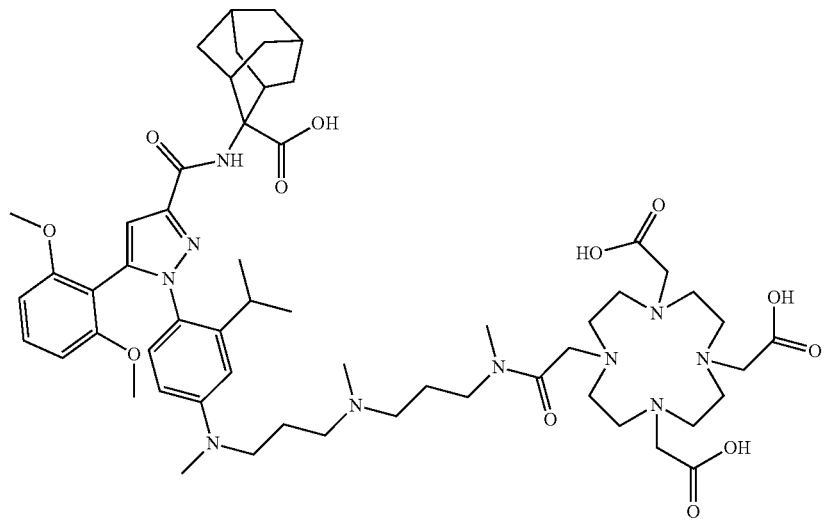 [SMILES: COc1cccc(OC)c1-c1cc(C(=O)NC2(C(=O)O)C3CC4CC(C3)CC2C4)nn1-c1ccc(N(C)CCCN(C)CCCN(C)C(=O)CN2CCN(CC(=O)O)CCN(CC(=O)O)CCN(CC(=O)O)CC2)cc1C(C)C]

The Synthetic Route to 1-1

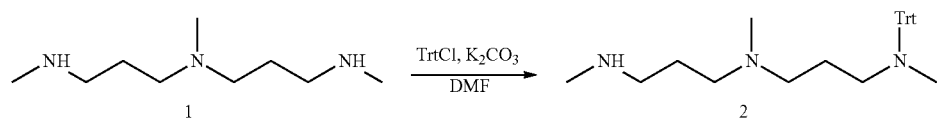

-continued
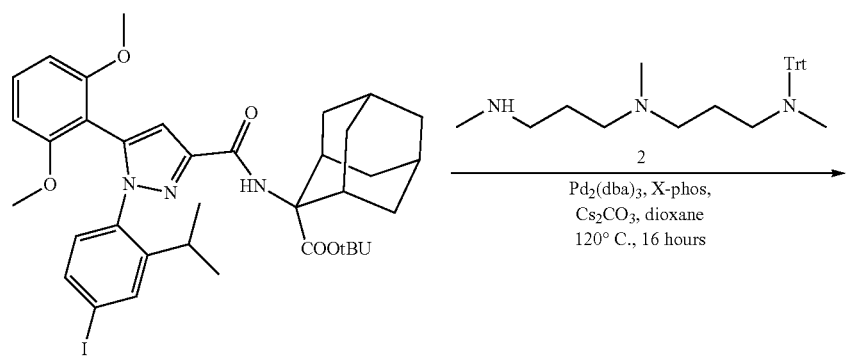
3
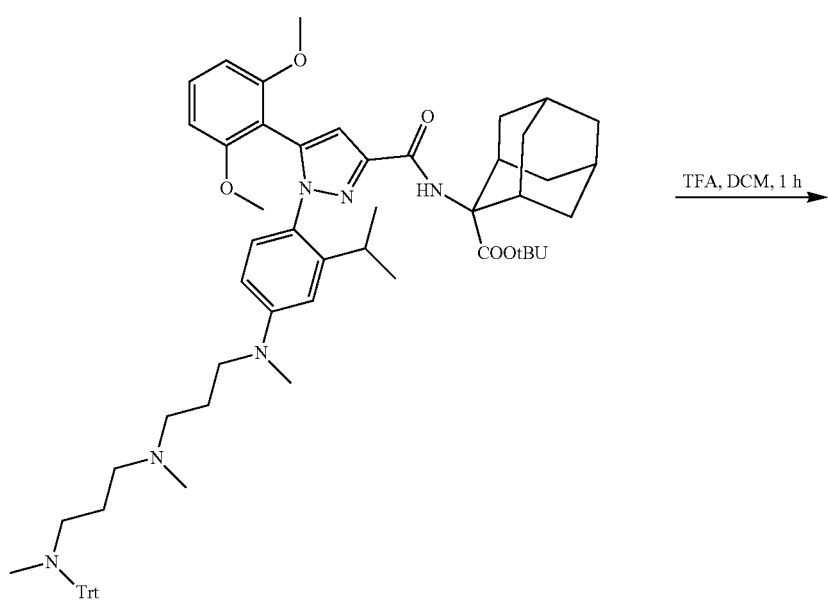
4
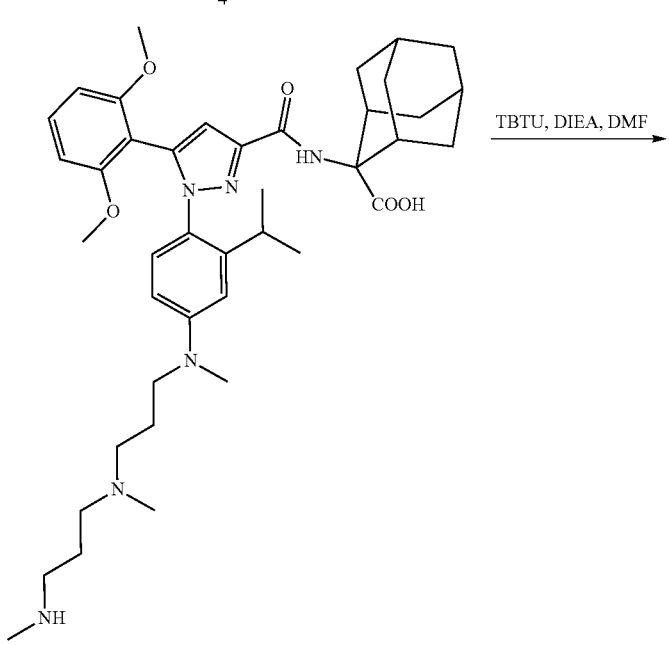
5

-continued
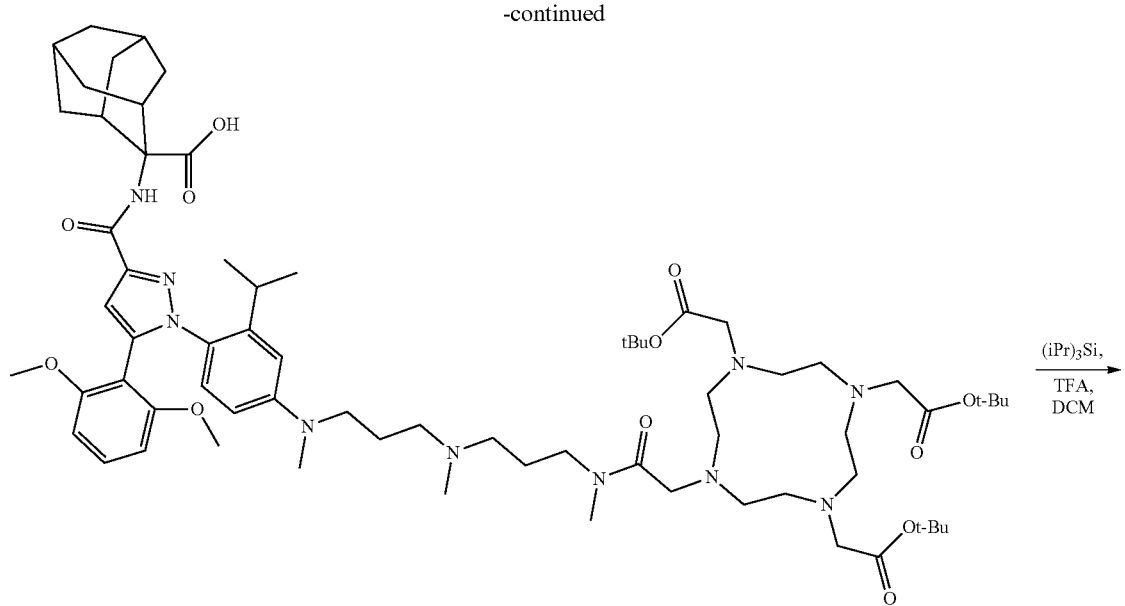
6
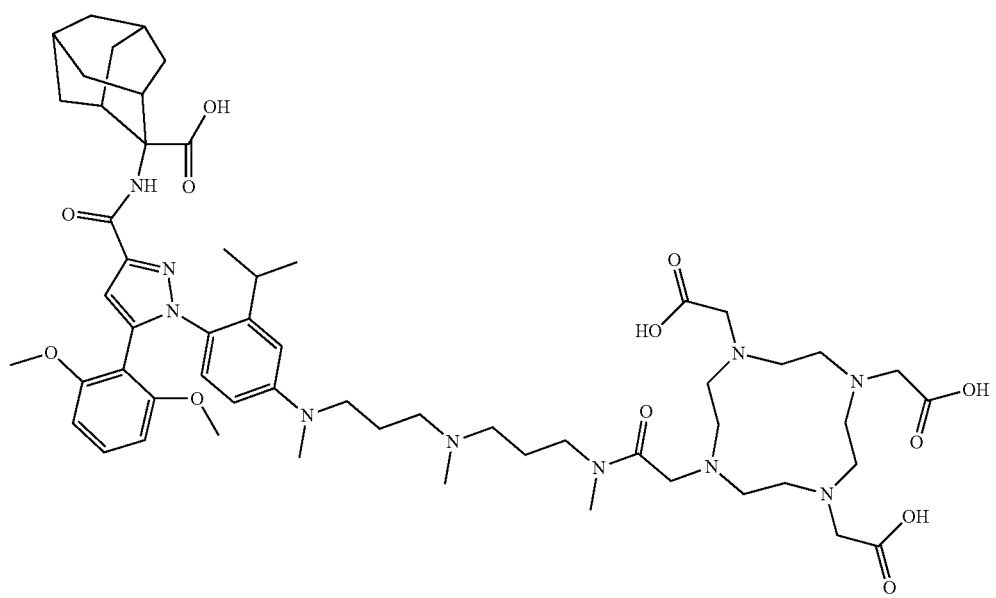
I-1

Synthesis of tert-butyl-2-(5-(2,6-dimethoxyphenyl)-1-(2-isopropyl-4-(methyl(3-(methyl(3-(methyl(trityl)amino)propyl)amino)propyl)amino)phenyl)-1H-pyrazole-3-carboxamido)adamantane-2-carboxylate (4)

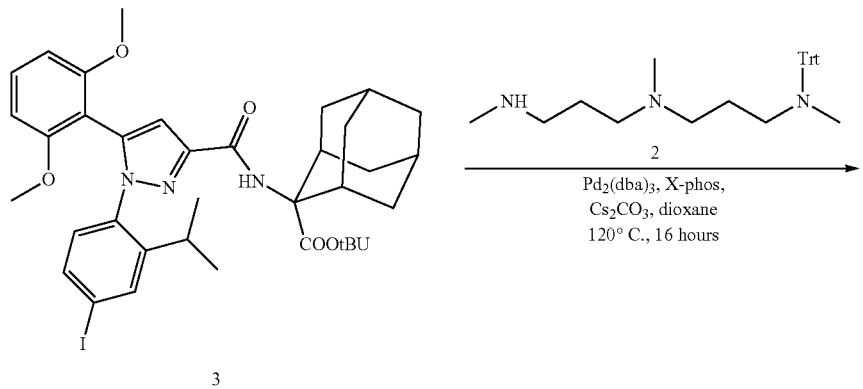

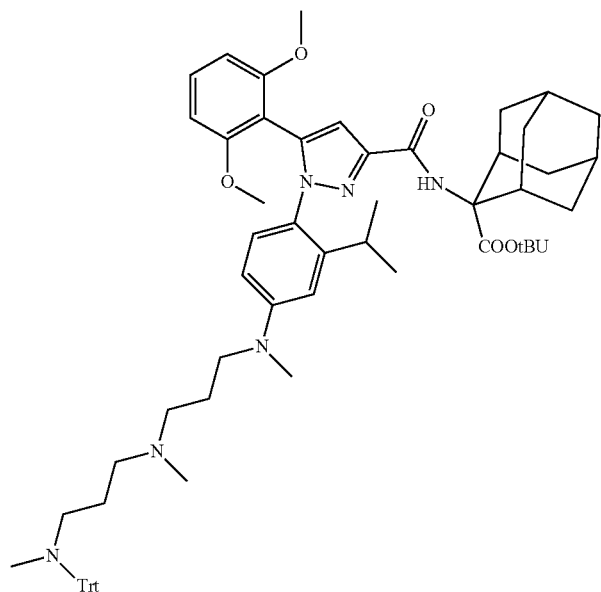

To a solution of compound 3 (350 mg, 0.48 mmol) in dioxane (10 mL) was added compound 2 (1.0 g, 2.10 mmol), $CS_2CO_3$ (471.5 mg, 1.45 mmol), x-phos (23.2 mg, 0.05 mmol) and $Pd_2(dba)_3$ (44.7 mg, 0.05 mmol). The reaction mixture was stirred at 120° C. under $N_2$ balloon overnight. The residue was diluted with $H_2O$ (20 mL) and extracted with Ethyl acetate (EA) (20 mL×2). The combined organic phases were dried over $Na_2SO_4$, filtered and concentrated. The residue was purified by flash chromatography on reverse phase silica gel using acetonitrile (ACN) and $H_2O$ as the mobile phase with a gradient of % ACN from 5% to 95% over 35 min to give compound 4 (370 mg, 76.7% yield) as yellow solid. Molecular weight calculated: 1012.6 g/mol. Determined by LC-MS: (M+H)+: 1013.6.

Synthesis of 2-(5-(2,6-dimethoxyphenyl)-1-(2-isopropyl-4-(methyl(4-methyl-7-(methylamino)heptyl)amino)phenyl)-1H-pyrazole-3-carboxamido)adamantane-2-carboxylic acid (5)

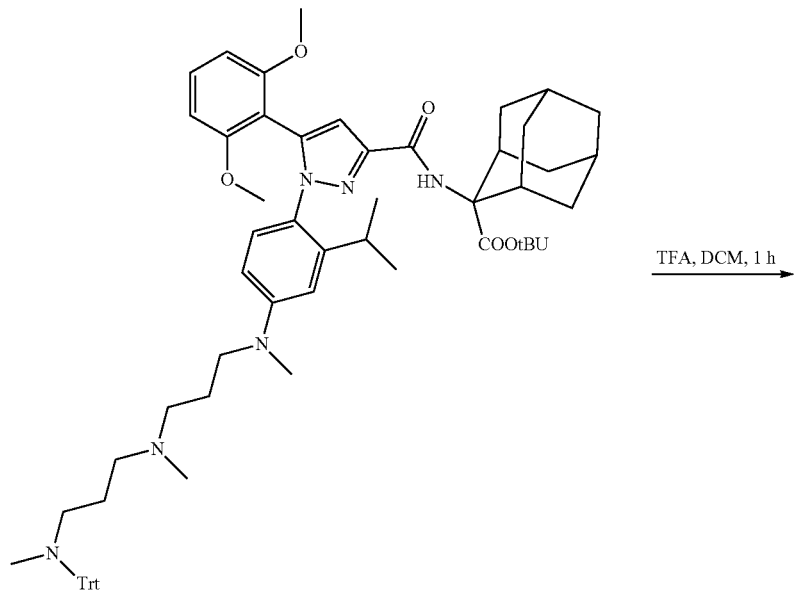

4

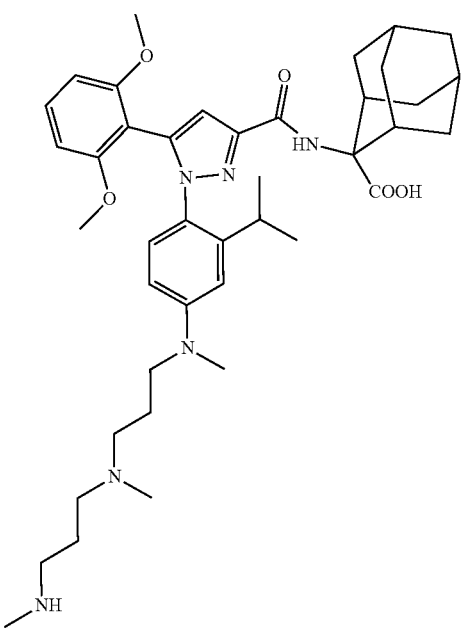

5

Compound 4 (370 mg, 0.37 mmol) was dissolved in TFA/DCM (2/10 mL), the resulting solution was stirred at r.t. for 1 hr. The solvent was removed by Rotavapor, and the residue was purified by prep-HPLC to give compound 5 (35 mg, 13.2% yield) as white solid. Molecular weight calculated: 713.5 g/mol. Determined by LC-MS: (M+H)+: 714.5.

Synthesis of 2-(5-(2,6-dimethoxyphenyl)-1-(2-iso-
propyl-4-(methyl(3-(methyl(3-(N-methyl-2-(4,7,10-
tris(2-(tert-butoxy)-2-oxoethyl)-1,4,7,10-tetraazacy-
clododecan-1-yl)acetamido)propyl)amino)propyl)
amino)phenyl)-1H-pyrazole-3-carboxamido)
adamantane-2-carboxylic acid (6)

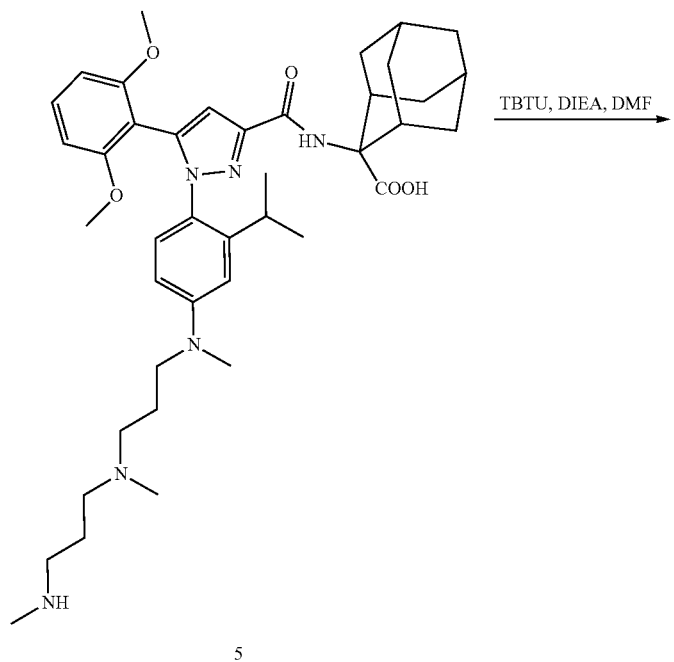

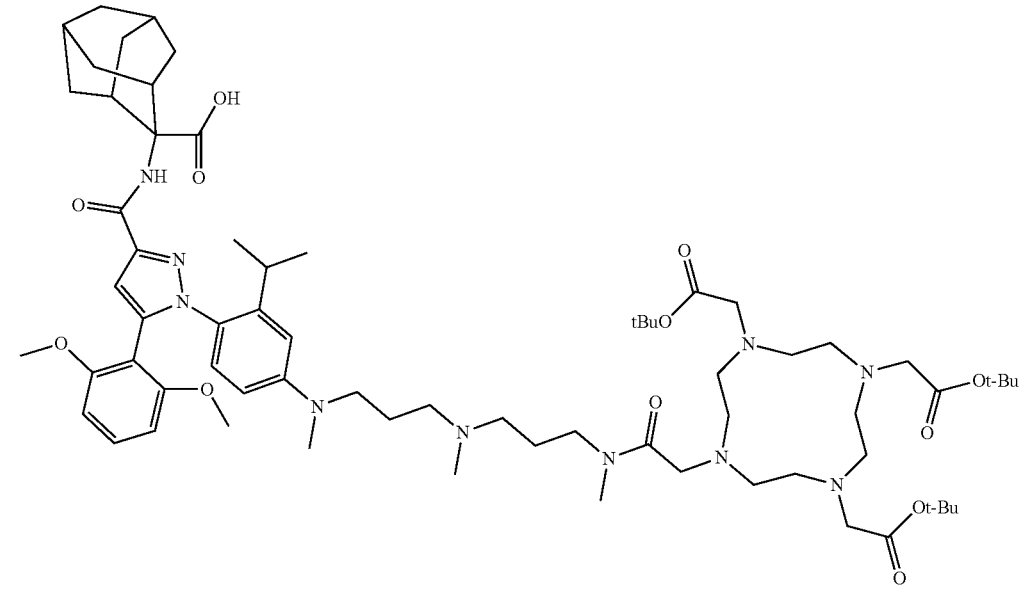

To a solution of DOTA-tris(t-Bu ester) (2-(4,7,10-tris(2-(tert-butoxy)-2-oxoethyl)-1,4,7,10-tetraazacyclododecan-1-yl)acetic acid) (42.1 mg, 0.07 mmol), TBTU (23.6 mg, 0.07 mmol) and DIEA (19.0 mg, 0.15 mmol) in DMF (15 mL). The reaction mixture was stirred at r.t. for 1 hr, added compound 5 (35.0 mg, 0.05 mmol), continued stirred at r.t. overnight. The residue was diluted with $H_2O$ (20 mL) and extracted with EA (20 mL×3). The combined organic phases were dried over $Na_2SO_4$, filtered and concentrated to give compound 6 (60 mg, crude) as yellow oil. Molecular weight calculated: 1268.8 g/mol. Determined by LC-MS: (M+H)+: 1269.8.

Synthesis of 2,2',2''-(10-(2-((3-((3-((4-(3-((2-carboxyadamantan-2-yl)carbamoyl)-5-(2,6-dimethoxyphenyl)-1H-pyrazol-1-yl)-3-isopropylphenyl)(methyl)amino)propyl)(methyl)amino)propyl)(methyl)amino)-2-oxoethyl)-1,4,7,10-tetraazacyclododecane-1,4,7-triyl)triacetic acid (I-1)

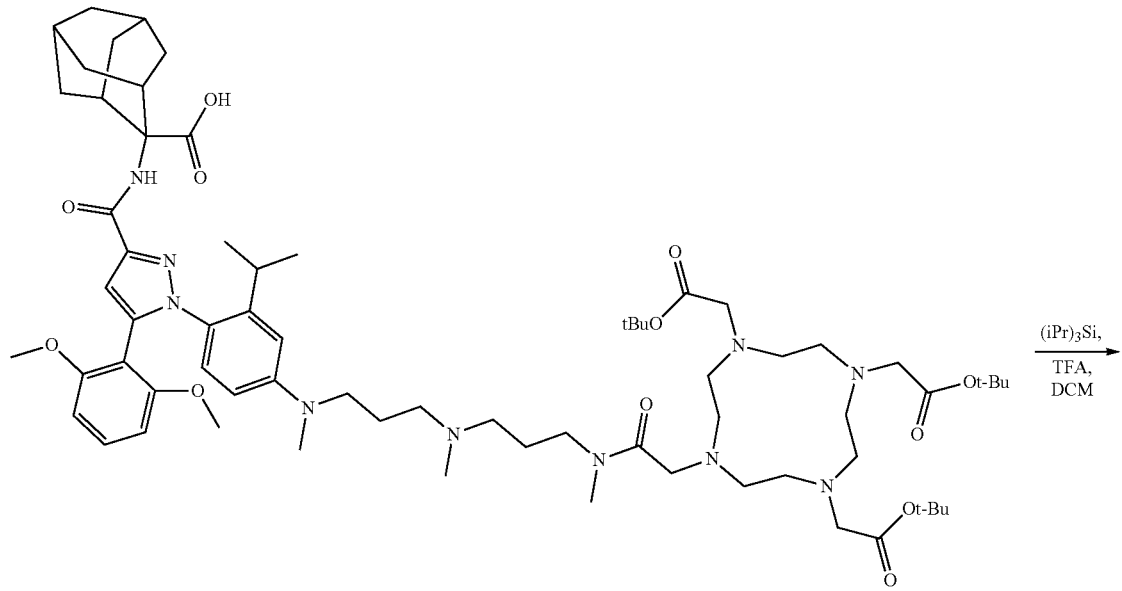

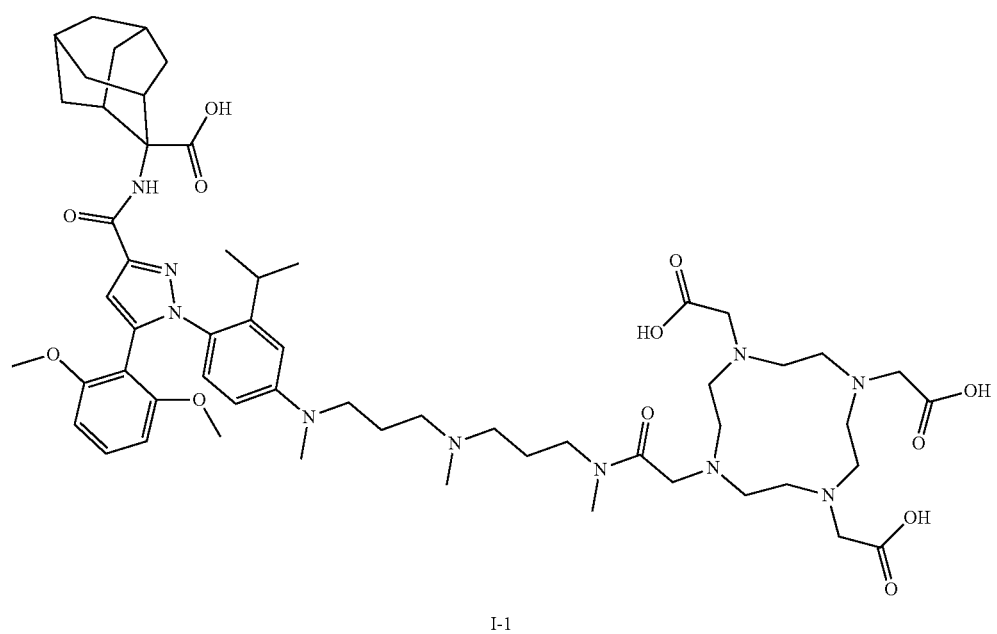 [SMILES: COc1cccc(OC)c1-c1cc(C(=O)NC2(C(=O)O)C3CC4CC(C3)CC2C4)nn1-c1ccc(N(C)CCCN(C)CCCN(C)C(=O)CN2CCN(CC(=O)O)CCN(CC(=O)O)CCN(CC(=O)O)CC2)cc1C(C)C ; [I-]]

To a solution of compound 6 (60 mg, crude) in TFA/DCM (3/3 mL), one drop of (iPr)₃SiH was added. The reaction mixture was stirred at r.t. overnight. The residue was purified by prep-HPLC to give I-1 (16.2 mg, 33.8% yield) as white solid. Molecular weight calculated: 1100.6 g/mol. Determined by LC-MS: (M+2H)2+: 551.5; (M+3H)3+: 368.0. Purity by UPLC (214 nm): 97.0%.

Example 2: Synthesis of I-2
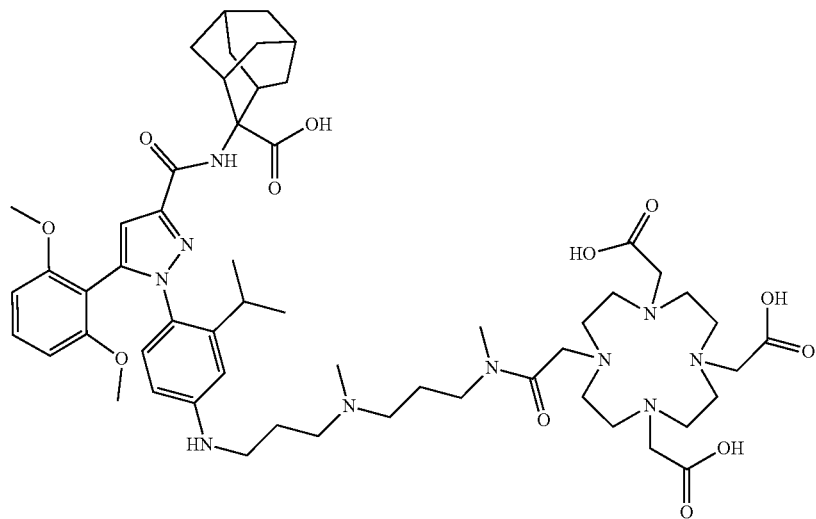 [SMILES: COc1cccc(OC)c1-c1cc(C(=O)NC2(C(=O)O)C3CC4CC(C3)CC2C4)nn1-c1ccc(NCCCN(C)CCCN(C)C(=O)CN2CCN(CC(=O)O)CCN(CC(=O)O)CCN(CC(=O)O)CC2)cc1C(C)C]
The Synthetic Route to I-2
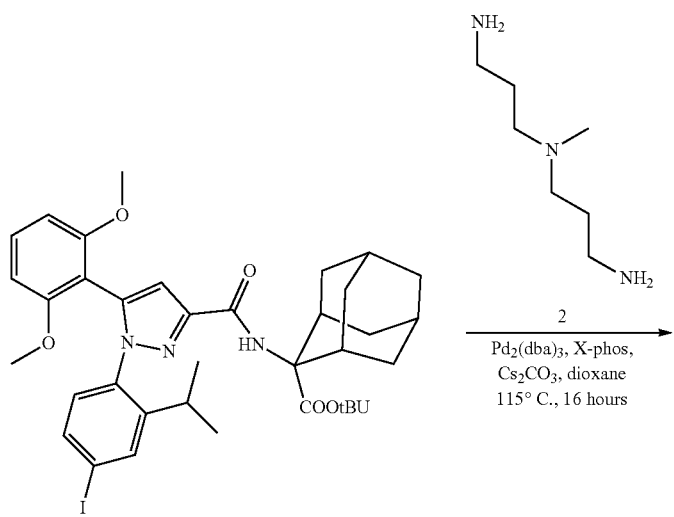

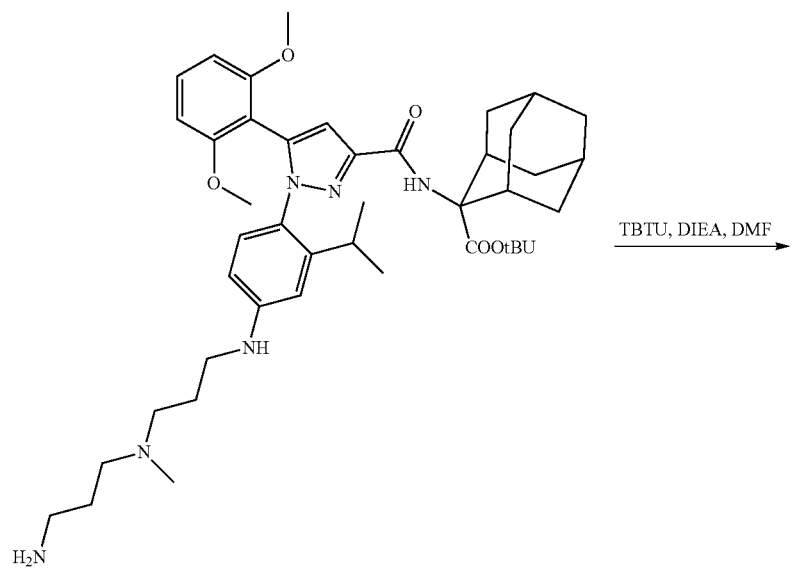
3
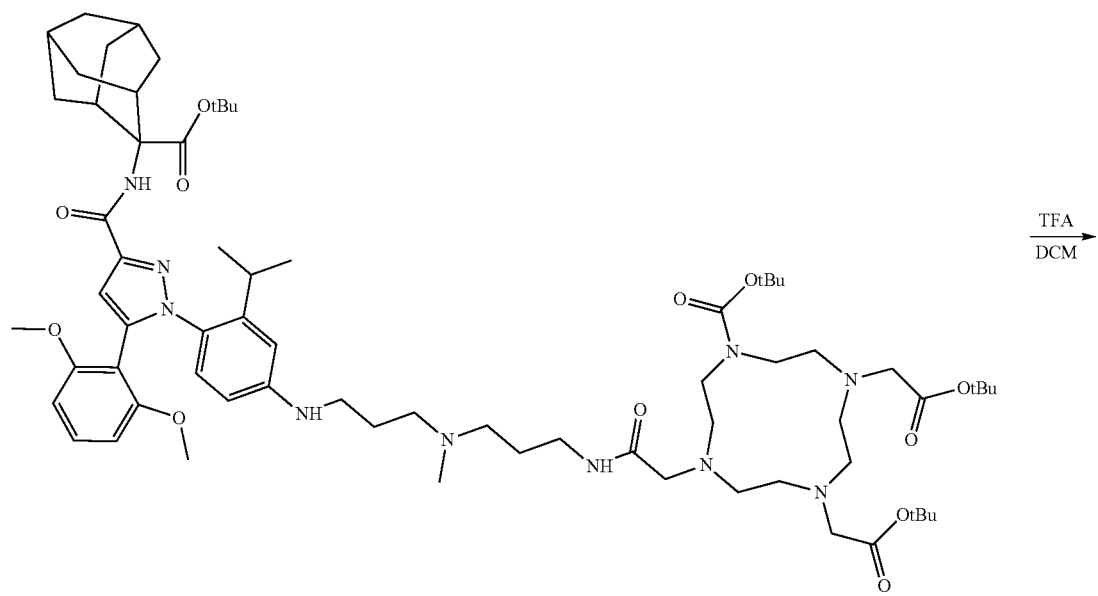
4

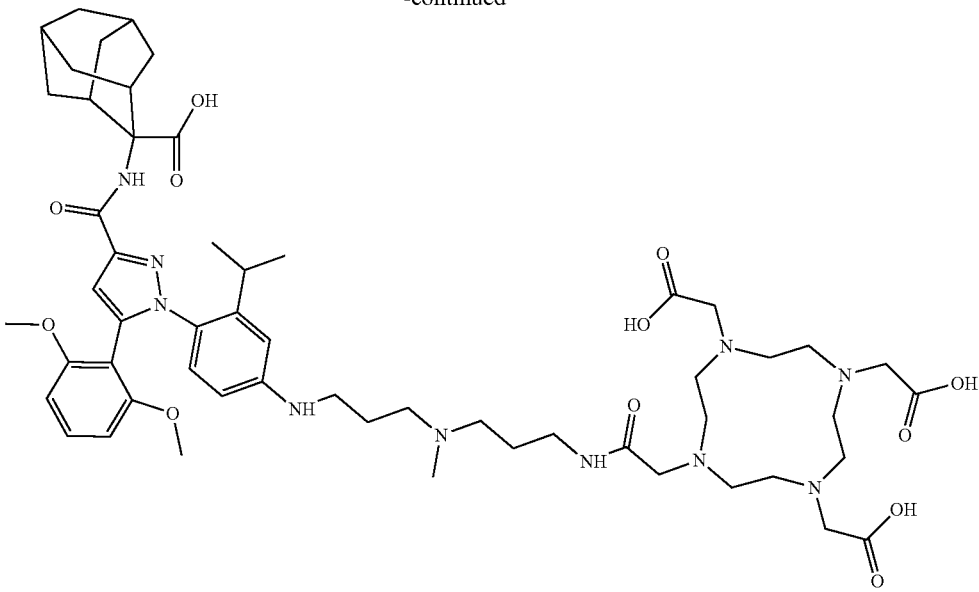

I-2

Synthesis of tert-butyl-2-(1-(4-((3-((3-aminopropyl)(methyl)amino)propyl)amino)-2-isopropylphenyl)-5-(2,6-dimethoxyphenyl)-1H-pyrazole-3-carboxamido)adamantane-2-carboxylate (3)

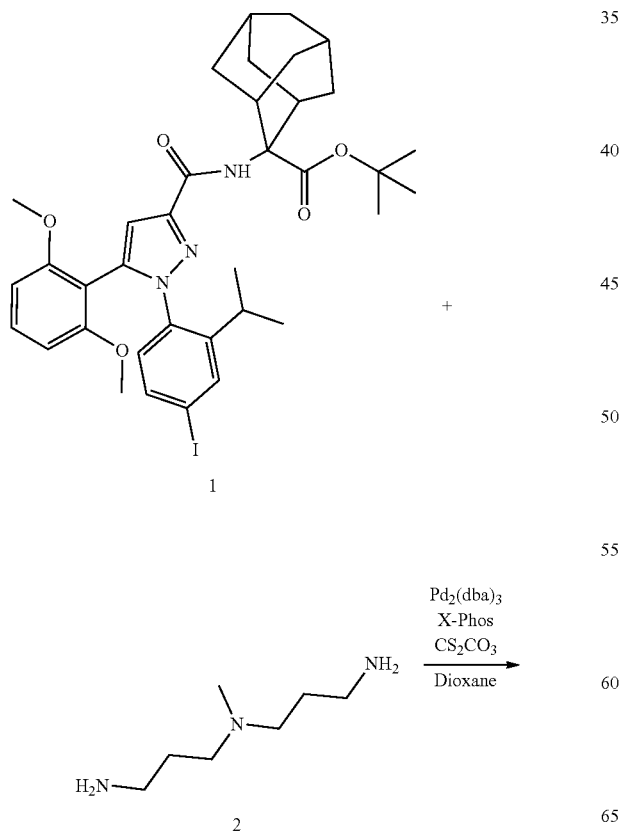

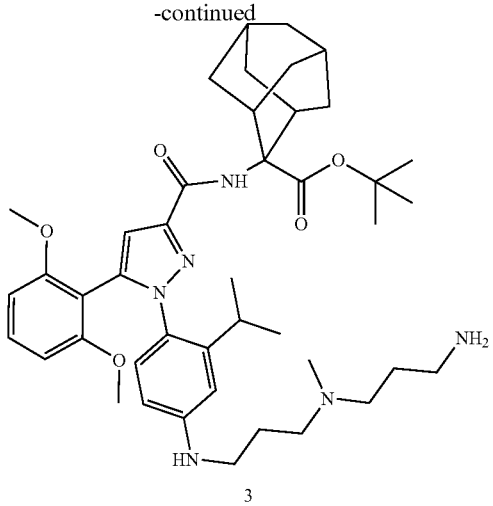

To a solution of compound 1 (2.0 g, 2.76 mmol) in dioxane (30 mL) was added compound 2 (1.60 mg, 11.04 mmol), $Cs_2CO_3$ (2.7 g, 8.28 mmol), x-phos (132 mg, 0.28 mmol) and $Pd_2(dba)_3$ (253 mg, 0.28 mmol). The reaction mixture was stirred at 115° C. under $N_2$ balloon overnight. The residue was diluted with $H_2O$ (20 mL) and extracted with EA (20 mL×2). The combined organic phases were dried over $Na_2SO_4$, filtered and concentrated. The residue was purified by flash chromatography on reverse phase silica gel using ACN and $H_2O$ as the mobile phase with a gradient of % ACN from 5% to 95% over 35 min to give compound 3 (750 mg, 37% yield) as yellow solid. Molecular weight calculated: 743 g/mol. Determined by LC-MS: (M+H)+: 744.

Synthesis of di-tert-butyl 2,2'-(7-(tert-butoxycarbonyl)-10-(2-((3-((3-((4-(3-((2-(tert-butoxycarbonyl)adamantan-2-yl)carbamoyl)-5-(2,6-dimethoxyphenyl)-1H-pyrazol-1-yl)-3-isopropylphenyl)amino)propyl)(methyl)amino)propyl)amino)-2-oxoethyl)-1,4,7,10-tetraazacyclododecane-1,4-diyl)diacetate (4)

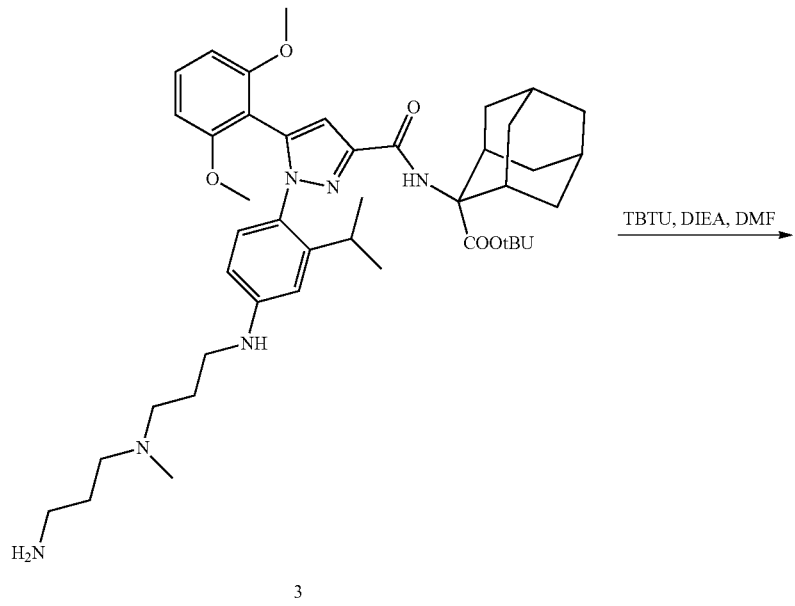

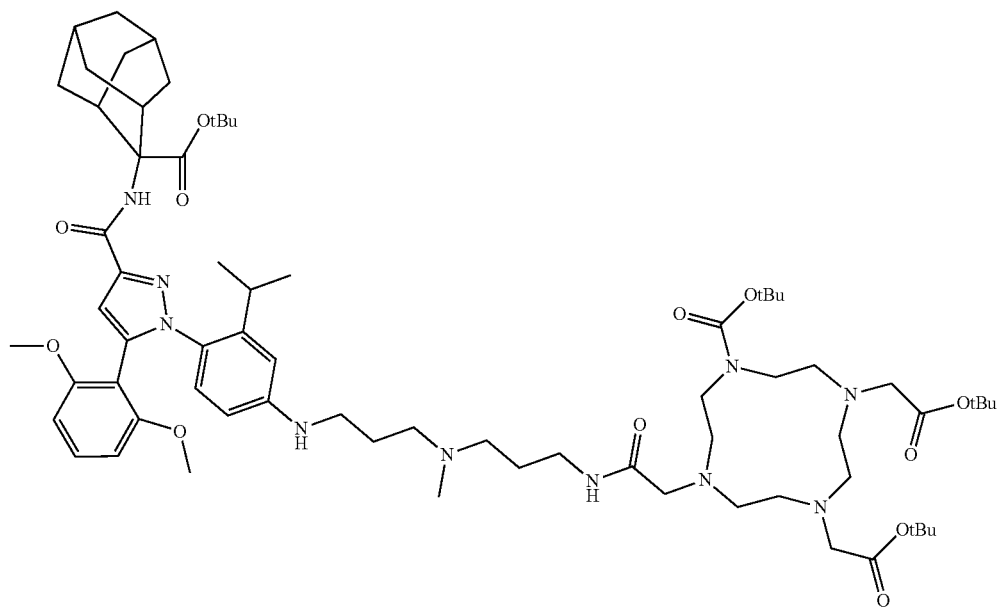

To a solution of DOTA-Tris(t-Bu ester) (2-(4,7,10-tris(2-(tert-butoxy)-2-oxoethyl)-1,4,7,10-tetraazacyclododecan-1-yl)acetic acid) (173.2 mg, 0.30 mmol), was added TBTU (97.2 mg, 0.30 mmol) and DIEA (78.1 mg, 0.61 mmol) in DMF (15 mL). The reaction mixture was stirred at r.t. for 1 hr before the addition of compound 3 (150.0 mg, 0.20 mmol), and the resulting mixture was stirred at r.t. overnight. The residue was diluted with $H_2O$ (20 mL) and extracted with EA (20 mL×3). The combined organic phases were dried over $Na_2SO_4$, filtered and concentrated to give compound 4 (120 mg, crude) as yellow oil. Molecular weight calculated: 1283.8 g/mol. Determined by LC-MS: (M+H)+: 1284.8.

Synthesis of 2,2',2''-(10-(2-((3-((3-((4-(3-((-2-carboxyadamantan-2-yl)carbamoyl)-5-(2,6-dimethoxyphenyl)-1H-pyrazol-1-yl)-3-isopropylphenyl)amino)propyl)(methyl)amino)propy)amino)-2-oxoethyl)-1,4,7,10-tetraazacyclododecane-1,4,7-triyl)triacetic acid (I-2)

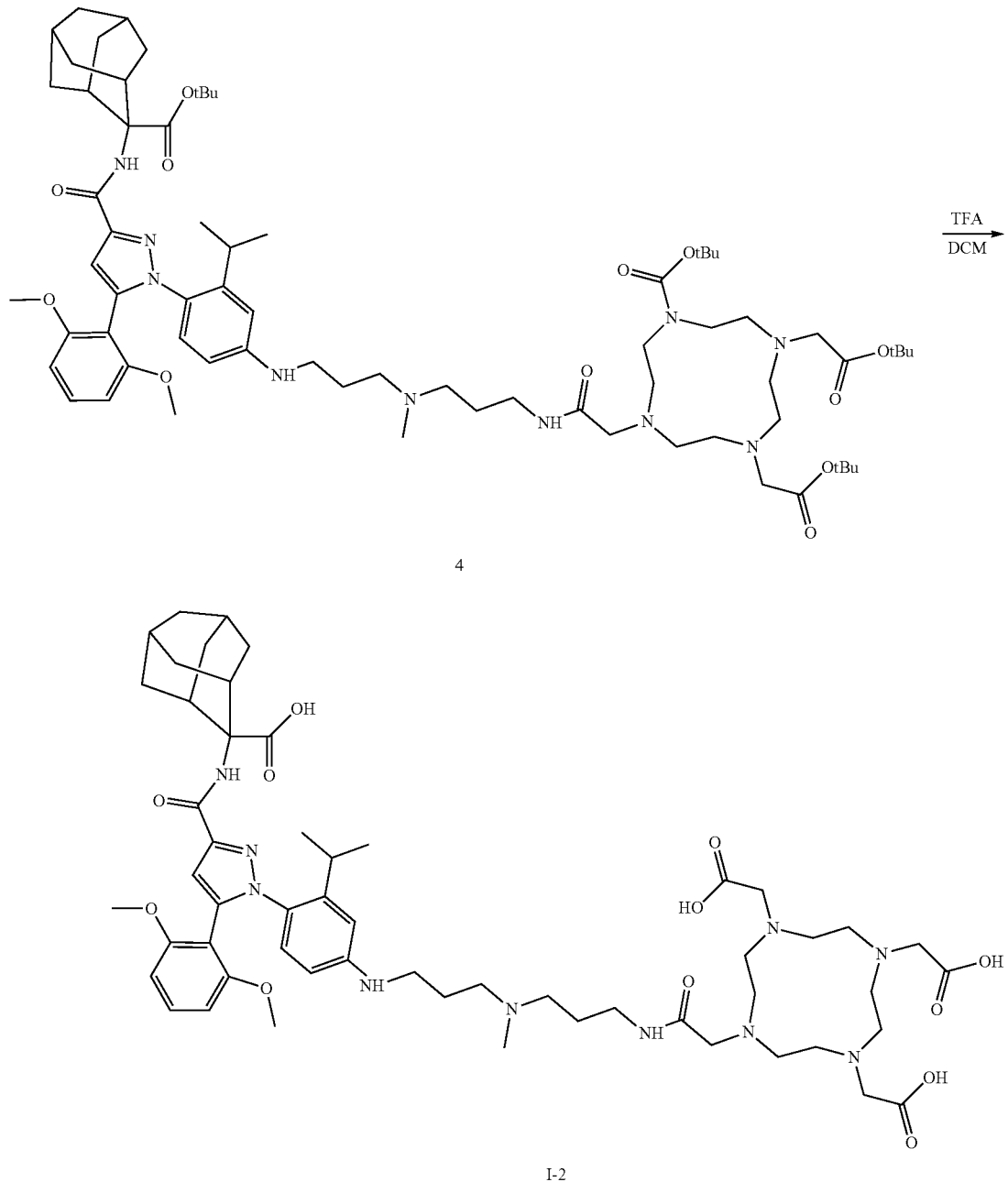

To a solution of compound 4 (120 mg, crude) in TFA/DCM (5/5 mL), (iPr)$_3$SiH (1 drop) was added. The reaction mixture was stirred at r.t. overnight. The solvent was removed by Rotavapor and the residue was purified by prep-HPLC to give I-2 (18.2 mg, 10.2% yield) as white solid. Molecular weight calculated: 1072.6 g/mol. Determined by LC-MS: (M+2H)2+: 537.4; (M+3H)3+: 358.8. Purity by UPLC (214 nm): 97.4%.

Example 3: Synthesis of I-3
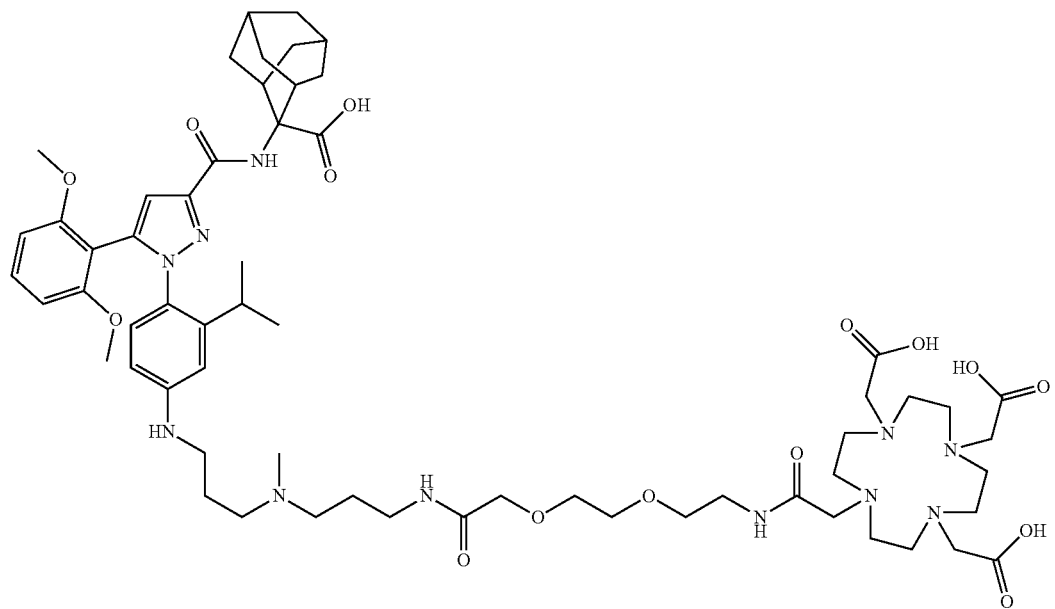 [SMILES: COc1cccc(OC)c1-c1cc(C(=O)NC2(C(=O)O)C3CC4CC(C3)CC2C4)nn1-c1ccc(NCCCN(C)CCCNC(=O)COCCOCCNC(=O)CN2CCN(CC(=O)O)CCN(CC(=O)O)CCN(CC(=O)O)CC2)cc1C(C)C]
The Synthetic Route to I-3
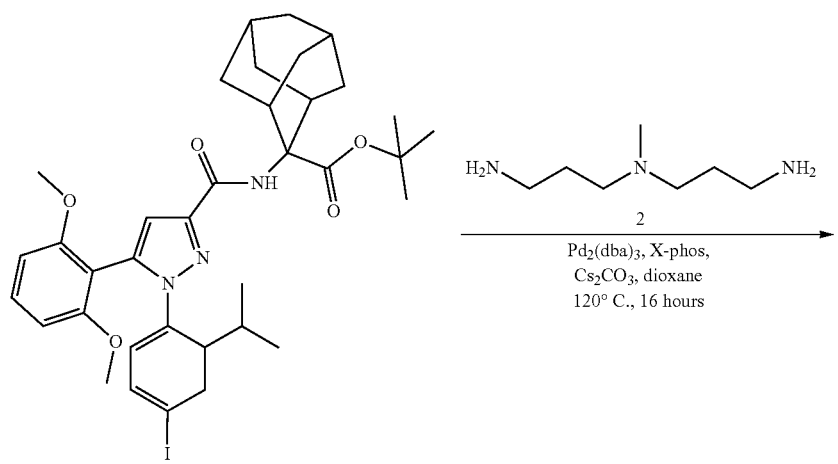

-continued
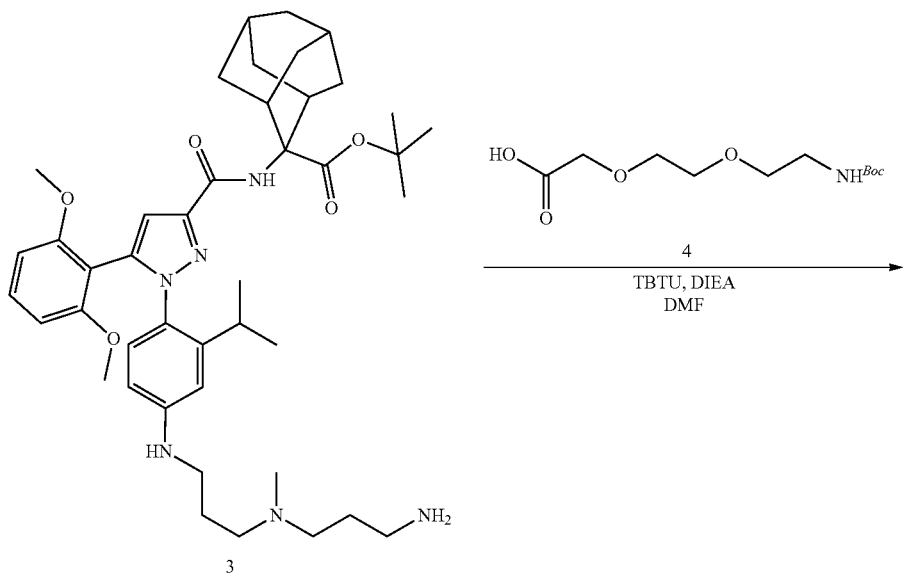
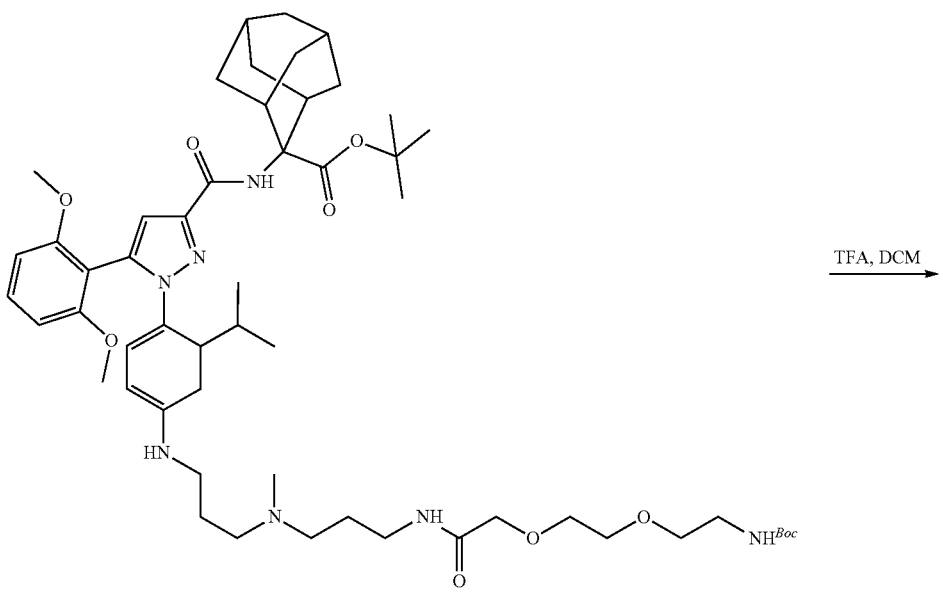

-continued
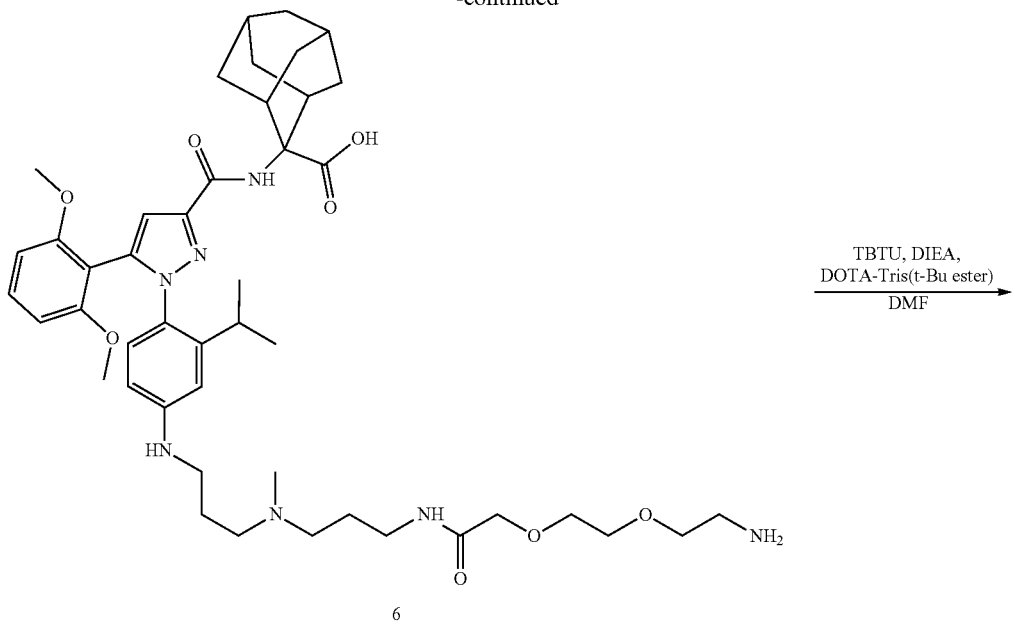
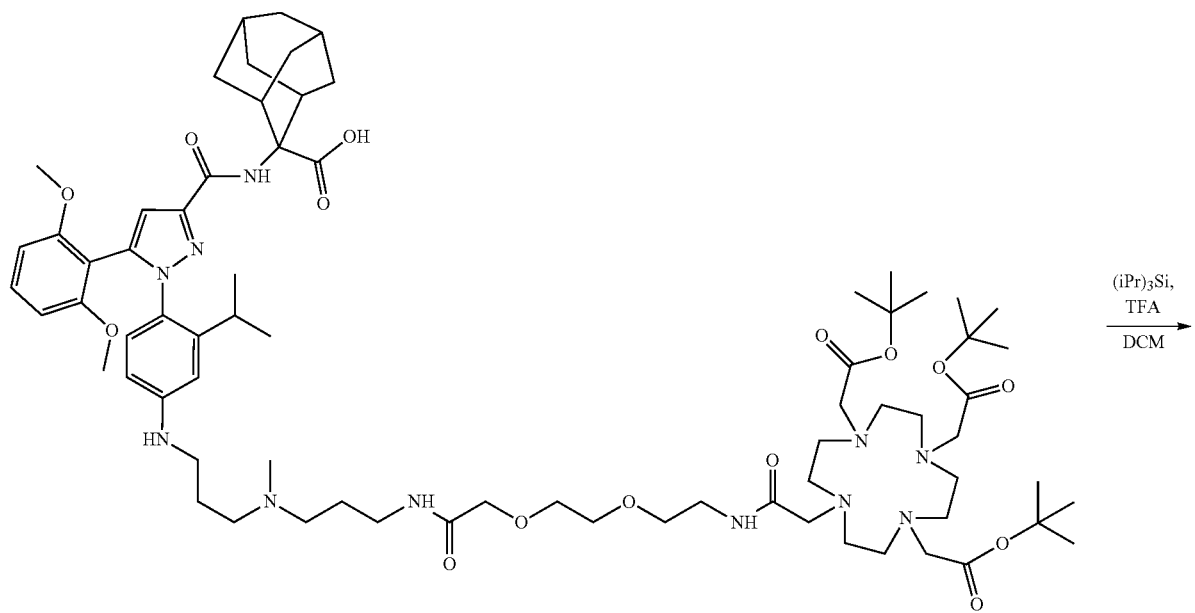

-continued
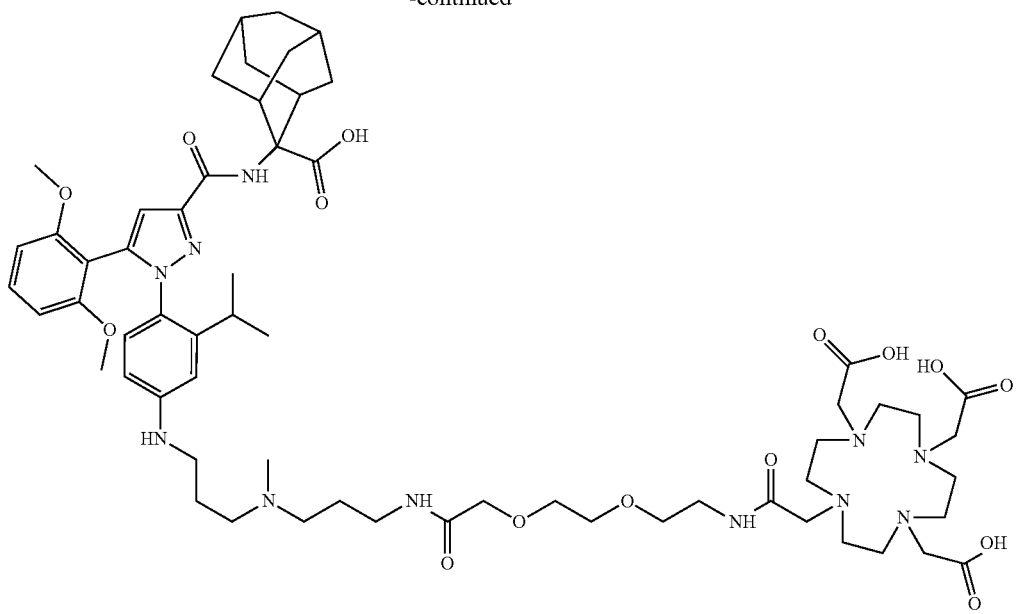
I-3
Synthesis of tert-butyl 2-(1-(4-((3-((3-aminopropyl)(methyl)amino)propyl)amino)-2-isopropylphenyl)-5-(2,6-dimethoxyphenyl)-1H-pyrazole-3-carboxamido)adamantane-2-carboxylate (3)
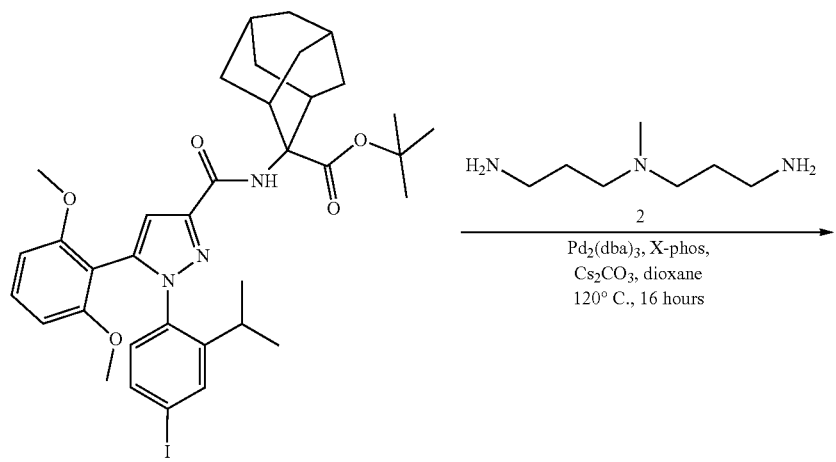

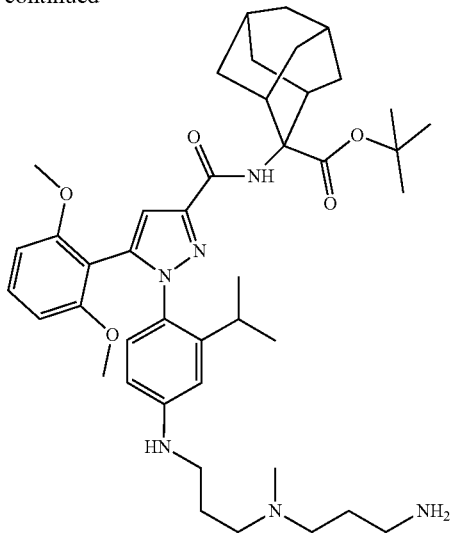

To a solution of compound 1 (2.0 g, 2.75 mmol) in dioxane (30 mL) was added compound 2 (599.2 mg, 4.13 mmol), $Cs_2CO_3$ (2.7 g, 8.27 mmol), x-phos (262.8 mg, 0.55 mmol) and $Pd_2(dba)_3$ (504.1 mg, 0.55 mmol). The reaction mixture was stirred at 120° C. under $N_2$ balloon overnight. The residue was diluted with $H_2O$ (20 mL) and extracted with EA (20 mL×2). The combined organic phases were dried over $Na_2SO_4$, filtered and concentrated. The residue was purified by flash chromatography on reverse phase silica gel (ACN/$H_2O$=5%~95%, 35 min) to give compound 3 (1.6 g, 85.8% yield) as yellow solid. Molecular weight calculated: 742.5 g/mol; Determined by LC-MS: (M+H)+: 743.5.

Synthesis of tert-butyl 2-(5-(2,6-dimethoxyphenyl)-1-(2-isopropyl-4-((2,2,18-trimethyl-4,13-dioxo-3,8,11-trioxa-5,14,18-triazahenicosan-21-yl)amino)phenyl)-1H-pyrazole-3-carboxamido)adamantane-2-carboxylate (5)

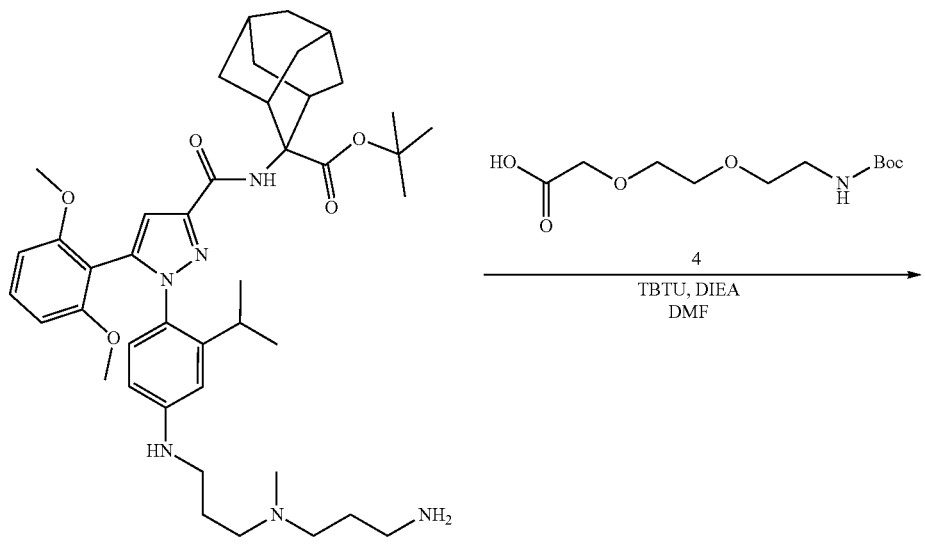

-continued

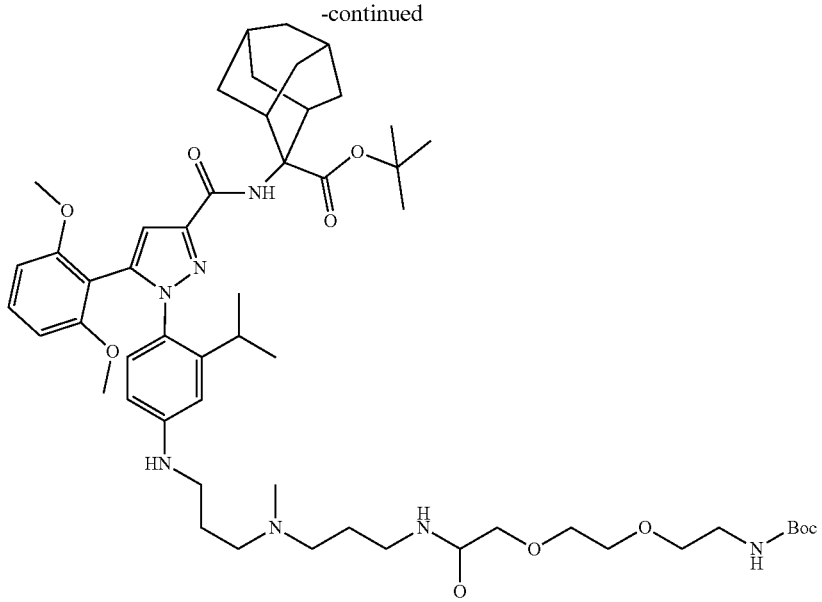

5

To a solution of compound 4 (100 mg, 0.35 mmol) in DMF (5 mL) in an ice-water bath was added DIEA (67.7 mg, 0.52 mmol) and TBTU (168.4 mmol, 0.52 mmol). The mixture was stirred for 30 min before compound 3 (280 mg, 0.35 mmol) was added. The reaction mixture was stirred at r.t. overnight. The residue was diluted with H₂O (20 mL) and extracted with EA (30 mL×3). The combined organic phases were dried over Na₂SO₄, filtered and concentrated to give compound 5 (200 mg, 57.8% yield) as brown oil. Molecular weight calculated: 987.6 g/mol; Determined by LC-MS: (M+H)+: 988.7.

Synthesis of 2-(1-(4-((1-amino-13-methyl-8-oxo-3,6-dioxa-9,13-diazahexadecan-16-yl)amino)-2-isopropylphenyl)-5-(2,8-dimethoxyphenyl)-1H-pyrazole-3-carboxamido)adamantane-2-carboxylic acid (6)

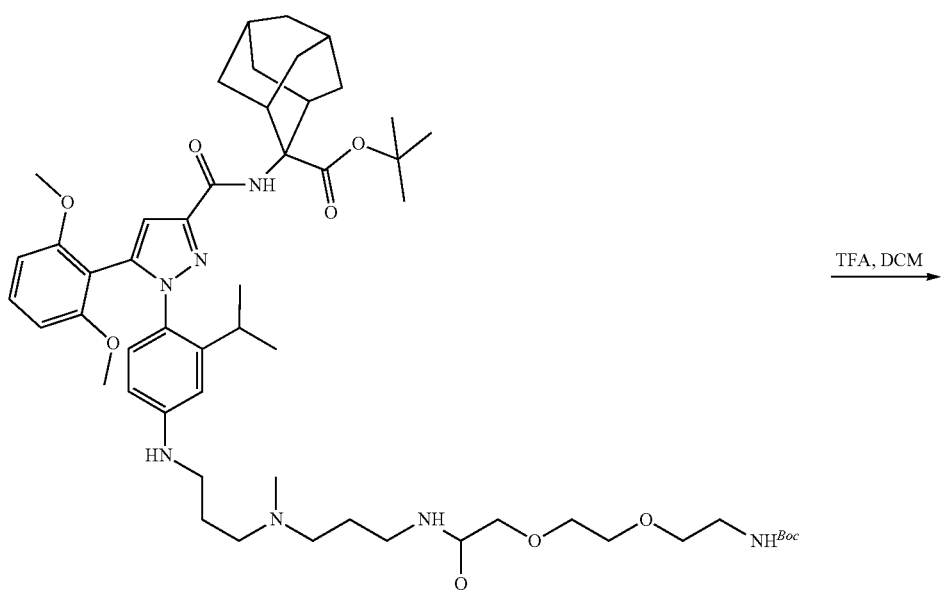

5

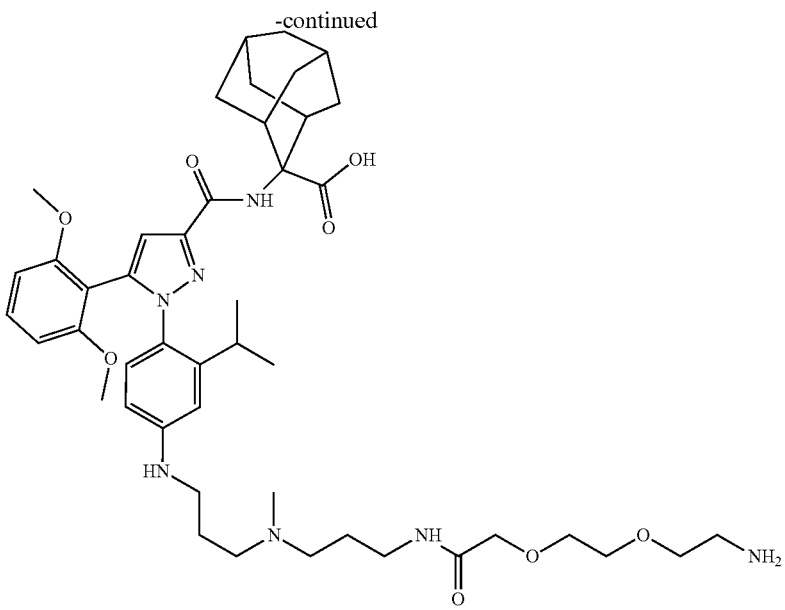

6

To a solution of compound 5 (200.0 mg, 0.20 mmol) in DCM (5 mL) was added TFA (1 mL). The reaction mixture was stirred at r.t. for 2 hr. The reaction mixture was concentrated and purified by prep-HPLC to give compound 6 (50 mg, 30% yield) as a white solid. Molecular weight calculated: 831.5 g/mol: Determined by LC-MS: (M+H)+: 832.5.

Synthesis of (5-(2,6-dimethoxyphenyl)-1-(2-isopropyl-4-((16-methyl-2,11-dioxo-1-(4,7,10-tris(2-(tert-butoxy)-2-oxoethyl)-1,4,7,10-tetraazacyclododecan-1-yl)-6,9-dioxa-3,12,16-triazanonadecan-19-yl) amino)phenyl)-1H-pyrazole-3-carboxamido) adamantane-2-carboxylic acid (7)

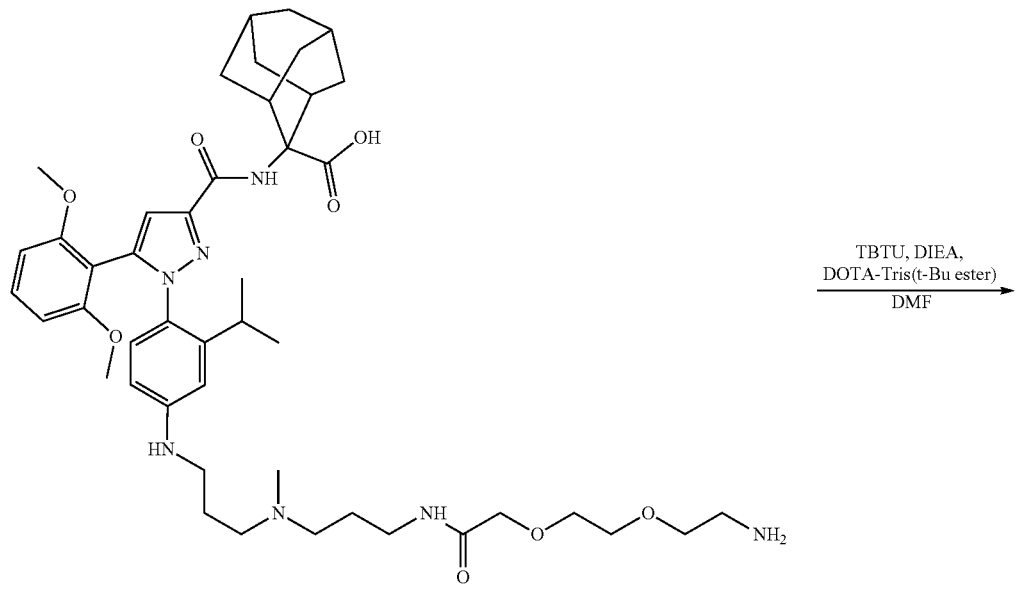

6

-continued

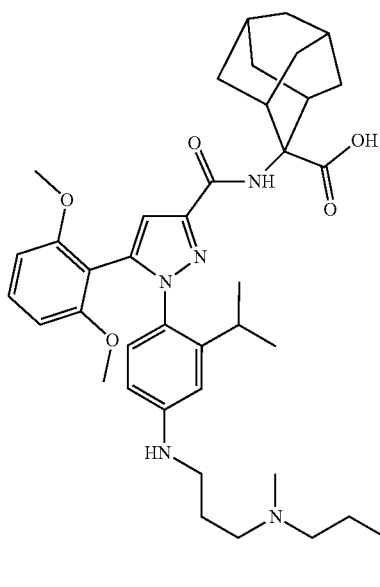
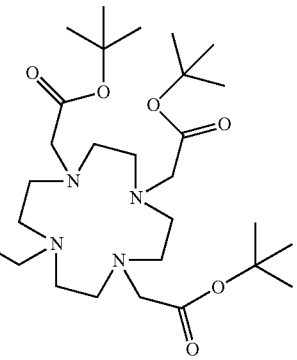

7

To a solution of DOTA-Tris(t-Bu ester) (2-(4,7,10-tris(2-(tert-butoxy)-2-oxoethyl)-1,4,7,10-tetraazacyclododecan-1-yl)acetic acid) (51.6 mg, 0.09 mmol), TBTU (28.9 mg, 0.09 mmol) and DIEA (11.6 mg, 0.18 mmol) in DMF (5 mL). The reaction mixture was stirred at r.t. for 1 hr before the addition of compound 6 (50.0 mg, 0.06 mmol), and the resulting mixture was stirred at r.t. overnight. The reaction mixture was diluted with H$_2$O (20 mL) and extracted with EA (20 mL×3). The combined organic phases were dried over Na$_2$SO$_4$, filtered and concentrated to give compound 7 (60 mg, crude) as yellow oil. Molecular weight calculated: 1385.9 g/mol: Determined by LC-MS: (M+H)+: 1386.9.

Synthesis of 2,2',2''-(10-(19-((4-(3-((2-carboxyadamantan-2-yl)carbamoyl)-5-(2,6 dimethoxyphenyl)-1H-pyrazol-1-yl)-3-isopropylphenyl)amino)-16-methyl-2,11-dioxo-6,9-dioxa-3,12,16-triazanonadecyl)-1,4,7,10-tetraazacyclododecane-1,4,7-triyl)triacetic acid (I-3)

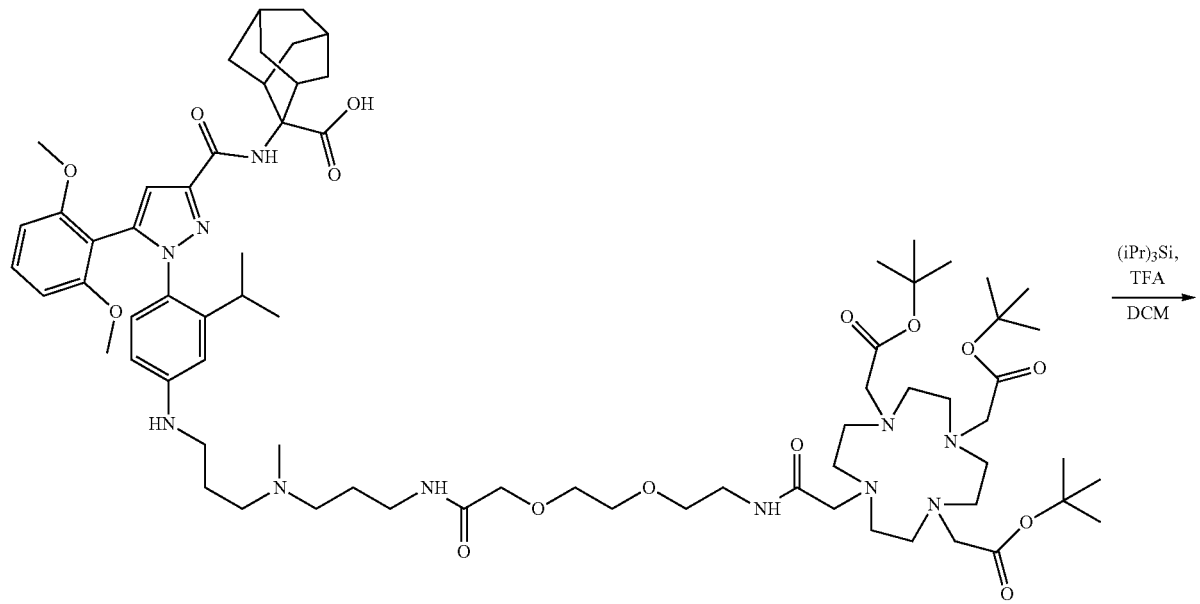

7

-continued
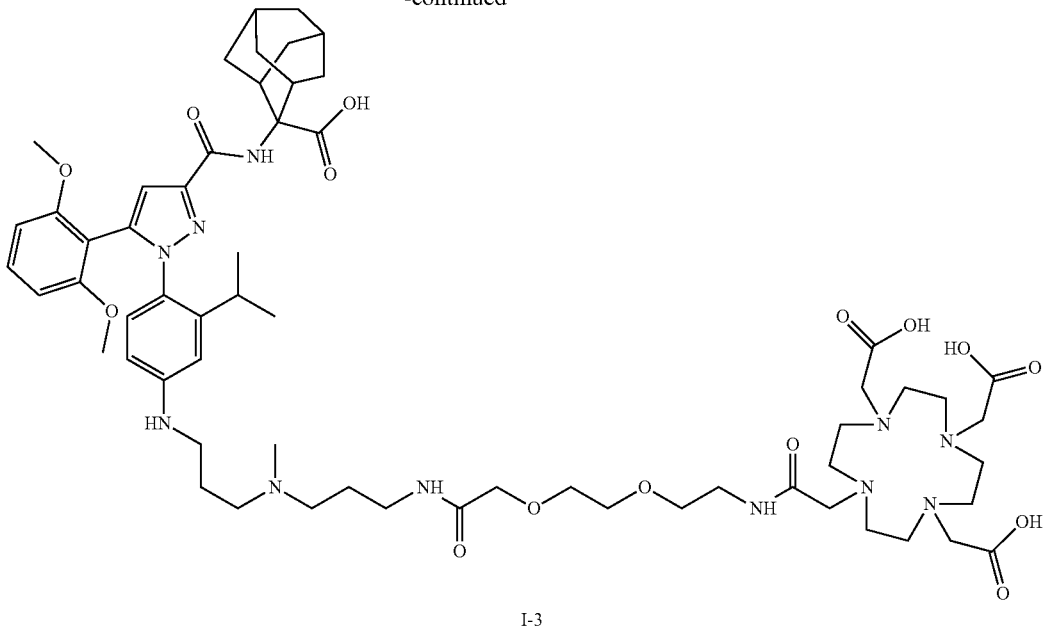
I-3
To a solution of compound 7 (60 mg, crude) in TFA/DCM (3/3 mL), (iPr)$_3$Si (1 drop) was added. The reaction mixture was stirred at r.t. overnight. The residue was purified by prep-HPLC to give I-3 (4.8 mg, 6.6% yield) as a white solid. Molecular weight calculated: 1217.7 g/mol; Determined by LC-MS: (M+2H)2+: 610.0. Purity by UPLC (214 nm): 77.2%.
Example 4: Synthesis of I-4
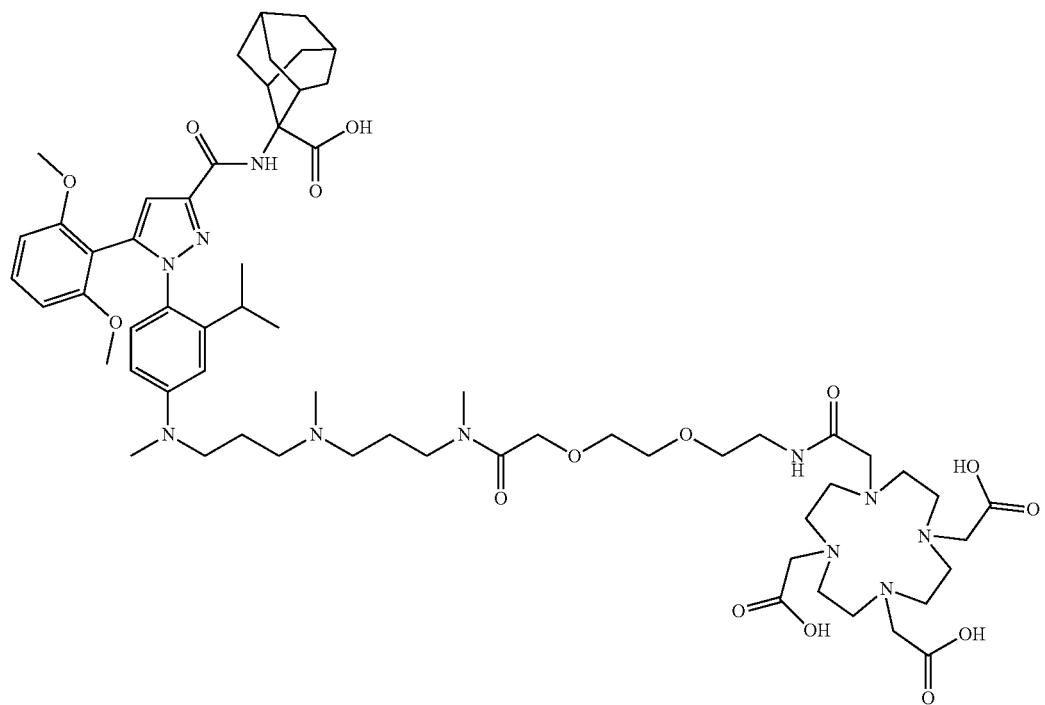 [SMILES: COc1cccc(OC)c1-c1cc(C(=O)NC2(C(=O)O)C3CC4CC(C3)CC2C4)nn1-c1ccc(N(C)CCCN(C)CCCN(C)C(=O)COCCOCCNC(=O)CN2CCN(CC(=O)O)CCN(CC(=O)O)CCN(CC(=O)O)CC2)cc1C(C)C]

The Synthetic Route of I-4
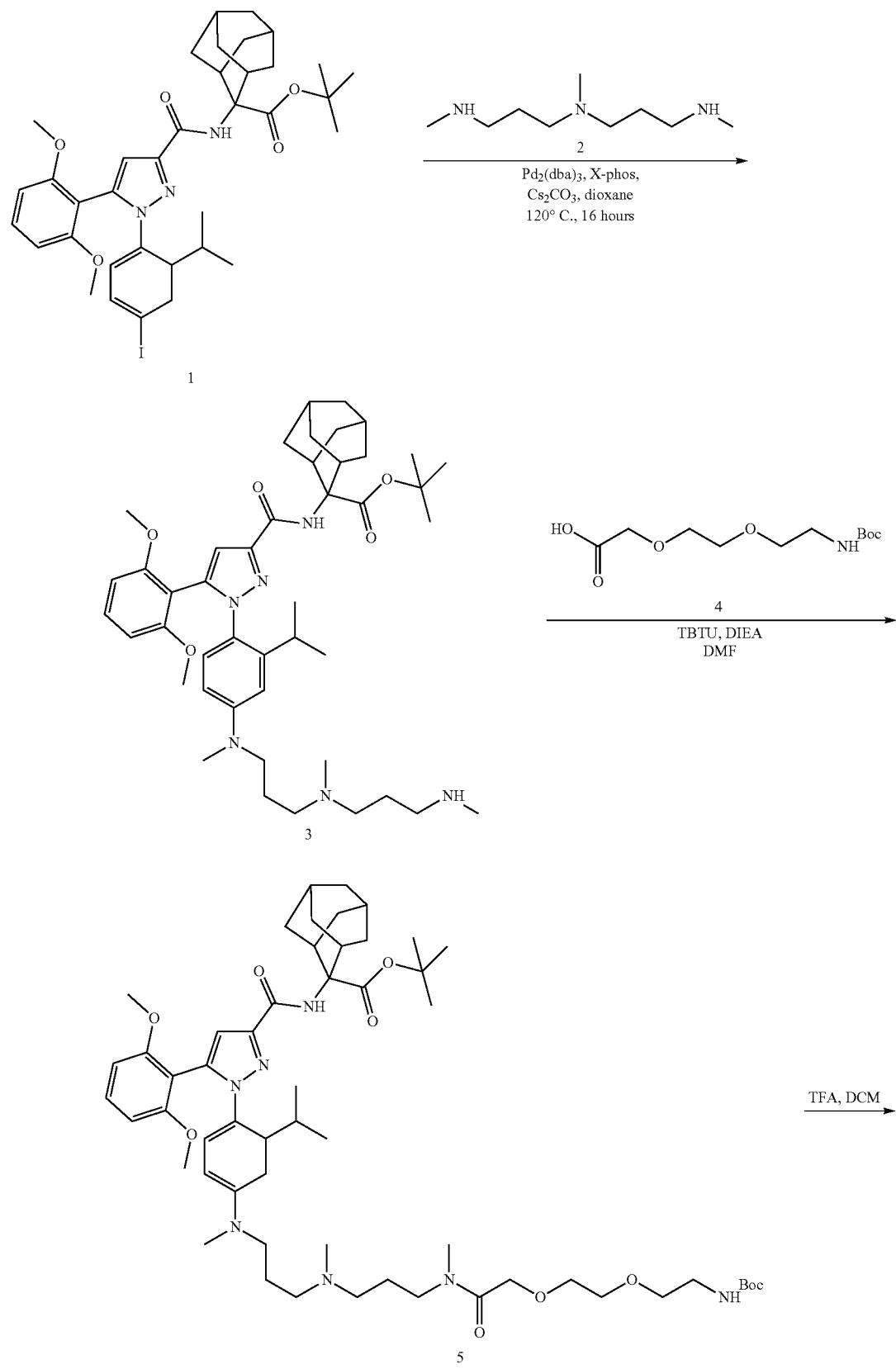

-continued
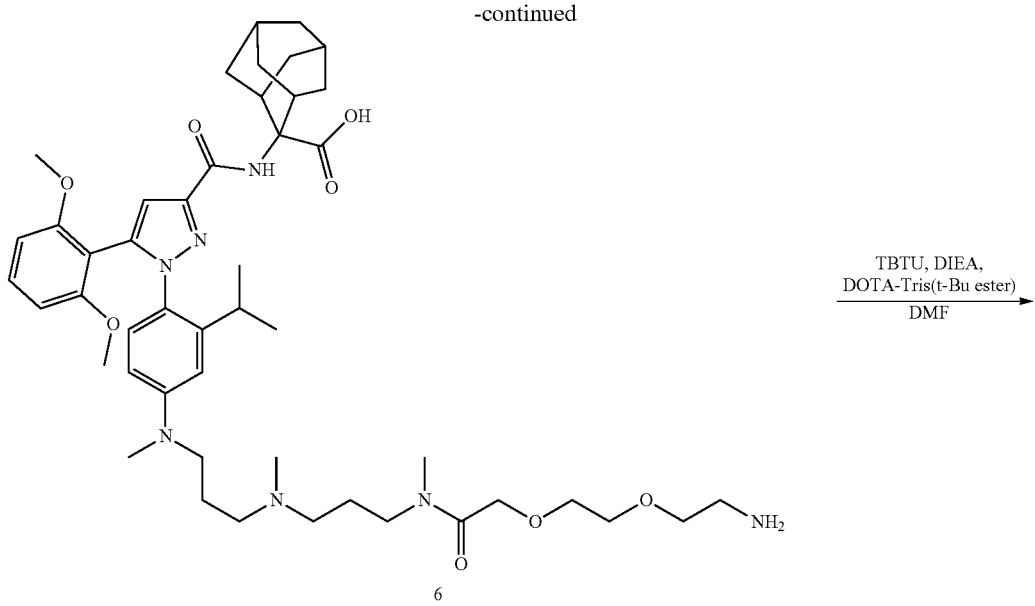
TBTU, DIEA,
DOTA-Tris(t-Bu ester)
———————————→
DMF
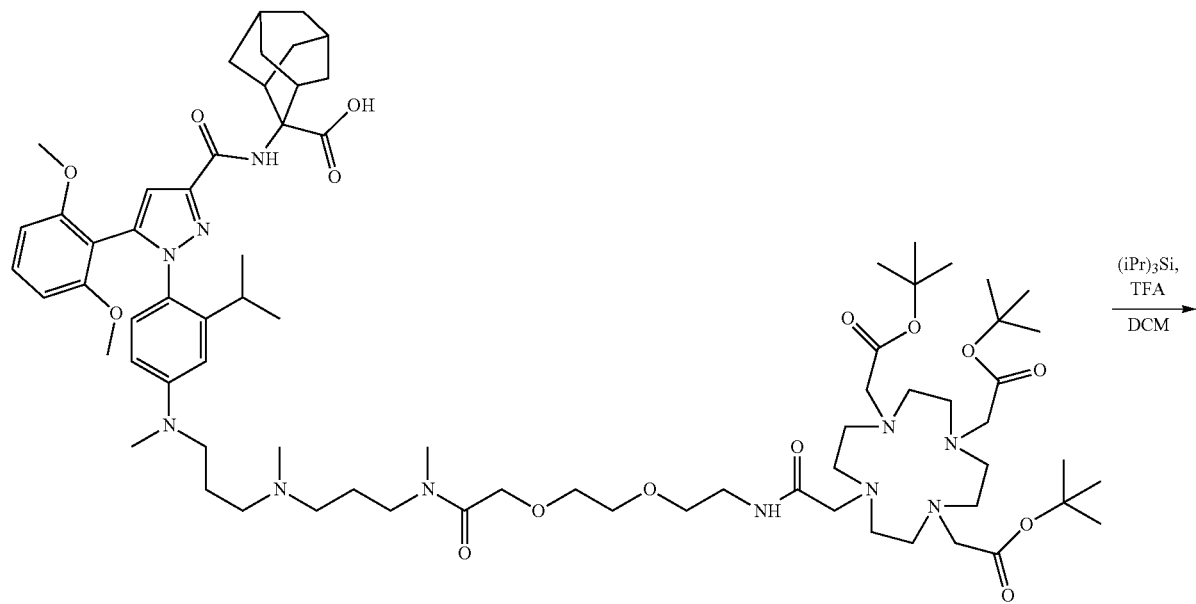
(iPr)₃Si,
TFA
———→
DCM

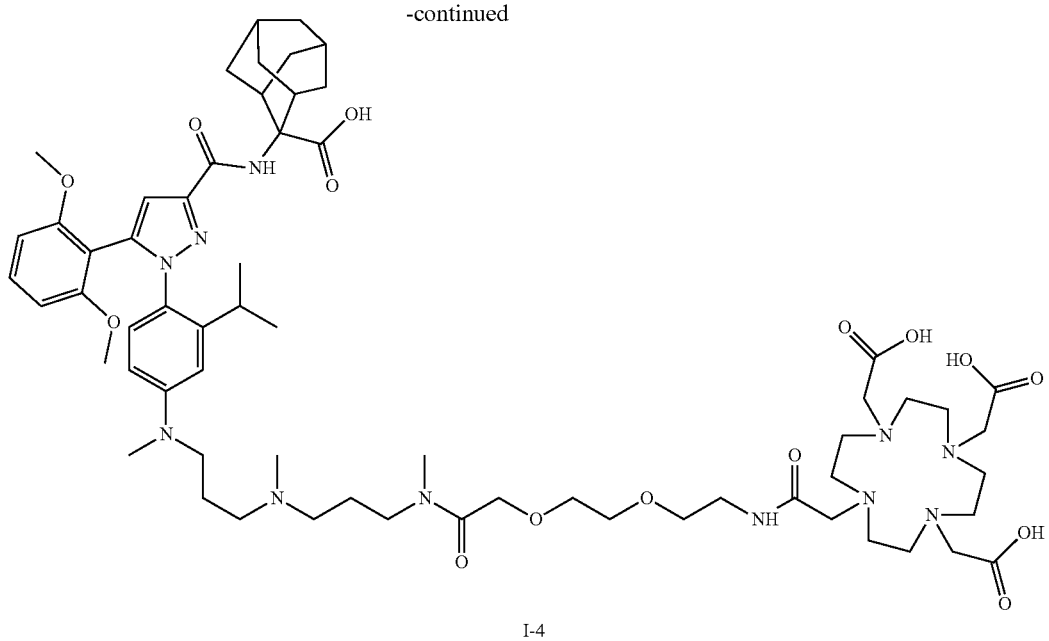
I-4
Synthesis of tert-butyl 2-(5-(2,6-dimethoxyphenyl)-1-(2-isopropyl-4 (methyl(3-(methyl(3-(methyl-amino)propyl)amino)propyl)amino)phenyl)-1H-pyrazole-3-carboxamido)adamantane-2-carboxylate (3)
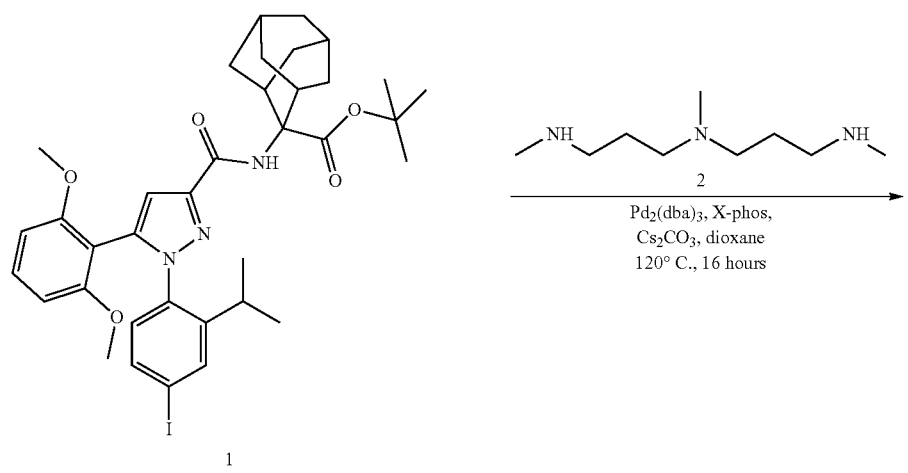

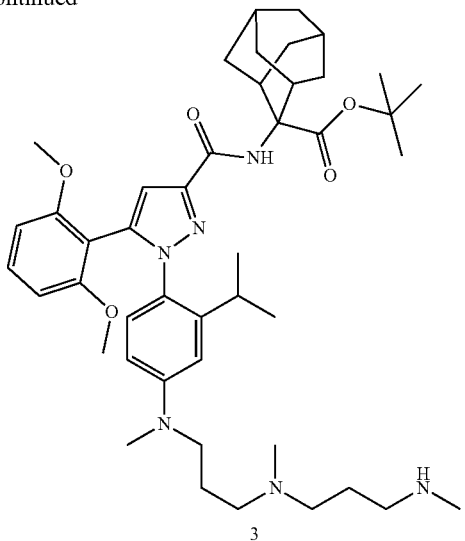

To a solution of compound 1 (2.0 g, 2.75 mmol) in dioxane (30 mL) was added compound 2 (714.9 mg, 4.13 mmol), $Cs_2CO_3$ (2.7 g, 8.27 mmol), x-phos (262.8 mg, 0.55 mmol) and $Pd_2(dba)3$ (504.1 mg, 0.55 mmol). The reaction mixture was stirred at 120° C. under $N_2$ balloon overnight. The residue was diluted with $H_2O$ (20 mL) and extracted with EA (20 mL×2). The combined organic phase was dried over $Na_2SO_4$, filtered and concentrated. The residue was purified by flash chromatography on reverse phase silica gel (ACN/$H_2O$=5%-95%, 35 min) to give compound 3 (800 mg, 38% yield) as yellow solid. Molecular weight calculated: 770.5 g/mol; Determined by LC-MS: (M+H)+: 771.5.

Synthesis of tert-butyl 2-(5-(2,6-dimethoxyphenyl)-1-(2-isopropyl-4-(methyl(2,2,14,18-tetramethyl-4,13-dioxo-3,8,11-trioxa-5,14,18-triazahenicosan-21-yl)amino)phenyl)-1H-pyrazole-3-carboxamido)adamantane-2-carboxylate (5)

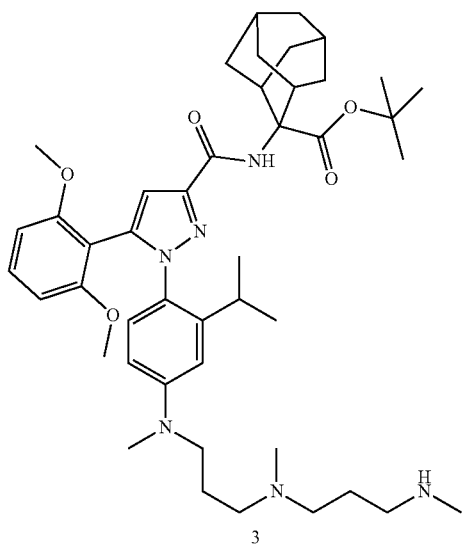 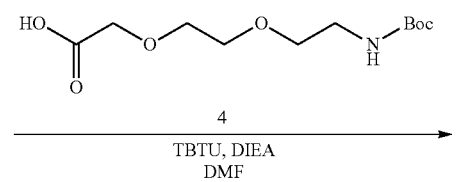

-continued

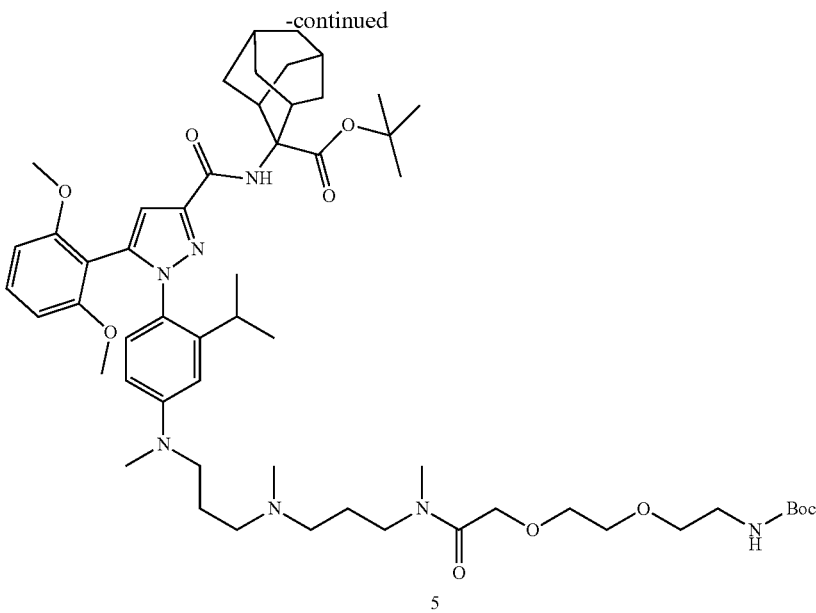

5

To a solution of compound 4 (61.4 mg, 0.23 mmol) in DMF (5 mL) in an ice-water bath, was added DIEA (90.4 mg, 0.70 mmol) and TBTU (112.4 mmol, 0.35 mmol). The mixture was stirred for 30 min before the addition of compound 3 (180 mg, 0.23 mmol). The resulting mixture was stirred at r.t. overnight, then diluted with H$_2$O (20 mL) and extracted with EA (30 mL×3). The combined organic phase was dried over Na$_2$SO$_4$, filtered and concentrated to give crude compound 5 (150 mg, 64% yield) as an orange oil. Molecular weight calculated: 1015.6 g/mol; Determined by LC-MS: (M+H)+: 1016.6.

Synthesis of (1-(4-((1-amino-9,13-dimethyl-8-oxo-3,6-dioxa-9,13-diazahexadecan-16-yl)(methyl)amino)-2-isopropylphenyl)-5-(2,6-dimethoxyphenyl)-1H-pyrazole-3-carboxamido)adamantane-2-carboxylic acid (6)

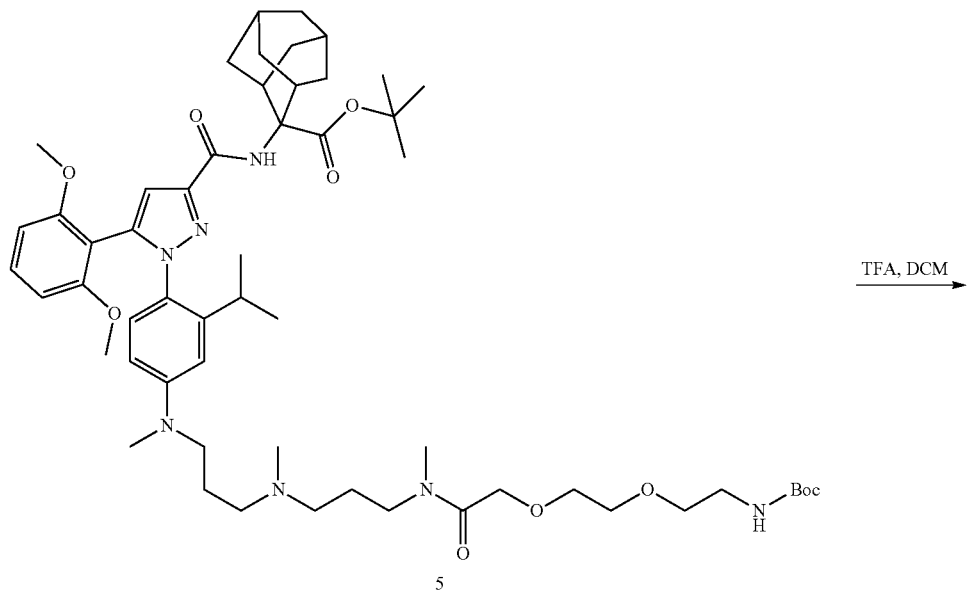

TFA, DCM

5

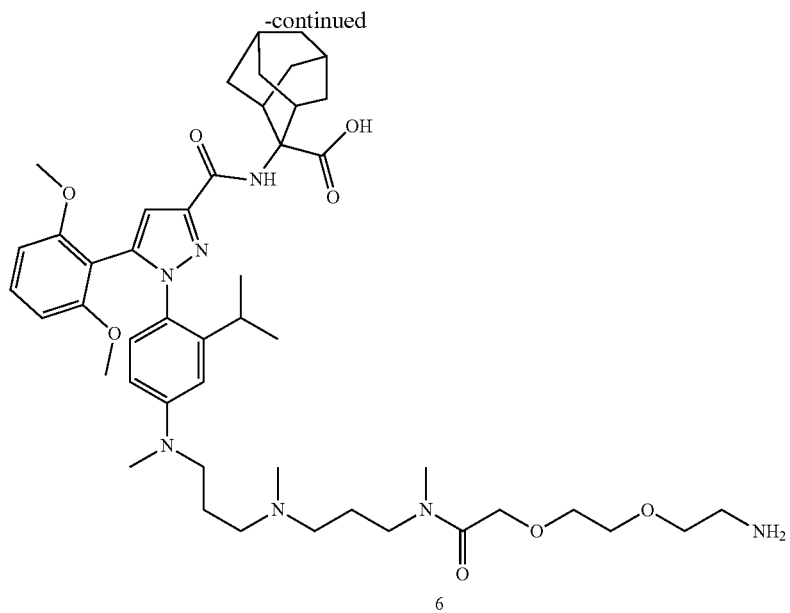

To a solution of compound 5 (150 mg, 0.15 mmol) in DCM (5 mL) was added TFA (1 mL). The reaction mixture was stirred at r.t. for 2 hr, then concentrated and purified by prep-HPLC to give compound 6 (50 mg, 39% yield) as a white solid. Molecular weight calculated: 859.5 g/mol; Determined by LC-MS: (M+H)+: 860.5.

Synthesis of 2-(5-(2,6-dimethoxyphenyl)-1-(4-((12,18-dimethyl-2,11-dioxo-1-(4,7,10-tris(2-(tert-butoxy)-2-oxoethyl)-1,4,7,10-tetraazacyclododecan-1-yl)-6,9-dioxa-3,12,16-triazanonadecan-19-yl)(methyl)amino)-2-isopropylphenyl)-1H-pyrazole-3-carboxamido)adamantane-2-carboxylic acid (7)

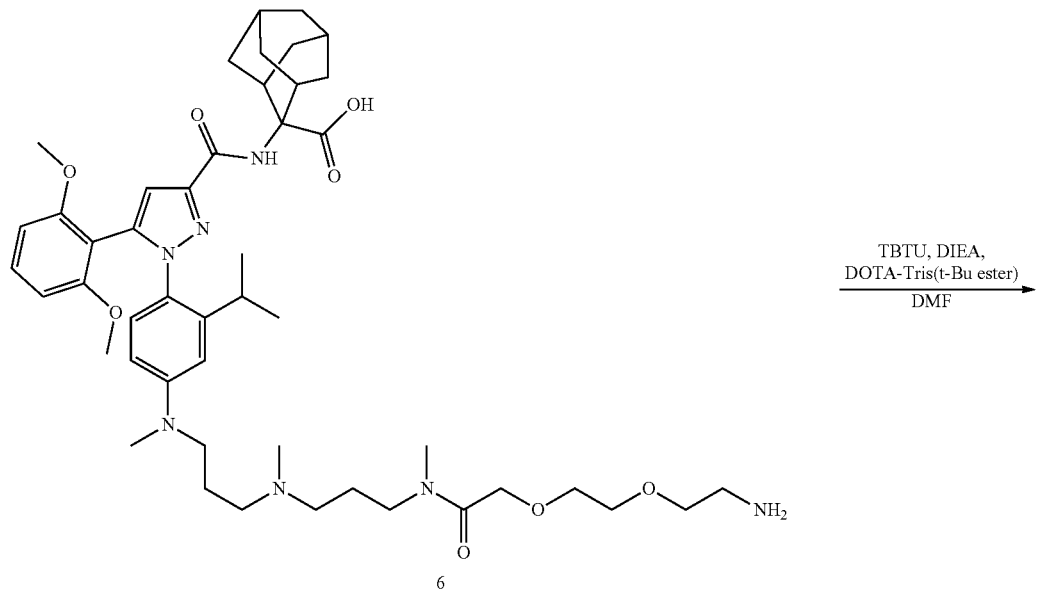

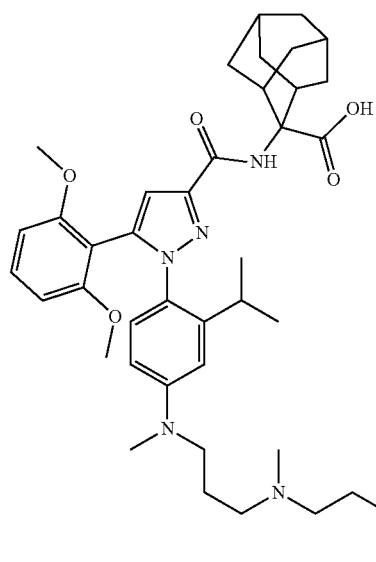

7

To a solution of 2-(4,7,10-tris(2-(tert-butoxy)-2-oxoethyl)-1,4,7,10-tetraazacyclododecan-1-yl)acetic acid (33.3 mg, 0.06 mmol), TBTU (30.0 mg, 0.09 mmol) and DIEA (22.5 mg, 0.17 mmol) in DMF (5 mL). The reaction mixture was stirred at r.t. for 1 hour, added compound 6 (50.0 mg, 0.06 mmol), continued stirred at r.t. for overnight. The residue was diluted with $H_2O$ (20 mL) and extracted with EA (20 mL×3). The combined organic phases were dried over $Na_2SO_4$, filtered and concentrated to give compound 6 (60 mg, crude) as yellow oil. Molecular weight calculated: 1413.9 g/mol; Determined by LC-MS: (M+H)+: 1414.9.

Synthesis of 2,2′,2″-(10-(2-(4-(3-((2-carboxyadamantan-2-yl)carbamoyl)-5-(2,6-dimethoxyphenyl)-1H-pyrazol-1-yl)-3-isopropylphenyl)-6,10-dimethyl-11,20-dioxo-13,16-dioxa-2,6,10,19-tetraazahenicosan-21-yl)-1,4,7,10-tetraazacyclododecane-1,4,7-triyl)triacetic acid (I-4)

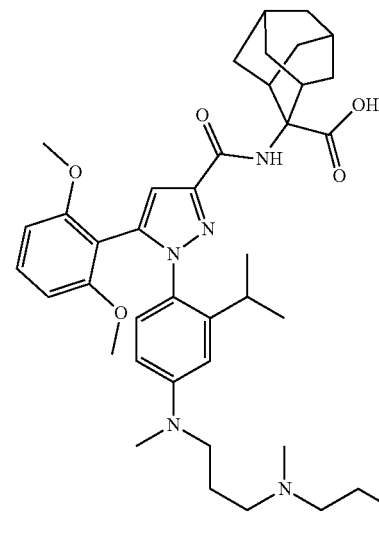 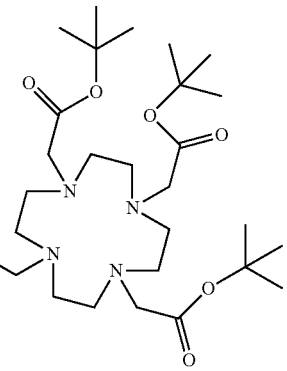

7

-continued
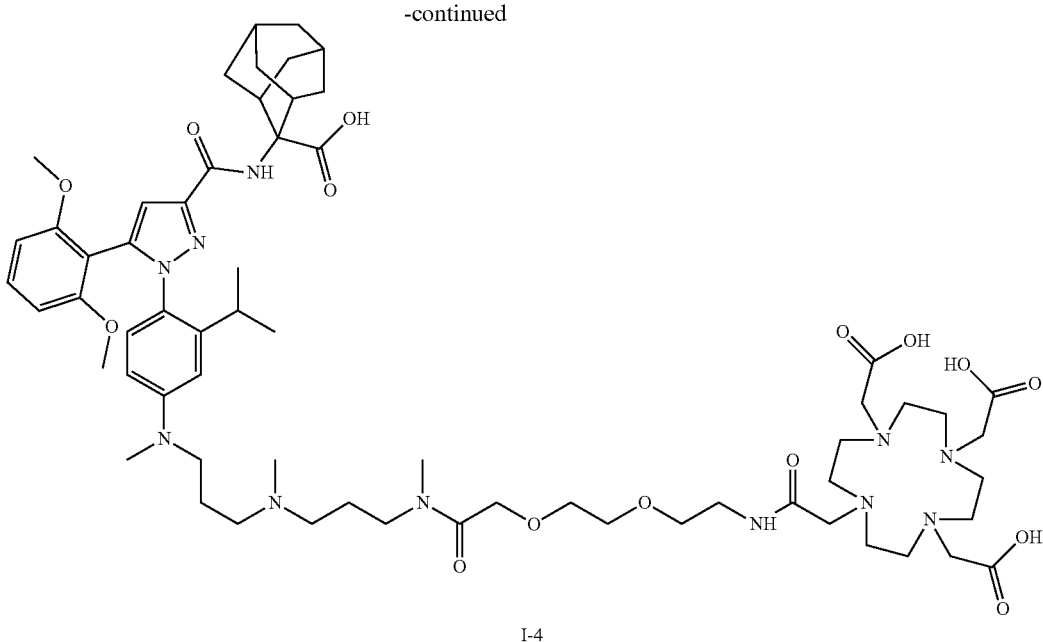
I-4
To a solution of compound 7 (60.0 mg, crude) in TFA/DCM (3/3 mL), (iPr)$_3$Si (1 drop) was added. The reaction mixture was stirred at r.t. overnight. The residue was purified by prep-HPLC to give I-4 (12.5 mg, 34% yield) as a white solid. Molecular weight calculated: 1245.7 g/mol: Determined by LC-MS: (M+2H)2+: 624.0. Purity by UPLC (214 nm): 97.7%.
Example 5. Synthesis of I-5
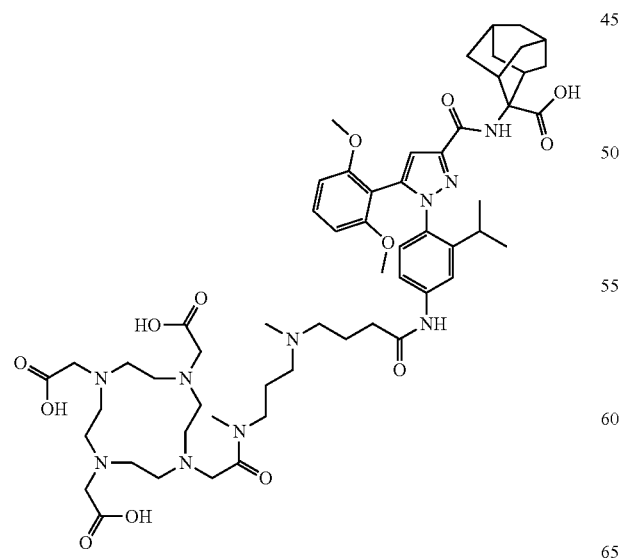

The Synthetic Route of I-5
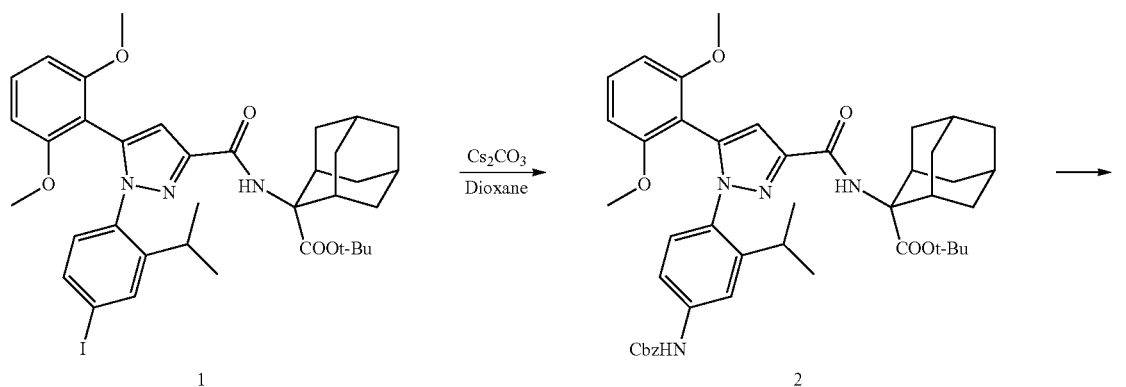
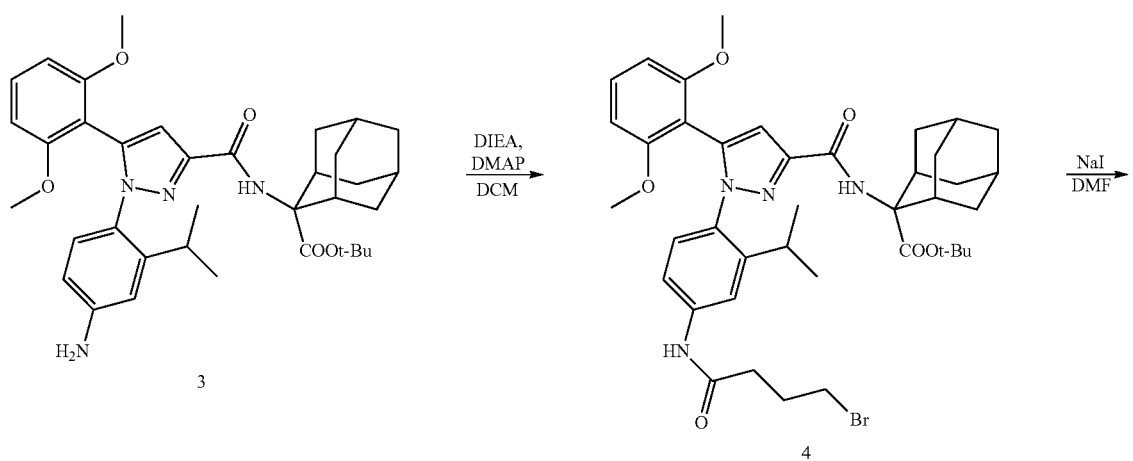
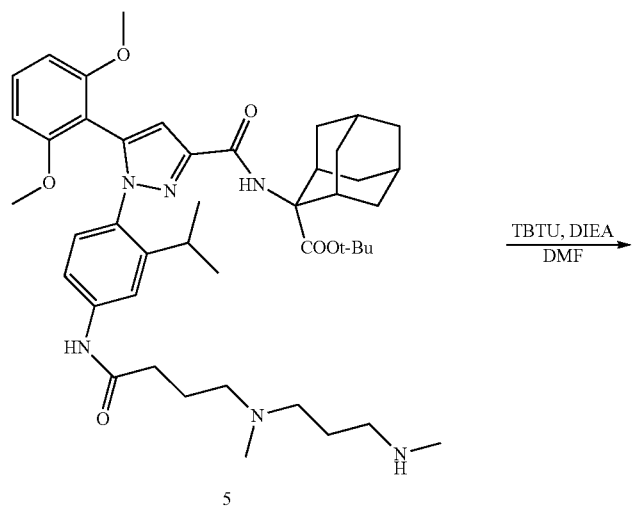

-continued
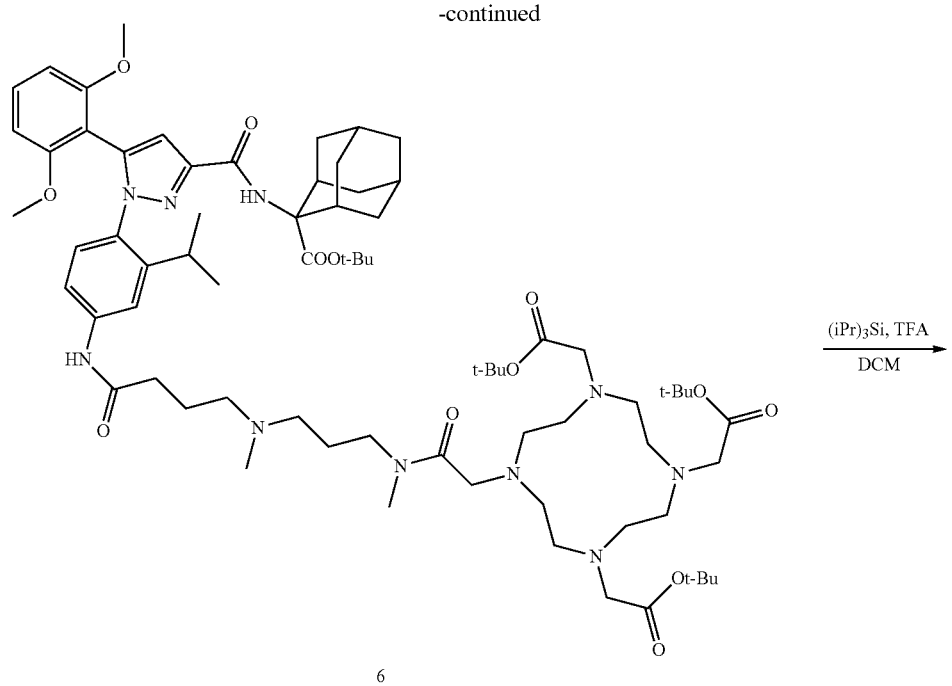
6
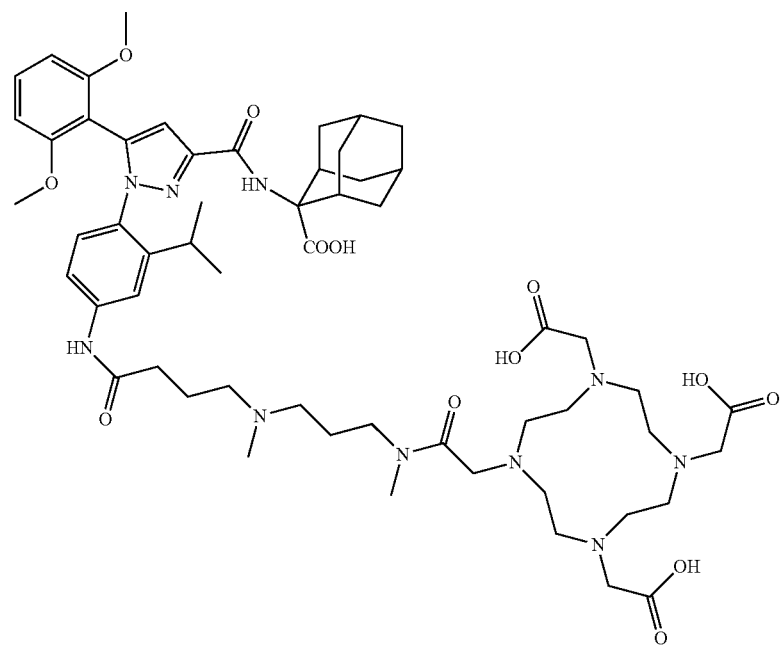
I-5

113

Synthesis of tert-butyl 2-(1-(4-(((benzyloxy)carbonyl)amino)-2-isopropylphenyl)-5-(2,6-dimethoxyphenyl)-1H-pyrazole-3-carboxamido)adamantane-2-carboxylate (2)

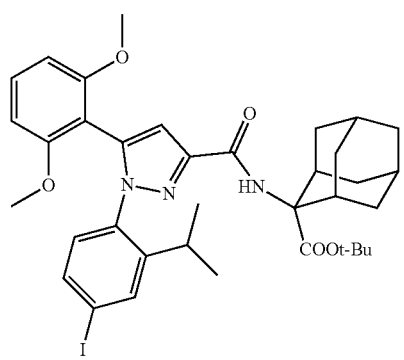

1

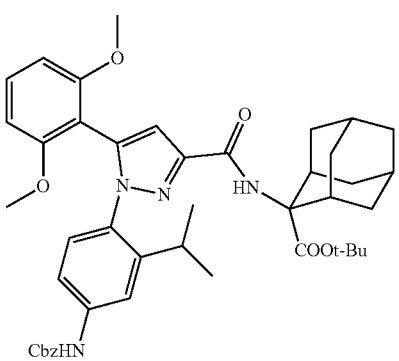

2

To a solution of compound 1 (200 mg, 0.28 mmol) in dioxane (20 mL) was added benzyl carbamate (83.3 mg, 0.56 mmol), Cs$_2$CO$_3$ (274 mg, 0.84 mmol), x-phos (67 mg, 0.14 mmol) and Pd$_2$(dba)$_3$ (26 mg, 0.028 mmol). The reaction mixture was stirred at 115° C. under N$_2$ balloon overnight. The reaction mixture was diluted with H$_2$O (20 mL) and extracted with EA (20 mL×2). The combined organic phases were dried over Na$_2$SO$_4$, filtered and concentrated. The residue was purified by flash chromatography on reverse phase silica gel using ACN and H$_2$O as the mobile phase with a gradient of % ACN from 5% to 95% over 35 min to give compound 2 (192 mg, 93% yield) as yellow solid. Molecular weight calculated: 748 g/mol. Determined by LC-MS: (M+H)+: 749.

114

Synthesis of tert-butyl 2-(1-(4-amino-2-isopropylphenyl)-5-(2,6-dimethoxyphenyl)-1H-pyrazole-3-carboxamido)adamantane-2-carboxylate (3)

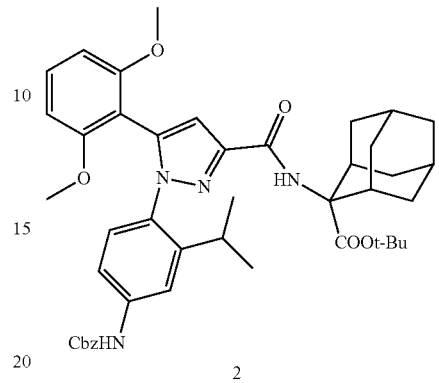

2

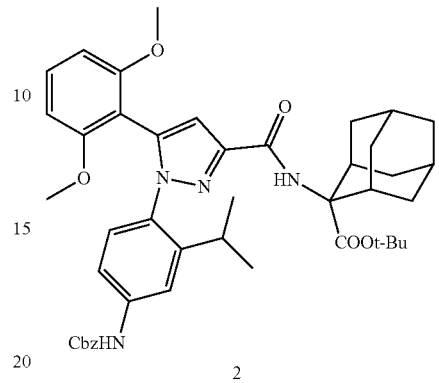

3

To a solution of compound 2 (200 mg, 0.27 mmol) in THF (10 mL) was added Pd/C (20 mg). The reaction mixture was stirred at r.t. for 4 hr. The reaction mixture was filtered, washed with THF (10 mL×2) and concentrated to give crude compound 3 (150 mg, 92% yield) as a yellow solid. Molecular weight calculated: 614 g/mol. Determined by LC-MS: (M+H)+: 615.

Synthesis of tert-butyl 2-(1-(4-(4-bromobutanamido)-2-isopropylphenyl)-5-(2,6-dimethoxyphenyl)-1H-pyrazole-3-carboxamido)adamantane-2-carboxylate (4)

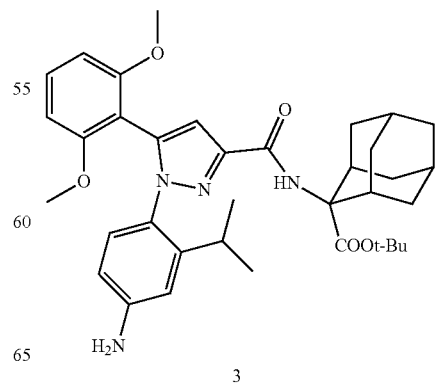

3

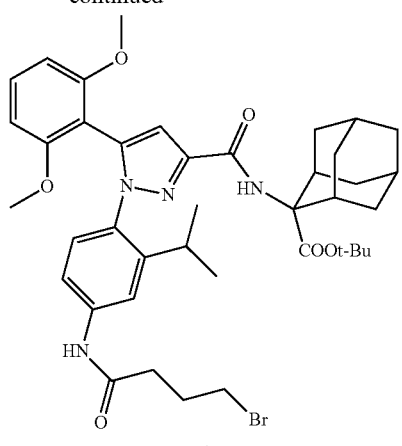

4

To a solution of compound 3 (100 mg, 0.18 mmol) in DCM (15 mL) was added 4-bromobutanoyl chloride (86.2 mg, 0.47 mmol), DIEA (90.4 mg, 0.70 mmol), and DMAP (3.2 mg, 0.02 mmol). The reaction mixture was stirred at 25° C. under N₂ balloon for 2 hr. The residue was diluted with H₂O (20 mL) and extracted with DCM (20 mL×3). The combined organic phases were dried over Na₂SO₄, filtered and concentrated. The residue was purified by prep-HPLC to give crude compound 4 (120 mg, 96% yield) as yellow oil. Molecular weight calculated: 764 g/mol. Determined by LC-MS: (M+H)+: 765.

5

To a solution of compound 4 (120 mg, 0.15 mmol) in DMF (5 mL) was added N₁,N₃-dimethylpropane-1,3-diamine (40.1 mg, 0.39 mmol), and NaI (23.6 mg, 0.15 mmol). The reaction mixture was stirred at 25° C. under N₂ balloon overnight. The residue was purified by prep-HPLC to give compound 5 (10 mg, 8% yield) as white solid. Molecular weight calculated: 785 g/mol. Determined by LC-MS: (M+H)+: 786.

Synthesis of tert-butyl 2-(5-(2,6-dimethoxyphenyl)-1-(2-isopropyl-4-(4-(methyl(3-(methylamino)propyl)amino)butanamido)phenyl)-1H-pyrazole-3-carboxamido)adamantane-2-carboxylate (5)

Synthesis of tri-tert-butyl 2,2',2''-(10-(2-((3-((4-((4-(3-((2-(tert-butoxycarbonyl)adamantan-2-yl)carbamoyl)-5-(2,6-dimethoxyphenyl)-1H-pyrazol-1-yl)-3-isopropylphenyl)amino)-4-oxobutyl)(methyl)amino)propyl)(methyl)amino)-2-oxoethyl)-1,4,7,10-tetraazacyclododecane-1,4,7-triyl)triacetate (6)

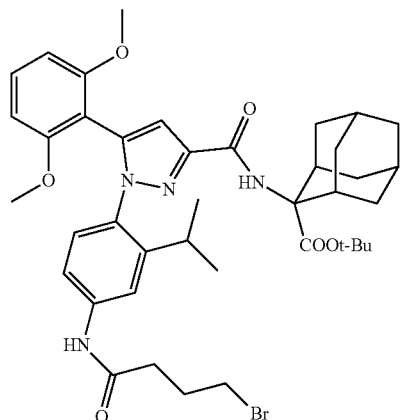

4

NaI / DMF →

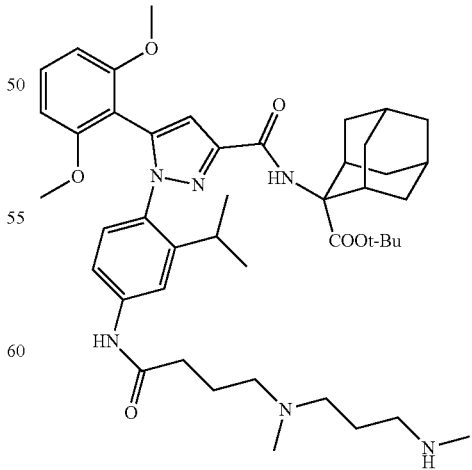

5

TBTU, DIEA / DMF →

-continued

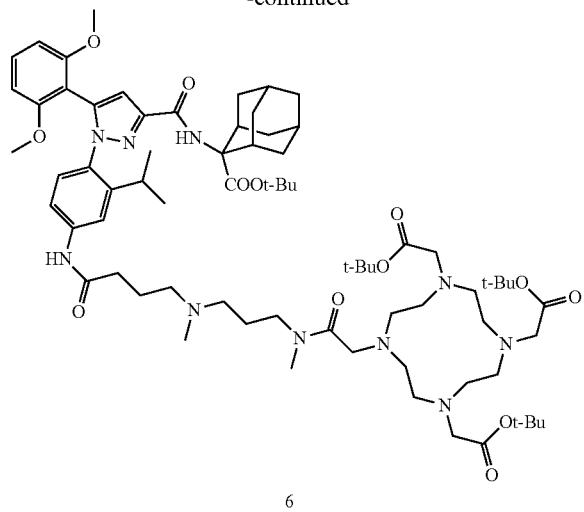

6

To a solution of DOTA-tris(t-Bu ester) (2-(4,7,10-tris(2-(tert-butoxy)-2-oxoethyl)-1,4,7,10-tetraazacyclododecan-1-yl)acetic acid) (10.9 mg, 0.02 mmol) in DMF (5 mL), was added TBTU (6.1 mg, 0.02 mmol) and DIEA (4.9 mg, 0.04 mmol). The reaction mixture was stirred at r.t. for 1 hr before the addition of compound 5 (10.0 mg, 0.01 mmol). The resulting mixture was stirred at r.t. overnight, then diluted with H₂O (20 mL) and extracted with EA (20 mL×3). The combined organic phases were dried over Na₂SO₄, filtered and concentrated to give compound 8 (20 mg, crude) as a yellow oil. Molecular weight calculated: 1339 g/mol. Determined by LC-MS: (M+H)+: 1340.

Synthesis of 2,2',2''-(10-(2-((3-((4-((4-(3-((2-carboxyadamantan-2-yl)carbamoyl)-5-(2,6-dimethoxyphenyl)-1H-pyrazol-1-yl)-3-isopropylphenyl)amino)-4-oxobutyl)(methy)amino)propyl)(methyl)amino)-2-oxoethyl)-1,4,7,10-tetraazacyclododecane-1,4,7-triyl)triacetic acid (I-5)

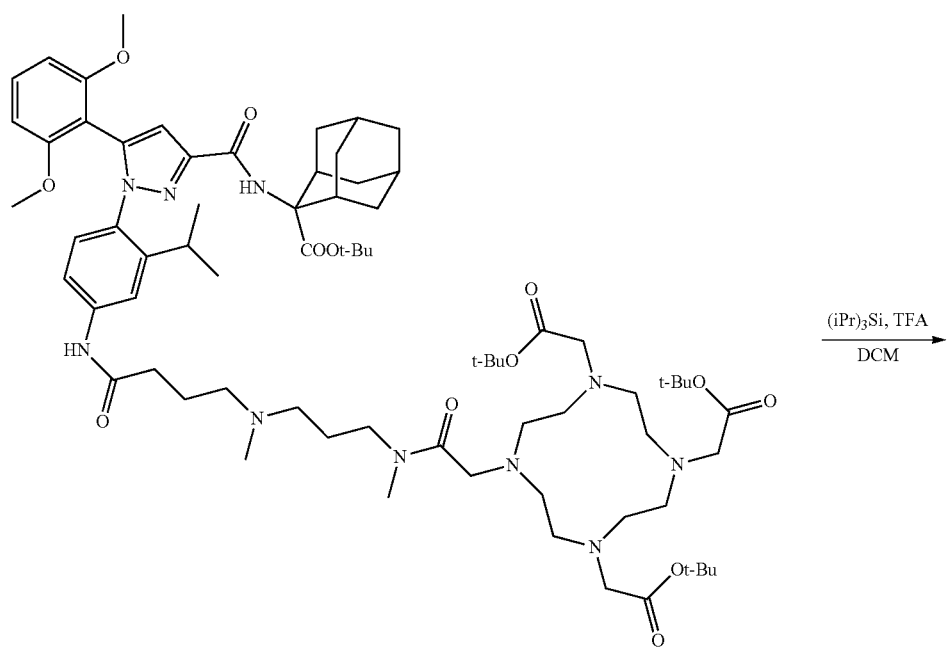

6

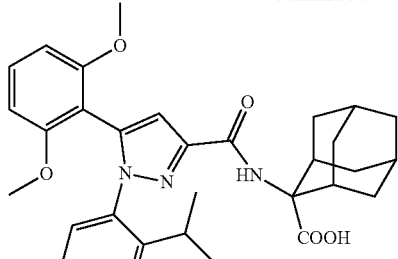
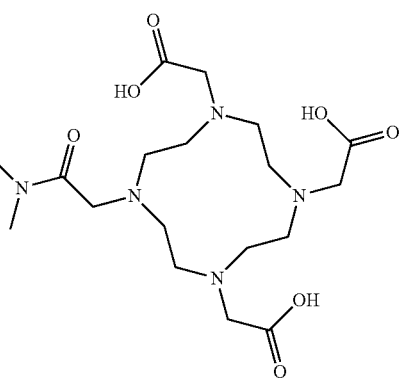
I-5
To a solution of compound 6 (20.1 mg, crude) in TFA/DCM (3/3 mL). (iPr)3SiH (1 drop) was added. The mixture was stirred at r.t. overnight. The solvent was removed by Rotavapor, and the residue was purified by prep-HPLC to give I-5 (5.4 mg, 34% yield) as a white solid. Molecular weight calculated: 1115.4 g/mol; Determined by LC-MS: (M+2H)2+: 558.8. Purity by UPLC (214 nm): >99%.
Example 6: Synthesis of I-6
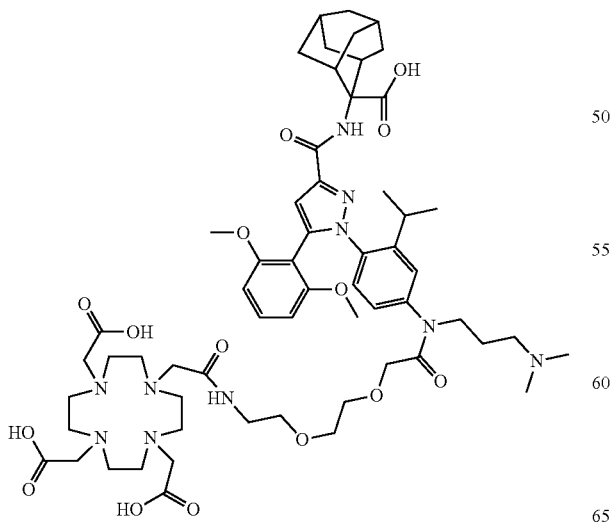

The Synthetic Route to I-6
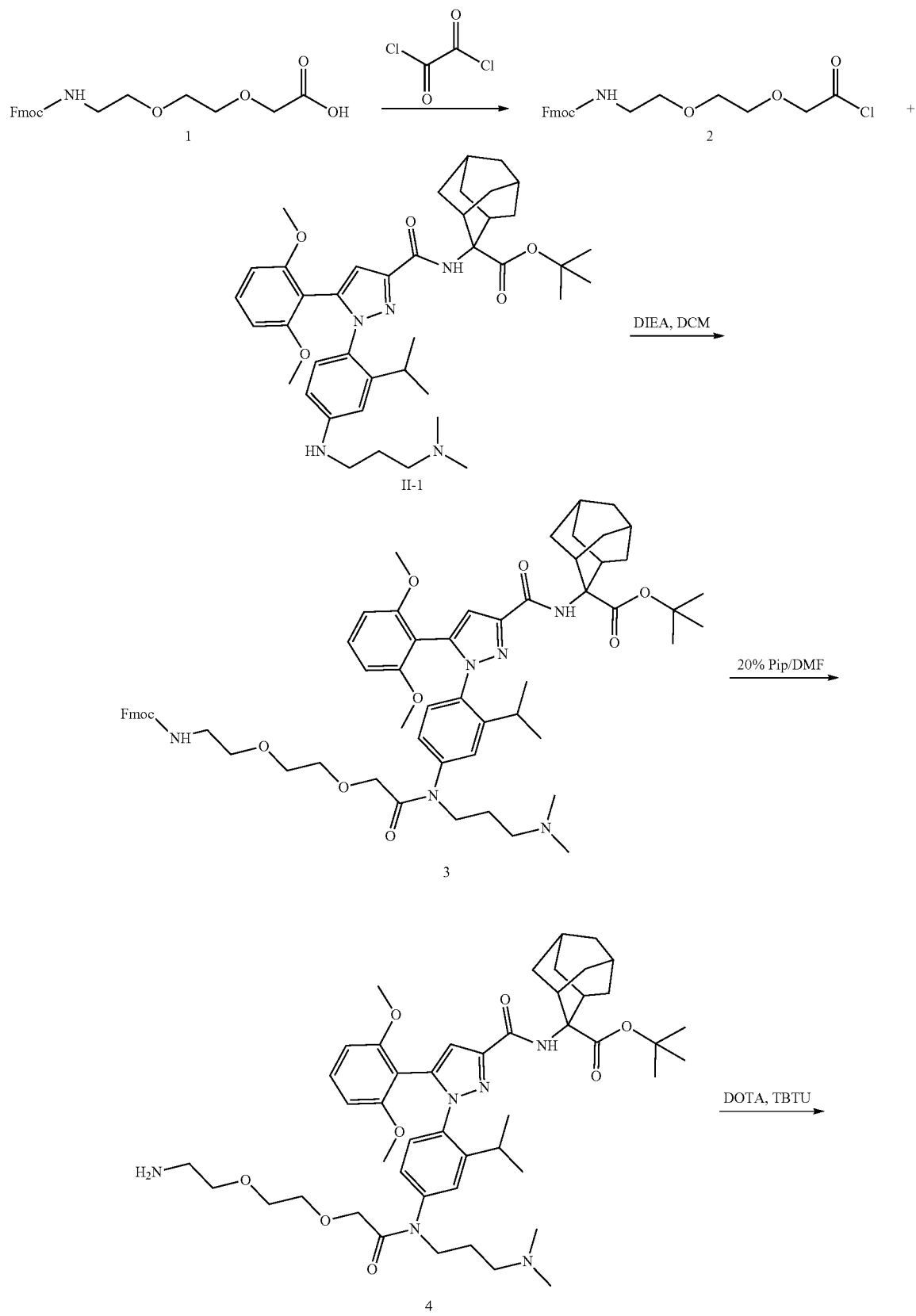

-continued

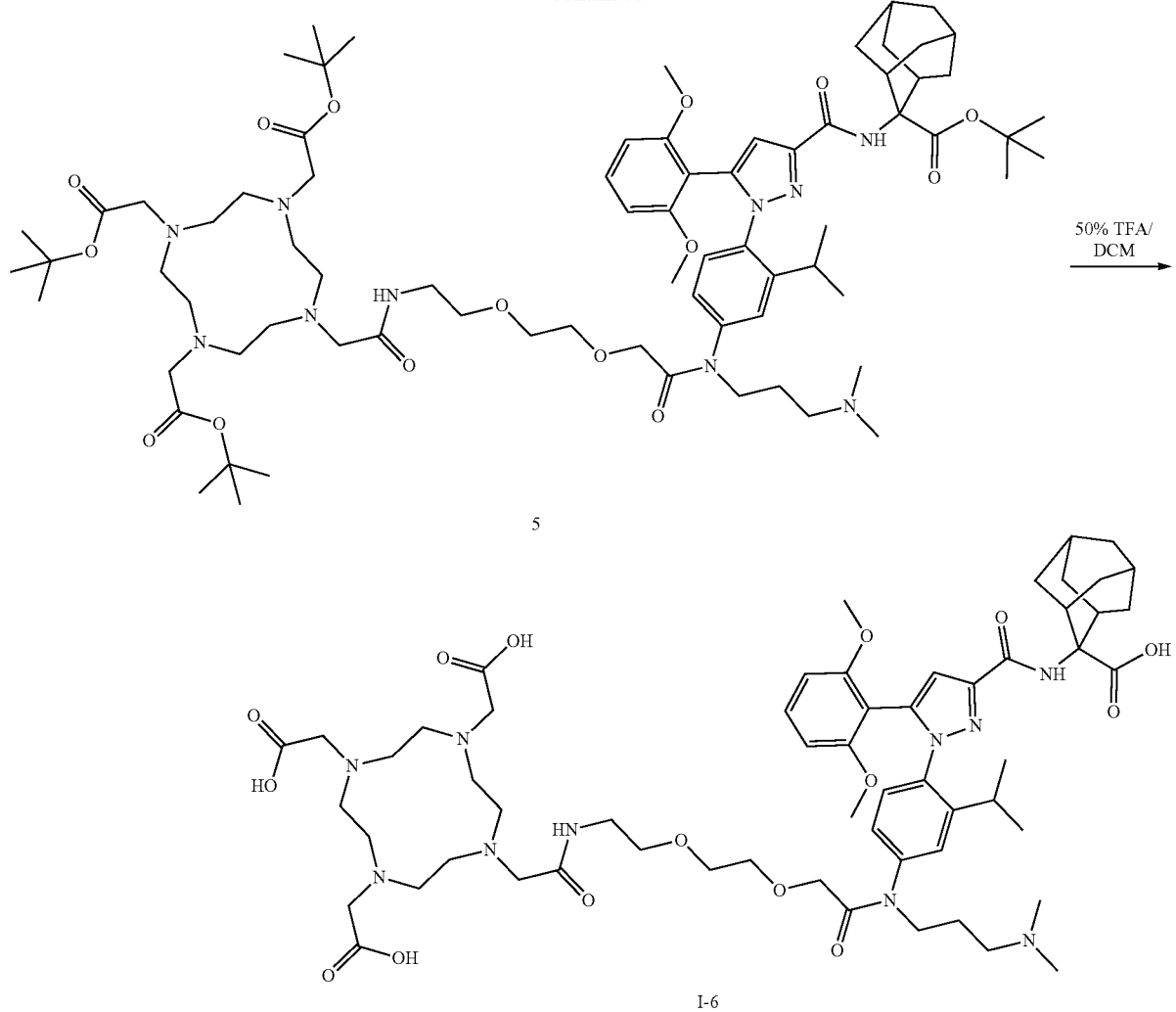

Synthesis of (9H-fluoren-9-yl)methyl(2-(2-(2-chloro-2-oxoethoxy)ethoxy)ethyl)carbamate (2)

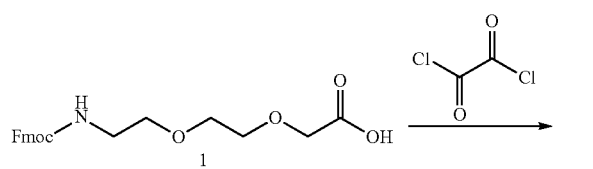

To a solution of compound 1 (560 mg, 1.45 mmol) in DCM (4 mL) was added oxalyl chloride (0.9 mL, 8.74 mmol) and DMF (0.05 mL) The reaction mixture was stirred at r.t. for 3 hr under N₂. The residue was concentrated and re-dissolved in DCM (4 mL).

Synthesis of Synthesis of tert-butyl-2-(1-(4-(2-(2-(2-aminoethoxy)ethoxy)-N-(3-(dimethylamino)propyl)acetamido)-2-isopropylphenyl)-5-(2,6-dimethoxyphenyl)-1H-pyrazole-3-carboxamido) adamantane-2-carboxylate (4)

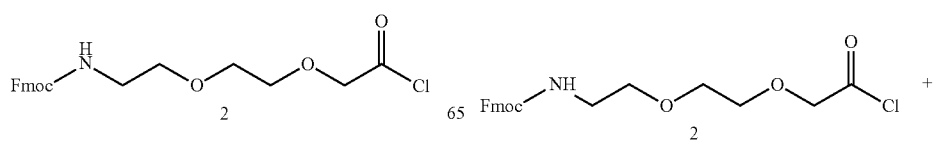

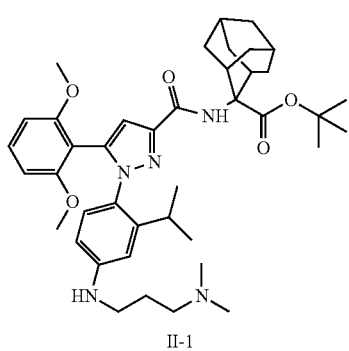

II-1

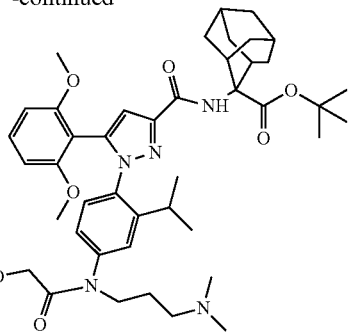

4

To a solution of compound II-1 (50 mg, 0.07 mmol) in DCM (1 mL) was added acyl chloride 2 in DCM solution (400 μL). The reaction mixture was stirred at r.t. for 3 hr. then concentrated. The residue was treated with 20% piperidine in DMF (0.25 mL) for 10 min. The crude solution was diluted by H$_2$O purified by prep-HPLC to give compound 5 (9 mg) as a white solid. Molecular weight calculated: 845.1 g/mol; Determined by LC-MS: (M+H)+: 848.1.

Synthesis of I-6

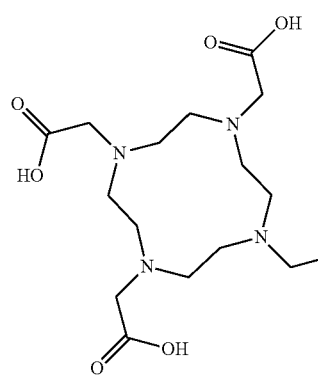

4

1. DOTA-Tris(t-Bu ester), TBTU, DIEA
2. 50% TFA/DCM

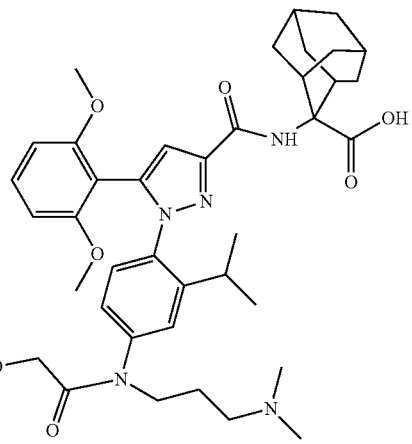

I-6

To a solution of compound 4 (9 mg, 0.012 mmol) in DMF (1 mL), was added DOTA-Tris (t-Bu ester) (8.1 mg, 0.014 mmoL), TBTU (6 mg, 0.018 mmoL) and DIEA (5 mg, 0.036 mmol). The reaction mixture was stirred at 25° C. for 2 hr. The residue was diluted with EA (5 mL) and extracted with H2O (5 mL×3). The combined organic phases were dried over Na$_2$SO$_4$, filtered and concentrated. The residue was treated with 50% TFA/DCM (2 mL) at r.t. for 16 hr. The solvent was removed by Rotavapor and the residue was purified by prep-HPLC to give I-6 (1.8 mg) as a white solid. Molecular weight calculated: 1175.4 g/mol; Determined by LC-MS: (M+2H)2+: 588.4; (M+3H)3+: 392.6. Purity by UPLC (214 nm): >99.0%.

Example 7: Synthesis of I-7

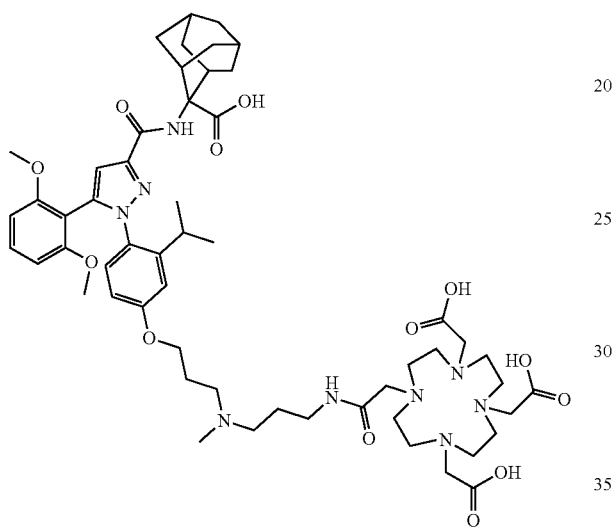

The Synthetic Route to I-7

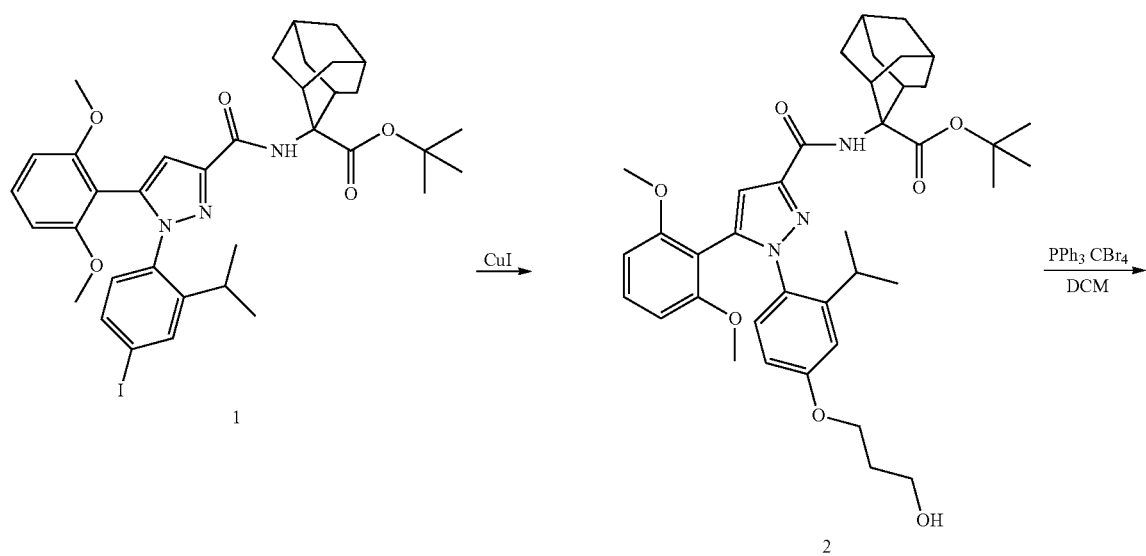

-continued
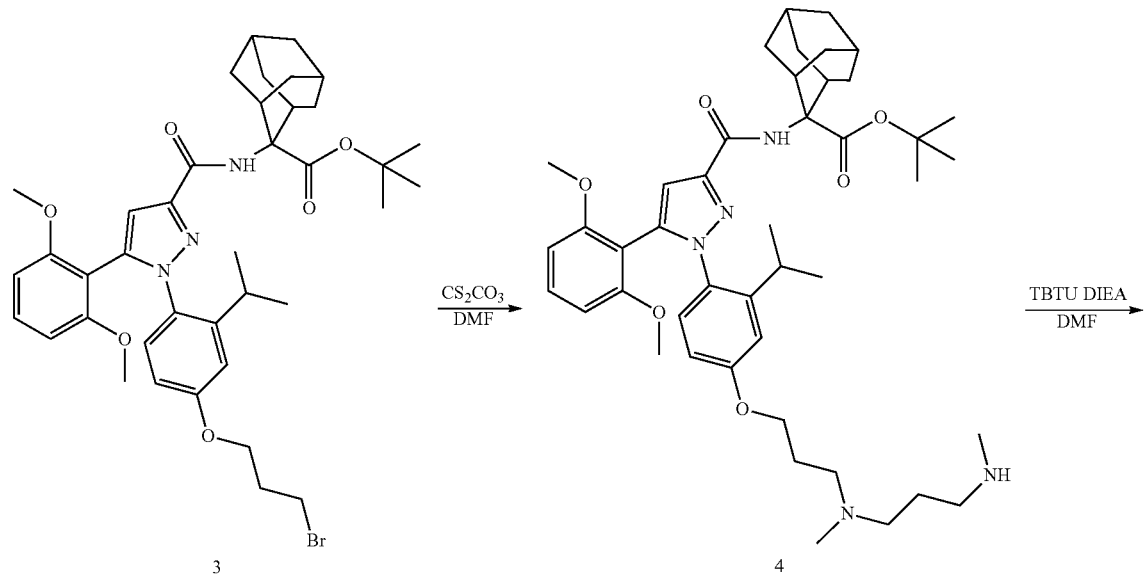
3 → 4
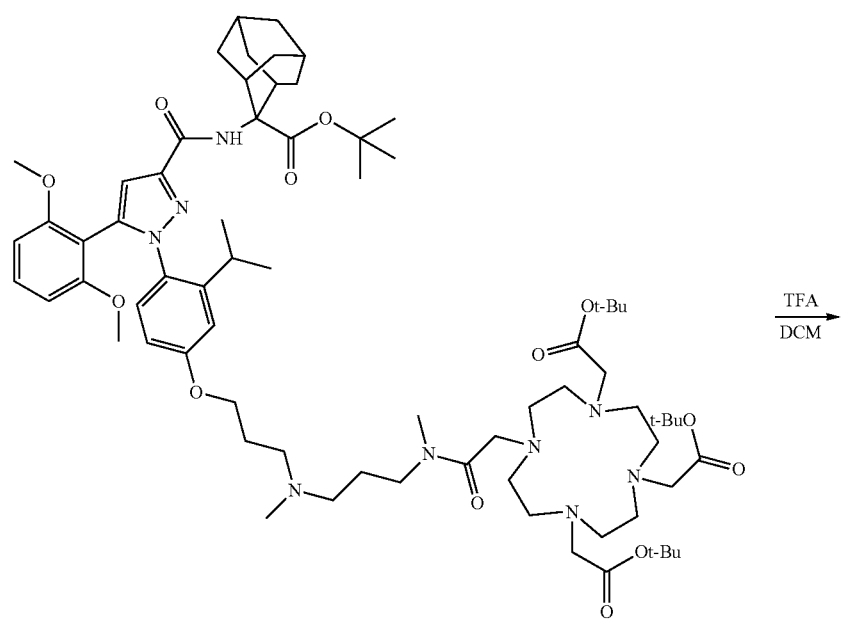
5

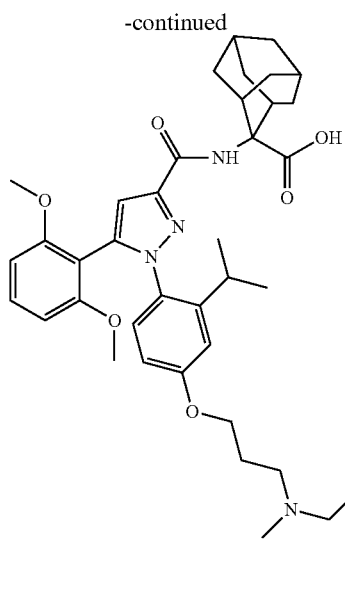

I-7

Synthesis of tert-butyl 2-(5-(2,6-dimethoxyphenyl)-1-(4-(3-hydroxypropoxy)-2-isopropylphenyl)-1H-pyrazole-3-carboxamido)adamantane-2-carboxylate (2)

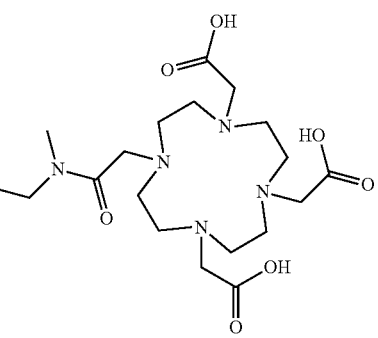

2

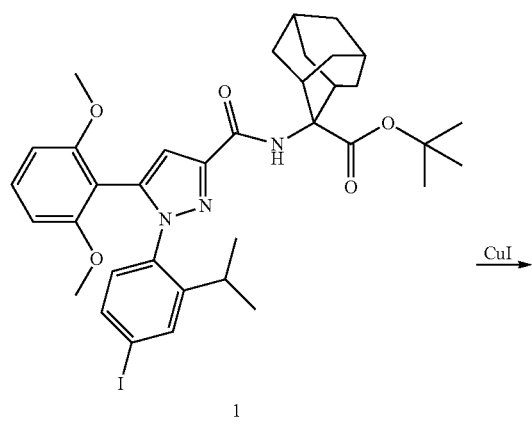

1

To a solution of compound 1 (600 mg, 0.83 mmol) in propane-1,3-diol (15 mL) was added CuI (158.1 mg, 0.83 mmol) and $Cs_2CO_3$ (808.6 mg, 2.48 mmol). The reaction mixture was stirred at 120° C. under $N_2$ balloon overnight. The residue was diluted with $H_2O$ (20 mL) and extracted with EA (20 mL×2). The combined organic phase was dried over $Na_2SO_4$, filtered and concentrated. The residue was purified by flash chromatography on silica gel (PE/EA=1/1) to give compound 2 (400 mg, 72% yield) as a yellow solid. Molecular weight calculated: 673.9 g/mol: Determined by LC-MS: (M+H)+: 674.8.

133

Synthesis of tert-butyl 2-(1-(4-(3-bromopropoxy)-2-isopropylphenyl)-5-(2,6-dimethoxyphenyl)-1H-pyrazole-3-carboxamido)adamantane-2-carboxylate (3)

134

Synthesis of tert-butyl 2-(5-(2,6-dimethoxyphenyl)-1-(2-isopropyl-4-(3-(methyl(3-(methylamino)propyl)amino)propoxy)phenyl)-1H-pyrazole-3-carboxamido)adamantane-2-carboxylate (4)

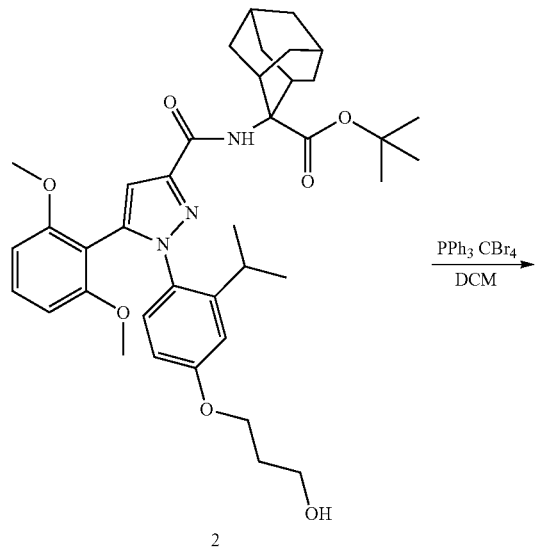

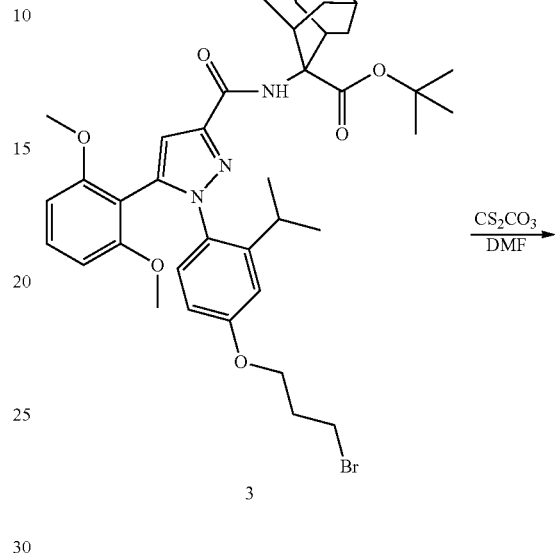

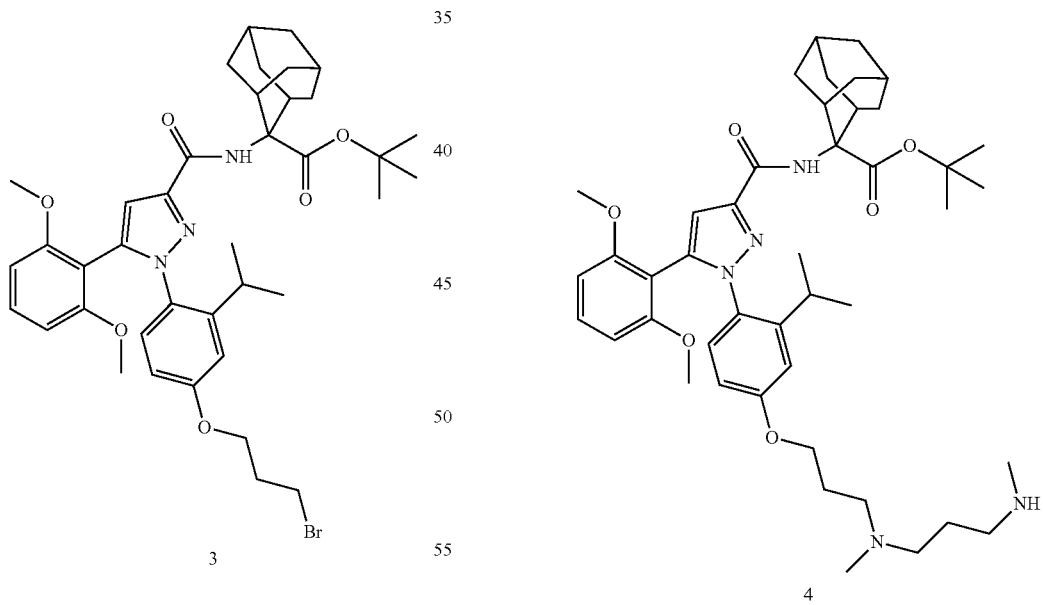

To a solution of compound 2 (50 mg, 0.07 mmol) in DCM (2 mL), was added PPh$_3$ (27.5 mg, 0.11 mmol) and CBr$_4$ (36.5 mg, 0.11 mmol). The reaction mixture was stirred at r.t. overnight. The residue was diluted with H$_2$O (10 mL) and extracted with DCM (10 mL×2). The combined organic phase was dried over Na$_2$SO$_4$, filtered and concentrated. The residue was purified by flash chromatography on silica gel (PE/EA=2/1) to give compound 3 (27.3 mg, 50% yield) as a yellow solid. Molecular weight calculated: 736.8 g/mol; Determined by LC-MS: (M+H)+: 737.8.

To a solution of compound 3 (95 mg, 0.13 mmol) in DMF (2 mL) was added N$^1$N$^3$-dimethylpropane-1,3-diamine (64.5 mg, 0.63 mmol) and Cs$_2$CO$_3$ (127.1 mg, 0.39 mmol). The reaction mixture was stirred at 80° C. under N$_2$ balloon overnight. The reaction mixture was concentrated and the residue was purified by Prep-HPLC to give compound 4 (30 mg, 31% yield) as a white solid. Molecular weight calculated: 758.0 g/mol; Determined by LC-MS: (M+H)+: 759.0.

Synthesis of tri-tert-butyl 2,2',2"-(10-(2-((3-((3-(4-(3-((2-(tert-butoxycarbonyl)adamantan-2-yl)carbamoyl)-5-(2,8-dimethoxyphenyl)-1H-pyrazol-1-yl)-3-isopropylphenoxy)propyl)(methyl)amino)propyl)(methyl)amino)-2-oxoethyl)-1,4,7,10-tetraazacyclododecane-1,4,7-triyl)triacetate (5)

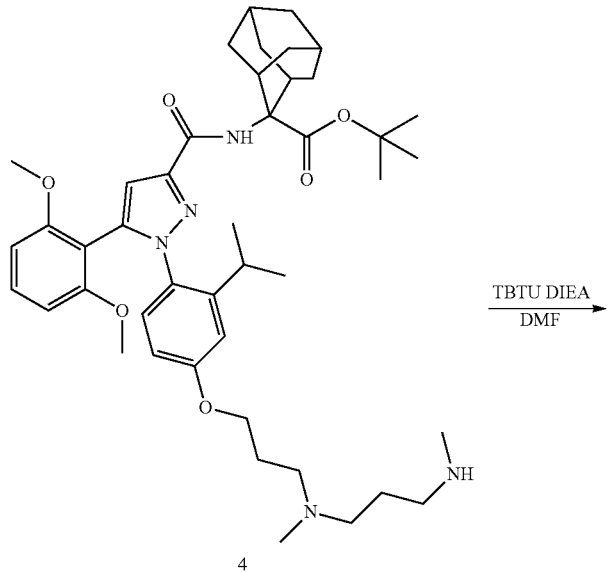

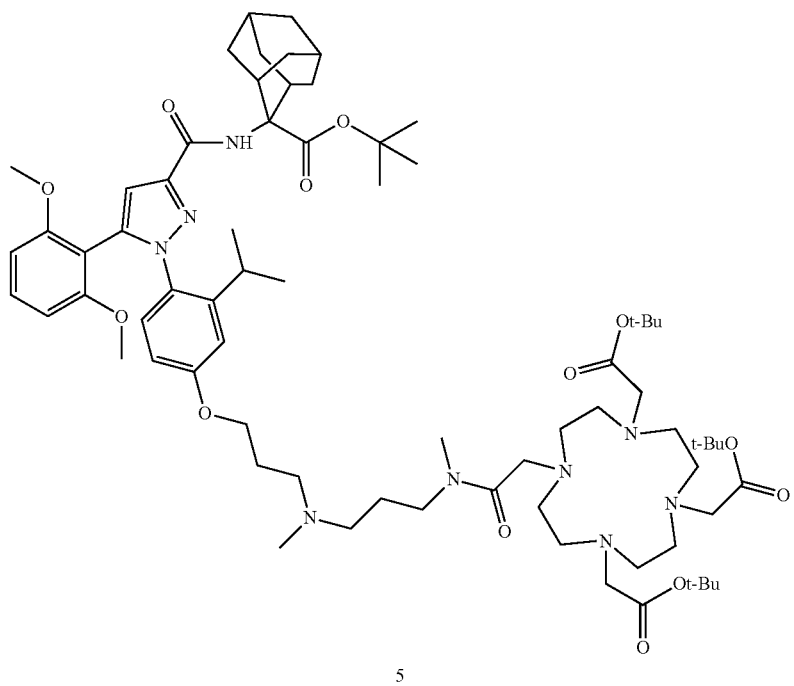

A mixture of DOTA-Tris (t-Bu ester) (2-(4,7,10-tris(2-(tert-butoxy)-2-oxoethyl)-1,4,7,10-tetraazacyclododecan-1-yl)acetic acid) (15 mg, 0026 mmol), TBTU (85 mg, 0.026 mmol), DIEA (4 mg, 0.026 mmol) in DMF (1 ml) was stirred at r.t. for 1 hr before the addition of compound 4 (10 mg, 0.013 mmol). The reaction mixture was stirred for 2 hr at 25° C. under $N_2$ balloon. The residue was diluted with $H_2O$ (20 mL) and extracted with EA (20 mL×2). The combined organic phase was dried over $Na_2SO_4$, filtered and concentrated to give compound 5 (10 mg, crude) as a yellow oil. Molecular weight calculated: 1311.8 g/mol; Determined by LC-MS: (M+2H)2+: 657.0.

Synthesis of 2,2',2"-(10-(2-((3-((3-(4-(3-((2-carboxyadamantan-2-yl)carbamoyl)-5-(2,6-dimethoxyphenyl)-1H-pyrazol-1-yl)-3 isopropylphenoxy)propyl)(methyl)amino)propyl)(methyl)amino)-2-oxoethyl)-1,4,7,10-tetraazacyclododecane-1,4,7-triyl)triacetic acid (I-7)

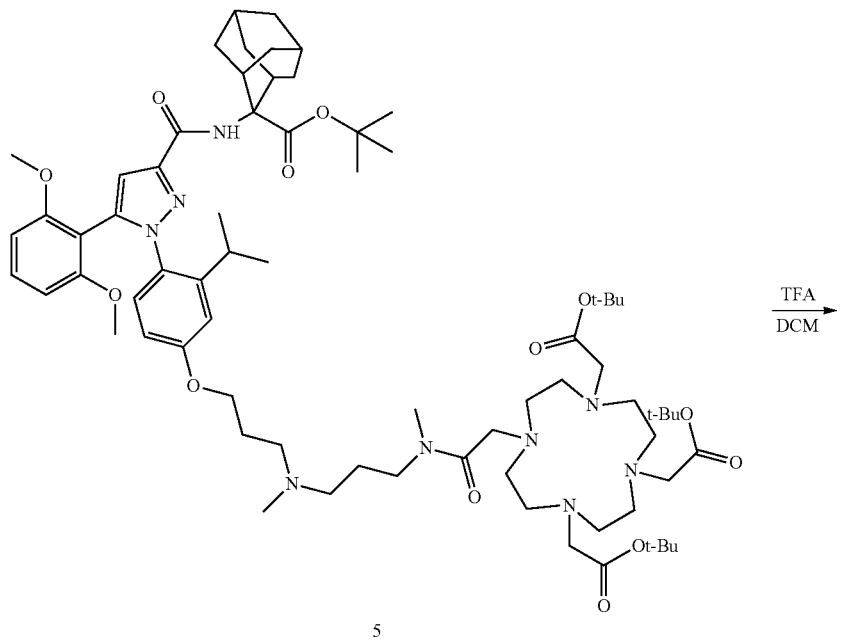

5

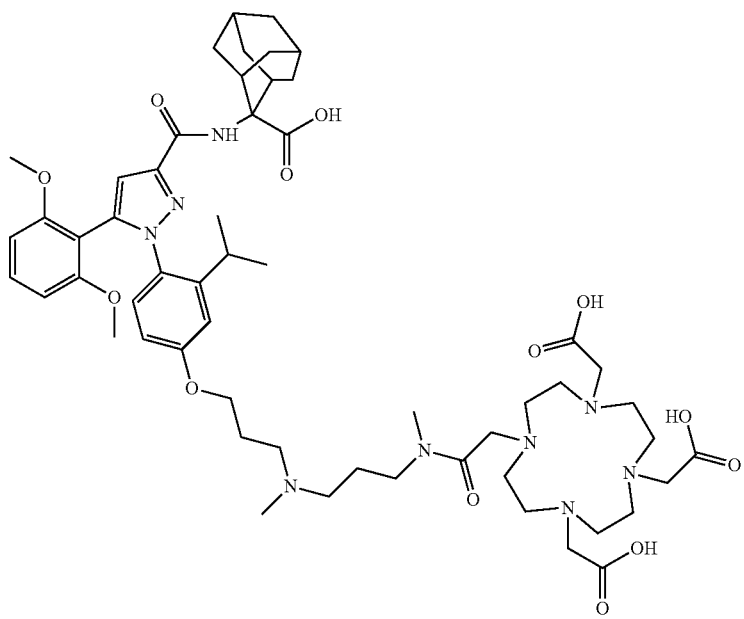

I-7

To a solution of compound 5(10 mg, crude) in TFA/DCM (I/mL), (iPr)₃Si (1 drop) was added, and the mixture was stirred at r.t. overnight. The solvent was removed by Rotavapor, and the residue was purified by prep-HPLC to give I-7 (4.3 mg, 52% yield) as a white solid. Molecular weight calculated: 1087.6 g/mol; Determined by LC-MS: (M+2H) 2+: 545.0. Purity by UPLC (214 nm): 96.6%.

Example 8: Synthesis of I-8
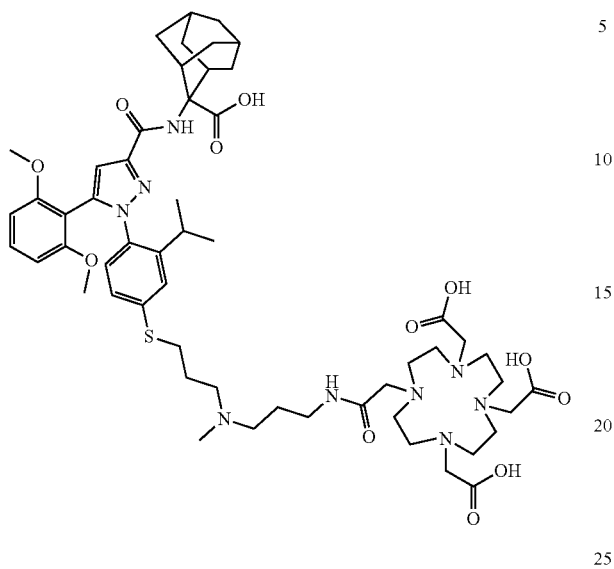
The Synthetic Route to I-8
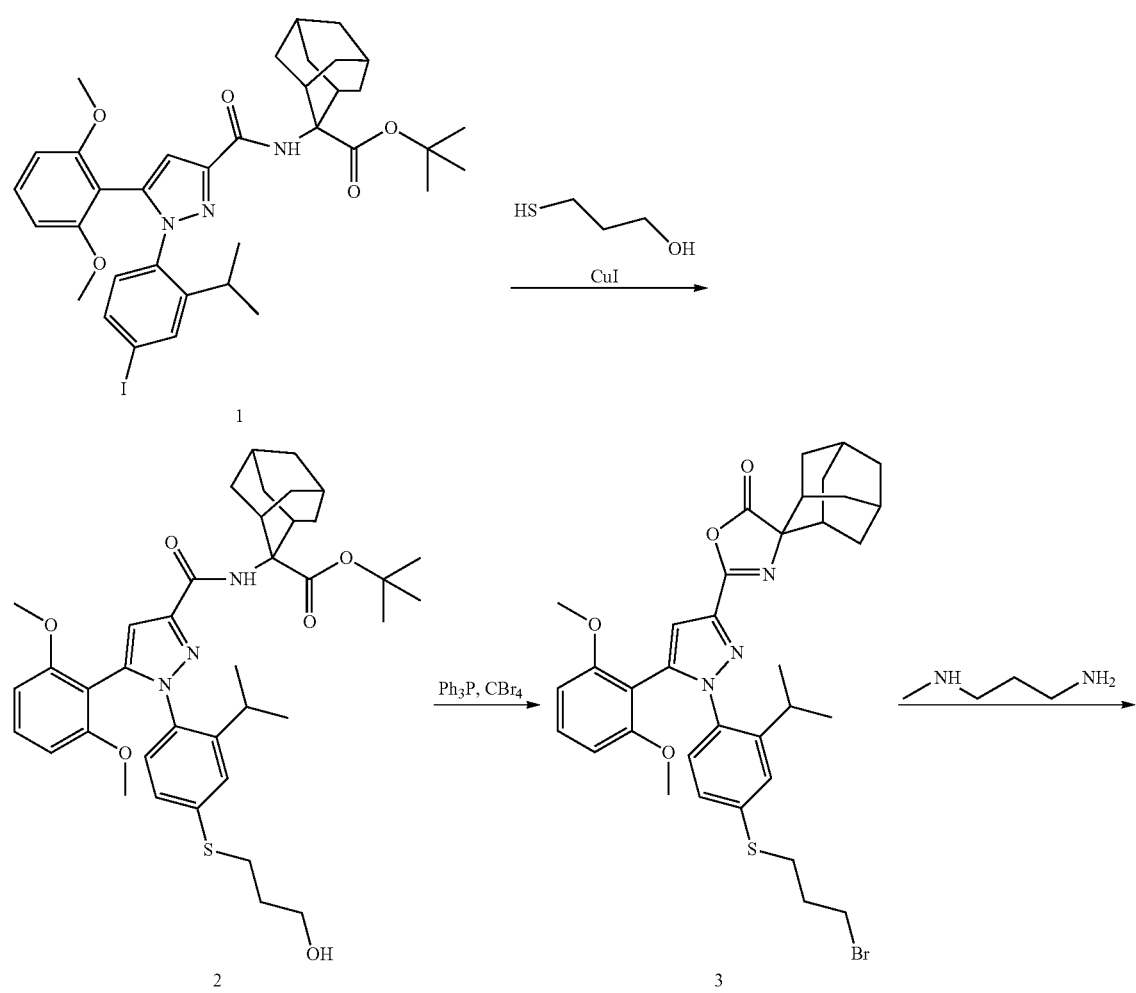

-continued
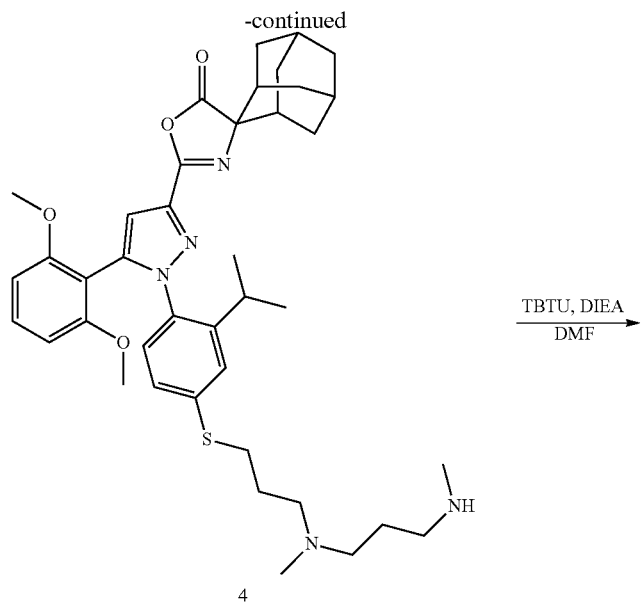
4
TBTU, DIEA
DMF →
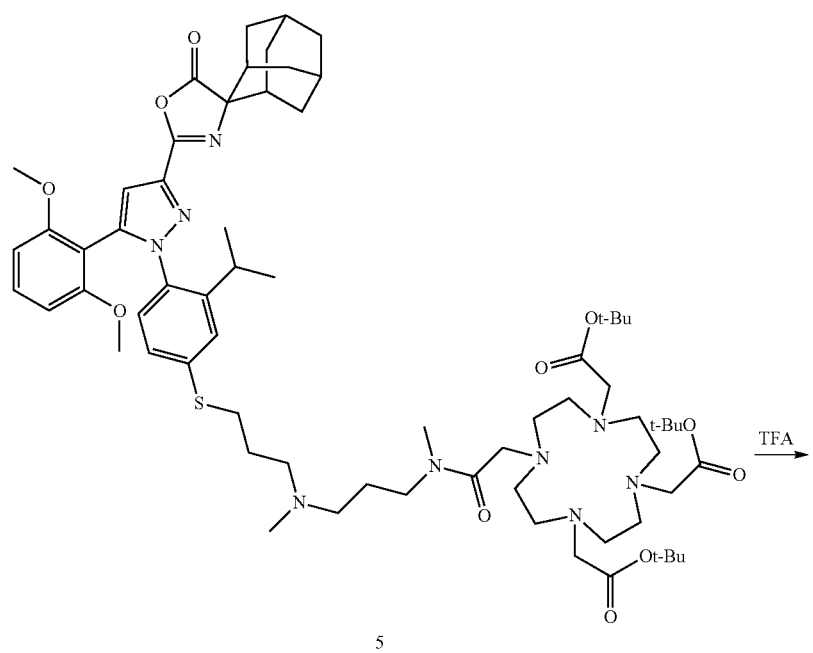
5
TFA →

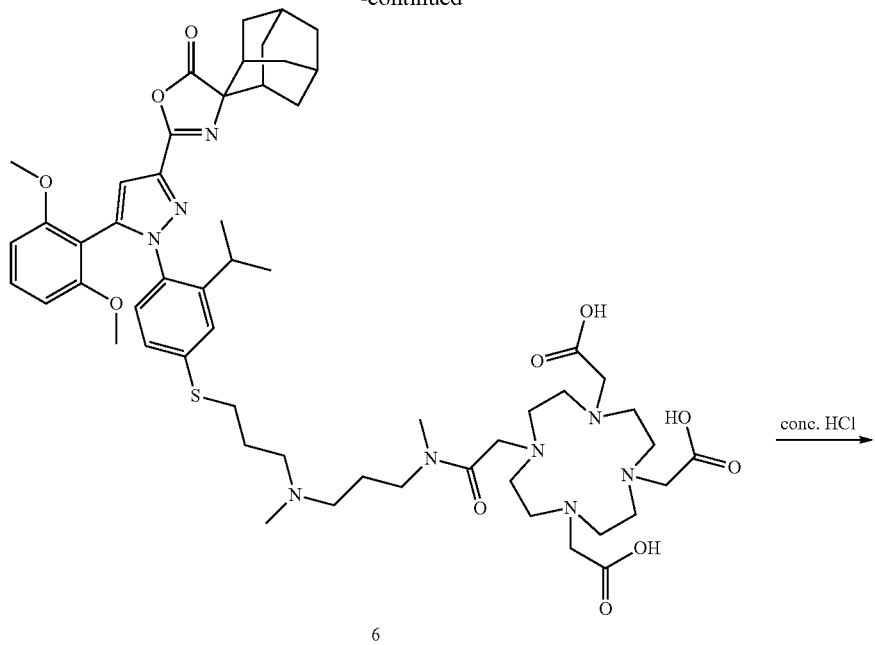
6
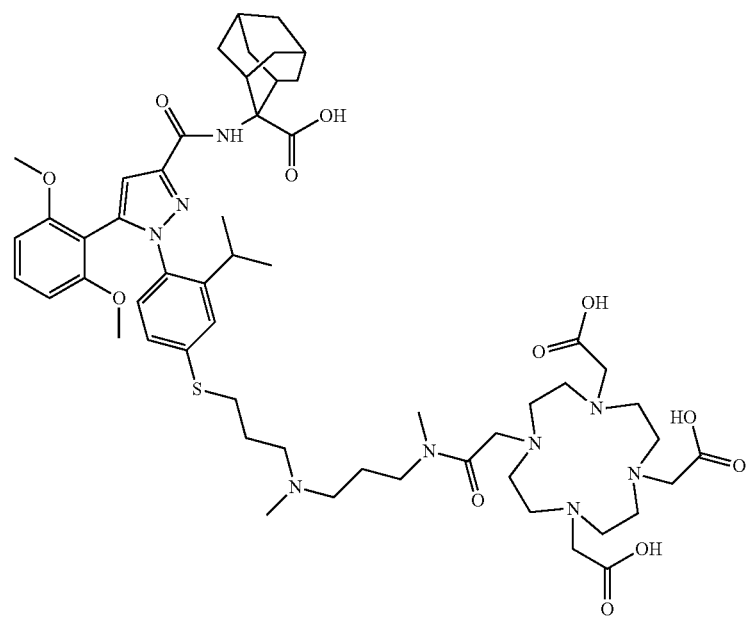
I-8

145

Synthesis of tert-butyl 2-(5-(2,6-dimethoxyphenyl)-1-(4-((3-hydroxypropyl)thio)-2-isopropylphenyl)-1H-pyrazole-3-carboxamido)adamantane-2-carboxylate (2)

146

Synthesis of 2'-(1-(4-((3-bromopropyl)thio)-2-isopropylphenyl)-5-(2,6-dimethoxyphenyl)-1H-pyrazol-3-yl)-5'H-spiro[adamantane-2,4'-oxazol]-5'-one (3)

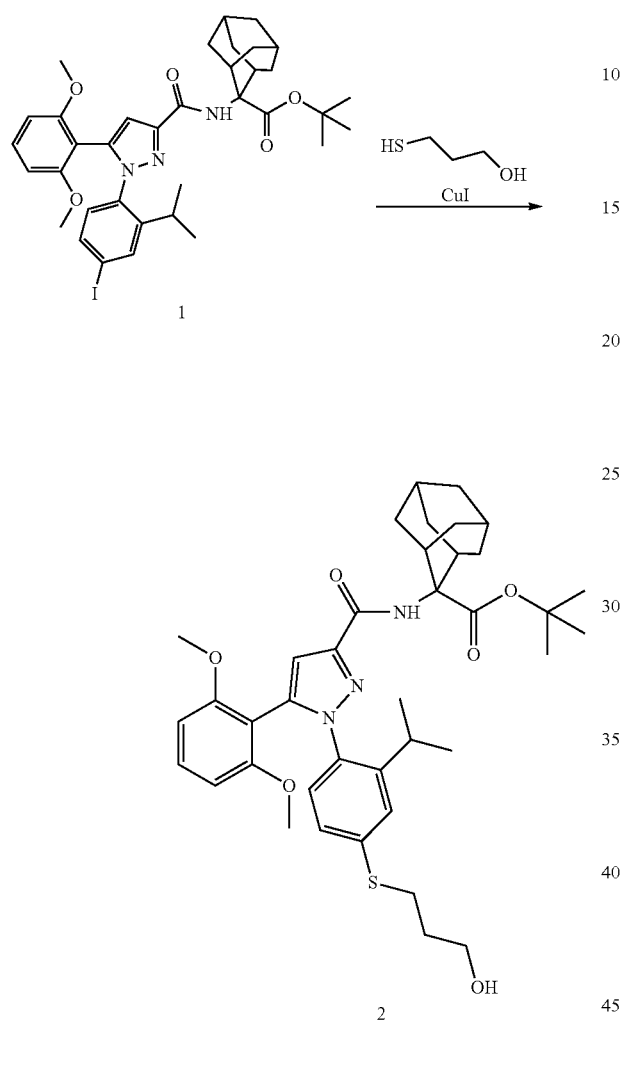

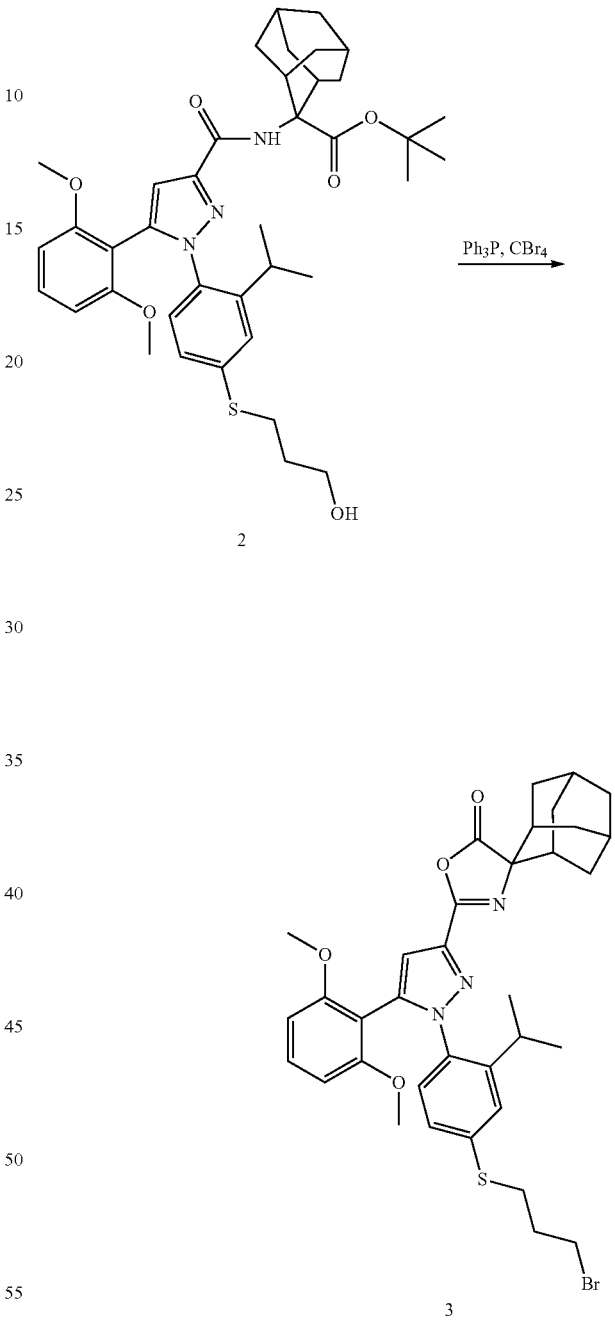

To a solution of compound 1 (500 mg, 0.69 mmol) in DMSO (10 mL) was added 3-mercaptopropan-1-ol (317 mg, 3.4 mmol), $CS_2CO_3$ (674 mg, 2.07 mmol) and CuI (131 mg, 0.89 mmol). The reaction mixture was stirred at 120° C. under $N_2$ balloon overnight. The residue was diluted with $H_2O$ (20 mL) and extracted with EA (20 mL×2). The combined organic phase was dried over $Na_2SO_4$, filtered and concentrated. The residue was purified by flash chromatography on reverse phase silica gel (ACN/H2O=2%~65%, 35 min) to give compound 2 (300 mg, 63% yield) as a white solid. Molecular weight calculated: 689.9 g/mol; Determined by LC-MS: (M+H)+: 690.9.

To a solution of compound 2 (250 mg, 0.38 mmol) in ACN (5 mL) was added $Ph_3P$ (427 mg, 1.63 mmol) and $CBr_4$ (541 mg, 1.63 mmol), and the mixture was stirred at 60° C. for 2 hr. The solvent was then removed by Rotavapor, and the residue was purified by flash chromatography on reverse phase silica gel (PE/EA=9/1) to give compound 3 (160 mg, 65% yield) as a white sold. Molecular weight calculated: 678.7 g/mol; Determined by LC-MS: (M+H)+: 679.7.

Synthesis of 2'-(5-(2,6-dimethoxyphenyl)-1-(2-isopropyl-4-((3-(methyl(3-(methylamino)propyl)amino)propyl)thio)phenyl)-1H-pyrazol-3-yl)-5'H-spiro[adamantane-2,4'-oxazol]-5'-one (4)

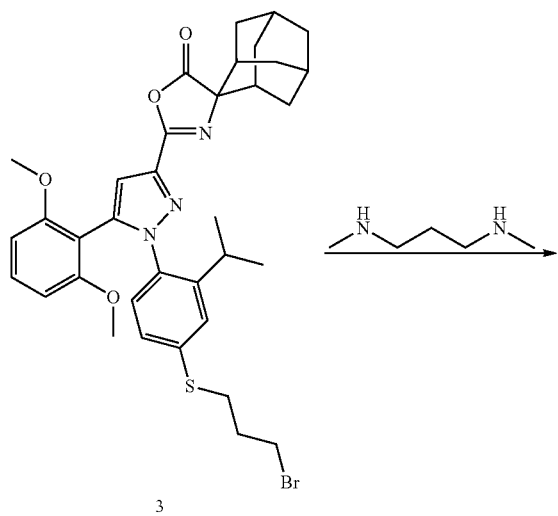

3

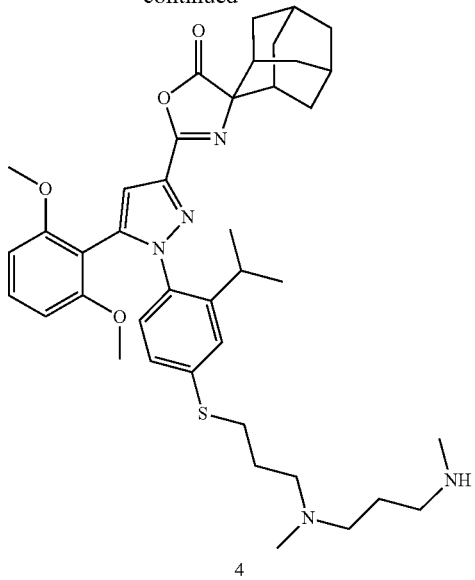

4

To a solution of compound 3 (20 mg, 0.03 mmol) in ACN (2 mL) was added $N^1,N^3$-dimethylpropane-1,3-diamine (9 mg, 0.09 mmol), KI (10 mg, 0.06 mmol), and $K_2CO_3$ (8.1 mg, 0.06 mmol). The resulting mixture was stirred at 80° C. under $N_2$ for 2 hr, filtered and the filtrate was concentrated and used directly in the next step. Molecular weight calculated: 700.0 g/mol; Determined by LC-MS: (M+H)+: 701.0.

Synthesis of tri-tert-butyl 2,2',2"-(10-(2-((3-((3-((4-(5-(2,6-dimethoxyphenyl)-3-(5'-oxo-5'H-spiro[adamantane-2,4'-oxazol]-2'-yl)-1H-pyrazol-1-yl)-3-isopropylphenyl)thio)propyl)(methyl)amino)propyl)(methyl)amino)-2-oxoethyl)-1,4,7,10-tetraazacyclododecane-1,4,7-triyl)triacetate (5)

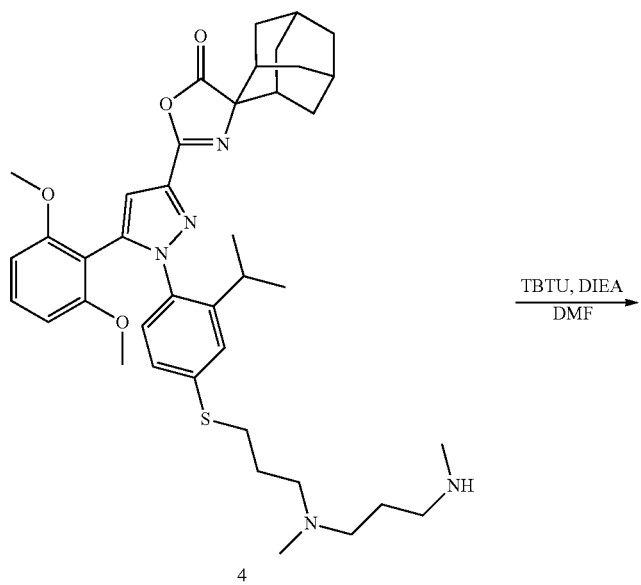

4

TBTU, DIEA
————————→
DMF

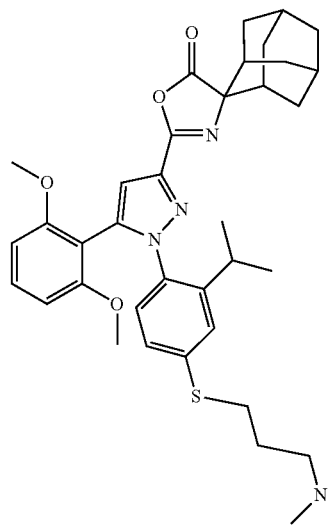

5

A mixture of DOTA Tris(t-Bu ester) (2-(4,7,10-tris(2-(tert-butoxy)-2-oxoethyl)-1,4,7,10-tetraazacyclododecan-1-yl)acetic acid) (33 mg, 0.057 mmol), TBTU (18.3 mg, 0.057 mmol), and DIEA (7.4 mg, 0.057 mmol) in DMF (1 mL) was stirred at r.t. for 1 hr before the addition of compound 4. The resulting reaction solution was stirred for 2 hr at 25° C. under $N_2$ balloon, then diluted with $H_2O$ (20 mL) and extracted with EA (20 mL×2). The combined organic phase was dried over $Na_2SO_4$, filtered and concentrated to give compound 6 (20 mg, crude) as a yellow oil. Molecular weight calculated: 1253.7 g/mol; Determined by LC-MS: (M+2H)2+: 628.0.

Synthesis of 2,2',2''-(10-(2-((3-((3-((4-(5-(2,6-dimethoxyphenyl)-3-(5'-oxo-5'H-spiro[adamantane-2,4'-oxazol]-2'-yl)-1H-pyrazol-1-yl)-3-isopropylphenyl)thio)propyl)(methy)amino)propyl)(methyl)amino)-2-oxoethyl)-1,4,7,10-tetraazacyclododecane-1,4,7-triyl)triacetic acid (8)

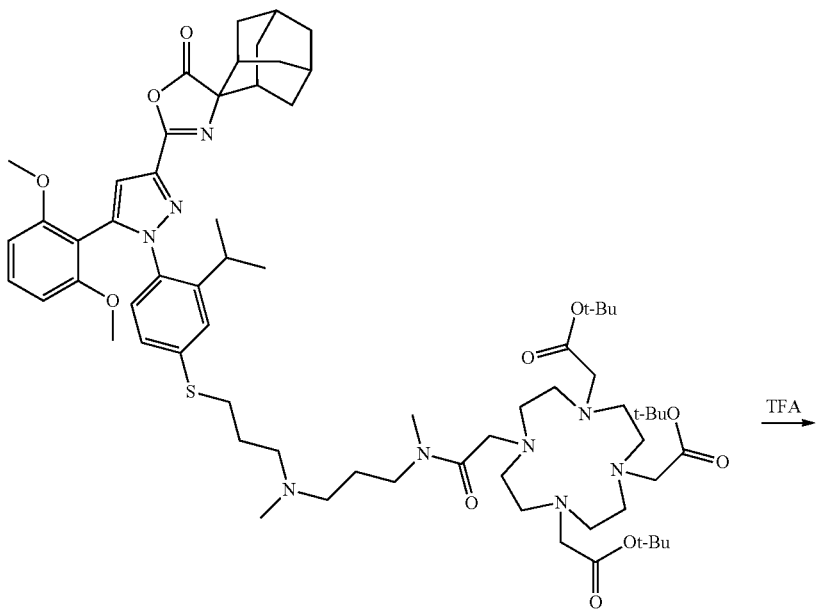

5

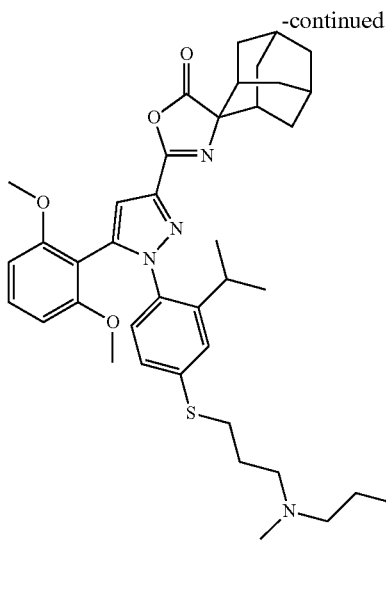

6

To a solution of compound 5 (20 mg, crude) in TFA/DCM (1/1 mL), was added 1 drop of (iPr)3Si. The resulting mixture was stirred at r.t. overnight. The solvent was removed in vacuo to give compound 6 (20 mg, crude) as a yellow oil. Molecular weight calculated: 1085.6 g/mol; Determined by LC-MS: (M+2H)2+: 543.8.

Synthesis of 2,2',2''-(10-(2-((3-((3-((4-(3-((2-carboxyadamantan-2-yl)carbamoyl)-5-(2,6-dimethoxyphenyl)-1H-pyrazol-1-yl)-3-isopropylphenyl)thio)propyl)(methyl)amino)propyl)(methyl)amino)-2-oxoethyl)-1,4,7,10-tetraazacyclododecane-1,4,7-triyl)triacetic acid (I-8)

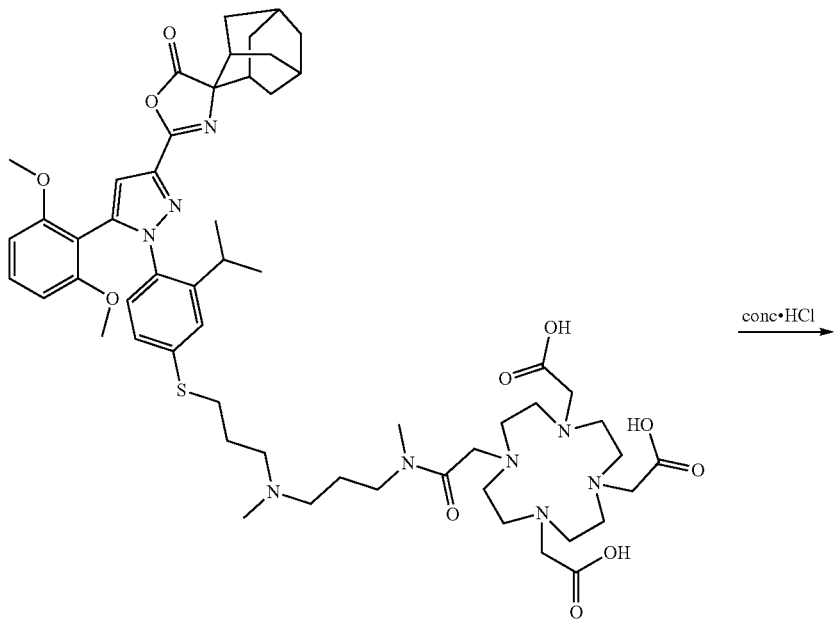

6

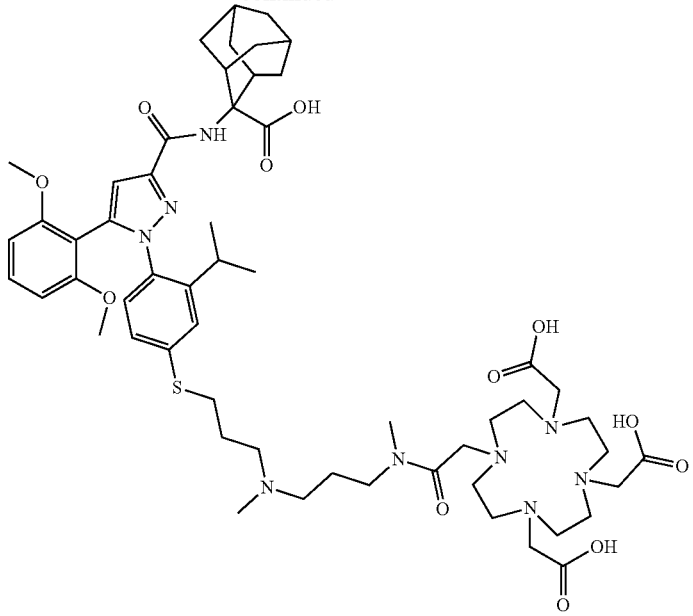
I-8
To a solution of compound 6 (20 mg, crude) In ACN (1 mL), was added one drop of conc. HCl. The resulting mixture was stirred at r.t. for 0.5 h, then the solvent was removed by Rotovapor and the residue was purified by prep-HPLC to give I-8 (5.5 mg, 27% yield) as a white solid. Molecular weight calculated: 1103.6 g/mol; Determined by LC-MS: (M+2H)2+: 553.0. Purity by UPLC (214 nm): 91.2%.
Example 9: Synthesis of I-9
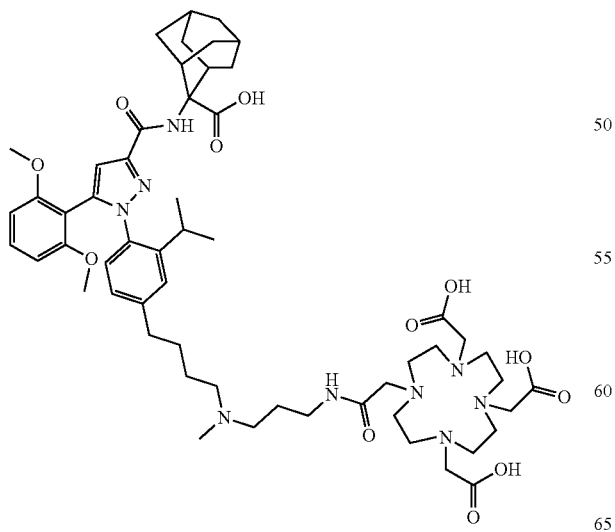

The Synthetic Route of I-9
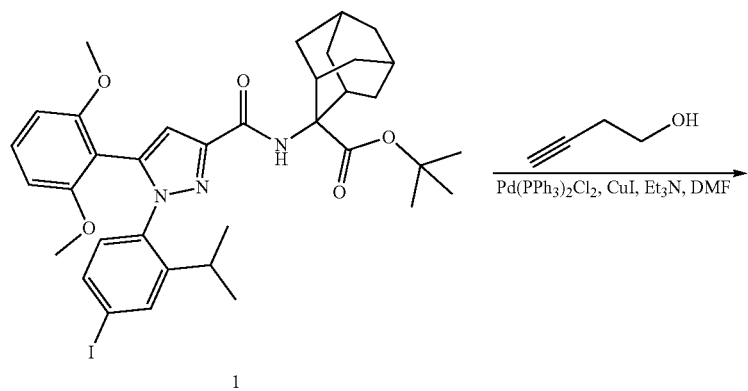
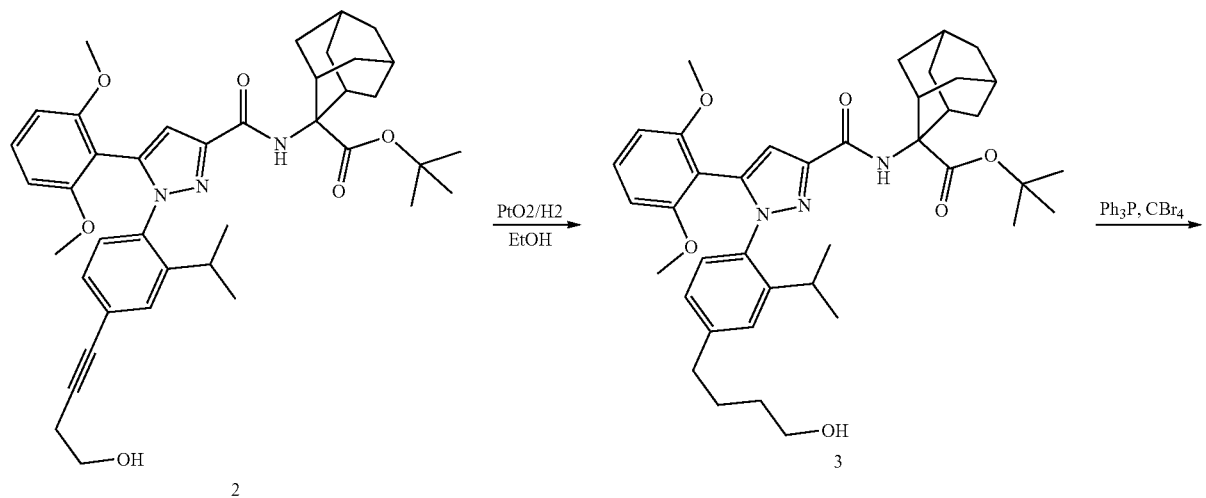
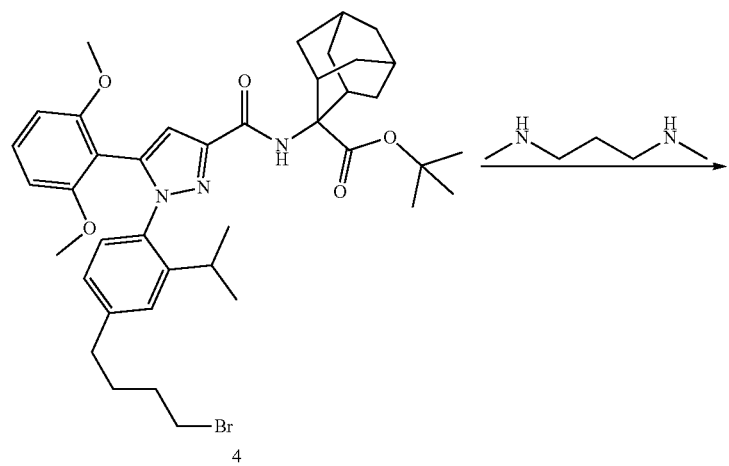

-continued
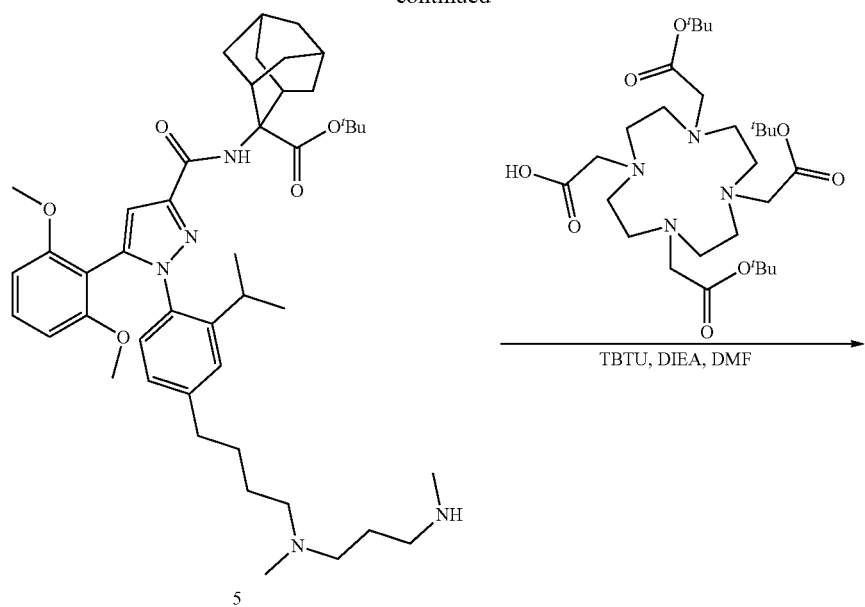
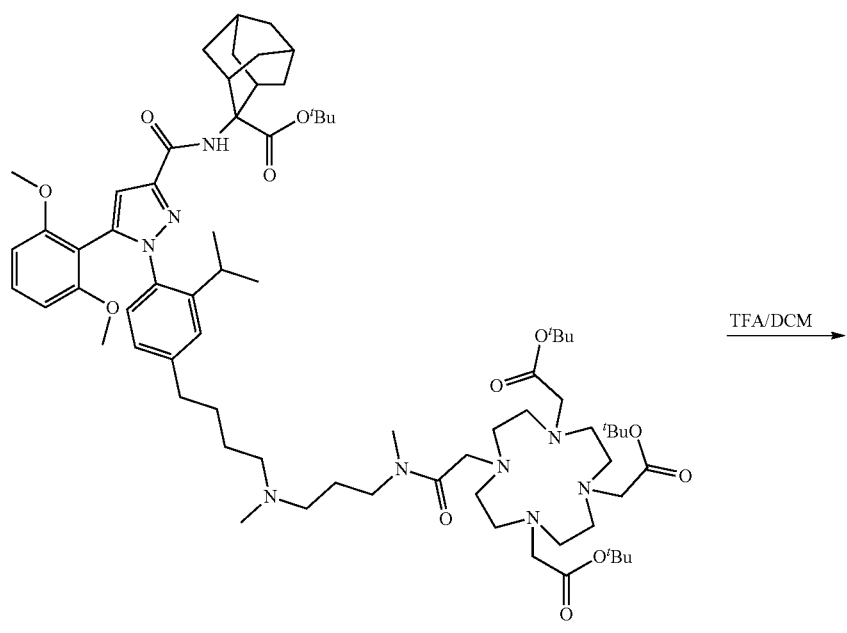

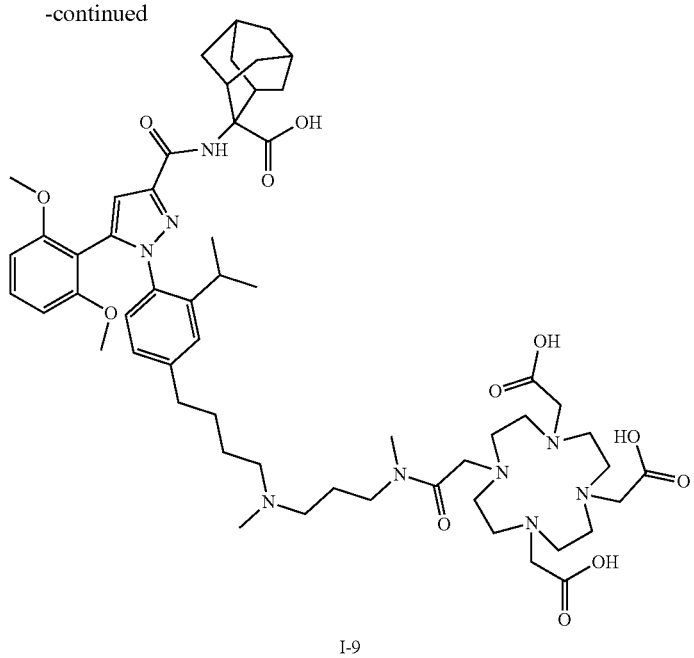

I-9

Synthesis of tert-butyl 2-(5-(2,6-dimethoxyphenyl)-1-(4-(4-hydroxybut-1-yn-1-yl)isopropylphenyl)-1H-pyrazole-3-carboxamido)adamantane-2-carboxylate (2)

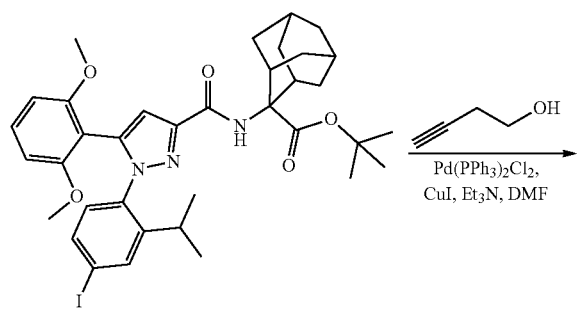

To a solution of compound 1 (500 mg, 0.69 mmol) in DMF (4 mL) was added but-3-yn-1-ol (96.6 mg, 1.38 mmol), Pd(PPh$_3$)$_2$Cl$_2$ (98.7 mg, 0.14 mmol), triethylamine (0.5 ml) and CuI (52.4 mg, 0.27 mmol). The reaction mixture was stirred at 120° C. for 3 hr under N$_2$ balloon, then diluted with H$_2$O (20 mL) and extracted with EA (20 mL×2). The combined organic phase was dried over Na$_2$SO$_4$, filtered and concentrated. The residue was purified by flash chromatography on reverse phase silica gel (PE/EA=72/28) to give compound 2 (460 mg, 100% yield) as a yellow solid. Molecular weight calculated: 667.4 g/mol; Determined by LC-MS: (M+H)+: 668.6.

Synthesis of tert-butyl 2-(5-(2,6-dimethoxyphenyl)-1-(4-(4-hydroxybutyl)-2-isopropylphenyl)-1H-pyrazole-3-carboxamido)adamantane-2-carboxylate (3)

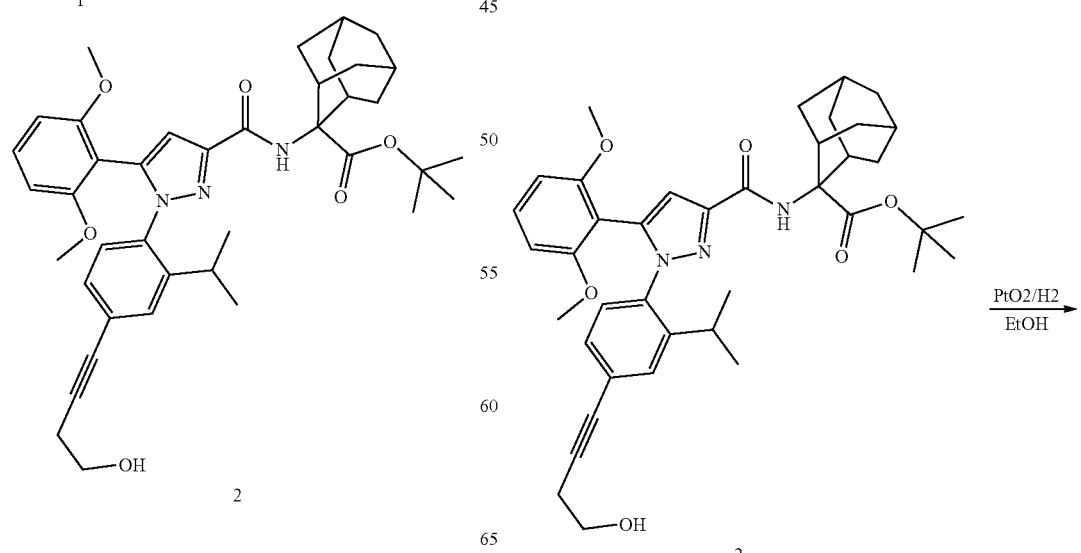

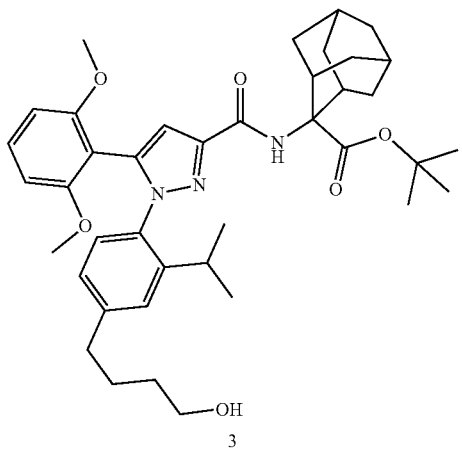

3

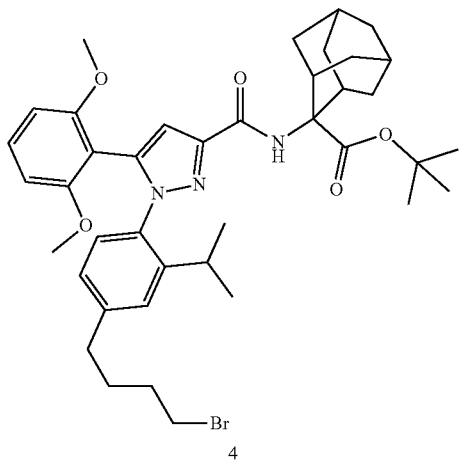

4

To a solution of compound 2 (460 mg, 0.69 mmol) in ethanol (5 mL) was added PtO₂ (31 mg, 0.14 mmol). The reaction mixture was stirred at 20° C. under a H₂ balloon for 16 hr. then filtered and concentrated. The crude product was purified by flash chromatography on reverse phase silica gel (PE/EA=6/4) to give compound 3 (385 mg, 83% yield) as a yellow solid. Molecular weight calculated: 671.4 g/mol; Determined by LC-MS: (M+H)+: 672.4.

To a solution of compound 3 (400 mg, 0.60 mmol) in ACN (5 mL) was added Ph₃P (702 mg, 2.68 mmol) and CBr₄ (890 mg, 2.68 mmol). The reaction mixture was stirred at 60° C. for 2 hr. The solvent was removed in vacuo, and the residue was purified by flash chromatography on reverse phase silica gel (PE/EA=82/18) to give compound 4 (270 mg, 61% yield) as a white solid. Molecular weight calculated: 733.3 g/mol: Determined by LC-MS: (M+H)+: 734.3.

Synthesis of tert-butyl 2-(1-(4-(4-bromobutyl)-2-isopropylphenyl)-5-(2,6-dimethoxyphenyl)-1H-pyrazole-3-carboxamido)adamantane-2-carboxylate (4)

Synthesis of tert-butyl 2-(5-(2,6-dimethoxyphenyl)-1-(2-isopropyl-4-(4-(methyl(3-(methylamino)propyl)amino)butyl)phenyl)-1H-pyrazole-3-carboxamido)adamantane-2-carboxylate (5)

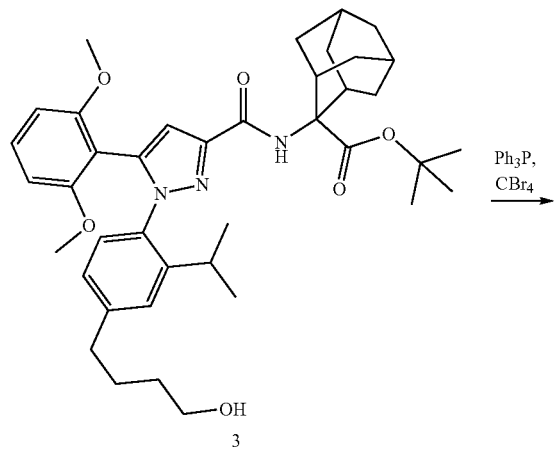

3

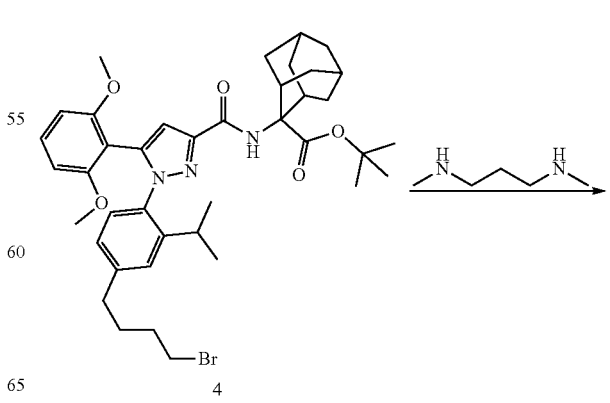

4

-continued

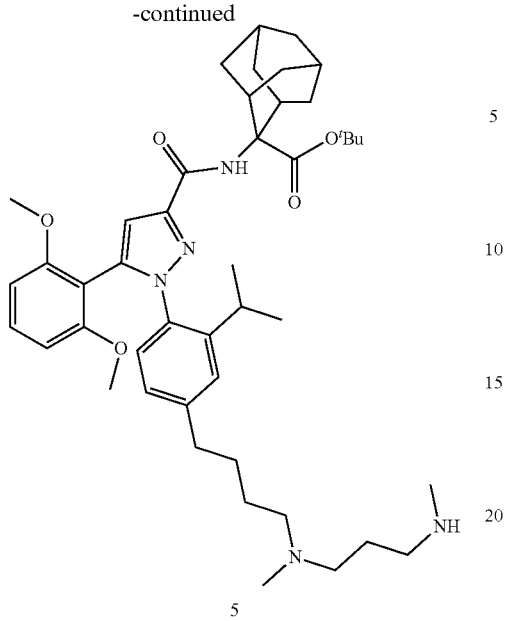

To a solution of compound 4 (50 mg, 0.07 mmol) in ACN (2 mL) was added $N^1,N^3$-dimethylpropane-1,3-diamine (20.9 mg, 0.2 mmol), KI (22.6 mg, 0.14 mmol), and $K_2CO_3$ (18.8 mg, 0.14 mmol). The reaction mixture was stirred at 80° C. under $N_2$ balloon for 2 hr. The solvent was removed in vacuo, and the residue was purified by flash chromatography on reverse phase silica gel (ACN/H2O=2%~80%, 35 min) to give compound 5 (15 mg, 29% yield) as a white solid. Molecular weight calculated: 755.5 g/mol; Determined by LC-MS: (M+H)+: 756.4.

Synthesis of tri-tert-butyl 2,2',2"-(10-(2-((3-((4-(4-(3-((2-(tert-butoxycarbonyl)adamantan-2-yl)carbamoyl)-5-(2,6-dimethoxyphenyl)-1H-pyrazol-1-yl)-3-isopropylphenyl)butyl)(methyl)amino)propyl)(methyl)amino)-2-oxoethyl)-1,4,7,10-tetraazacyclododecane-1,4,7-triyl)triacetate (6)

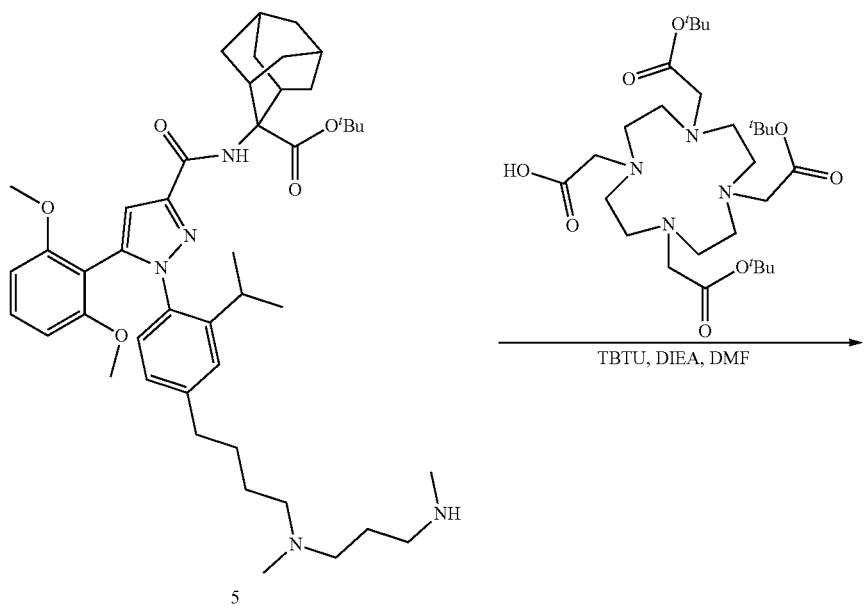

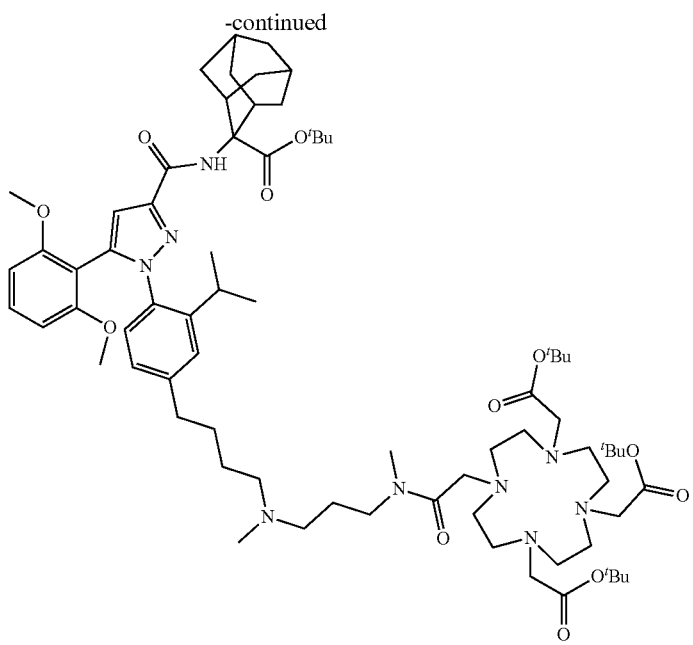

6

A mixture of DOTA-Tris(t-Bu ester) (2-(4,7,10-tris(2-(tert-butoxy)-2-oxoethyl)-1,4,7,10-tetraazacyclododecan-1-yl)acetic acid) (15 mg, 0.026 mmol), TBTU (8.5 mg, 0.026 mmol), DIEA (3.4 mg, 0.026 mmol) in DMF (1 ml) was stirred at r.t. for 1 hr before the addition of compound 5 (10 mg, 0.013 mmol). The reaction mixture was stirred for another 2 h under $N_2$ balloon, then diluted with $H_2O$ (20 mL) and extracted with EA (20 mL×2). The combined organic phase was dried over $Na_2SO_4$, filtered and concentrated to give compound 6 (10 mg, crude) as a yellow oil.

Synthesis of 2,2',2''-(10-(2-((3-((4-(4-(3-((2-carboxyadamantan-2-yl)carbamoyl)-5-(2,6-dimethoxyphenyl)-1H-pyrazol-1-yl)-3-isopropylphenyl)butyl)(methyl)amino)propyl)(methyl)amino)-2-oxoethyl)-1,4,7,10-tetraazacyclododecane-1,4,7-triyl)triacetic acid (I-9)

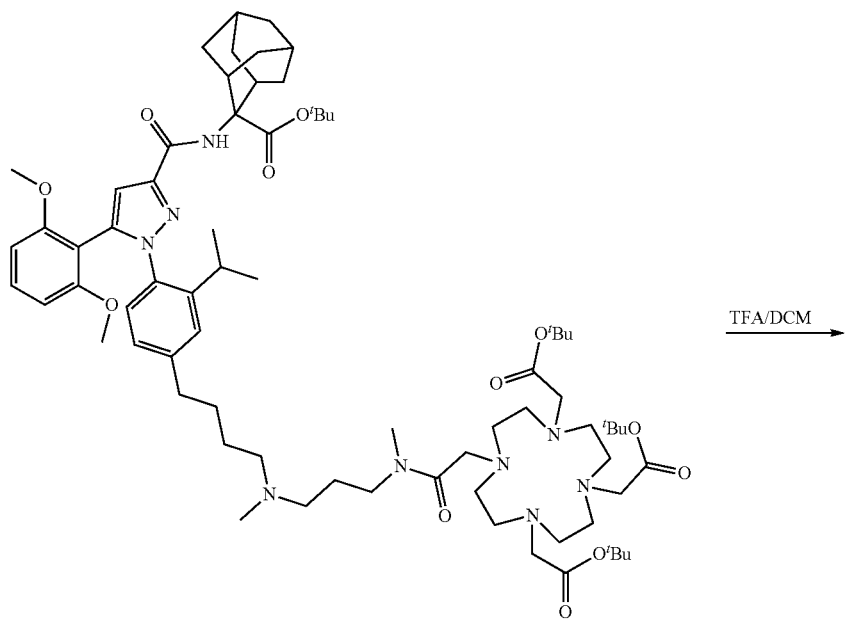

6

TFA/DCM →

-continued
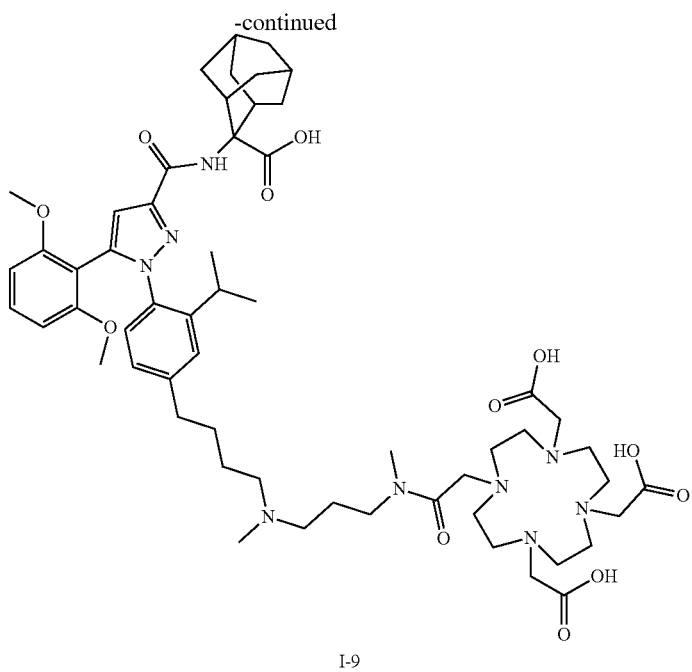
I-9
To a solution of compound 6 (10 mg, crude) in DCM (1 mL), was added A (1 ml). The reaction mixture was stirred at r.t. for 2 hr. The solvent was removed in vacuo and the residue was purified by prep-HPLC to give I-9 (1.5 mg, 18% yield) as a white solid. Molecular weight calculated: 1088.3 g/mol; Determined by LC-MS: (M+2H)2+: 544.0. Purity by UPLC (214 nm): 90.7%.
Example 10: Synthesis of I-10
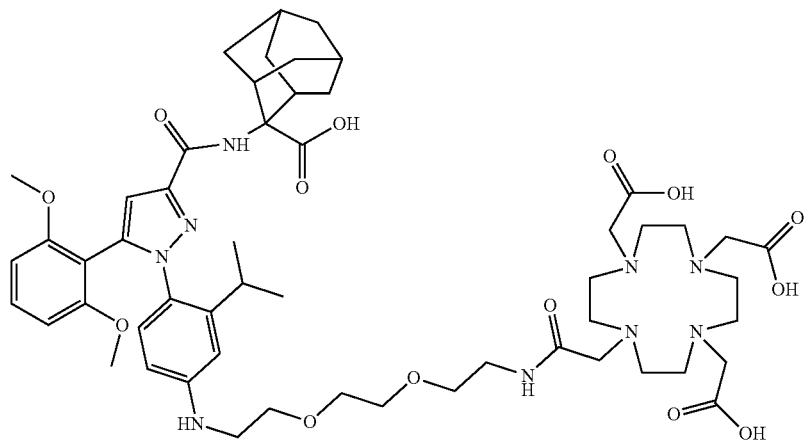 [SMILES: COc1cccc(OC)c1-c1cc(C(=O)NC2(C(=O)O)C3CC4CC(C3)CC2C4)nn1-c1ccc(NCCOCCOCCNC(=O)CN2CCN(CC(=O)O)CCN(CC(=O)O)CCN(CC(=O)O)CC2)cc1C(C)C]

The Synthetic Route to I-10
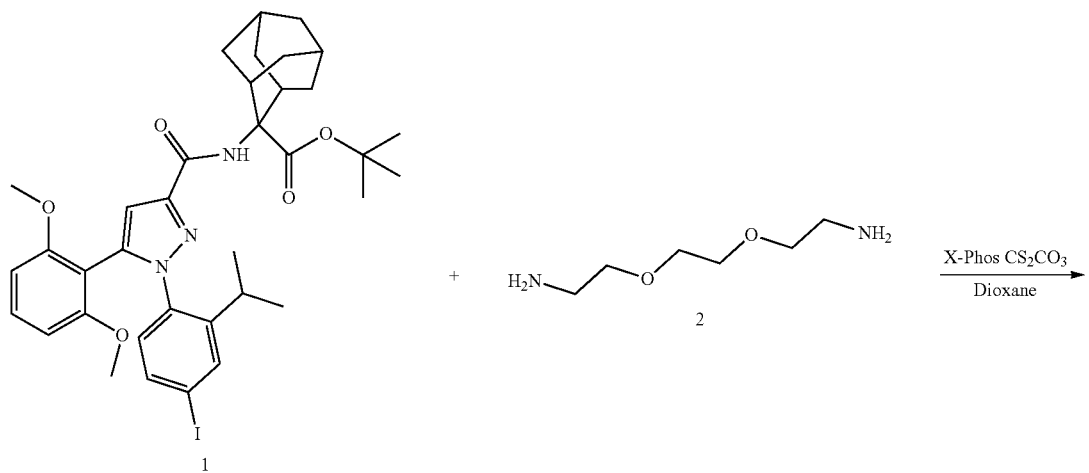
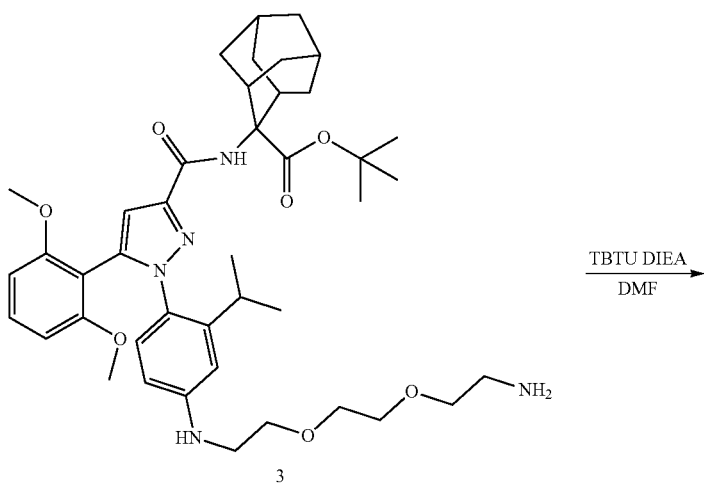
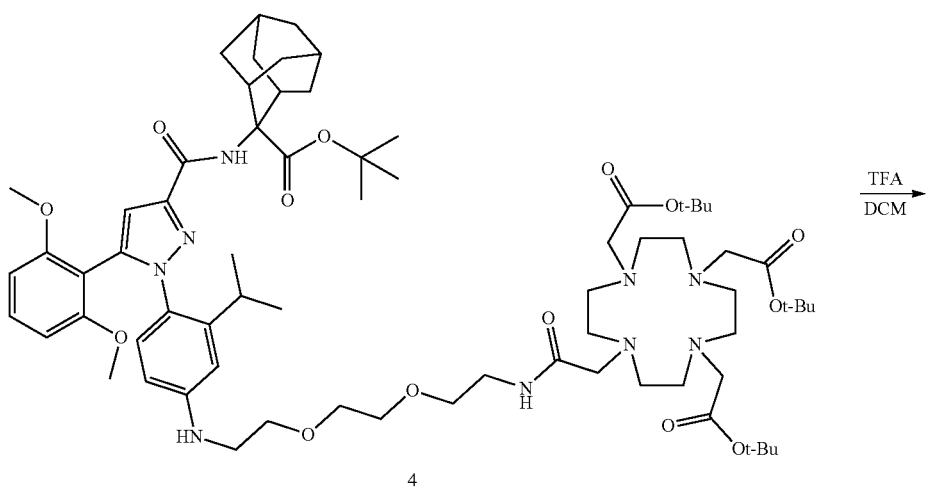

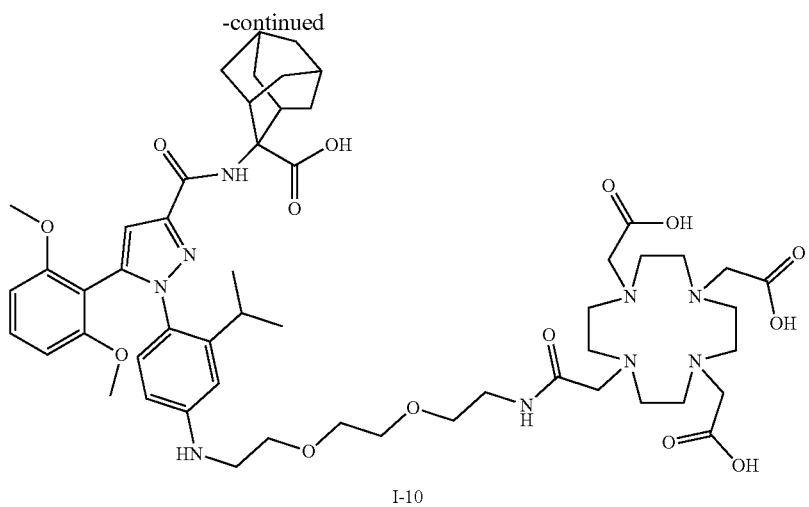

I-10

Synthesis of tert-butyl 2-(1-(4-((2-(2-(2-aminoeth-oxy)ethoxy)ethyl)amino)-2-isopropylphenyl)-5-(2,6-dimethoxyphenyl)-1H-pyrazole-3-carboxamido)adamantane-2-carboxylate (3)

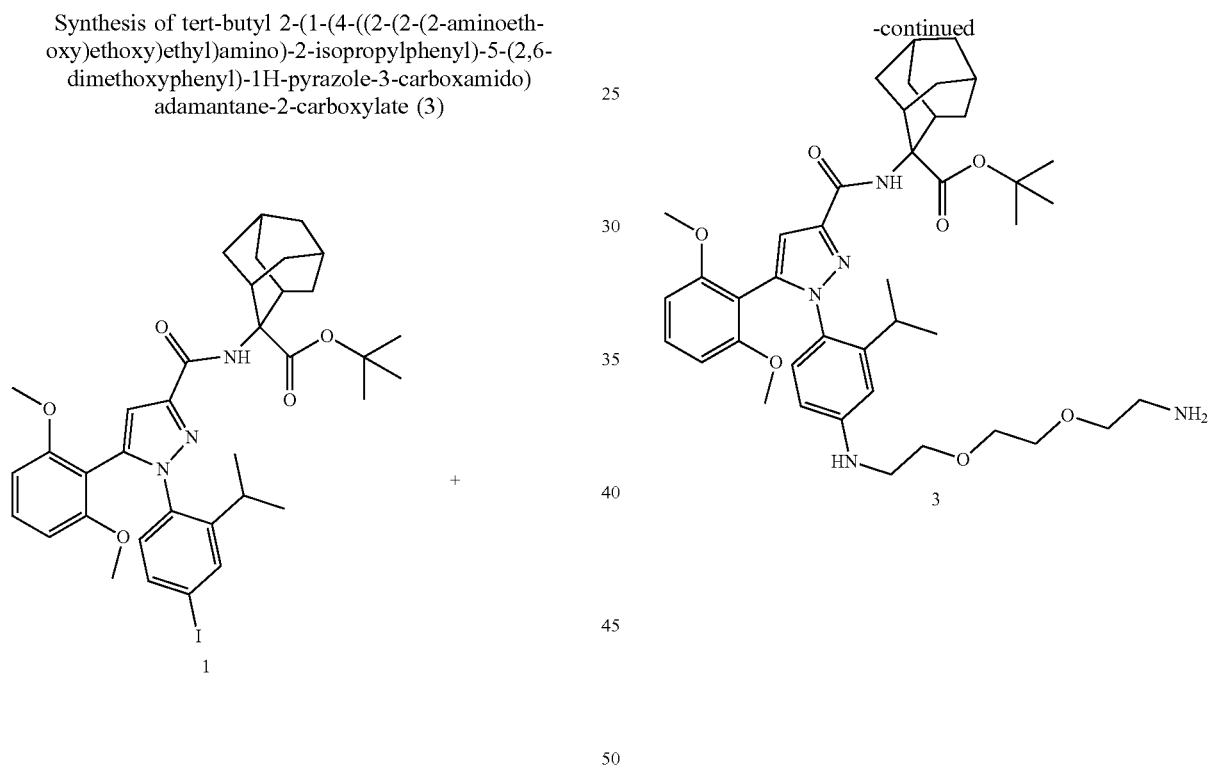

To a solution of compound 1 (300 mg, 0.41 mmol) in dioxane (20 mL) was added compound 2 (304 mg, 2.05 mmol), $Cs_2CO_3$ (401 mg, 1.23 mmol), x-phos (97.7 mg, 0.21 mmol) and $Pd_2(dba)_3$ (187.7 mg, 0.21 mmol). The reaction mixture was stirred at 115° C. under $N_2$ balloon overnight. The residue was diluted with $H_2O$ (20 mL) and extracted with EA (20 mL×2). The combined organic phase was dried over $Na_2SO_4$, filtered and concentrated. The residue was purified by flash chromatography on reverse phase silica gel using ACN and $H_2O$ as the mobile phase with a gradient of % ACN from 5% to 95% over 35 min) to give compound 3 (120 mg, 38% yield) as a yellow solid. Molecular weight calculated: 771 g/mol; Determined by LC-MS: (M+H)+: 772.

Synthesis of tri-tert-butyl 2,2',2"-(10-(2-((2-(2-(2-((4-(3-((2-(tert-butoxycarbonyl)adamantan-2-yl)carbamoyl)-5-(2,6-dimethoxyphenyl)-1H-pyrazol-1-yl)-3-isopropylphenyl)amino)ethoxy)ethoxy)ethyl)amino)-2-oxoethyl)-1,4,7,10-tetraazacyclododecane-1,4,7-triyl)triacetate (4)

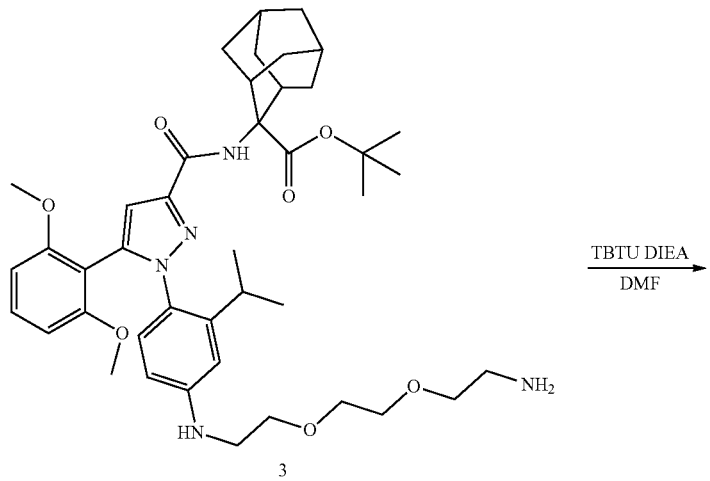

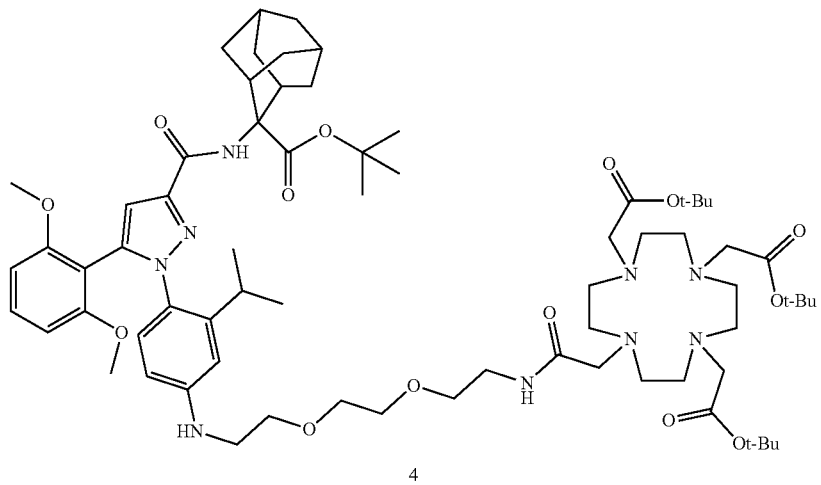

To a solution of DOTA-tris(t-Bu ester) (57.6 mg, 0.1 mmol) in DMF (2 mL) was added TBTU (32.1 mg, 0.1 mmol) and DIEA (27.09 mg, 0.21 mmol). After 10 min compound 3 (50 mg, 0.07 mmol) was added. The reaction mixture was stirred at r.t. overnight. The residue was diluted with H$_2$O (20 mL) and extracted with EA (20 mL×2). The combined organic phase was dried over Na$_2$SO$_4$, filtered and concentrated. The residue was purified by flash chromatography on reverse phase silica gel using ACN and H$_2$O as the mobile phase with a gradient of % ACN from 5% to 95% over 35 min to give compound 4 (30 mg, 34% yield) as a yellow solid. Molecular weight calculated: 1300 g/mol; Determined by LC-MS: (M+H)+: 1301.0.

Synthesis of 2,2',2"-(10-(2-((2-(2-(2-((4-(3-((2-car-boxyadamantan-2-yl)carbamoyl)-5-(2,6-dimethoxy-phenyl)-1H-pyrazol-1-yl)-3-isopropylphenyl)amino)ethoxy)ethoxy)ethyl)amino)-2-oxoethyl)-1,4,7,10-tetraazacyclododecane-1,4,7-triyl)triacetic acid (I-10)

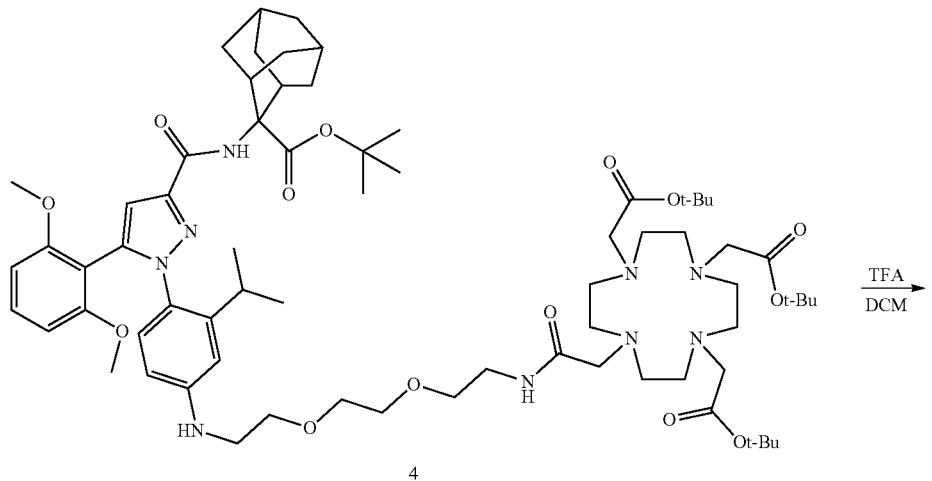

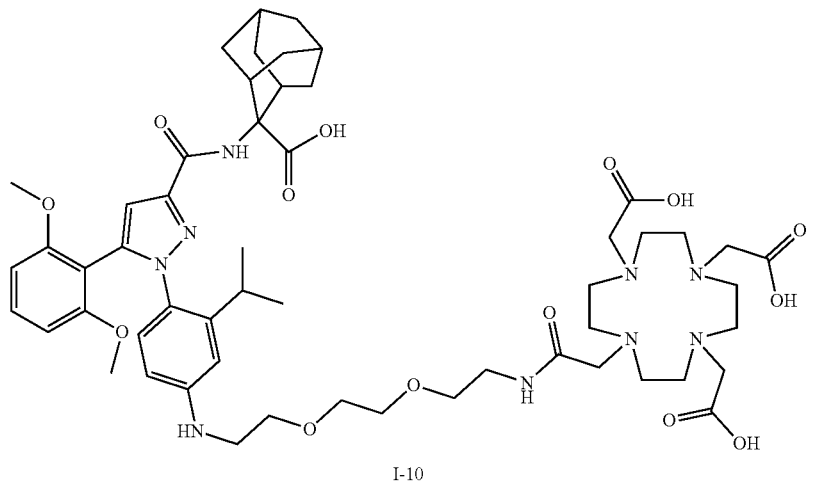

To a solution of compound 4 (30 mg, 0.023 mmol) in DCM (1 mL) was added TFA (1 mL). The reaction mixture was stirred at r.t. for 2 hr. The reaction mixture was concentrated and the residue was purified by Prep-HPLC to give compound I-10 (10 mg, 40% yield) as a white solid. Molecular weight calculated: 1076.3 g/mol; Determined by LC-MS: (M+2H)2+: 539.0. Purity by UPLC (214 nm): >99%.

Example 11: Synthesis of I-11
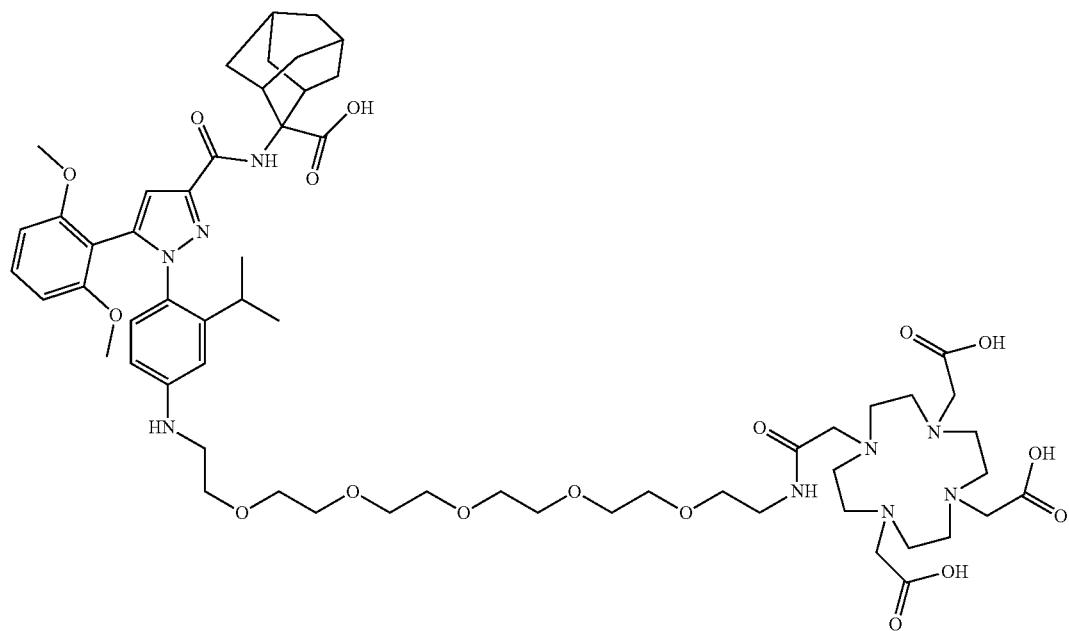 [SMILES: COc1cccc(OC)c1-c1cc(C(=O)NC2(C(=O)O)C3CC4CC(C3)CC2C4)nn1-c1ccc(NCCOCCOCCOCCOCCOCCNC(=O)CN2CCN(CC(=O)O)CCN(CC(=O)O)CCN(CC(=O)O)CC2)cc1C(C)C]
The Synthetic Route to I-11
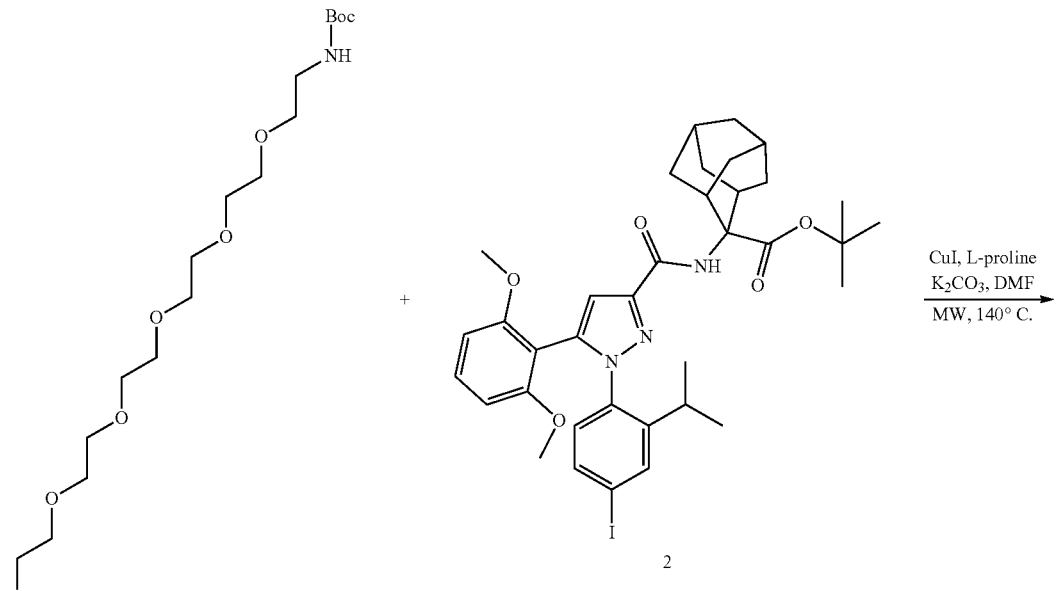

-continued
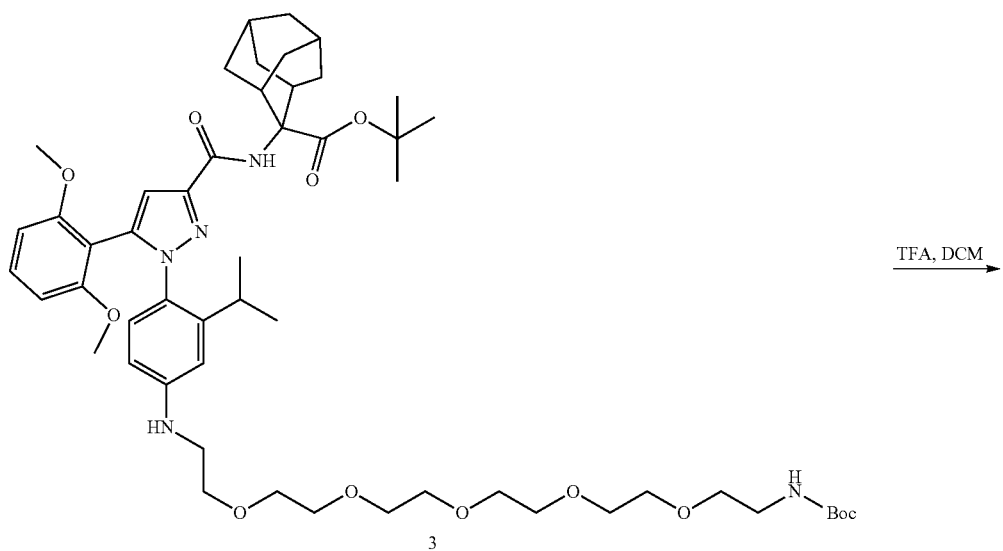
3
TFA, DCM →
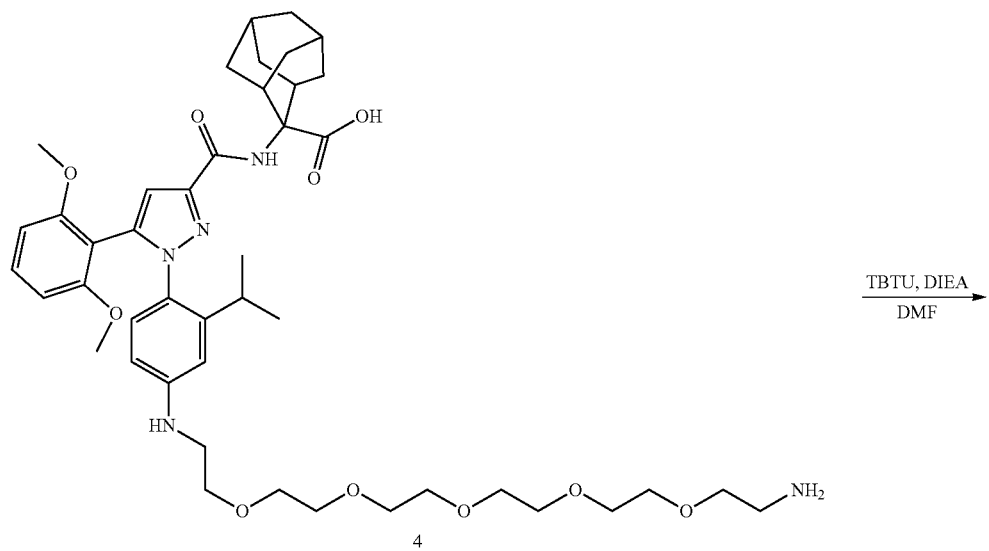
4
TBTU, DIEA
DMF →

181
182
-continued
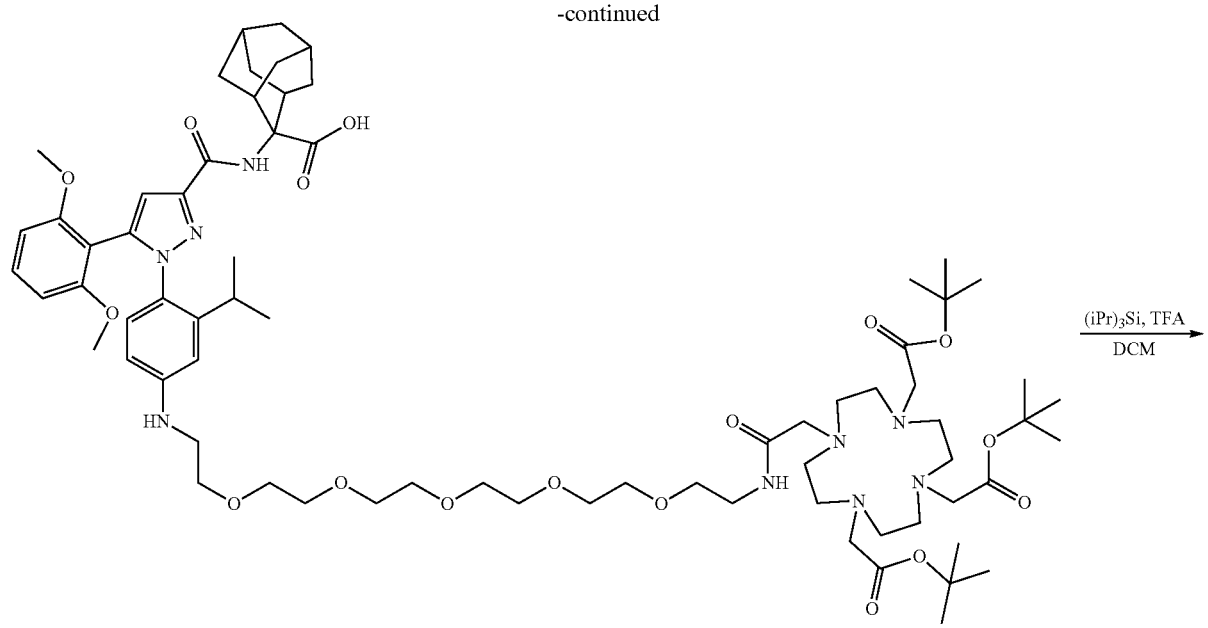
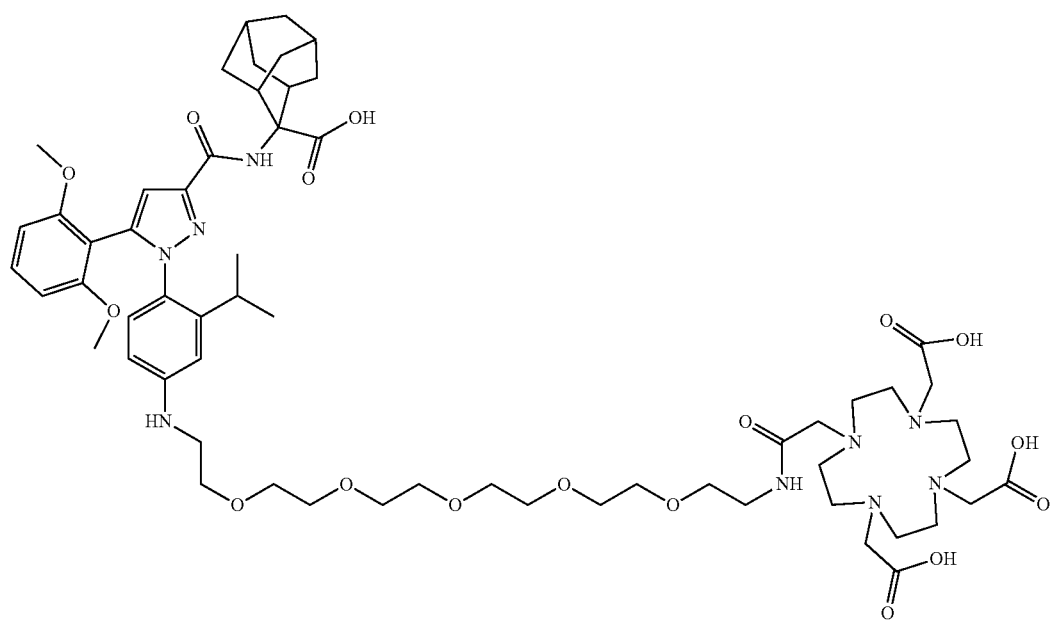
I-11

Synthesis of tert-butyl 2-(5-(2,6-dimethoxyphenyl)-1-(4-((2,2-dimethyl-4-oxo-3,8,11,14,17,20-hexaoxa-5-azadocosan-22-yl)amino)-2-isopropylphenyl)-1H-pyrazole-3-carboxamido)adamantane-2-carboxylate (3)

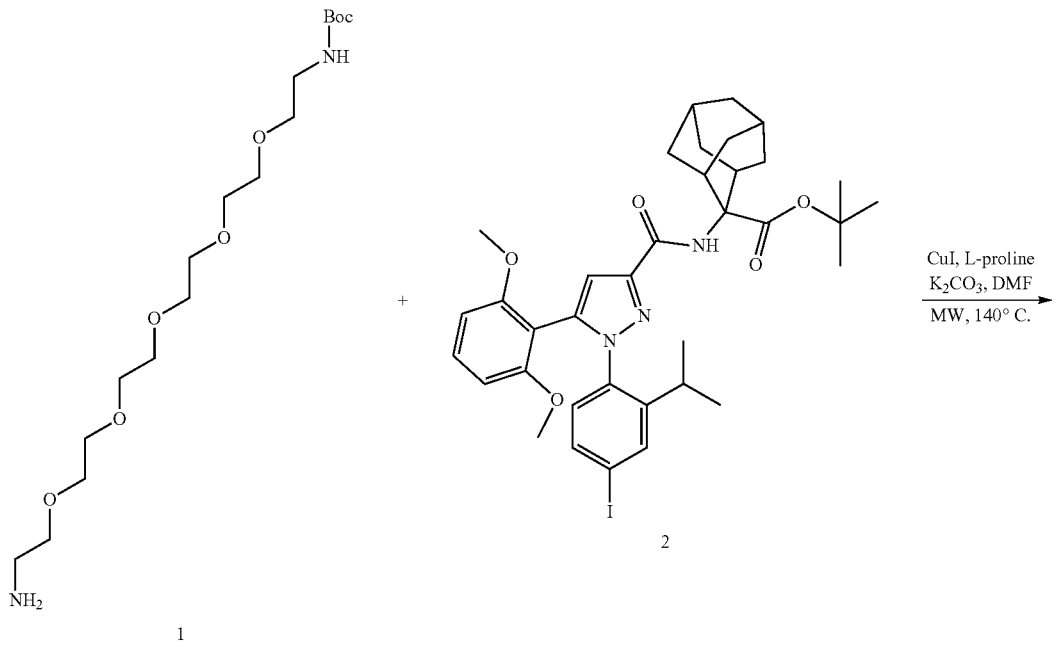

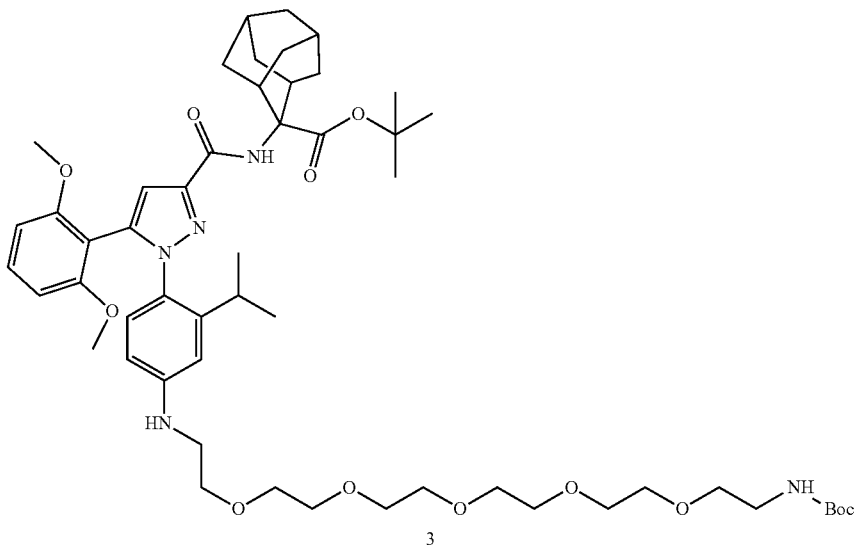

A solution of compound 1 (250 mg, 0.658 mmol), compound 2 (434.2 mg, 0.598 mmol), L-proline (13.76 mg, 0.120 mmol), CuI (22.73 mg, 0.120 mmol) and $K_2CO_3$ (165.07 mg, 1.20 mmol) in DMF (5 mL) was stirred under Ar at 140° C. (microwave) for 3 hr. The mixture was poured into $H_2O$ (30 mL) and extracted with EtOAc (3×30 mL). The combined organic phase was washed with brine, dried over $Na_2SO_4$. The residue was purified by flash chromatography on reverse phase silica gel (ACN/$H_2O$=5%~95%, 35 min) to give compound 3 (50.0 mg, 8.6% yield) as a white solid. Molecular weight calculated: 977.6 g/mol; Determined by LC-MS: (M+H)+: 978.7.

Synthesis of 2-(1-(4-(((17-amino-3,6,9,12,15-pentaoxaheptadecyl)amino)-2-isopropylphenyl)-5-(2,6-dimethoxyphenyl)-1H-pyrazole-3-carboxamido)adamantane-2-carboxylic acid (4)

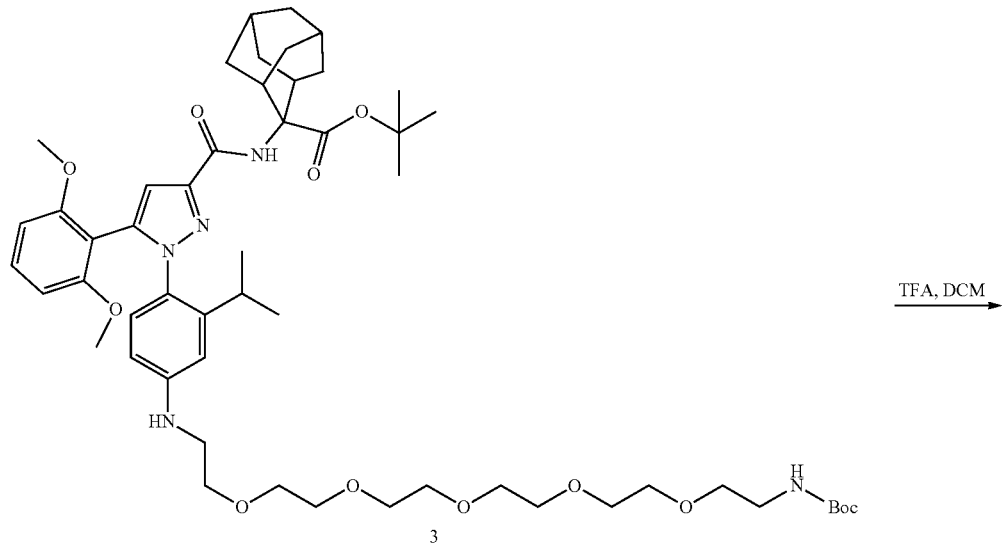

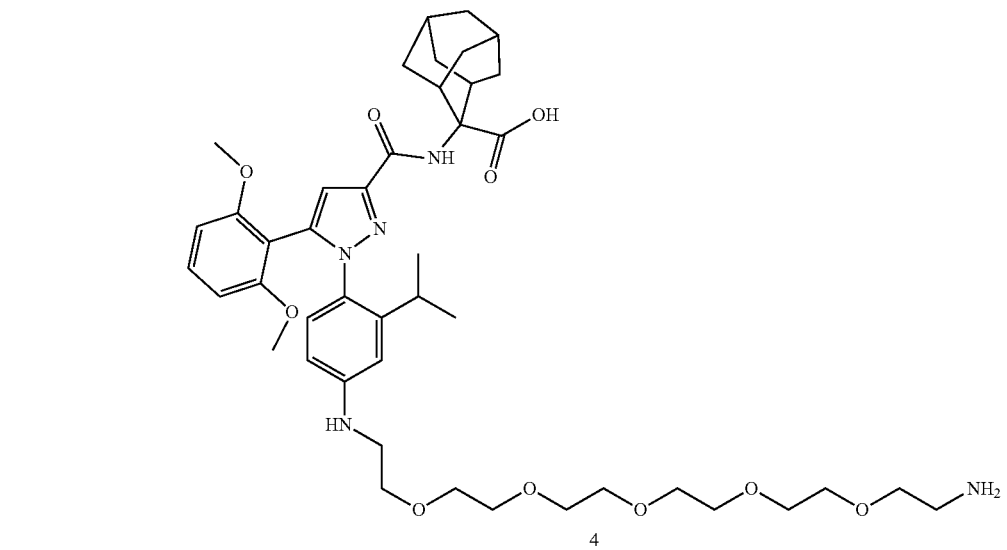

A solution of compound 3 (50.0 mg, crude) in TFA/DCM (1/3 ml) was stirred at r.t. for 2 hr. The solvent was removed by Rotavapor and the residue was purified by prep-HPLC to give compound 4 (15 mg, 36% yield) as a white solid. Molecular weight calculated: 821.5 g/mol; Determined by LC-MS: (M+H)+: 822.1.

Synthesis of 2-(5-(2,6-dimethoxyphenyl)-1-(2-isopropyl-4-((2-oxo-1-(4,7,10-tris(2-(tert-butoxy)-2-oxoethyl)-1,4,7,10-tetraazacyclododecan-1-yl)-8,9,12,15,18-pentaoxa-3-azaicosan-20-yl)amino)phenyl)-1H-pyrazole-3-carboxamido)adamantane-2-carboxylic acid (5)

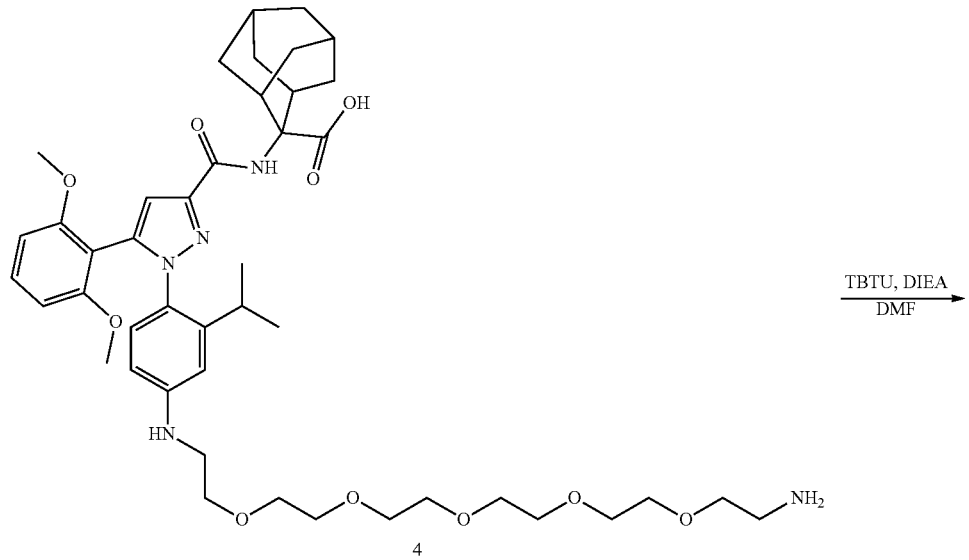

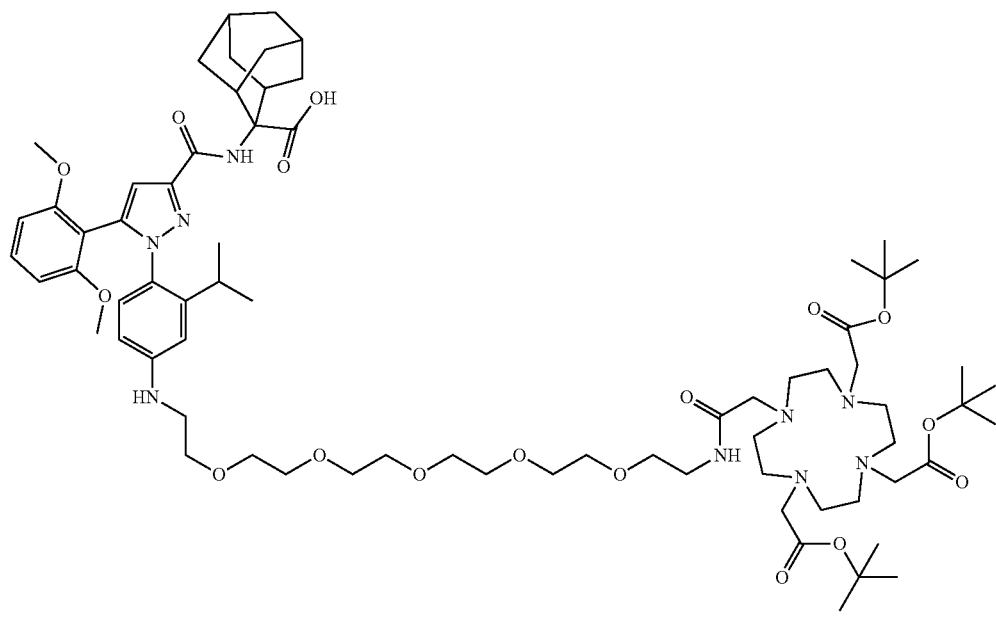

To a solution of DOTA Tris(t-Bu ester) (2-(4,7,10-tris(2-(tert-butoxy)-2-oxoethyl)-1,4,7,10-tetraazacyclododecan-1-yl)acetic acid) (15.7 mg, 0.03 mmol). In DMF (5 mL), was added TBTU (8.8 mg, 0.03 mmol) and DIEA (7.1 mg, 0.08 mmol). The reaction mixture was stirred at r.t. for 1 h before the addition of compound 4 (15.0 mg, 0.02 mmol). The resulting solution was stirred at r.t. overnight, diluted with H$_2$O (20 mL) and extracted with EtOAc (20 mL×3). The combined organic phase was dried over Na$_2$SO$_4$, filtered and concentrated to give compound 5 (30.8 mg, crude) as a yellow oil. Molecular weight calculated: 1375.8 g/mol; Determined by LC-MS: (M+H)+: 1376.9.

Synthesis of 2,2',2''-(10-(20-((4-(3-((2-carboxyadamantan-2-yl)carbamoyl)-5-(2,6-dimethoxyphenyl)-1H-pyrazol-1-yl)-3-Isopropylphenyl)amino)-2-oxo-6,9,12,15,18-pentaoxa-3-azaicosyl)-1,4,7,10-tetraazacyclododecane-1,4,7-triyl)triacetic acid (I-11)

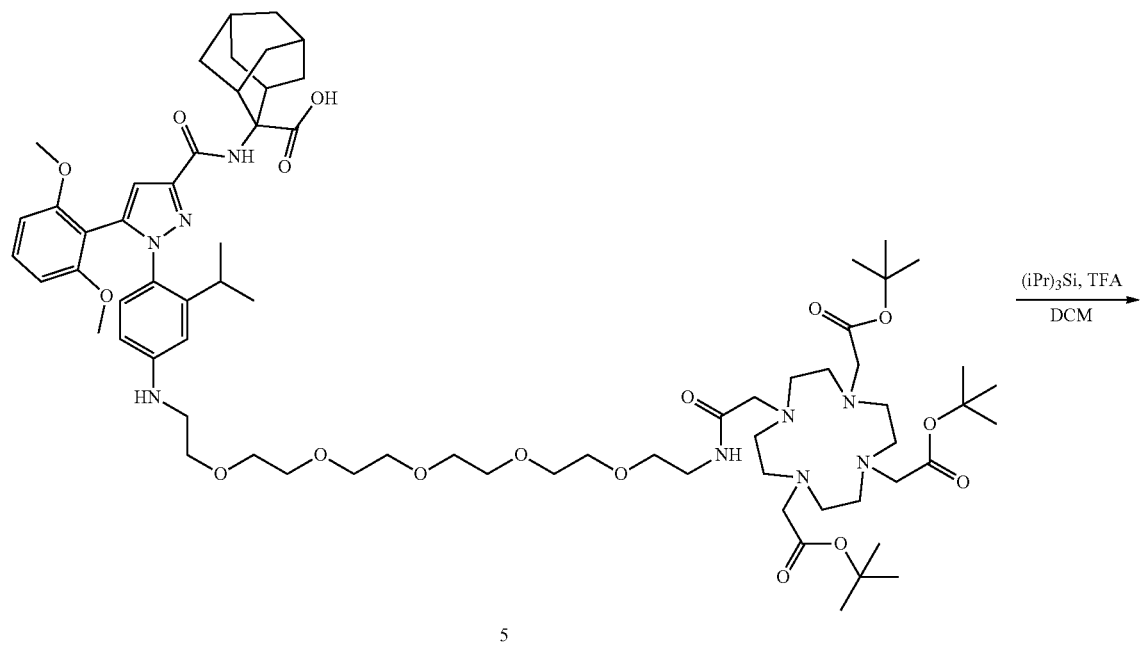

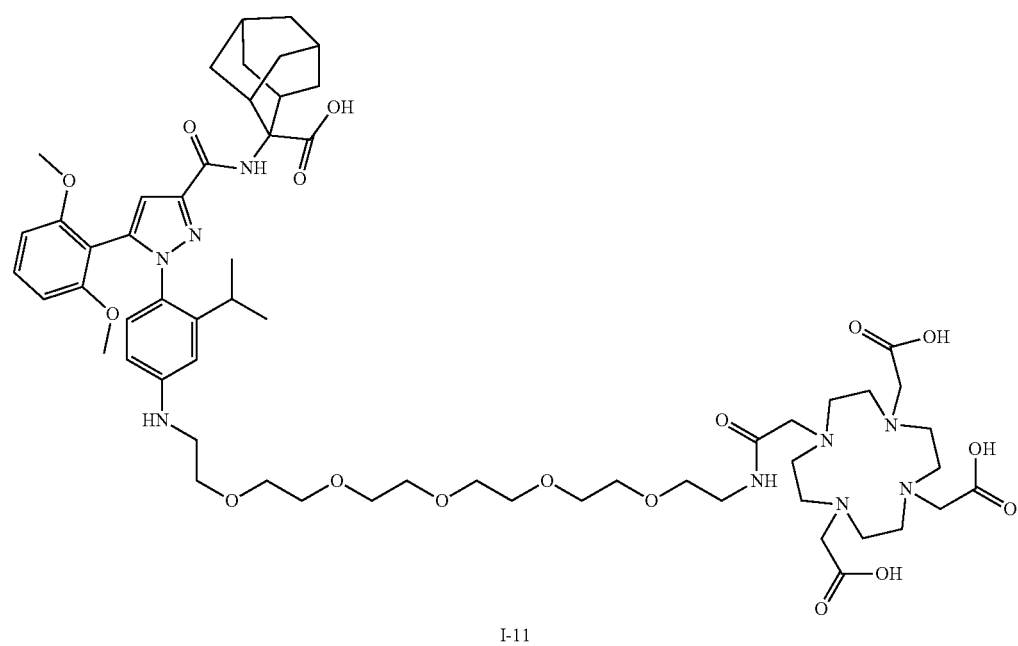

I-11

To a solution of compound 5 (30.8 mg, crude) in TFA/DCM (3/3 mL), (iPr)3Si (1 drop) was added. The reaction mixture was stirred at r.t. overnight. The solvent was removed by Rotavapor and the residue was purified by prep-HPLC to give I-11 (7.2 mg, 33.1% yield) after freeze-drying as a white solid. Molecular weight calculated: 1208.4 g/mol; Determined by LC-MS: (M+2H)2+: 805.0. Purity by UPLC (214 nm): 97.0%.

Example 12: Synthesis of I-12

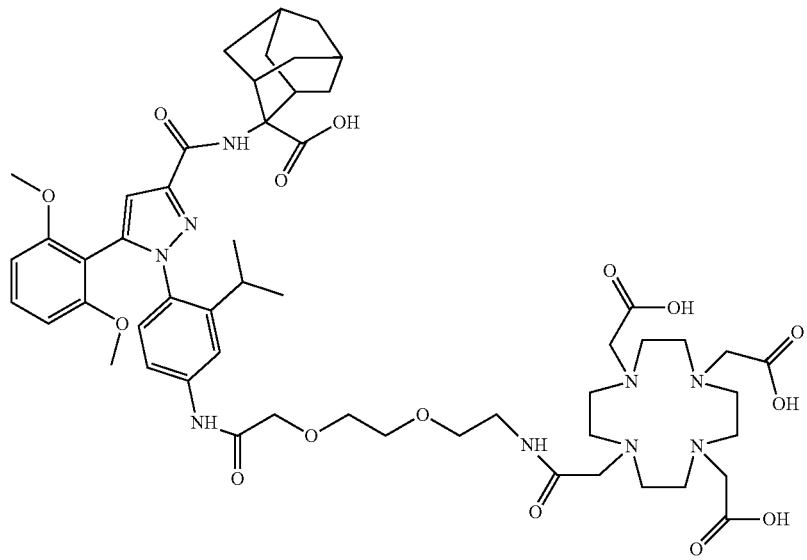 [SMILES: COc1cccc(OC)c1-c1cc(C(=O)NC2(C(=O)O)C3CC4CC(C3)CC2C4)nn1-c1ccc(NC(=O)COCCOCCNC(=O)CN2CCN(CC(=O)O)CCN(CC(=O)O)CCN(CC(=O)O)CC2)cc1C(C)C]

Compound I-12 was prepared following a similar route of synthesizing Compound I-6 as described above.
Molecular weight (average) calculated: 1090.2 g/mol
Determined by LC-MS: (M+H)+1090.4; (M+2H)2+: 545.8;
Purity by UPLC (214 nm): >99.0%

Example 13: Synthesis of I-13

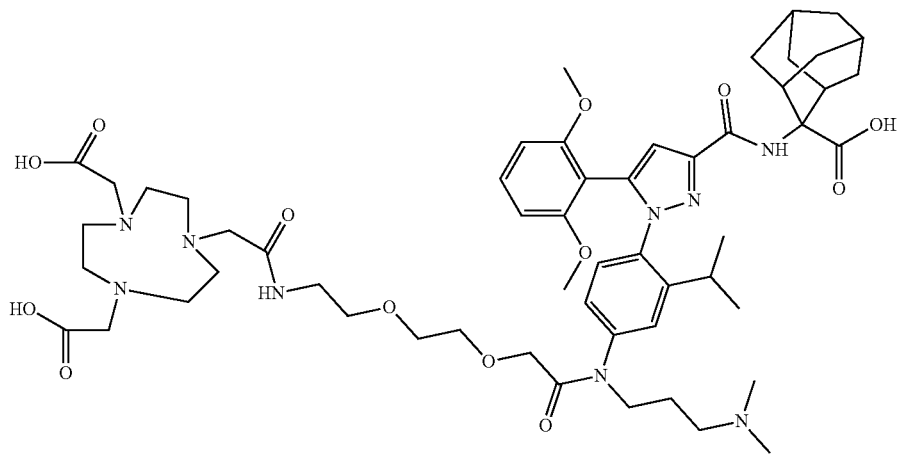 [SMILES: COc1cccc(OC)c1-c1cc(C(=O)NC2(C(=O)O)C3CC4CC(C3)CC2C4)nn1-c1ccc(N(CCCN(C)C)C(=O)COCCOCCNC(=O)CN2CCN(CC(=O)O)CCN(CC(=O)O)CC2)cc1C(C)C]

Compound I-13 was prepared following a similar route of synthesizing Compound I-6 as described previously.
Molecular weight (average) calculated: 1074.3 g/mol
Determined by LC-MS: (M+H)+: 1075.4; (M+2H)2+: 537.8
Purity by UPLC (214 nm): 90%

Example 14: Synthesis of I-14
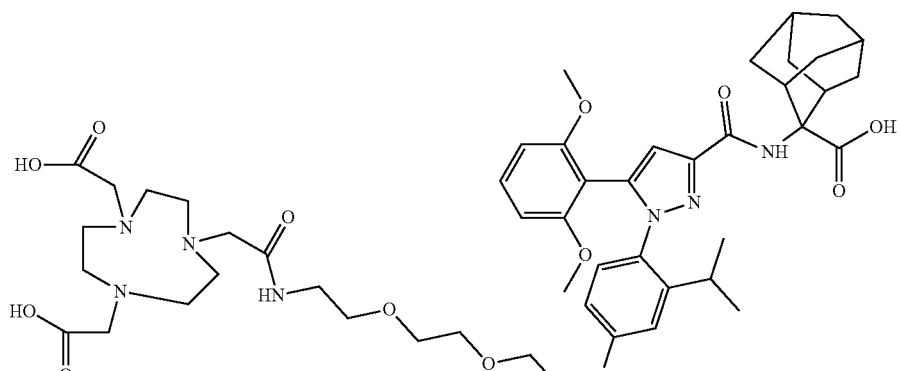
Compound I-14 was prepared following a similar route of synthesizing Compound I-10 as described previously.
Molecular weight (average) calculated: 975.1 g/mol
Determined by LC-MS: (M+H)+: 976.4; (M+2H)2+: 488.4
Purity by UPLC (214 nm): 95.8%
Synthesis of Exemplary Compounds of Formula II of the Application
Example 15: II-1
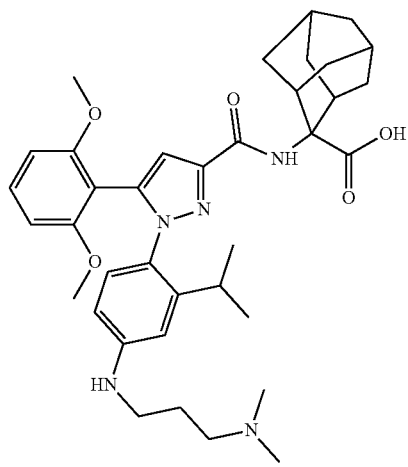 [SMILES: COc1cccc(OC)c1-c1cc(C(=O)NC2(C(=O)O)C3CC4CC(C3)CC2C4)nn1-c1ccc(NCCCN(C)C)cc1C(C)C]
The Synthetic Route to II-1
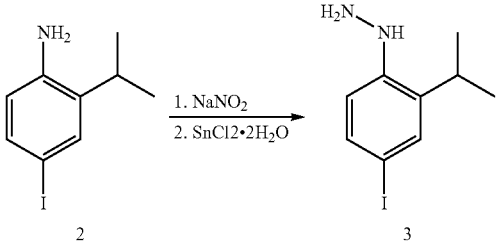

Synthesis of 4-iodo-2-isopropylaniline (2)

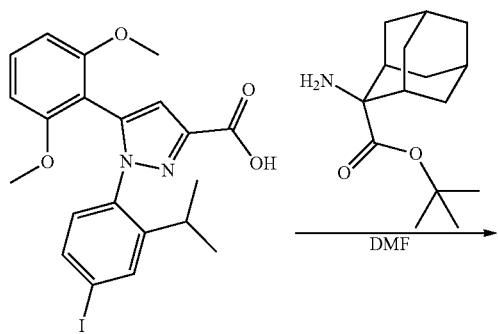

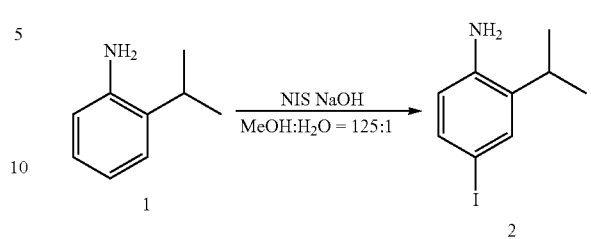

To a solution of compound 1 (5.00 g, 37.04 mmol) in MeOH/H₂O=125/1 (126 mL) was added NaOH (2.96 g, 74.07 mmol) and NIS (8.75 g, 38.89 mmol) at −40° C. for 20 min. The reaction mixture was stirred at r.t. overnight. The reaction mixture was concentrated, and the residue was diluted with H₂O (50 mL) and extracted with EA (50 mL×2). The combined organic phase was dried over Na₂SO₄, filtered and concentrated. The residue was purified by silica gel column chromatography (PE/EA=10/1-5/1) to give compound 2 (8.34 g, 86% yield) as a yellow oil. Molecular weight calculated: 261 g/mol. Determined by LC-MS: (M+H)+: 262.

Synthesis of (4-iodo-2-isopropylphenyl)hydrazine (3)

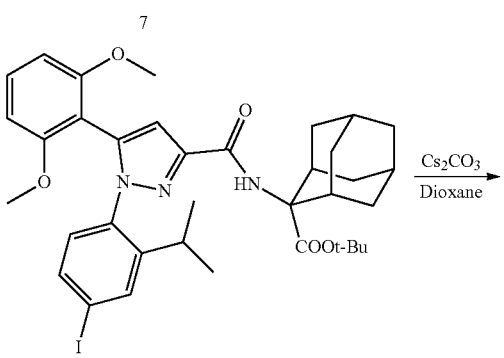

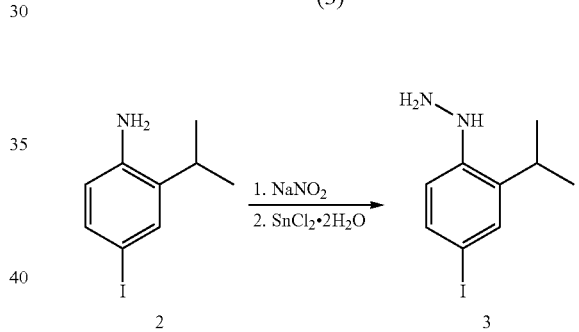

To a solution of compound 2 (1.0 g, 3.83 mmol) in 6 N HCl (0.8 mL) was added NaNO₂ (0.53 g, 7.66 mmol) in 2 mL of H₂O at 0° C. for 2 min. After 1 hr, SnCl₂·H₂O (2.85 g, 12.64 mmol) in 2 mL of 6 N HCl was added at 0° C. over 2 min. The reaction mixture was stirred at r.t. for 3 hr. The reaction mixture was filtered, washed with Et₂O (10 mL) and concentrated to compound 3 (0.61 g, 58% yield) as a yellow solid. Molecular weight calculated: 276 g/mol. Determined by LC-MS: (M+H)+: 277.

Synthesis of methyl 5-(2,6-dimethoxyphenyl)-1-(4-iodo-2-isopropylphenyl)-1H-pyrazole-3-carboxylate (6)

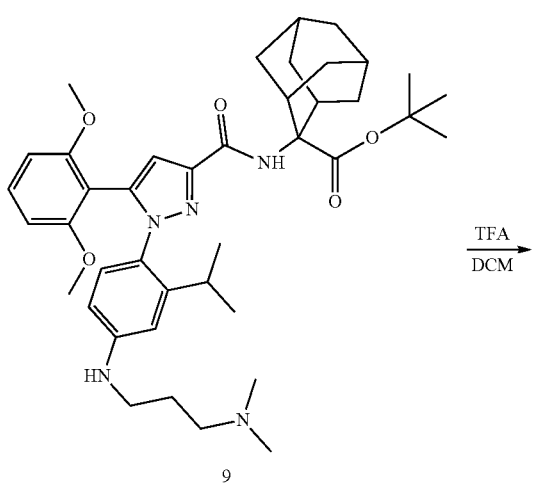

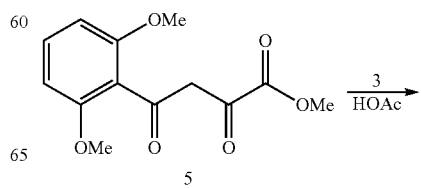

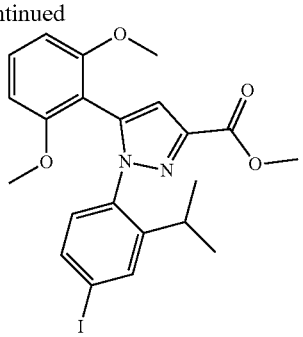

6

To a solution of compound 5 (600 mg, 2.25 mmol) in AcOH (20 mL) was added compound 3 (747 mg, 2.7 mmol) at r.t. and then the reaction mixture was stirred at 60° C. overnight. The reaction mixture was cooled down to r.t., adjusted to pH>7 with Na$_2$CO$_3$ solution and extracted with EA (50 mL×3). The combined organic phase was dried over Na$_2$SO$_4$, filtered and concentrated. The residue was purified by silica gel column chromatography (PE/EA=3/1) to give compound 6 (638 mg, 56% yield) as a yellow solid. Molecular weight calculated: 506 g/mol. Determined by LC-MS: (M+H)+: 507. $^1$H NMR (400 MHz, CDCl$_3$) δ: 7.50 (s, 1H), 7.45 (d, J=8.0 Hz, 1H), 7.26 (m, 1H), 7.04 (d. J=8.0 Hz, 1H), 6.93 (s, 1H), 6.46 (J=8.0 Hz, 2H), 3.94 (s, 3H), 3.64 (s, 6H), 2.61 (m, 1H), 0.94 (brs, 6H).

Synthesis of 5-(2,6-dimethoxyphenyl)-1-(4-iodo-2-isopropylphenyl)-1H-pyrazole-3-carboxylic acid (7)

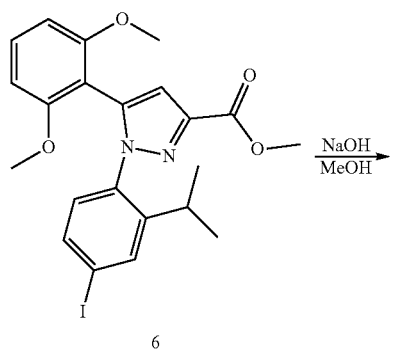

6

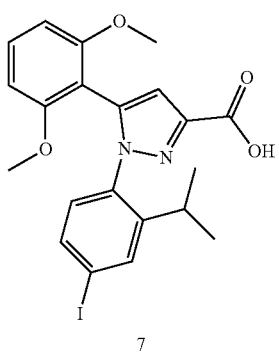

7

To a solution of compound 6 (560 mg, 1.11 mmol) in MeOH (10 mL) was added NaOH (88.5 mg, 2.22 mmol) at r.t. The reaction mixture was stirred at 60° C. overnight. The reaction mixture was concentrated, and the residue was purified by flash chromatography on reverse phase silica gel using ACN and H$_2$O as the mobile phase with a gradient of % ACN from 5% to 95% over 35 min to give compound 7 (500 mg, 92% yield) as a yellow solid. Molecular weight calculated: 492 g/mol. Determined by LC-MS: (M+H)+: 493.

Synthesis of tert-butyl 2-(5-(2,6-dimethoxyphenyl)-1-(4-iodo-2-isopropylphenyl)-1H-pyrazole-3-carboxamido)adamantane-2-carboxylate (8)

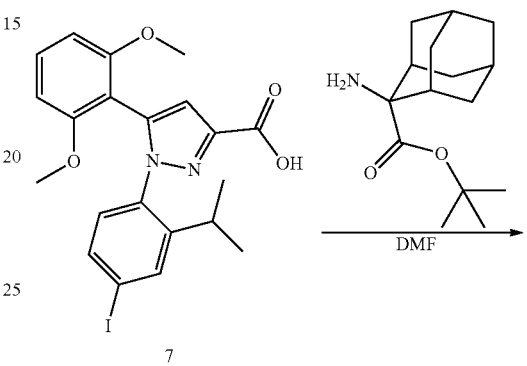

7

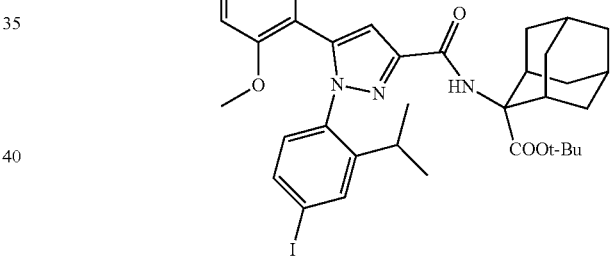

8

To a solution of compound 7 (400 mg, 0.81 mmol) in DMF (15 mL) in an ice-water bath, was added DIEA (313.5 mg, 2.43 mmol) and PyBOP (632.3 mmol, 1.22 mmol). The mixture was stirred for 10 min. before the addition of tert-butyl 2-aminoadamantane-2-carboxylate (244.2 mg, 0.97 mmol). The reaction mixture was stirred at 90° C. overnight. The residue was diluted with H$_2$O (20 mL) and extracted with EA (20 mL×2). The combined organic phase was dried over Na$_2$SO$_4$, filtered and concentrated. The residue was purified by flash chromatography on reverse phase silica gel using ACN and H$_2$O as the mobile phase with a gradient of % ACN from 5% to 95% over 35 min to give compound 8 (240 mg, 41% yield) as a yellow solid. Molecular weight calculated: 725 g/mol. Determined by LC-MS: (M+H)+: 726. $^1$H NMR (400 MHz, DMSO-d6) δ: 7.70 (d, J=2.0, 1H), 7.54 (dd, J=8.4, 2.0 Hz, 1H), 7.33 (d, J=8.4, 1H), 7.28 (d, J=3.2, 1H), 6.93 (d, J=8.4 Hz, 1H), 6.65 (s, 1H), 6.62 (d, J=8.8 Hz, 2H), 3.64 (s, 6H), 2.50 (m, 3H), 2.01-1.93 (m, 4H), 1.80-1.60 (m 8H), 1.39 (s, 9H), 1.03 (d, J=6.4 Hz, 6H).

199
Synthesis of tert-butyl 2-(5-(2,6-dimethoxyphenyl)-1-(4-((3-(dimethylamino)propyl)amino)-2-isopropylphenyl)-1H-pyrazole-3-carboxamido)adamantane-2-carboxylate (9)

200
Synthesis of 2-(5-(2,6-dimethoxyphenyl)-1-(4-((3-(dimethylamino)propyl)amino)-2-isopropylphenyl)-1H-pyrazole-3-carboxamido)adamantane-2-carboxylic acid (II-1)

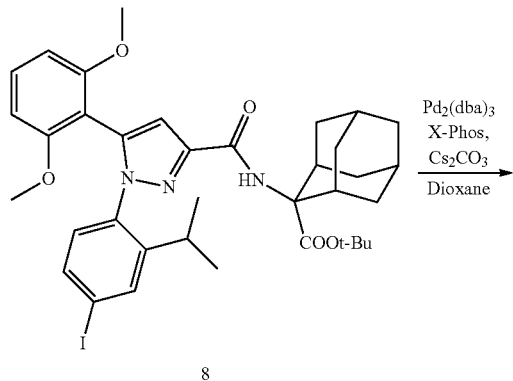

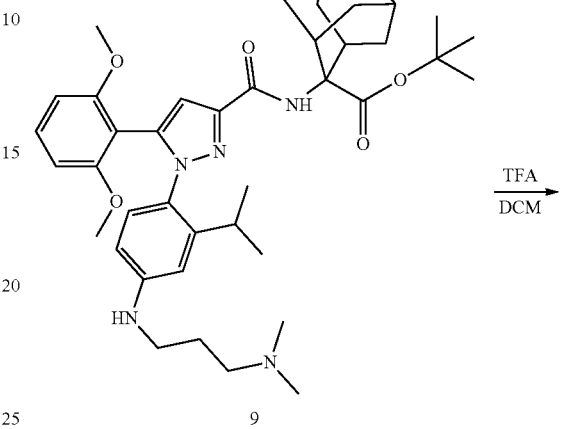

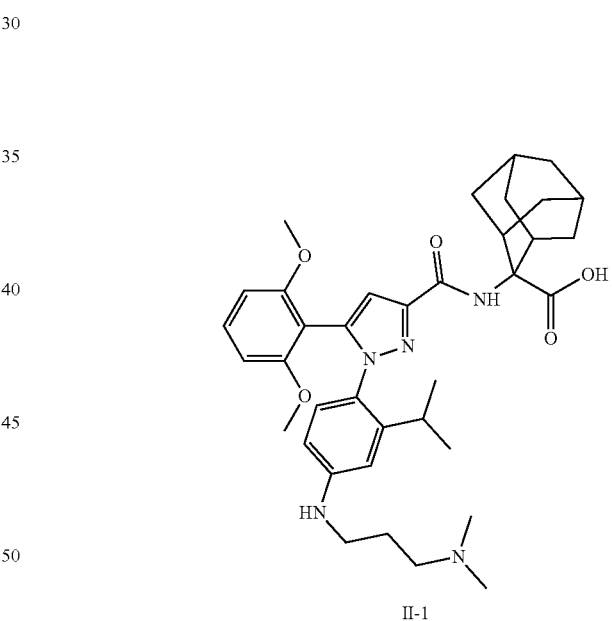

To a solution of compound 8 (50 mg, 0.07 mmol) in dioxane (15 mL) was added N,N-Dimethyl-1,3-propanediamine (8.4 mg, 0.08 mmol), Cs$_2$CO$_3$ (68.5 mg, 0.21 mmol), x-phos (16.7 mg, 0.04 mmol) and Pd$_2$(dba)$_3$ (36.6 mg, 0.04 mmol). The reaction mixture was stirred at 115° C. under N$_2$ balloon overnight. The residue was diluted with H$_2$O (20 mL) and extracted with EA (20 mL×2). The combined organic phase was dried over Na$_2$SO$_4$, filtered and concentrated. The residue was purified by flash chromatography on reverse phase silica gel with a gradient of % ACN from 5% to 95% over 35 min to give compound 9 (30 mg, 82% yield) as a yellow solid. Molecular weight calculated: 700.0 g/mol. Determined by LC-MS: (M+H)+: 701.0.

To a solution of compound 9 (30 g, 0.042 mmol) in DCM (10 mL) was added TFA (5 mL). The reaction mixture was stirred at r.t. for 2 hr. The reaction mixture was concentrated and the residue was purified by prep-HPLC to give II-1 (10 mg, 36% yield) as a white solid. Molecular weight calculated: 643.8 g/mol. Determined by LC-MS: (M+H)+: 644.4. Purity by UPLC (214 nm): 97.2%. $^1$H NMR (400 MHz, DMSO-d$_6$) δ: 12.39 (brs, 1H), 9.34 (brs, 1H), 7.30-7.26 (m, 2H), 6.91 (d, J=8.4 Hz, 1H), 6.59 (t, J=7.0 Hz, 3H), 8.41 (d, J=2.4 Hz, 1H), 6.30-6.27 (m, 1H), 5.88 (brs, 1H), 3.65 (s, 6H), 3.11 (t, J=7.6 Hz, 2H), 3.04 (t, J=6.6 Hz, 2H), 2.77 (s, 6H), 2.49-2.45 (m, 2H), 1.95 (d, J=12.4 Hz, 2H), 1.88-1.81 (m, 2H), 1.76-1.81 (m, 10H), 1.01 (s, 6H).

Example 16: II-2
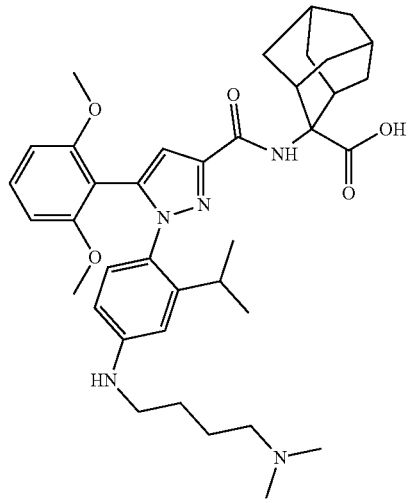 [SMILES: COc1cccc(OC)c1-c1cc(C(=O)NC2(C(=O)O)C3CC4CC(C3)CC2C4)nn1-c1ccc(NCCCCN(C)C)cc1C(C)C]
The Synthetic Route to II-2
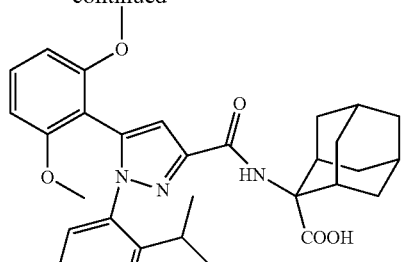
II-2
Synthesis of tert-butyl 2-(5-(2,6-dimethoxyphenyl)-1-(4-((4-(dimethylamino)butyl)amino)-2-isopropylphenyl)-1H-pyrazole-3-carboxamido)adamantane-2-carboxylate (3)
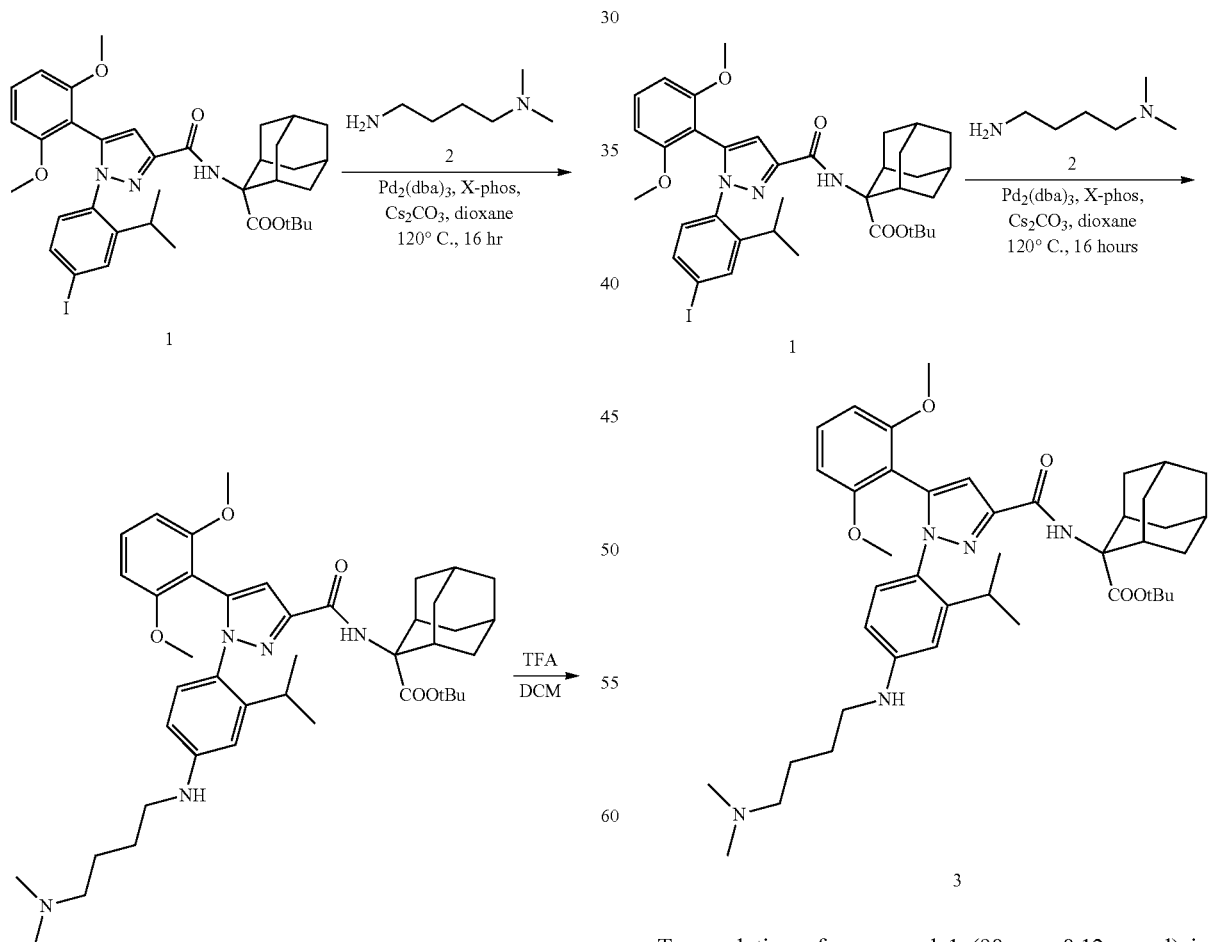
To a solution of compound 1 (90 mg, 0.12 mmol) in dioxane (5 mL) was added compound 2 (17.3 mg, 0.15 mmol), $Cs_2COS$ (121.2 mg, 0.37 mmol), x-phos (5.7 mg, 0.01 mmol) and Pd$_2$(dba)$_3$ (11.0 mg, 0.01 mmol). The reaction mixture was stirred at 120° C. under N$_2$ balloon overnight. The reaction solution was diluted with H$_2$O (20 mL) and extracted with EA (20 mL×2). The combined organic phase was dried over Na$_2$SO$_4$, filtered and concentrated. The residue was purified by flash chromatography on reverse phase silica gel (ACN/H$_2$O=5%-95%, 35 min) to give compound 3 (35 mg, 41% yield) as an orange oil. Molecular weight calculated: 713.5 g/mol; Determined by LC-MS: (M+H)+. 714.5.

Synthesis of 2-(5-(2,6-dimethoxyphenyl)-1-(4-((4-(dimethylamino)butyl)amino)-2-isopropylphenyl)-1H-pyrazole-3-carboxamido)adamantane-2-carboxylic acid (II-2)

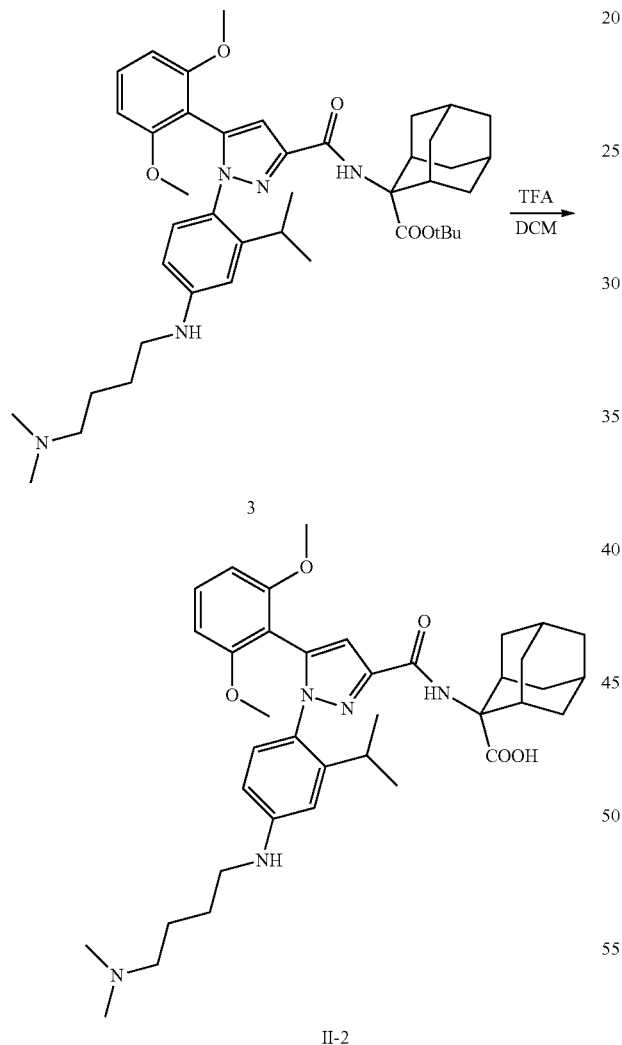

To a solution of compound 2 (35 mg, 0.05 mmol) in DCM (2 mL) was added TFA (2 mL). The reaction mixture was stirred at r.t. for 4 hr. The reaction mixture was concentrated by Rotavapor and the residue was purified by prep-HPLC to give compound II-2 (8.2 mg, 31% yield) as a white solid. Molecular weight calculated: 657.4 g/mol; Determined by LC-MS: (M+H)+: 658.4. Purity by UPLC (214 nm): 98.6%.

Example 17: II-3

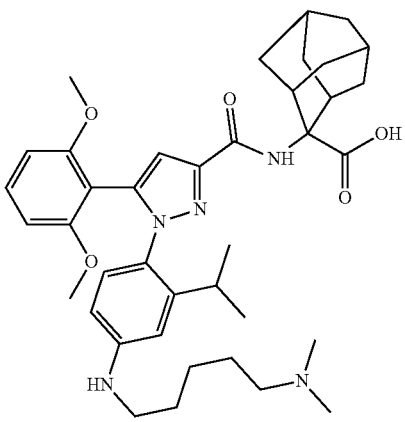 [SMILES: COc1cccc(OC)c1-c1cc(C(=O)NC2(C(=O)O)C3CC4CC(C3)CC2C4)nn1-c1ccc(NCCCCCN(C)C)cc1C(C)C]

The Synthetic Route to II-3

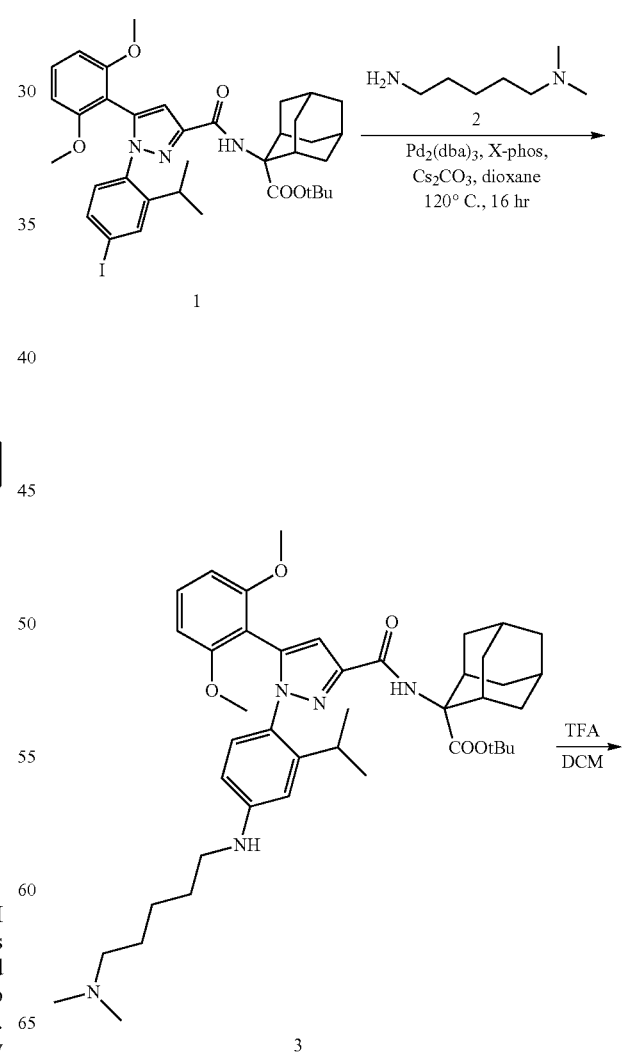

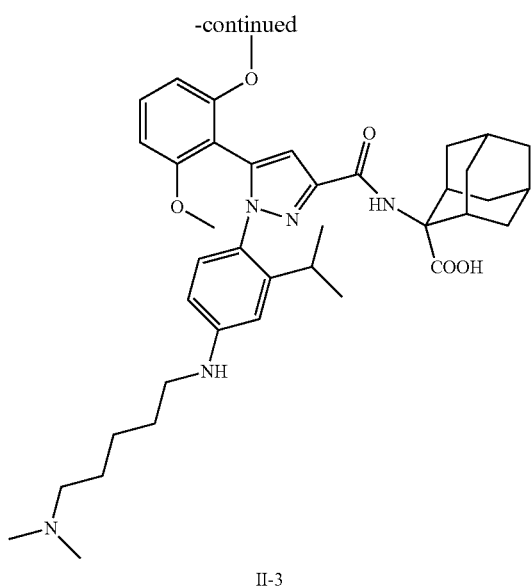

II-3

Synthesis of tert-butyl 2-(5-(2,6-dimethoxyphenyl)-1-(4-((5-(dimethylamino)pentyl)amino)-2-isopropylphenyl)-1H-pyrazole-3-carboxamido)adamantane-2-carboxylate (3)

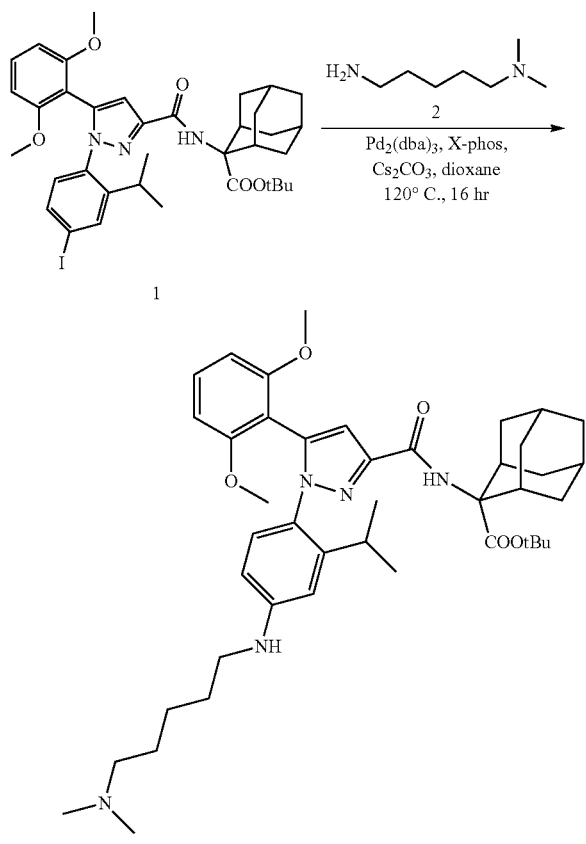

To a solution of compound 1 (90 mg, 0.12 mmol) in dioxane (5 mL) was added compound 2 (19.4 mg, 0.15 mmol), $CS_2CO_3$ (121.2 mg, 0.37 mmol), x-phos (5.7 mg, 0.01 mmol) and $Pd_2(dba)_3$ (11.0 mg, 0.01 mmol). The reaction mixture was stirred at 120° C. under $N_2$ balloon overnight. The residue was diluted with $H_2O$ (20 mL) and extracted with EA (20 mL×2). The combined organic phase was dried over $Na_2SO_4$, filtered and concentrated. The residue was purified by flash chromatography on reverse phase silica gel ($ACN/H_2O$=5%-95%, 35 min) to give compound 3 (30 mg, 34% yield) as orange oil. Molecular weight calculated: 727.5 g/mol; Determined by LC-MS: (M+H)+: 728.5.

Synthesis of 2-(5-(2,6-dimethoxyphenyl)-1-(4-((5-(dimethylamino)pentyl)amino)-2-isopropylphenyl)-1H-pyrazole-3-carboxamido)adamantane-2-carboxylic acid (II-3)

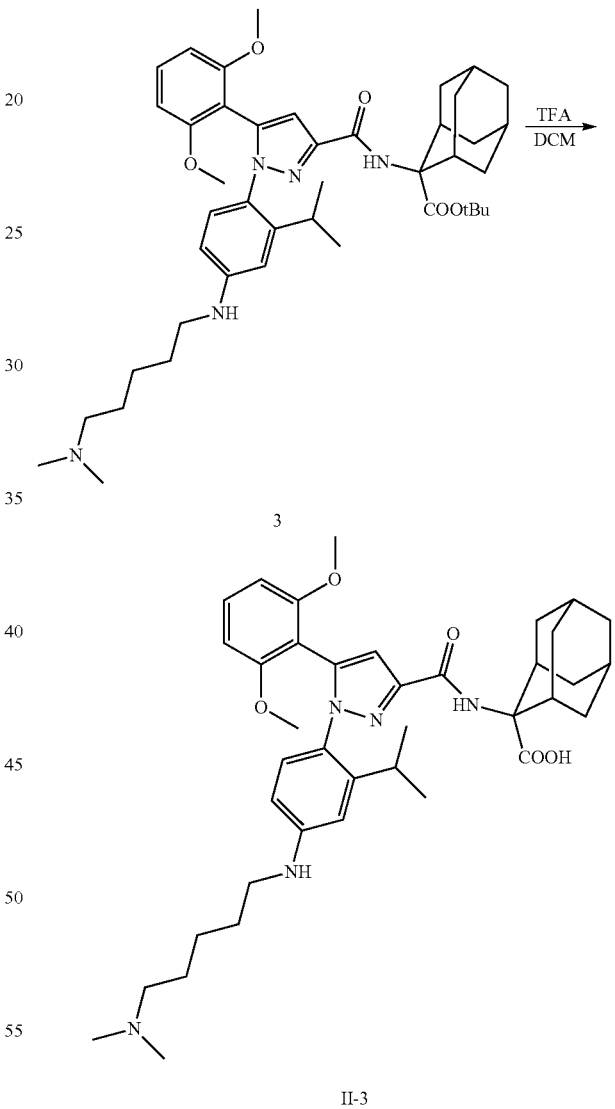

To a solution of compound 3 (30.0 mg, 0.05 mmol) in DCM (2 mL) was added TFA (2 mL). The reaction mixture was stirred at r.t. for 4 hr. The reaction solution was concentrated by Rotavapor and the residue was purified by prep-HPLC to give compound II-3 (8.2 mg, 30% yield) as a white solid. Molecular weight calculated: 671.4 g/mol; Determined by LC-MS: (M+H)+: 672.3. Purity by UPLC (214 nm): >99.0%.

Synthesis of Comparator Compounds of the Application
Example 18: Comparator 1 (C-1, DOTA-NT-20.3)
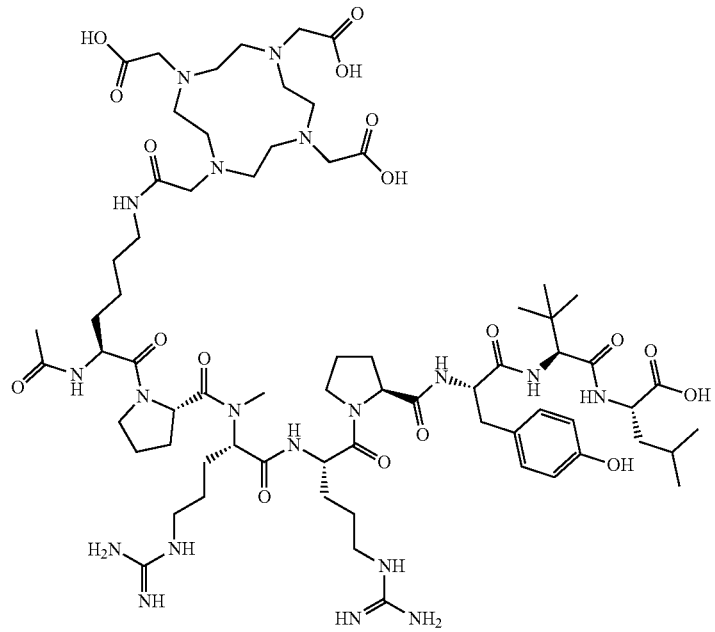 [SMILES: CC(=O)N[C@@H](CCCCNC(=O)CN1CCN(CC(=O)O)CCN(CC(=O)O)CCN(CC(=O)O)CC1)C(=O)N1CCC[C@H]1C(=O)N(C)[C@@H](CCCNC(=N)N)C(=O)N[C@@H](CCCNC(=N)N)C(=O)N1CCC[C@H]1C(=O)N[C@@H](Cc1ccc(O)cc1)C(=O)N[C@H](C(=O)N[C@@H](CC(C)C)C(=O)O)C(C)(C)C]
C-1 was prepared by following standard solid-phase peptide synthesis. Molecular weight calculated: 1484.8 g/mol. Determined by LC-MS: (M+2H)2+: 743.4; (M+3H)3+: 495.8. Purity by UPLC (214 nm): >99%.
Example 19: Comparator 2 (C-2, 3BP-227)
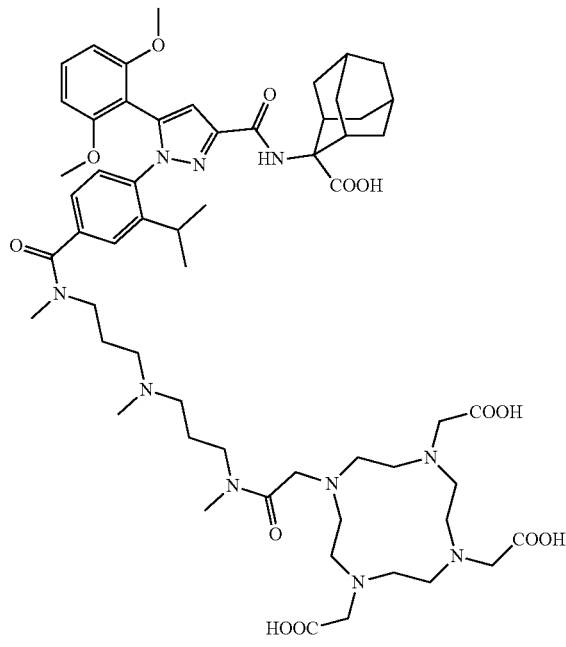 [SMILES: COc1cccc(OC)c1-c1cc(C(=O)NC2(C(=O)O)C3CC4CC(C3)CC2C4)nn1-c1ccc(C(=O)N(C)CCCN(C)CCCN(C)C(=O)CN2CCN(CC(=O)O)CCN(CC(=O)O)CCN(CC(=O)O)CC2)cc1C(C)C]
The Synthetic Route to C-2
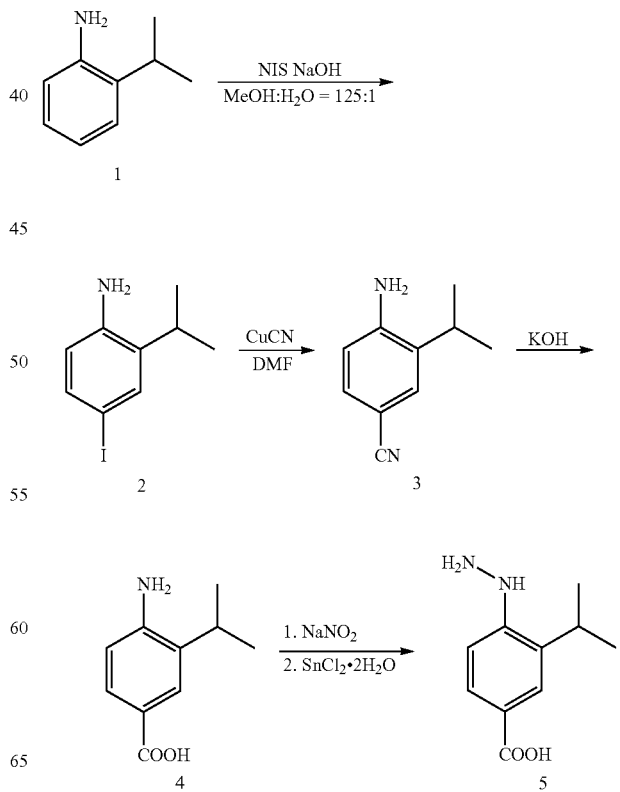

-continued
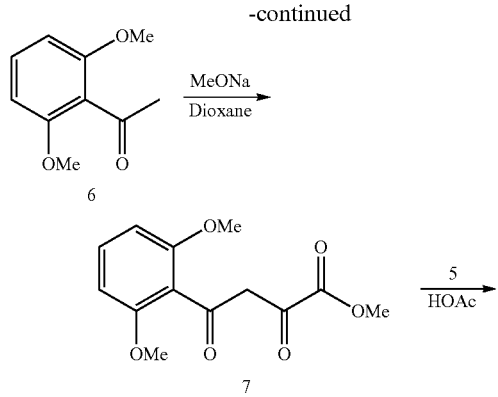
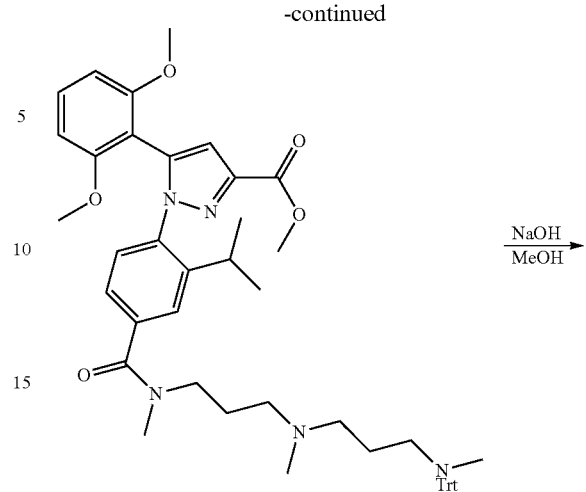
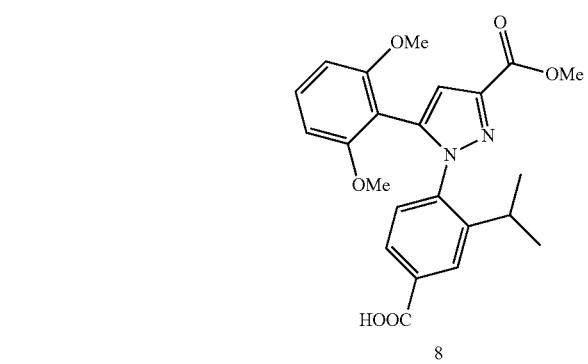
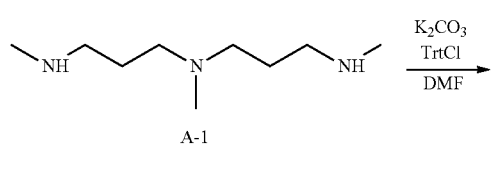
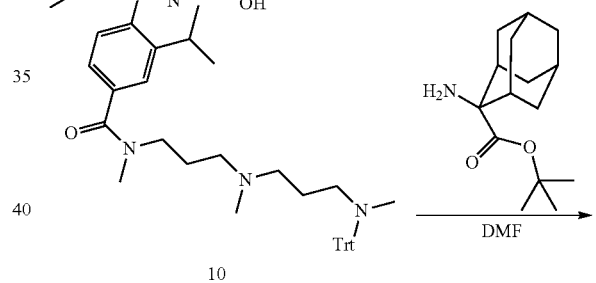
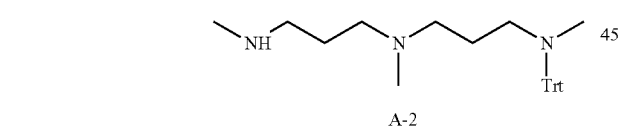
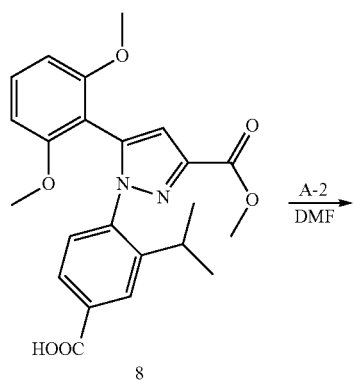
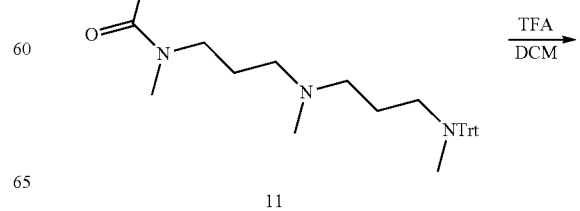

211 -continued

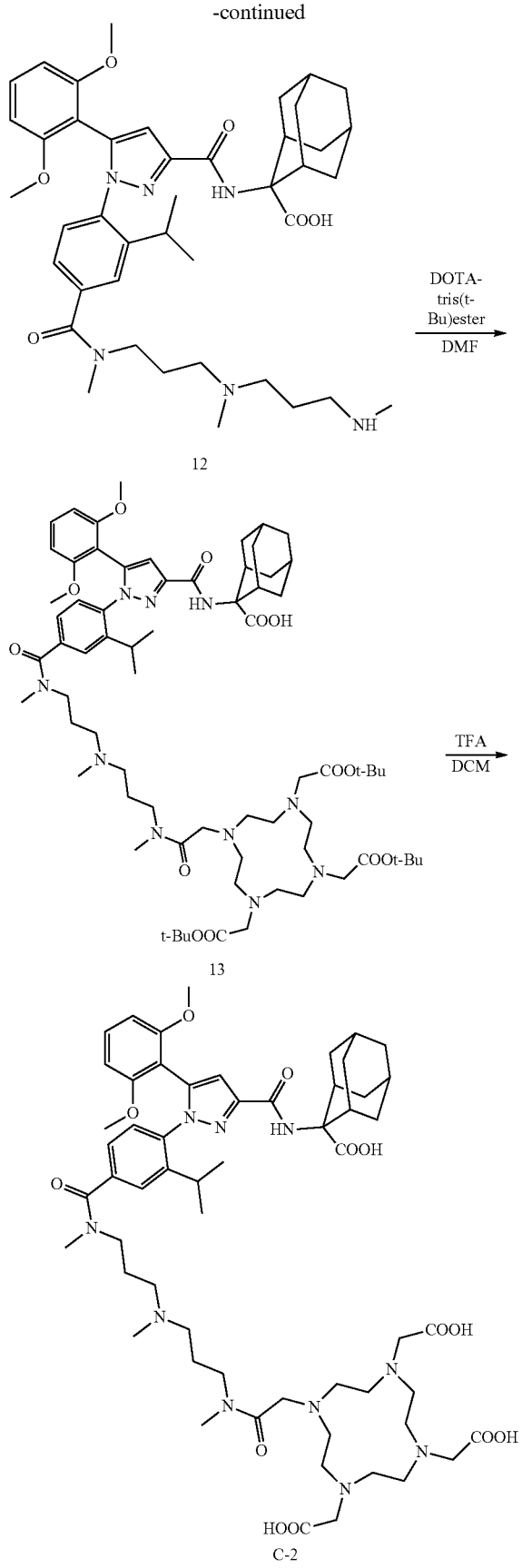

212

Synthesis of 4-Iodo-2-isopropylaniline (2)

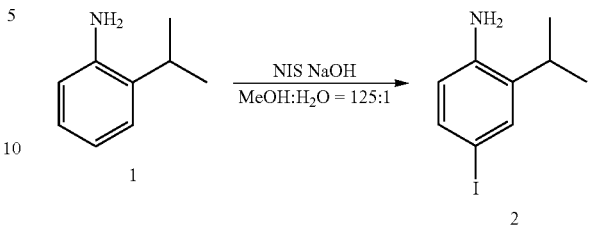

To a solution of compound 1 (5.00 g, 37.04 mmol) in MeOH/H$_2$O=125/1 (128 mL) was added NaOH (2.96 g, 74.07 mmol) and N-iodosuccinimide (NIS) (8.75 g, 38.89 mmol) at −40° C. for 20 min. The reaction mixture was stirred at r.t. overnight. The reaction mixture was concentrated. The residue was diluted with H$_2$O (50 mL) and extracted with ethyl acetate (50 mL×2). The combined organic phases were dried over Na$_2$SO$_4$, filtered and concentrated. The residue was purified by silica gel column chromatography (petroleum/ethyl acetate=10/1-5/1) to give compound 2 (8.34 g, 88% yield) as a yellow oil. Molecular weight (average) calculated: 281 g/mol. Determined by LC-MS: (M+H)+: 262.

Synthesis of 4-amino-3-isopropylbenzonitrile (3)

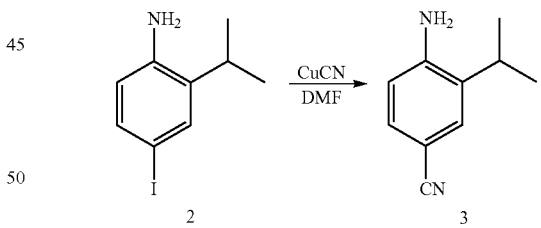

To a solution of compound 2 (5.0 g, 19.2 mmol) in DMF (20 mL) was added CuCN (5.15 g, 57.5 mmol). The reaction mixture was stirred at 140° C. for 4 hr. The reaction mixture was diluted with H$_2$O (20 mL) and extracted with ethyl acetate (30 mL×2). The combined organic phases were dried over Na$_2$SO$_4$, filtered and concentrated. The residue was purified by silica gel column chromatography (petroleum/ethyl acetate=10/1-3/1) to give compound 3 (2.7 g, 88% yield) as brown solid. Molecular weight (average) calculated: 160 g/mol, Determined by LC-MS: (M+H)+: 161. $^1$H NMR (400 MHz, CDCl$_3$) δ: 7.38 (d, J=2.0 Hz, 1H), 7.30-7.27 (m, 1H), 6.64 (d, J=8.0 Hz, 1H), 2.87-2.77 (m, 1H), 1.28-1.24 (m, 6H).

Synthesis of 4-amino-3-isopropylbenzoic acid (4)

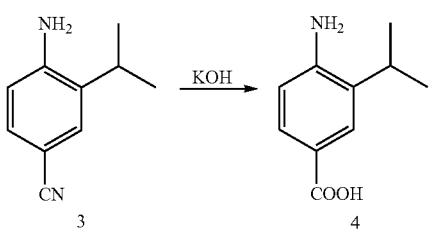

To a solution of compound 3 (2.7 g, 16.86 mmol) in ethylene glycol/H$_2$O (9 mL/3 mL) was added KOH (3.71 g, 67.44 mmol). The reaction mixture was stirred at 140° C. for 4 hr. The reaction mixture was cooled down to r.t., adjusted to pH=3 with 3 N HCl and extracted with ethyl acetate (30 mL×3). The combined organic phases were dried over Na$_2$SO$_4$, filtered and concentrated. The residue was purified by silica gel column chromatography (PE/EA=3/1) to give compound 4 (2.7 g, 90% yield) as a yellow solid. Molecular weight (average) calculated: 179 g/mol. Determined by LC-MS: (M+H)+: 180. $^1$H NMR (400 MHz, DMSO-d$_6$) δ: 11.95 (brs, 1H), 7.61 (d, J=2.0 Hz, 1H), 7.05 (d, J=2.0 Hz, 1H), 7.48 (d, J=2.0 Hz, 1H), 5.68 (s, 2H), 3.00-2.90 (m, 1H), 1.16 (s, 3H), 1.14 (s, 3H).

Synthesis of 4-hydrazinyl-3-isopropylbenzoic acid (5)

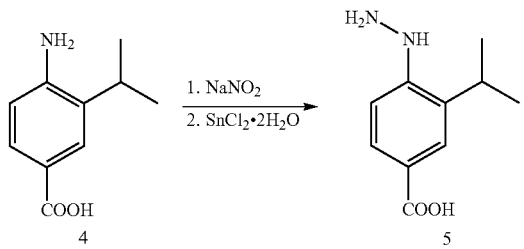

To a solution of compound 4 (1.0 g, 5.58 mmol) in 6 N HCl (1 mL) was added NaNO$_2$ (0.77 g, 11.17 mmol) in 1 mL of H$_2$O at 0° C. for 2 min. After 1 hr, SnCl$_2$H$_2$O (2.52 g, 11.17 mmol) in 2 mL of 6 N HCl was added at 0° C. for 2 min. The reaction mixture was stirred at r.t. for 3 hr. The reaction mixture was filtered, washed with Et$_2$O (10 mL) and concentrated to compound 5 (0.7 g, 70% yield) as a yellow solid. Molecular weight (average) calculated: 194 g/mol. Determined by LC-MS: (M+H)+: 195. $^1$H NMR (400 MHz, DMSO-d$_6$) δ: 10.53 (s, 2H), 7.77 (d, J=1.6 Hz, 1H), 7.42-7.16 (m, 1H), 7.05 (d, J=8.4 Hz, 1H), 323-3.14 (m, 1H), 1.23-1.16 (m, 6H). MS Calcd: 194; MS Found: 195 ([M+H]$^+$).

Synthesis of methyl 4-(2,6-dimethoxyphenyl)-2,4-dioxobutanoate (7)

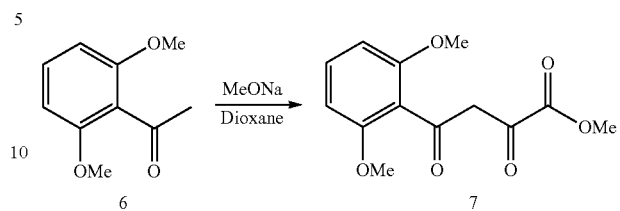

To a solution of compound 6 (10 g, 55.5 mmol) in dioxane (50 mL) was added dimethyl oxalate (8.19 g, 69.4 mmol) and MeONa (5.4 mol/mL, 11.3 mL, 61.05 mmol) at r.t. The reaction mixture was stirred at 70° C. overnight. The reaction mixture was cooled down to r.t., adjusted to pH=5 with 3 N HCl and extracted with ethyl acetate (50 mL×3). The combined organic phase was dried over Na$_2$SO$_4$, filtered and concentrated. The residue was purified by silica gel column chromatography (petroleum/ethyl acetate=5/1) to give compound 7 (14 g, 95% yield) as a yellow solid. Molecular weight (average) calculated: 268 g/mol. Determined by LC-MS: (M+H)+: 267.

Synthesis of 4-(5-(2,6-dimethoxyphenyl)-3-(methoxycarbonyl)-1H-pyrazol-1-yl)-3-isopropyl-benzoic acid (8)

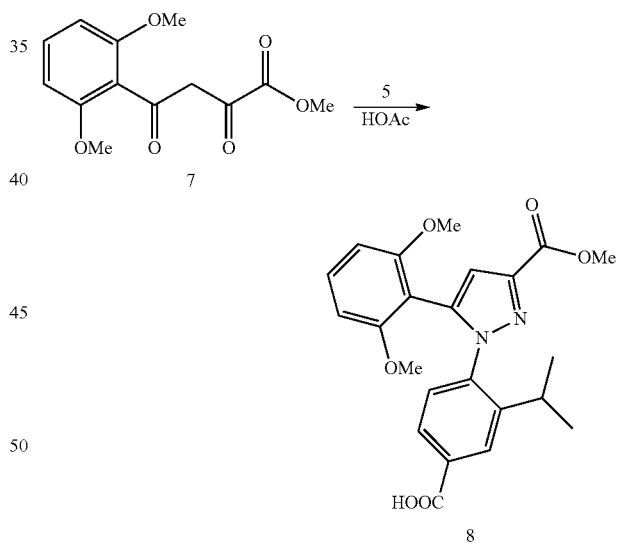

To a solution of compound 7 (8.0 g, 30 mmol) in acetic acid (50 mL) was added compound 5 (12.44 g, 45 mmol) at r.t. and then the reaction mixture was stirred at 60° C. overnight. The reaction mixture was cooled down to r.t., adjusted to pH>7 with Na$_2$CO$_3$ solution and extracted with ethyl acetate (50 mL×3). The combined organic phase was dried over Na$_2$SO$_4$, filtered and concentrated. The residue was purified by silica gel column chromatography (PE/EA=3/1) to give compound 8 (8.0 g, 53% yield) as a yellow solid. Molecular weight calculated: 424.2 g/mol. Determined by LC-MS: (M+H)+: 425.0. $^1$H NMR (400 MHz, DMSO-d$_6$) δ: 13.14 (brs, 1H), 7.85 (d, J=1.6 Hz, 1H), 7.77-7.75 (m, 1H), 7.32-7.27 (m, 2H), 6.86 (s, 1H), 6.60 (d, J=8.8 Hz, 2H), 3.84 (s, 3H), 3.61 (s, OH), 2.67-2.59 (m, 1H), 0.95 (d, J=6.0 Hz, 6H).

Synthesis of $N^1,N^3$-dimethyl-$N^1$-(3-(methylamino) propyl)-$N^3$-tritylpropane-1,3-diamine (A-2)

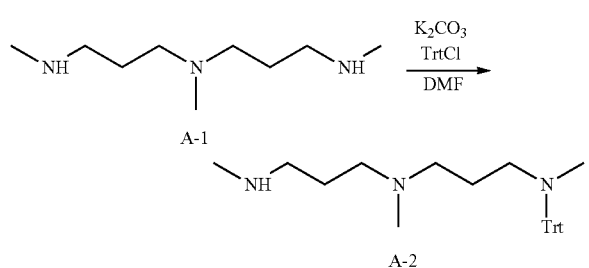

To a solution of N-Methyl-N,N-bis[3-(methylamino)propyl]amine A-1 (2.0 g, 13.8 mmol) in DMF (25 mL) in an ice-water bath was added $K_2CO_3$ (7.6 g, 55.2 mmol), and TrtCl (3.8 g, 13.8 mmol). The reaction mixture was stirred at r.t. overnight. The residue was diluted with $H_2O$ (20 mL) and extracted with EA (50 mL×3). The combined organic phases were dried over $Na_2SO_4$, filtered and concentrated to give compound A-2 (2.2 g, crude) as yellow oil. Molecular weight calculated: 415 g/mol. Determined by LC-MS: (M+H)+: 416.

Synthesis of methyl 5-(2,6-dimethoxyphenyl)-1-(2-isopropyl-4-(methyl(3-(methyl(3-(methyl(trityl) amino)propyl)amino)propyl)carbamoyl)phenyl)-1H-pyrazole-3-carboxylate (9)

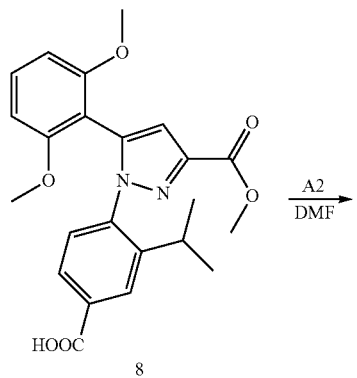

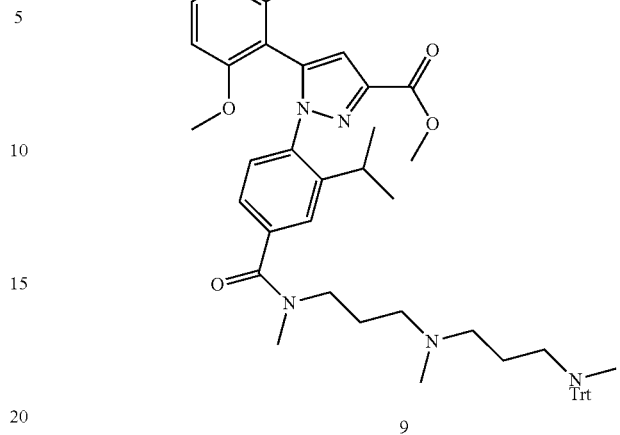

To a solution of compound 8 (1.5 g, 3.54 mmol) in DMF (20 mL) was added HATU (2.02 g, 5.31 mmol) and DIEA (1.37 g, 10.62 mmol). The mixture was stirred for 10 min before the addition of compound A-2 (1.76 g, 4.24 mmol). The reaction mixture was stirred at r.t. overnight. The residue was diluted with $H_2O$ (20 mL) and extracted with EA (20 mL×2). The combined organic phases were dried over $Na_2SO_4$, filtered and concentrated. The residue was purified by flash chromatography on reverse phase silica gel using ACN and $H_2O$ as the mobile phase with a gradient of % ACN from 5% to 95% over 35 min to give compound 9 (2.07 g, 71% yield) as a yellow solid. Molecular weight calculated: 821 g/mol. Determined by LC-MS: (M+H-Trt)+: 580.

Synthesis of 5-(2,6-dimethoxyphenyl)-1-(2-isopropyl-4-(methyl(3-(methyl(3-(methyl(trityl)amino) propyl)amino)propyl)carbamoyl)phenyl)-1H-pyrazole-3-carboxylic acid (10)

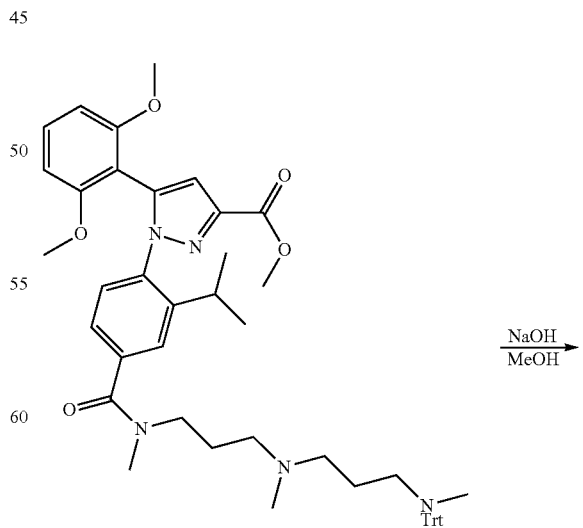

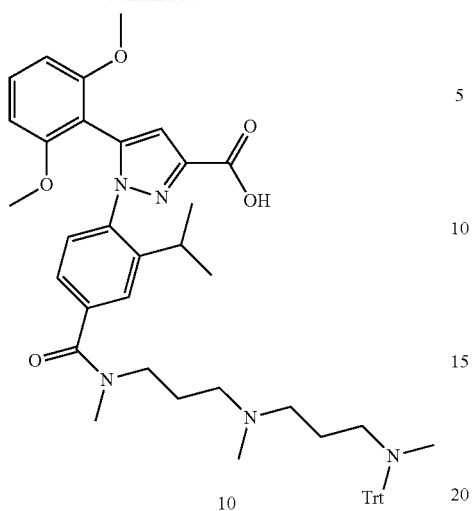

10

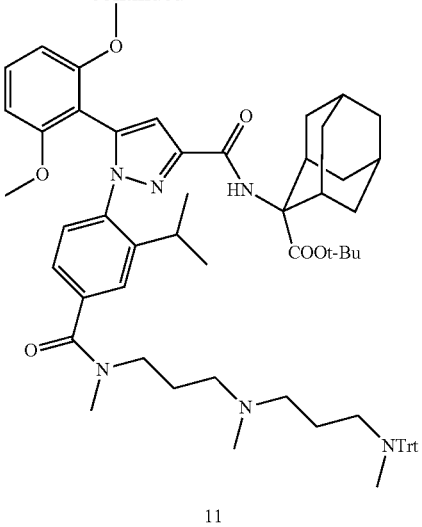

11

To a solution of compound 9 (2.07 g, 2.52 mmol) in MeOH (10 mL) was added NaOH (201.8 mg, 5.04 mmol) at r.t. The reaction mixture was stirred at 60° C. overnight. The reaction mixture was concentrated. The residue was purified by flash chromatography on reverse phase silica gel using ACN and H₂O as the mobile phase with a gradient of % ACN from 5% to 95% over 35 min) to give compound 10 (1.8 g, 90% yield) as a yellow solid. Molecular weight calculated: 807 g/mol. Determined by LC-MS: (M+H)+: 808.

To a solution of compound 10 (200 mg, 0.25 mmol) in DMF (15 mL) in an ice bath, was added DIEA (97 mg, 0.75 mmol) and PyBOP (195 mg, 0.80 mmol). The mixture was stirred for 10 min before the addition of tert-butyl 2-aminoadamantane-2-carboxylate (75 mg, 0.30 mmol). The reaction mixture was stirred at 60° C. overnight, then diluted with H₂O (20 mL) and extracted with EA (20 mL×2). The combined organic phase was dried over Na₂SO₄, filtered and concentrated. The residue was purified by flash chromatography on reverse phase silica gel using ACN and H₂O as the mobile phase with a gradient of % ACN from 5% to 95% over 35 min to give compound 11 (180 mg, 70% yield) as a yellow solid. Molecular weight calculated: 1040 g/mol. Determined by LC-MS: (M+H)+: 1041

Synthesis of 2-(5-(2,6-dimethoxyphenyl)-1-(2-isopropyl-4-(methyl(3-(methyl(3-(methylamino)propyl)amino)propyl)carbamoyl)phenyl)-1H-pyrazole-3-carboxamido)adamantane-2-carboxylic acid (12)

Synthesis of tert-butyl 2-(5-(2,8-dimethoxyphenyl)-1-(2-isopropyl-4-(methyl(3-(methyl(3-(methyl(trityl)amino)propy)amino)propy)carbamoyl)phenyl)-1H-pyrazole-3-carboxamido)adamantane-2-carboxylate (11)

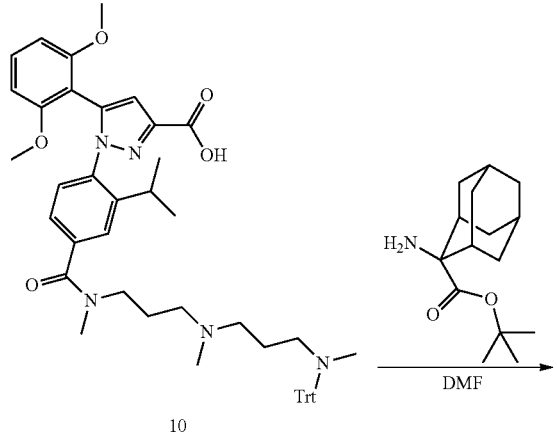

10

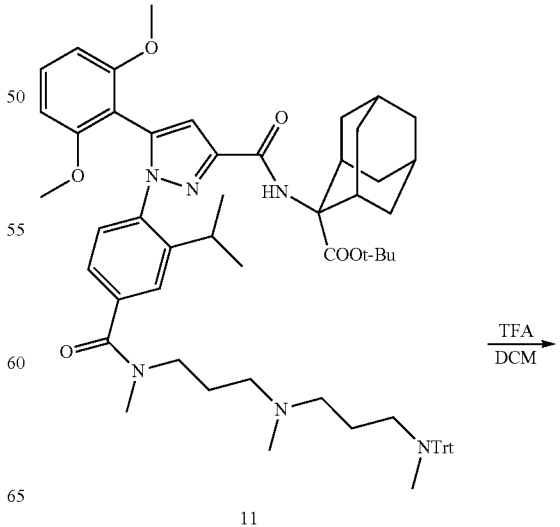

11

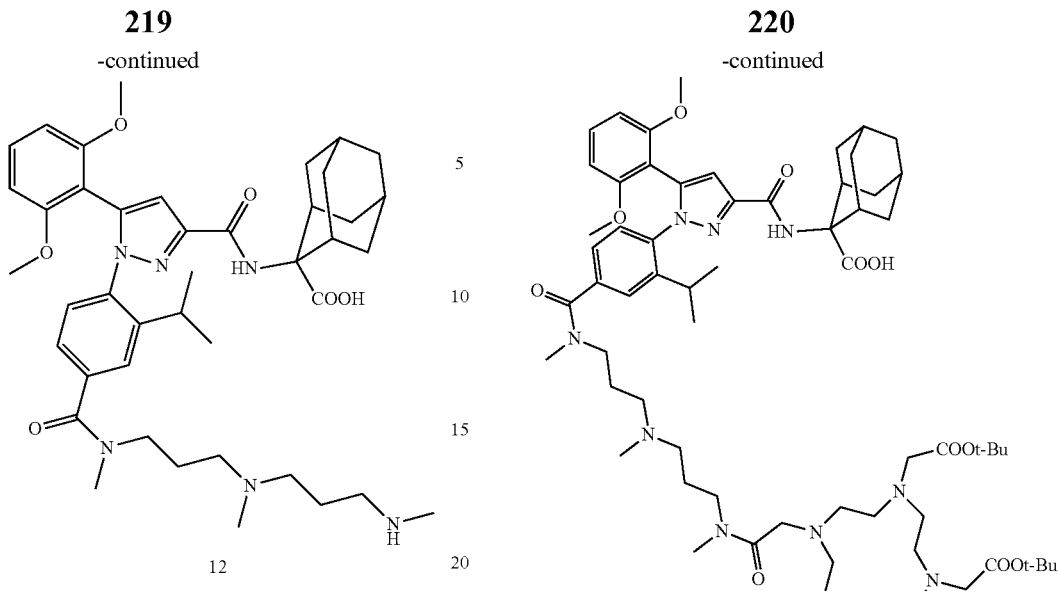

To a solution of compound 11 (1.0 g, 0.98 mmol) in DCM (10 mL) was added TFA (5 mL). The reaction mixture was stirred at r.t. for 3 hr. The reaction mixture was concentrated to give crude compound 12 (600 mg, 84% yield) as a yellow solid which was used for next step without further purification. Molecular weight calculated: 742 g/mol. Determined by LC-MS: (M+H)+: 743.

Synthesis of 2-(5-(2,6-dimethoxyphenyl)-1-(2-isopropyl-4-(methyl(3-(methyl(3-(N-methyl-2-(4,7,10-tris(2-(tert-butoxy)-2-oxoethyl)-1,4,7,10-tetraazacyclododecan-1-yl)acetamido)propyl)amino)propyl)carbamoyl)phenyl)-1H-pyrazole-3-carboxamido)adamantane-2-carboxylic acid (13)

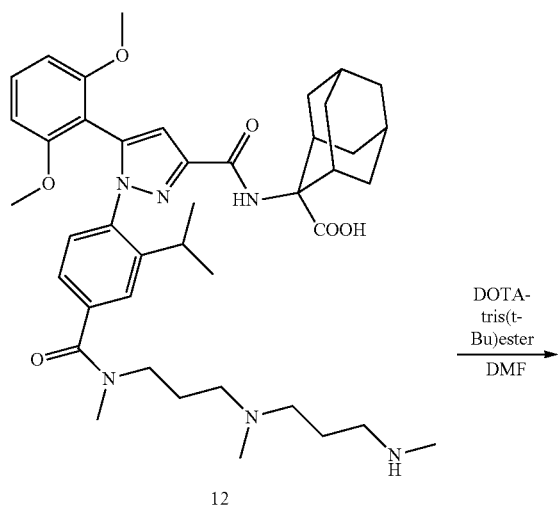

To a solution of DOTA-tris(t-Bu) ester (347 mg, 0.61 mmol) in DMF (10 mL) was added TBTU (260 mg, 0.81 mmol) and DIEA (156.7 mg, 1.22 mmol). The mixture was stirred for 10 min before the addition of compound 12 (300 mg, 0.41 mmol) was added. The reaction mixture was stirred at r.t. overnight, then diluted with $H_2O$ (20 mL) and extracted with EA (20 mL×2). The combined organic phase was dried over $Na_2SO_4$, filtered and concentrated. The residue was purified by flash chromatography on reverse phase silica gel using ACN and $H_2O$ as the mobile phase with a gradient of % ACN from 5% to 95% over 35 min to give compound 13 (150 mg, 29% yield) as yellow solid. Molecular weight calculated: 1297.7 g/mol. Determined by LC-MS: (M+H)+: 1298.7.

Synthesis of 2,2',2''-(10-(2-((3-((3-(4-(3-((2-carboxyadamantan-2-yl)carbamoyl)-5-(2,6-dimethoxyphenyl)-1H-pyrazol-1-yl)-3-isopropyl-N-methylbenzamido)propyl)(methyl)amino)propyl)(methyl)amino)-2-oxoethyl)-1,4,7,10-tetraazacyclododecane-1,4,7-triyl)triacetic acid (C-2)

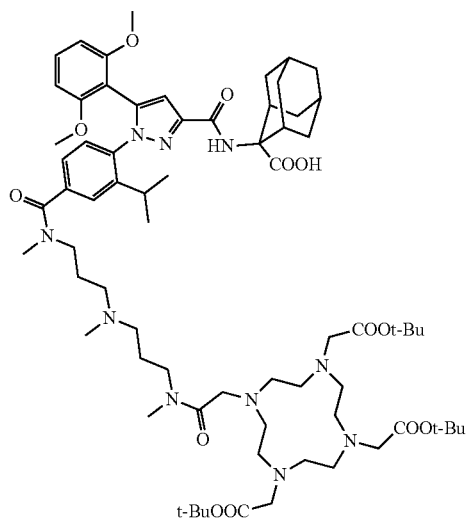

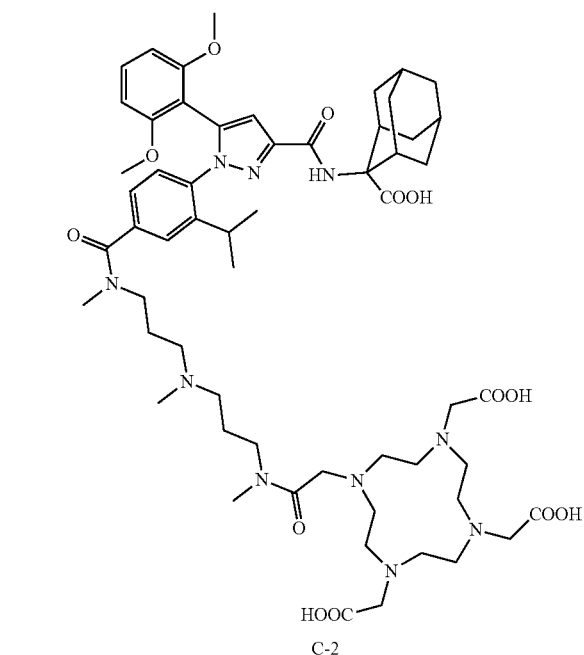

To a solution of compound 13 (150 mg, 0.12 mmol) in DCM (2 mL) was added TFA (1 mL). The reaction mixture was stirred at r.t. overnight. The reaction mixture was concentrated and the residue was purified by Prep-HPLC to give compound C-2 (33.3 mg, 26% yield) as a white solid. Molecular weight calculated: 1129.4 g/mol. Determined by LC-MS: (M+2H)2+: 565.4. Purity by UPLC (214 nm): 94.4%

Example 20: Comparator 3 (C-3, SR142948, Purchased from Tocris, Bristol, United Kingdom)

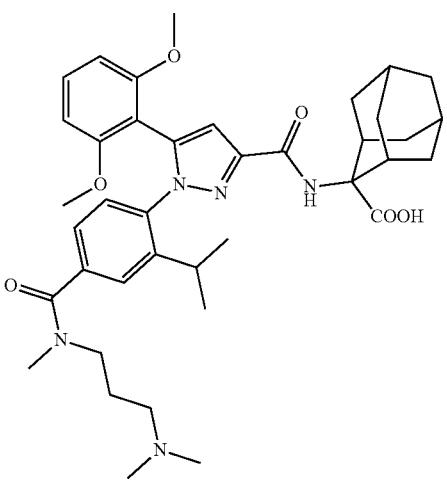 [SMILES: COc1cccc(OC)c1-c1cc(C(=O)NC2(C(=O)O)C3CC4CC(C3)CC2C4)nn1-c1ccc(C(=O)N(C)CCCN(C)C)cc1C(C)C]

Example 21: Comparator 4 (C-4) (Ref: WO9632382 A1 1996-10-17)

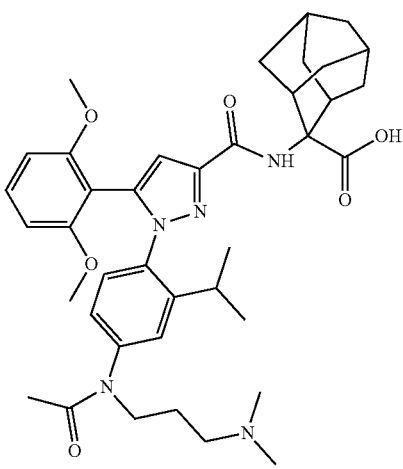 [SMILES: COc1cccc(OC)c1-c1cc(C(=O)NC2(C(=O)O)C3CC4CC(C3)CC2C4)nn1-c1ccc(N(CCCN(C)C)C(C)=O)cc1C(C)C]

Example 22: Comparator 5 (C-5) (Ref: https//pubs.acs.org/doi/10.1021/acs.jmedchem.1c00523))

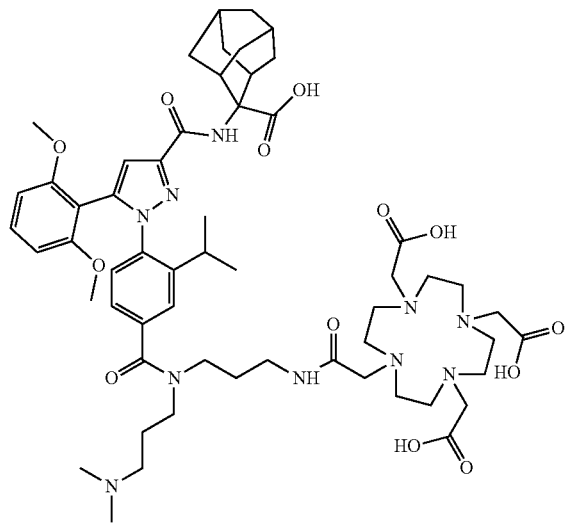 [SMILES: COc1cccc(OC)c1-c1cc(C(=O)NC2(C(=O)O)C3CC4CC(C3)CC2C4)nn1-c1ccc(C(=O)N(CCCNC(=O)CN2CCN(CC(=O)O)CCN(CC(=O)O)CCN(CC(=O)O)CC2)CCCN(C)C)cc1C(C)C]

Molecular weight (average) calculated: 1115.3 g/mol
Determined by LC-MS: (M+H)+1116.3; (M+2H)2+: 558.4;
Purity by UPLC (214 nm): 95.6%
B: Biological Data Example 23 Stability Study of Exemplary Radionuclide Labeled Compounds of the Present Application Exemplary compounds of the present application were labeled with $^{177}$Lu to evaluate stability of the compounds after radionuclide labeling. Briefly, 4 µL exemplary compounds in DMSO stock solution (2000 µM) and 2 mCi $^{177}$Lu (ITM Isotope Technologies Munich) were mixed together in 0.5 M NaOAc buffer (20-50 µL, pH=4.5), followed by incubation at 95° C. for 15 min. Then the labeled complexes were subject to radio-TLC analysis (a polyamide film using methanol and 1M ammonium acetate as the mobile phase, v/v: 4:1, detected by Mini Scan) and radio-HPLC analysis (column: Shim-pack GIST 5 µm 4.6*150 mm; buffer A: 0.2% formic acid H2O; buffer B: 0.1% formic acid acetonitrile; flow rate: 1 mL/min; gradient: 0-5 min: 10% B to 95% B; then 5-8 min: 95% B).

After radionuclide labeling, the complexes were diluted to ~1.5 mCi/0.30 mL by PBS (pH 7.4) or PBS with 3 mg/mL ascorbic acid (pH 7.4). Then the diluted samples were incubated at room temperature, followed by stability analysis via radio-HPLC at 0, 4, 24, 48, 72, 120 h of incubation, respectively. FIG. 1 illustrates stability analysis of a representative complex $^{177}$Lu—I-7. As shown in FIG. 1, after incubation over 120 h, the structure of the labeled complex remained stable and no significant degradation was detected.

Example 24 Binding Affinities of the Exemplary Compounds of the Present Application The binding affinities of test compounds were determined by a radioligand competitive binding assay using $^{177}$Lu labeled C-1 as the reference radioligand.

Briefly, 100 µL HT-29 cells expressing human NTSR-1 at a density of 1~2×10$^6$ cells/mL were mixed with binding buffer (RPMI-1640 medium supplemented with 0.25% bovine serum albumin) in each well of the 96-well filter plate (Millipore). Then the cells in each well were incubated with $^{177}$Lu—C-1 (0.55 µCi/well) and the test compound under 37° C. for 1 hr (n=3). After incubation, unbound $^{177}$Lu—C-1 and the test compound in each well was removed by filtration using a Multiscreen vacuum manifold (Millipore) and the cells were further rinsed with the binding buffer for 5 times. The cells from each well were then collected and radioactivity of the cells in each well was individually measured by γ counter (2480 WIZARD2, PerkinElmer). The best-fit $IC_{50}$ value of test compounds (inhibitory concentration when 50% of the bound $^{177}$Lu—C-1 on cells were displaced) were calculated by fitting the data with nonlinear regression using GraphPad Prism 8.0.1.

Figure 2:
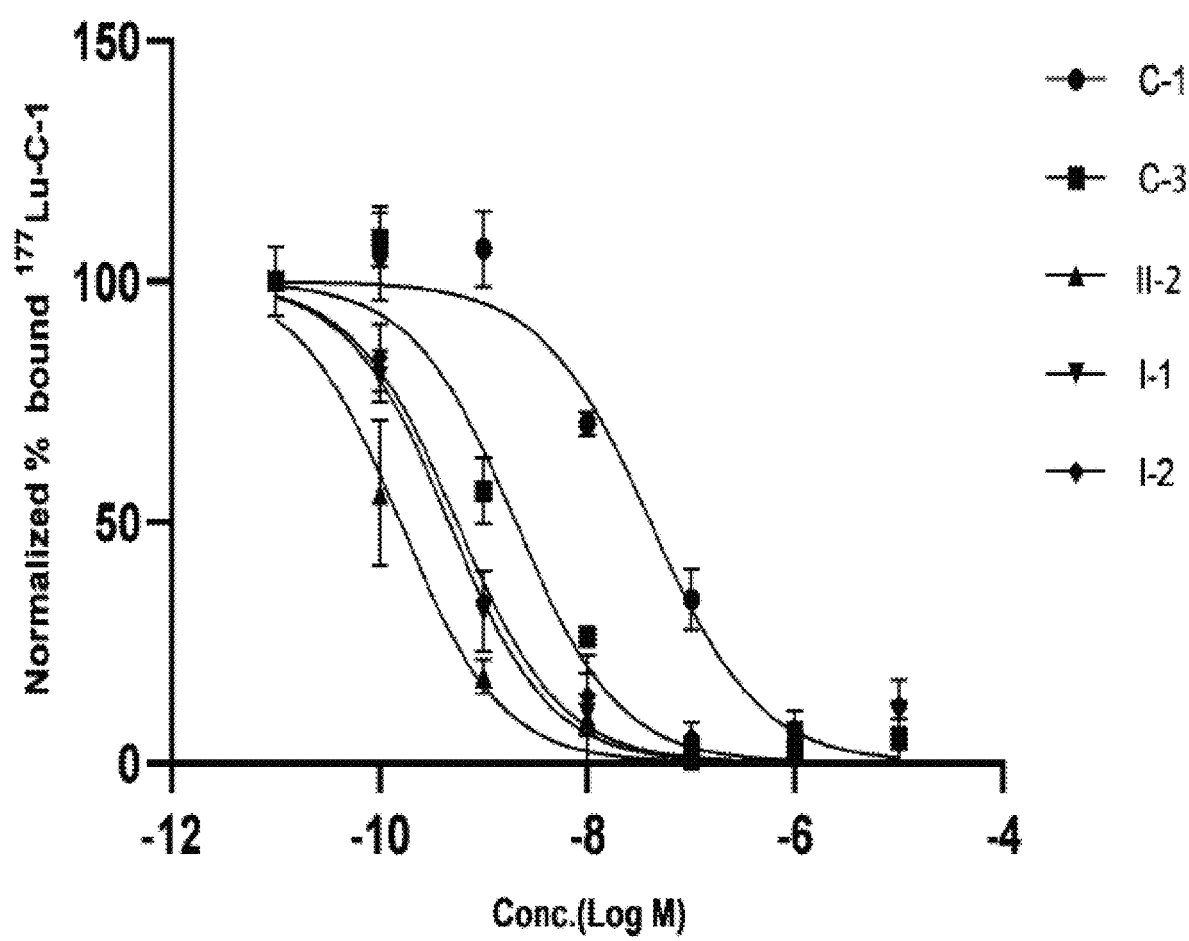
FIG. 2 illustrates the binding affinity of exemplary compounds of the application in the radioligand competitive binding assay.
Figure 3A:
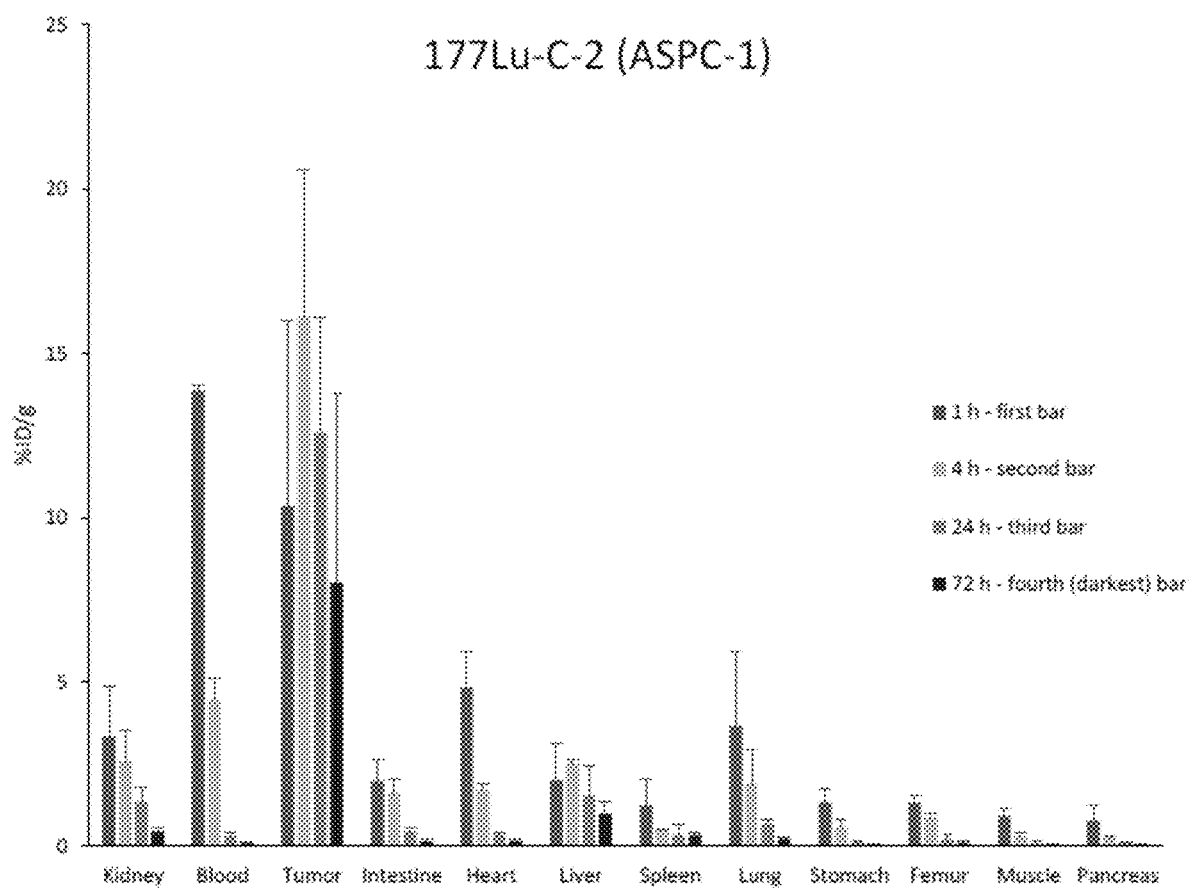
FIGS. 3A-3D illustrate biodistribution of comparative and exemplary complexes $^{177}$Lu—C-2, $^{177}$Lu—I-5, $^{177}$Lu—I-10 and $^{177}$Lu—I-7 in different organs/tissues of the ASPC-1 tumor bearing mice.
Figure 3B:
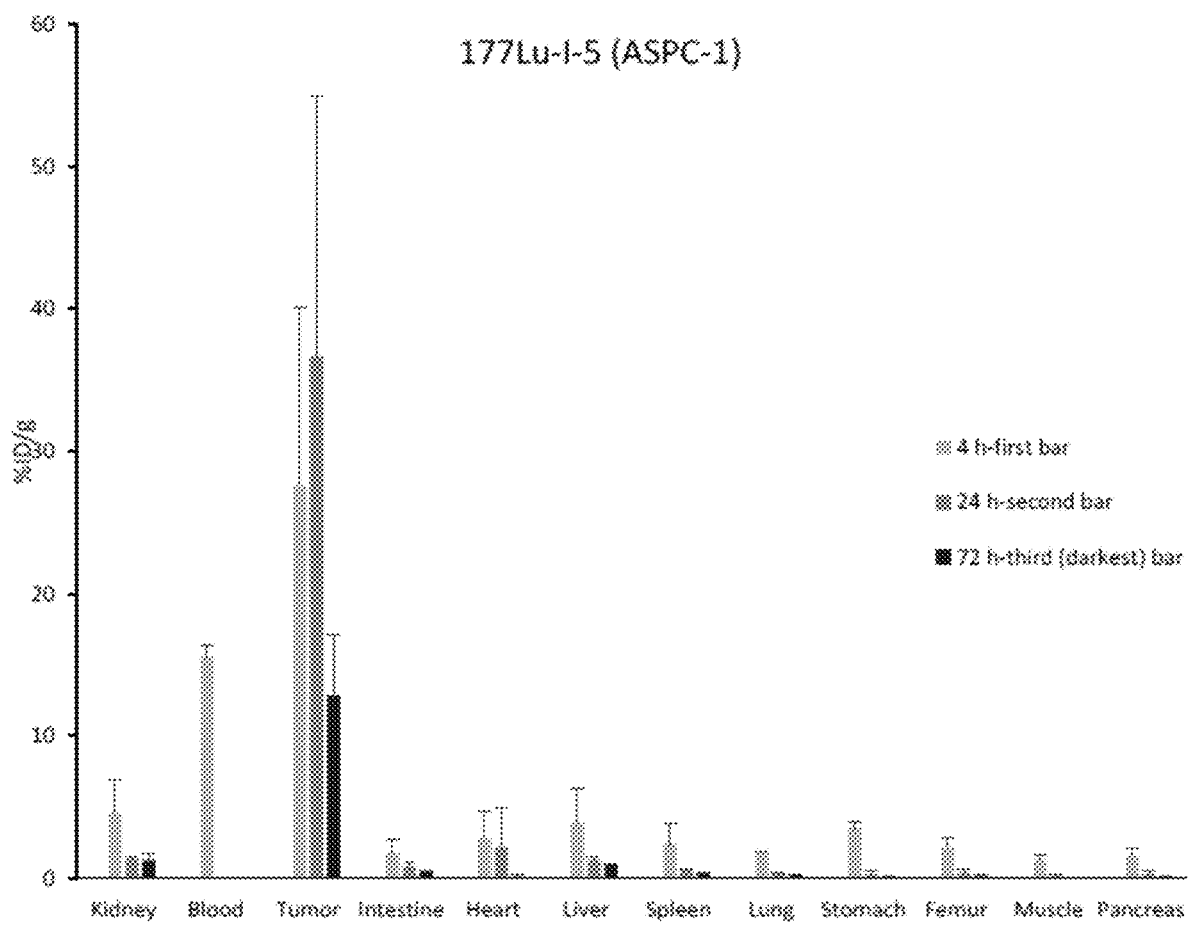
Figure 3C:
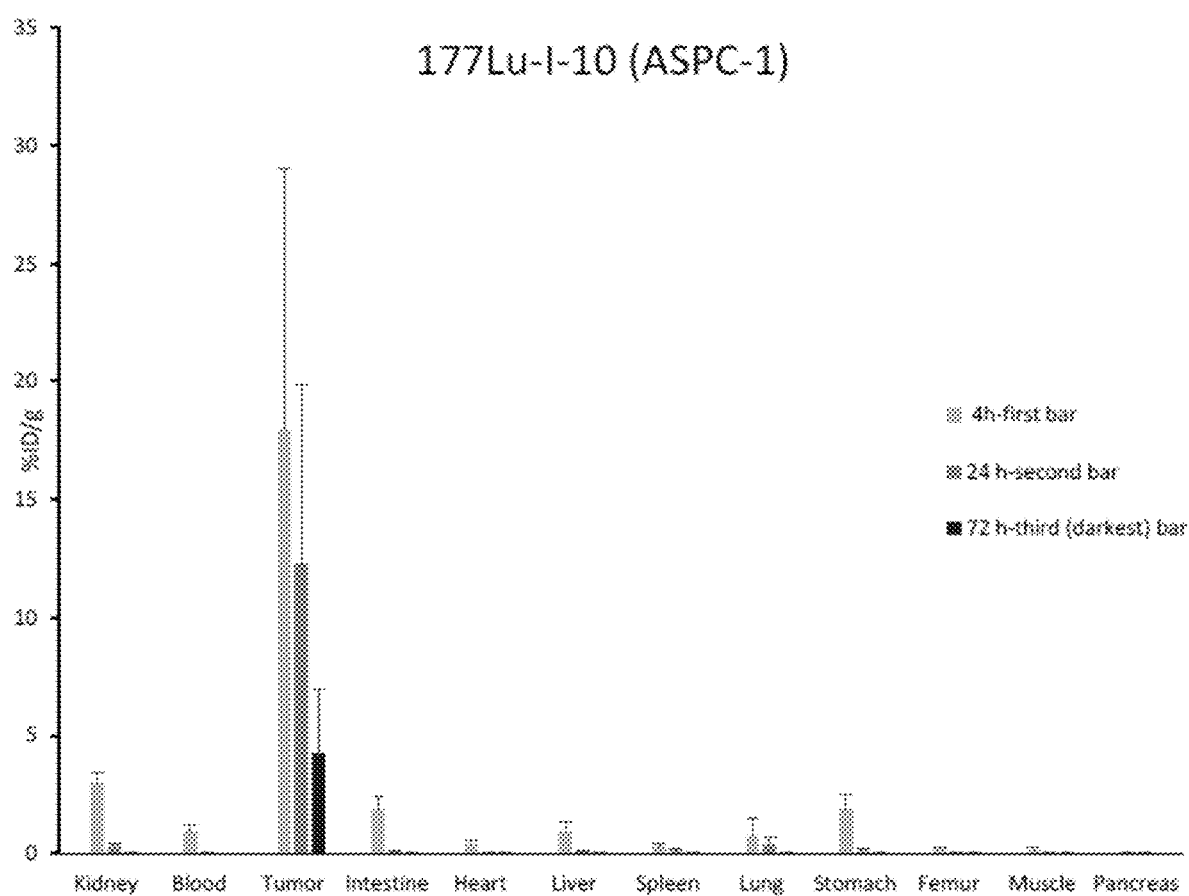
Figure 3D:
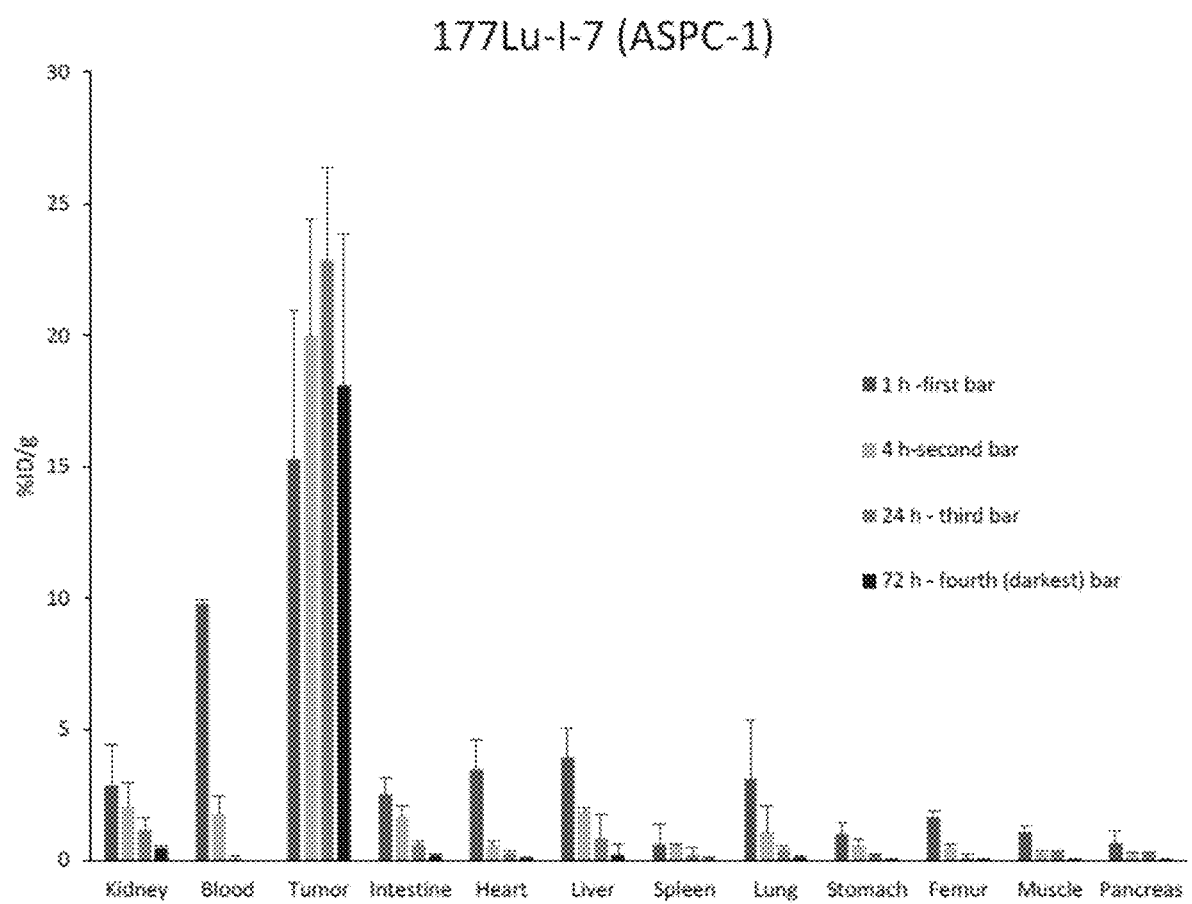

Table 1 and FIG. 2 illustrate the results from representative test compounds in a single radioligand competitive binding assay. As shown in Table 1 and FIG. 2, the compounds I-1, I-2 and II-2 displayed higher binding affinity as compared to the comparator compound C-1 or C-3.

TABLE 1

IC50 of the representative compounds from a single radioligand competitive binding assay

| Nonlin fit Summary table | Log IC$_{50}$ | | | IC$_{50}$ (nM) | | |
|---|---|---|---|---|---|---|
| | Mean | +Error | −Error | Mean | +Error | −Error |
| C-1 | −7.394 | 0.183 | 0.182 | 4.035E−08 | 2.110E−08 | 1.379E−08 |
| C-3 | −8.688 | 0.204 | 0.197 | 2.049E−09 | 1.230E−09 | 7.485E−10 |
| I-1 | −9.333 | 0.145 | 0.144 | 4.646E−10 | 1.845E−10 | 1.314E−10 |
| I-2 | −9.253 | 0.169 | 0.164 | 5.591E−10 | 2.668E−10 | 1.756E−10 |
| I-2 | −9.802 | 0.193 | 0.181 | 1.578E−10 | 8.837E−11 | 5.388E−11 |

Table 2 further illustrate mean IC$_{50}$ of the test compounds in the radioligand competitive binding assay from multiple experiments, as well as the relative binding affinities as compared to C-1 (calculated by Mean IC$_{50}$ of C-1/Mean IC$_{50}$ of the test compound)

TABLE 2

Mean IC50 and relative binding affinity of the test compounds

| Compound | Mean IC$_{50}$ | Relative Binding Affinity |
|---|---|---|
| C-1 (in vitro binding assay ref) | 3.22E−08 | 1.00 |
| C-2 (3BP-227) | 4.46E−09 | 7.2 |
| C-3 (SR142948) | 2.35E−09 | 13.7 |
| C-4 | 3.90E−10 | 22.0 |
| I-1 | 3.9E−10 | 82.6 |
| I-2 | 4.21E−10 | 76.5 |
| I-3 | 6.20E−11 | 519.8 |
| I-4 | 5.99E−11 | 538.2 |
| I-5 | 2.20E−10 | 146.4 |
| I-6 | 1.05E−08 | 3.1 |
| I-7 | 2.06E−10 | 156.7 |
| I-8 | 4.51E−10 | 71.4 |
| I-9 | 1.32E−10 | 243.5 |
| I-10 | 1.14E−09 | 28.3 |
| I-11 | 3.23E−10 | 99.8 |

TABLE 2-continued

Mean IC50 and relative binding affinity of the test compounds

| Compound | Mean IC$_{50}$ | Relative Binding Affinity |
|---|---|---|
| I-12 | 2.89E−09 | 11.2 |
| I-13 | 2.20E−09 | 14.6 |
| I-14 | 2.96E−09 | 10.9 |
| II-1 | 2.98E−10 | 107.6 |
| II-2 | 1.10E−10 | 293.0 |
| II-3 | 6.02E−11 | 535.2 |

Based on the radioligand competitive binding assay, it can be seen that the compounds of the present application are all highly active against NTSR-1 with IC$_{50}$ values in the range of about 0.01 nM to about 1 nM, suggesting the structure of the linkers connecting the aromatic motifs of the molecule and the chelators could have unexpected impact on the binding affinity.

Binding affinities of the representative compounds were also evaluated by FLIPR assay. Neurotensin receptor 1 belongs to the G-protein coupled receptors (GPCR) family. Activation of NTSR-1 by its ligand Neurotensin can induce intracellular-calcium mobilization. In FLIPR assay, the test compound and Neurotensin were incubated together with cells expressing NTSR-1 to measure inhibition of the intracellular-calcium mobilization by the test compound so that to evaluate its binding affinity.

Briefly, HEK293 cells stably expressing human NTSR-1 were plated in 384-well plates. 20 ul cell suspension at a concentration of $10 \times 10^5$ per ml was seeded in each well and incubated at 37° C. 5% CO$_2$ overnight. Then the cells in each well were mixed with 20 ul probenecid assay buffer, 20 ul 8 uM Fluo-4 Direct™ Loading Buffer, 6×EC80 of Neurotensin and 10 µl of the diluted test compound, and incubated at 37° C. 5% CO$_2$ for 50 min followed by incubation at room temperature for 10 min. The plate was then subject to FLIPR analysis.

Table 3 illustrates the mean IC$_{50}$ of the test compounds in FLIPR assay. As can be seen from Table 3, the compounds of the present application 1-5, 1-6 and 1-7 all displayed lower IC$_{50}$ as compared to the comparator compound C-2, further suggesting their superior binding affinities than C2.

TABLE 3

Mean IC$_{50}$ of the test compounds in FLIPR Assays

| Compound | IC$_{50}$ (nM) |
|---|---|
| C-2 | 45.42 |
| I-5 | 26.95 |
| I-6 | 16.24 |
| I-7 | 11.70 |

Example 25 Biodistribution of the Radionuclide Labeled Complexes of the Present Application The BALB/c nude mice (Charles River, Beijing) were utilized to establish the xenografted model for biodistribution study. All animal care and experimental procedure were performed by following the animal protocols approved by the ethics committee of China Institute of Radiation Protection.

Briefly, each mouse was inoculated with approximately $4 \times 10^6$ ASPC-1 cells (human pancreatic cancer cell line) or HT-29 cells (human colorectal adenocarcinoma cell line) expressing human NTSR-1 by subcutaneous injection at rear flank. After inoculation, the xenografted tumors were allowed to grow for ~2-4 weeks till the tumor weight reached to about 0.05 to 0.50 g (0.20 g in average).

Biodistribution studies were performed by administrating the radionuclide labeled test compound at a dose of ~30-50 µCi (100 µL in 0.9% NaCl, ~1.11-1.85 MBq, with specific activity 30-250 µCi/nmol) to each animal through tail vein injection.

At different time points after the administration, the mice treated with each compound were euthanized. The tissues and organs of the animals in each group were collected, excised, weighed, and analyzed in a PerkinElmer 2480 WIZARD2γ counter, and the percent injected dose (% ID) and % ID/g of each organ or tissue were calculated.

Tables 4-12 below illustrate the biodistribution of the test complexes in APSC-1 tumor-bearing mice at 1, 4, 24, and at 72 hours, including $^{177}$Lu—C-2, $^{177}$Lu—C-5, $^{177}$Lu—I-1, $^{177}$Lu—I-2, $^{177}$Lu—I-5, $^{177}$Lu—I-6, $^{177}$Lu—I-7, $^{177}$Lu—I-8, and $^{177}$Lu—I-10.

FIGS. 3A-3D illustrate the biodistribution of representative $^{177}$Lu-labeled complexes $^{177}$Lu—C-2, $^{177}$Lu—I-5, $^{177}$Lu—I-10 and $^{177}$Lu—I-7 in ASPC-1 tumor-bearing mice at different time points after administration.

TABLE 4

Biodistribution of $^{177}$Lu-C-2 in ASPC-1 tumor-bearing mice (n = 3)

| Organ/Tissue | % ID/g (1 h) | % ID/g (4 h) | % ID/g (24 h) | % ID/g (72 h) |
|---|---|---|---|---|
| Kidney | 3.34 ± 1.53 | 2.6 ± 0.93 | 1.36 ± 0.42 | 0.46 ± 0.08 |
| Blood | 13.87 ± 0.17 | 4.46 ± 0.64 | 0.31 ± 0.1 | 0.09 ± 0.01 |
| Tumor | 10.34 ± 5.66 | 16.13 ± 4.47 | 12.6 ± 3.52 | 8.03 ± 5.76 |
| Intestine | 1.98 ± 0.63 | 1.62 ± 0.41 | 0.44 ± 0.11 | 0.15 ± 0.06 |
| Heart | 4.83 ± 1.1 | 1.72 ± 0.18 | 0.37 ± 0.07 | 0.16 ± 0.04 |
| Liver | 2.01 ± 1.1 | 2.51 ± 0.12 | 1.53 ± 0.93 | 0.99 ± 0.37 |
| Spleen | 1.25 ± 0.78 | 0.49 ± 0.04 | 0.35 ± 0.3 | 0.34 ± 0.1 |
| Lung | 3.67 ± 2.25 | 1.92 ± 0.99 | 0.69 ± 0.14 | 0.23 ± 0.06 |
| Stomach | 1.35 ± 0.42 | 0.6 ± 0.23 | 0.15 ± 0.04 | 0.05 ± 0 |
| Femur | 1.34 ± 0.23 | 0.89 ± 0.11 | 0.22 ± 0.13 | 0.12 ± 0.03 |
| Muscle | 0.93 ± 0.21 | 0.31 ± 0.1 | 0.1 ± 0.05 | 0.06 ± 0.03 |
| Pancreas | 0.8 ± 0.47 | 0.27 ± 0.06 | 0.1 ± 0.02 | 0.07 ± 0.03 |

TABLE 5

Biodistribution of $^{177}$Lu-C-5 in ASPC-1 tumor-bearing mice (n = 3)

| Organ/Tissue | % ID/g (1 h) | % ID/g (4 h) |
|---|---|---|
| Kidney | 0.87 ± 0.05 | 0.33 ± 0.09 |
| Blood | 3.18 ± 0.24 | 0.22 ± 0.07 |
| Tumor | 14.96 ± 6.57 | 13.06 ± 6.54 |
| Intestine | 1.28 ± 0.11 | 0.42 ± 0.16 |
| Heart | 1.46 ± 0.24 | 0.16 ± 0.06 |
| Liver | 0.84 ± 0.43 | 0.79 ± 0.08 |
| Spleen | 0.26 ± 0.05 | 0.08 ± 0.03 |
| Lung | 1.66 ± 0.93 | 0.3 ± 0.15 |
| Stomach | 0.55 ± 0.13 | 0.4 ± 0.22 |
| Femur | 0.53 ± 0.04 | 0.13 ± 0.1 |
| Muscle | 0.31 ± 0.05 | 0.06 ± 0.02 |
| Pancreas | 0.26 ± 0.05 | 0.06 ± 0.02 |

TABLE 6

Biodistribution of $^{177}$Lu-I-1 in ASPC-1 tumor-bearing mice (n = 3)

| Organ/Tissue | % ID/g (4 h) | % ID/g (24 h) | % ID/g (72 h) |
|---|---|---|---|
| Kidney | 3.66 ± 2.51 | 3.16 ± 1.81 | 1.3 ± 0.61 |
| Blood | 2.08 ± 0.14 | 0.06 ± 0.02 | 0.04 ± 0.01 |
| Tumor | 6.93 ± 0.71 | 22.56 ± 1.81 | 7.23 ± 4.46 |
| Intestine | 0.98 ± 0.2 | 0.37 ± 0.07 | 0.51 ± 0.1 |
| Heart | 0.68 ± 0.5 | 0.24 ± 0.1 | 0.18 ± 0.03 |
| Liver | 1.81 ± 0.43 | 0.97 ± 0.45 | 1.06 ± 0.46 |
| Spleen | 0.42 ± 0.16 | 0.53 ± 0.25 | 0.24 ± 0.08 |
| Lung | 0.64 ± 0.1 | 0.31 ± 10.1 | 0.33 ± 0.28 |
| Stomach | 0.57 ± 0.16 | 0.28 ± 0.17 | 0.1 ± 0.02 |
| Femur | 0.72 ± 0.05 | 0.19 ± 0.09 | 0.15 ± 0.06 |
| Muscle | 0.47 ± 0.25 | 0.13 ± 0.05 | 0.06 ± 0.01 |
| Pancreas | 0.41 ± 0.28 | 0.18 ± 0.09 | 0.07 ± 0.04 |

TABLE 7

Biodistribution of $^{177}$Lu-I-2 in ASPC-1 tumor-bearing mice (n = 3)

| Organ/Tissue | % ID/g (4 h) | % ID/g (24 h) | % ID/g (72 h) |
|---|---|---|---|
| Kidney | 2.03 ± 0.38 | 2.39 ± 0.77 | 1.69 ± 1.04 |
| Blood | 9.23 ± 0.36 | 0.28 ± 0.03 | 0.07 ± 0.01 |
| Tumor | 23.11 ± 18.15 | 25.61 ± 1.69 | 15.44 ± 5.61 |
| Intestine | 2.00 ± 0.18 | 1.00 ± 0.18 | 0.55 ± 0.11 |
| Heart | 3.78 ± 0.03 | 0.4 ± 0.13 | 0.18 ± 0.1 |
| Liver | 5.15 ± 1.65 | 1.66 ± 0.55 | 1.02 ± 0.44 |
| Spleen | 1.05 ± 0.65 | 1.07 ± 0.31 | 0.19 ± 0.03 |
| Lung | 1.77 ± 0.37 | 0.39 ± 0.11 | 0.17 ± 0.02 |
| Stomach | 0.86 ± 0.1 | 0.43 ± 0.27 | 0.22 ± 0.1 |
| Femur | 1.4 ± 0.79 | 0.39 ± 0.1 | 0.111 ± 0.09 |
| Muscle | 1.48 ± 1.16 | 0.23 ± 0.14 | 0.05 ± 0.03 |
| Pancreas | 0.54 ± 0.14 | 0.32 ± 0.15 | 0.08 ± 0.02 |

TABLE 8

Biodistribution of $^{177}$Lu-I-5 in ASPC-1 tumor-bearing mice (n = 3)

| Organ/Tissue | %ID/g (4 h) | %ID/g (24 h) | %ID/g (72 h) |
|---|---|---|---|
| Kidney | 4.57 ± 2.28 | 1.37 ± 0.17 | 1.29 ± 0.49 |
| Blood | 15.51 ± 0.77 | 0.09 ± 0.01 | 0.02 ± 0 |
| Tumor | 27.56 ± 12.51 | 36.67 ± 18.25 | 12.83 ± 4.23 |
| Intestine | 1.81 ± 0.87 | 0.82 ± 0.31 | 0.51 ± 0.04 |
| Heart | 2.82 ± 1.88 | 2.18 ± 2.71 | 0.15 ± 0.13 |
| Liver | 3.87 ± 2.36 | 1.27 ± 0.29 | 0.96 ± 0.07 |
| Spleen | 2.39 ± 1.4 | 0.63 ± 0.05 | 0.34 ± 0.04 |
| Lung | 1.841 ± 0.07 | 0.33 ± 0.06 | 0.23 ± 0.07 |
| Stomach | 3.52 ± 0.4 | 0.28 ± 0.2 | 0.15 ± 0.05 |
| Femur | 2.21 ± 0.63 | 0.38 ± 0.23 | 0.17 ± 0.09 |
| Muscle | 1.29 ± 0.37 | 0.17 ± 0.08 | 0.05 ± 0.01 |
| Pancreas | 1.57 ± 0.5 | 0.3 ± 0.24 | 0.1 ± 0.04 |

TABLE 9

Biodistribution of $^{177}$Lu-I-6 in ASPC-1 tumor-bearing mice (n = 3)

| Organ/Tissue | % ID/g (1 h) | % ID/g (4 h) |
|---|---|---|
| Kidney | 3.71 ± 0.24 | 2.39 ± 0.37 |
| Blood | 0.38 ± 0.06 | 0.04 ± 0.01 |
| Tumor | 12.71 ± 4.57 | 13.64 ± 2.5 |
| Intestine | 0.77 ± 0.31 | 0.22 ± 0.06 |
| Heart | 0.22 ± 0.12 | 0.12 ± 0.03 |
| Liver | 0.51 ± 0.22 | 0.53 ± 0.16 |
| Spleen | 0.09 ± 0.01 | 0.13 ± 0.03 |
| Lung | 0.54 ± 0.04 | 0.17 ± 0.08 |
| Stomach | 0.27 ± 0.19 | 0.21 ± 0.05 |
| Femur | 0.12 ± 0.01 | 0.12 ± 0.09 |
| Muscle | 0.06 ± 0 | 0.08 ± 0.02 |
| Pancreas | 0.11 ± 0.03 | 0.06 ± 0.02 |

TABLE 10

Biodistribution of $^{177}$Lu-I-7 in ASPC-1 tumor-bearing mice (n = 3)

| Organ/Tissue | % ID/g (1 h) | % ID/g (4 h) | % ID/g (24 h) | % ID/g (72 h) |
|---|---|---|---|---|
| Kidney | 2.85 ± 0.45 | 2.05 ± 0.48 | 1.2 ± 0.17 | 0.48 ± 0.12 |
| Blood | 9.79 ± 1.66 | 1.8 ± 0.62 | 0.07 ± 0.01 | 0.01 ± 0 |
| Tumor | 15.27 ± 8.72 | 19.97 ± 10.42 | 22.83 ± 1.14 | 18.07 ± 0.98 |
| Intestine | 2.53 ± 0.58 | 1.69 ± 0.45 | 0.62 ± 0.04 | 0.19 ± 0.07 |
| Heart | 3.47 ± 0.56 | 0.58 ± 0.32 | 0.29 ± 0.14 | 0.08 ± 0.01 |
| Liver | 3.93 ± 0.43 | 1.88 ± 1.00 | 0.84 ± 0.09 | 0.23 ± 0.01 |
| Spleen | 0.63 ± 0.19 | 0.58 ± 0.15 | 0.23 ± 0.11 | 0.06 ± 0.01 |
| Lung | 3.12 ± 1.25 | 1.1 ± 0.49 | 0.43 ± 0.14 | 0.13 ± 0.1 |
| Stomach | 1.01 ± 0.82 | 0.58 ± 0.59 | 0.21 ± 0.08 | 0.04 ± 0.01 |
| Femur | 1.65 ± 0.23 | 0.49 ± 0.25 | 0.12 ± 0.04 | 0.06 ± 0.03 |
| Muscle | 1.1 ± 0.3 | 0.27 ± 0.2 | 0.34 ± 0.3 | 0.011 ± 0.01 |
| Pancreas | 0.67 ± 0.28 | 0.24 ± 0.22 | 0.29 ± 0.21 | 0.02 ± 0.01 |

TABLE 11

Biodistribution of $^{177}$Lu-I-8 in ASPC-1 tumor-bearing mice (n = 4)

| Organ/Tissue | % ID/g (4 h) | % ID/g (24 h) |
|---|---|---|
| Kidney | 3.09 ± 1.79 | 1.47 ± 1.07 |
| Blood | 6.25 ± 1.53 | 0.23 ± 0.12 |
| Tumor | 16.7 ± 10.49 | 26.12 ± 10.63 |
| Intestine | 3.51 ± 1.14 | 1.00 ± 0.34 |
| Heart | 2.39 ± 0.51 | 0.5 ± 0.12 |
| Liver | 7.4 ± 2.9 | 1.86 ± 0.97 |
| Spleen | 0.71 ± 0.16 | 1.22 ± 0.22 |
| Lung | 2.92 ± 2.09 | 0.55 ± 0.34 |
| Stomach | 1.74 ± 1.36 | 0.69 ± 0.46 |
| Femur | 0.89 ± 0.74 | 0.4 ± 0.16 |
| Muscle | 0.54 ± 0.28 | 0.34 ± 0.14 |
| Pancreas | 0.53 ± 0.09 | 0.6 ± 0.2 |

TABLE 12

Biodistribution of $^{177}$Lu-I-10 in ASPC-1 tumor-bearing mice (n = 3)

| Organ/Tissue | % ID/g (4 h) | % ID/g (24 h) | % ID/g (72 h) |
|---|---|---|---|
| Kidney | 3.02 ± 0.39 | 0.31 ± 0.11 | 0.04 ± 0.01 |
| Blood | 0.93 ± 0.29 | 0.04 ± 0.00 | 0.01 ± 0.00 |
| Tumor | 17.97 ± 11.04 | 12.27 ± 7.59 | 4.24 ± 2.71 |
| Intestine | 1.86 ± 0.58 | 0.14 ± 0.01 | 0.04 ± 0.01 |
| Heart | 0.41 ± 0.13 | 0.04 ± 0.02 | 0.01 ± 0.01 |
| Liver | 0.96 ± 0.4 | 0.14 ± 0.01 | 0.06 ± 0.02 |
| Spleen | 0.3 ± 0.14 | 0.12 ± 0.05 | 0.02 ± 0.01 |
| Lung | 0.74 ± 0.72 | 0.4 ± 0.26 | 0.05 ± 0.03 |
| Stomach | 1.88 ± 0.59 | 0.1 ± 0.07 | 0.04 ± 0.01 |
| Femur | 0.23 ± 0.06 | 0.04 ± 0.02 | 0.02 ± 0 |
| Muscle | 0.13 ± 0.12 | 0.01 ± 0.01 | 0.011 ± 0.01 |
| Pancreas | 0.07 ± 0.01 | 0.04 ± 0.02 | 0.01 ± 0 |

Figure 4A:
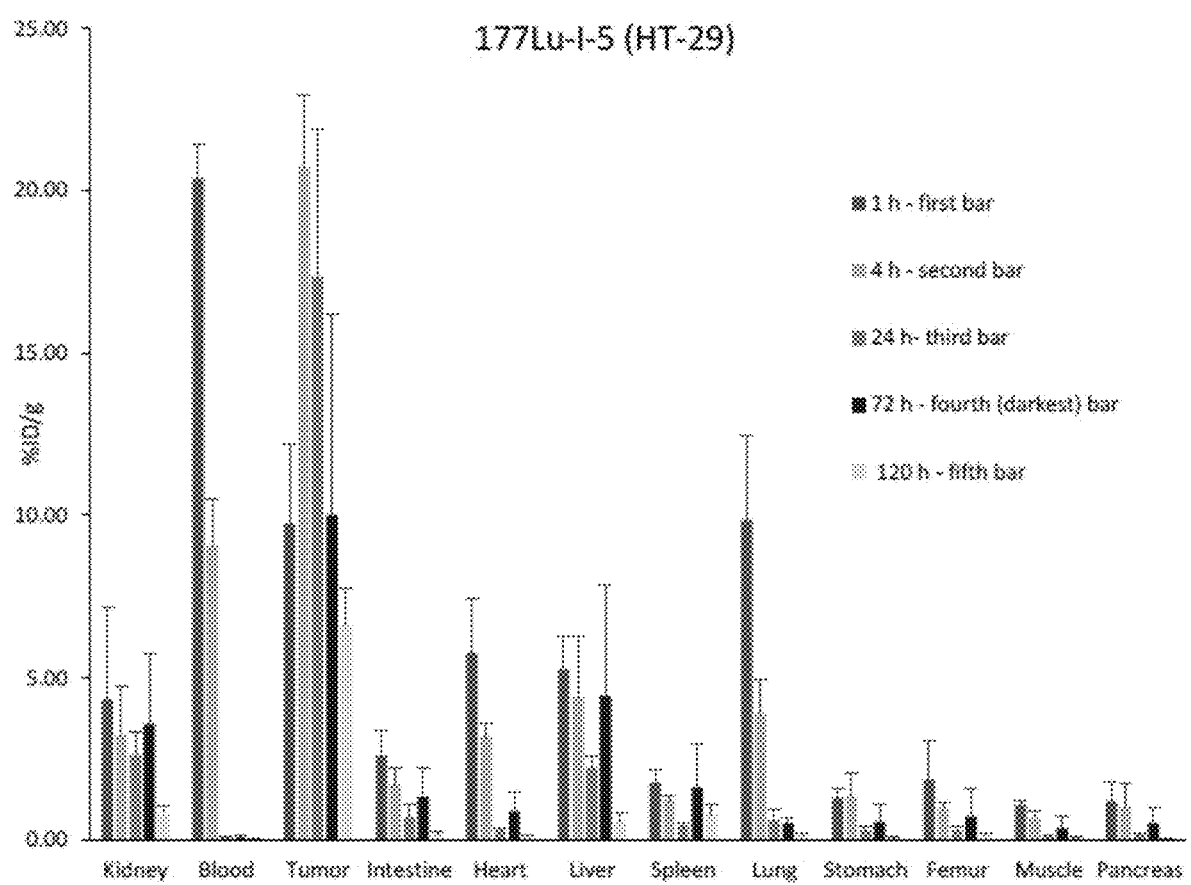
FIGS. 4A-4B illustrate biodistribution of comparative and exemplary complexes $^{177}$Lu—I-5, and $^{177}$Lu—I-7 in different organs/tissues of the HT-29 tumor bearing mice.
Figure 4B:
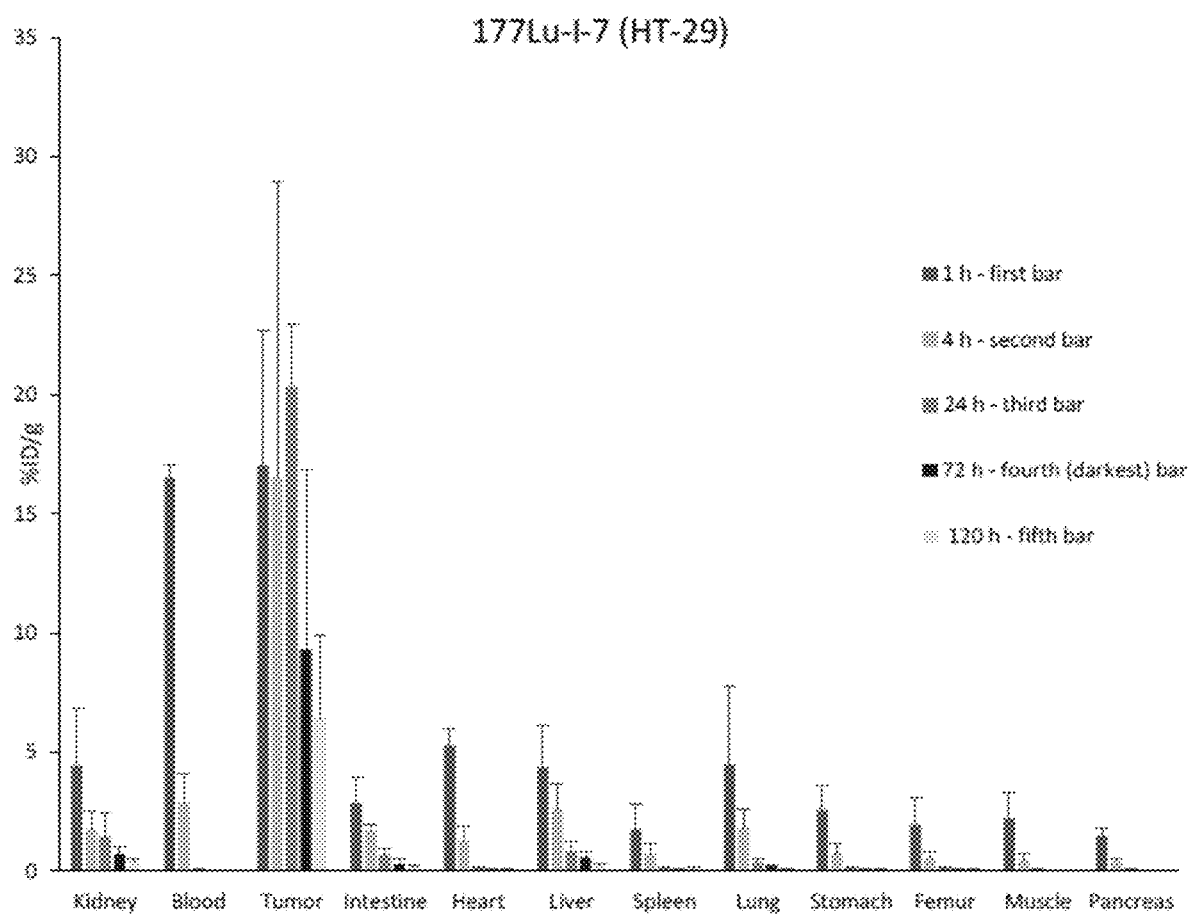

Tables 13-15 show the biodistribution of $^{177}$Lu—I-5, $^{177}$Lu—I-6, and $^{177}$Lu—I-7 in HT-29 tumor-bearing mice at different time points after administration. FIGS. 4A-4B further show the biodistribution of representative $^{177}$Lu-labeled compounds $^{177}$Lu—I-5, and $^{177}$Lu—I-7 In HT-29 tumor-bearing mice at different time points after administration.

TABLE 13

Biodistribution of $^{177}$Lu-I-5 in HT-29 tumor-bearing mice (n = 3)

| Organ/Tissue | % ID/g (1 h) | % ID/g (4 h) | % ID/g (24 h) | % ID/g (72 h) | % ID/g (120 h) |
|---|---|---|---|---|---|
| Kidney | 4.34 ± 2.82 | 3.22 ± 1.54 | 2.61 ± 0.72 | 3.55 ± 2.21 | 0.81 ± 0.23 |
| Blood | 20.4 ± 1.06 | 9.07 ± 1.42 | 0.07 ± 0.02 | 0.09 ± 0.07 | 0.01 ± 0 |
| Tumor | 9.74 ± 2.44 | 20.7 ± 2.21 | 17.4 ± 4.53 | 10.02 ± 6.15 | 6.61 ± 1.12 |
| Intestine | 2.59 ± 0.76 | 1.7 ± 0.53 | 0.7 ± 0.39 | 1.33 ± 0.88 | 0.17 ± 0.06 |
| Heart | 5.76 ± 1.66 | 3.15 ± 0.43 | 0.31 ± 0.07 | 0.89 ± 0.56 | 0.13 ± 0.02 |
| Liver | 5.26 ± 1.02 | 4.41 ± 1.88 | 2.21 ± 0.36 | 4.44 ± 3.4 | 0.55 ± 0.3 |
| Spleen | 1.76 ± 0.41 | 1.22 ± 0.16 | 0.43 ± 0.09 | 1.61 ± 1.35 | 0.8 ± 0.32 |
| Lung | 9.85 ± 2.58 | 3.88 ± 1.04 | 0.62 ± 0.32 | 0.5 ± 0.19 | 0.12 ± 0.1 |
| Stomach | 1.29 ± 0.31 | 1.35 ± 0.68 | 0.29 ± 0.11 | 0.54 ± 0.53 | 0.07 ± 0.01 |
| Femur | 1.84 ± 1.19 | 0.99 ± 0.18 | 0.29 ± 0.1 | 0.73 ± 0.82 | 0.13 ± 0.05 |
| Muscle | 1.07 ± 0.14 | 0.66 ± 0.21 | 0.12 ± 0.04 | 0.37 ± 0.34 | 0.06 ± 0.02 |
| Pancreas | 1.18 ± 0.61 | 1.01 ± 0.71 | 0.15 ± 0.06 | 0.51 ± 0.5 | 0.05 ± 0.02 |

TABLE 14

Biodistribution of $^{177}$Lu-I-6 in HT-29 tumor-bearing mice (n = 3)

| Organ/Tissue | % ID/g (1 h) | % ID/g (4 h) |
|---|---|---|
| Kidney | 5.9 ± 4.85 | 5.14 ± 2.21 |
| Blood | 3.2 ± 1.07 | 0.08 ± 0.03 |
| Tumor | 10.31 ± 4.72 | 7.53 ± 3.52 |
| Intestine | 1.21 ± 0.06 | 0.27 ± 0.07 |
| Heart | 1.17 ± 0.24 | 0.12 ± 0.03 |
| Liver | 1.28 ± 0.47 | 0.83 ± 0.27 |
| Spleen | 0.45 ± 0.19 | 0.26 ± 0.1 |
| Lung | 1.66 ± 1.17 | 0.27 ± 0.04 |
| Stomach | 0.69 ± 0.23 | 0.32 ± 0.2 |
| Femur | 0.68 ± 0.18 | 0.2 ± 0.03 |
| Muscle | 0.57 ± 0.15 | 0.09 ± 0.04 |
| Pancreas | 0.62 ± 0.25 | 0.14 ± 0.02 |

TABLE 15

Biodistribution of $^{177}$Lu-I-7 in HT-29 tumor-bearing mice (n = 3)

| Organ/Tissue | % ID/g (1 h) | % ID/g (4 h) | % ID/g (24 h) | % ID/g (72 h) | % ID/g (120 h) |
|---|---|---|---|---|---|
| Kidney | 4.41 ± 2.41 | 1.73 ± 0.79 | 1.43 ± 1.04 | 0.7 ± 0.3 | 0.4 ± 0.15 |
| Blood | 16.51 ± 0.56 | 2.85 ± 1.23 | 0.06 ± 0.02 | 0.03 ± 0 | 0.01 ± 0 |
| Tumor | 17.04 ± 5.68 | 16.52 ± 12.39 | 20.35 ± 2.62 | 9.3 ± 7.53 | 6.42 ± 3.46 |
| Intestine | 2.84 ± 1.07 | 1.71 ± 0.23 | 0.66 ± 0.29 | 0.29 ± 0.23 | 0.19 ± 0.01 |
| Heart | 5.28 ± 0.74 | 1.31 ± 0.53 | 0.16 ± 0.01 | 0.11 ± 0.01 | 0.05 ± 0.03 |
| Liver | 4.35 ± 1.78 | 2.59 ± 1.08 | 0.85 ± 0.38 | 0.57 ± 0.21 | 0.24 ± 0.04 |
| Spleen | 1.73 ± 1.08 | 0.71 ± 0.41 | 0.14 ± 0.03 | 0.08 ± 0.01 | 0.1 ± 0.04 |
| Lung | 4.47 ± 3.31 | 1.81 ± 0.77 | 0.35 ± 0.14 | 0.23 ± 0.01 | 0.07 ± 0.02 |
| Stomach | 2.58 ± 1.00 | 0.76 ± 0.38 | 0.14 ± 0.03 | 0.06 ± 0.01 | 0.061 ± 0.03 |
| Femur | 1.95 ± 1.15 | 0.56 ± 0.23 | 0.11 ± 0.02 | 0.06 ± 0.03 | 0.07 ± 0.02 |
| Muscle | 2.2 ± 1.08 | 0.44 ± 0.26 | 0.05 ± 0.03 | 0.03 ± 0.01 | 0.04 ± 0.02 |
| Pancreas | 1.48 ± 0.29 | 0.38 ± 0.17 | 0.07 ± 0.04 | 0.03 ± 0.01 | 0.04 ± 0.01 |

Table 16 illustrates radionuclide uptake by tumor relative other tissues in ASPC-1 tumor-bearing mice at 1 or 4 hours after administrating $^{177}$Lu—C5 and the representative compound of the present application $^{177}$Lu—I-6. As can be seen from Table 16, compared to $^{177}$Lu—C5, $^{177}$Lu—I-6 displayed a significantly higher tumor uptake relative to blood, liver and lung.

TABLE 16

Comparison of the uptake ratio between tumor and selected normal organs of $^{177}$Lu-C5 and $^{177}$Lu-I-6 in ASPC-1 tumor-bearing mice.

| | Tumor/Blood | Tumor/Liver | Tumor/Lung | Tumor/Kidney |
|---|---|---|---|---|
| $^{177}$LU-I-6 @ 1 h | 33.3 | 25.0 | 23.7 | 3.42 |
| $^{177}$Lu-C5 @ 1 h | 4.7 | 17.9 | 9.0 | 17.2 |
| $^{177}$Lu-I-6 @ 4 h | 364 | 25.9 | 79.3 | 5.70 |
| $^{177}$Lu-C5 @ 4 h | 60.5 | 16.6 | 43.3 | 40.0 |

Table 17 shows a comparison of the uptake AUC (0-72 hour) of comparator $^{177}$Lu—C2 and representative $^{177}$Lu-labeled compounds of the present application in ASPC-1 tumor-bearing mice. As shown in Table 17, the representative $^{177}$Lu-labeled complexes of the present application $^{177}$Lu—I-7, $^{177}$Lu—I-5, $^{177}$Lu—I-1, and $^{177}$Lu—I-2 all displayed significantly higher tumor AUC over 72 hours as compared to $^{177}$Lu—C2. In addition, the ratio of tumor AUC verse normal organ AUC has been significantly improved in $^{177}$Lu—I-7, $^{177}$Lu—I-5, $^{177}$Lu—I-1. $^{177}$Lu—I-2 and $^{177}$Lu—I-10 groups.

TABLE 17

Comparison of the uptake AUC (0-72 hour) of selected comparator and exemplary $^{177}$Lu-labeled complexes in ASPC-1 tumor-bearing mice.

| Organ/Tissue | AUC (0-72 h) | | | | | |
|---|---|---|---|---|---|---|
| | C-2 | I-7 | I-5 | I-1 | I-2 | I-10 |
| Kidney | 93.93 | 81.35 | 132.6 | 182.3 | 146.3 | 47.7 |
| Blood | 91.79 | 42.79 | 189.4 | 28.1 | 121.8 | 12.7 |
| Tumor | 827.02 | 1470.10 | 1885.4 | 1023.7 | 1518.2 | 734.4 |
| Intestine | 41.19 | 50.07 | 61.9 | 36.3 | 71.2 | 28.2 |
| Heart | 45.82 | 25.15 | 111.6 | 20.5 | 63.5 | 6.5 |
| Liver | 108.58 | 63.63 | 112.6 | 80.2 | 142.9 | 17.9 |
| Spleen | 28.18 | 17.09 | 58.3 | 28.8 | 53.7 | 8.2 |
| Lung | 58.38 | 36.66 | 39.0 | 26.1 | 38.5 | 23.5 |
| Stomach | 15.78 | 16.69 | 55.5 | 18.6 | 30.4 | 26.8 |
| Femur | 23.21 | 14.26 | 43.5 | 18.7 | 32.6 | 4.6 |
| Muscle | 10.11 | 17.07 | 22.4 | 11.5 | 26.6 | 2.3 |
| Pancreas | 9.77 | 14.40 | 31.7 | 12.5 | 19.4 | 2.3 |
| Tumor/Kidney | 8.80 | 18.1 | 14.2 | 5.6 | 10.4 | 15.4 |
| Tumor/Blood | 9.0 | 34.4 | 10.0 | 36.5 | 12.5 | 58.0 |
| Tumor/Liver | 7.61 | 23.1 | 16.7 | 12.8 | 10.6 | 41.1 |
| Tumor/Lung | 14.2 | 40.1 | 48.3 | 39.3 | 39.4 | 31.3 |

The above biodistribution studies have demonstrated that all the complexes of the present application displayed good to excellent tumor uptake of the radionuclide and favorable tumor AUC verse normal organ AUC ratios. The uptake of radionuclide in tumor and normal organs including blood, kidney and liver were found to be greatly impacted by the linkers connecting the aromatic motifs of the molecule and the chelators. In addition, it was also found that the structural variations in the linker regions play roles in determining the tumor residence time of radionuclide and more significantly the wash-out kinetics of the radionuclide in normal organs such as blood, kidney, liver, lung etc.

Example 26 SPECT/CT Imaging Study of $^{177}$Lu-Labeled Complexes

ASPC-1 tumor-bearing mice were IV-injected with about 120 μCi of $^{177}$Lu-labeled complexes, then anesthetized under 2% isoflurane/oxygen gas and placed on the scanner. SPECT/CT images were acquired in three bed positions for 30 min using a MILabs SPECT scanner. Whole-body SPECT images were acquired at 1 h, 4 h, 24 and 72 h after injecting the radiotracers.

Figure 5:
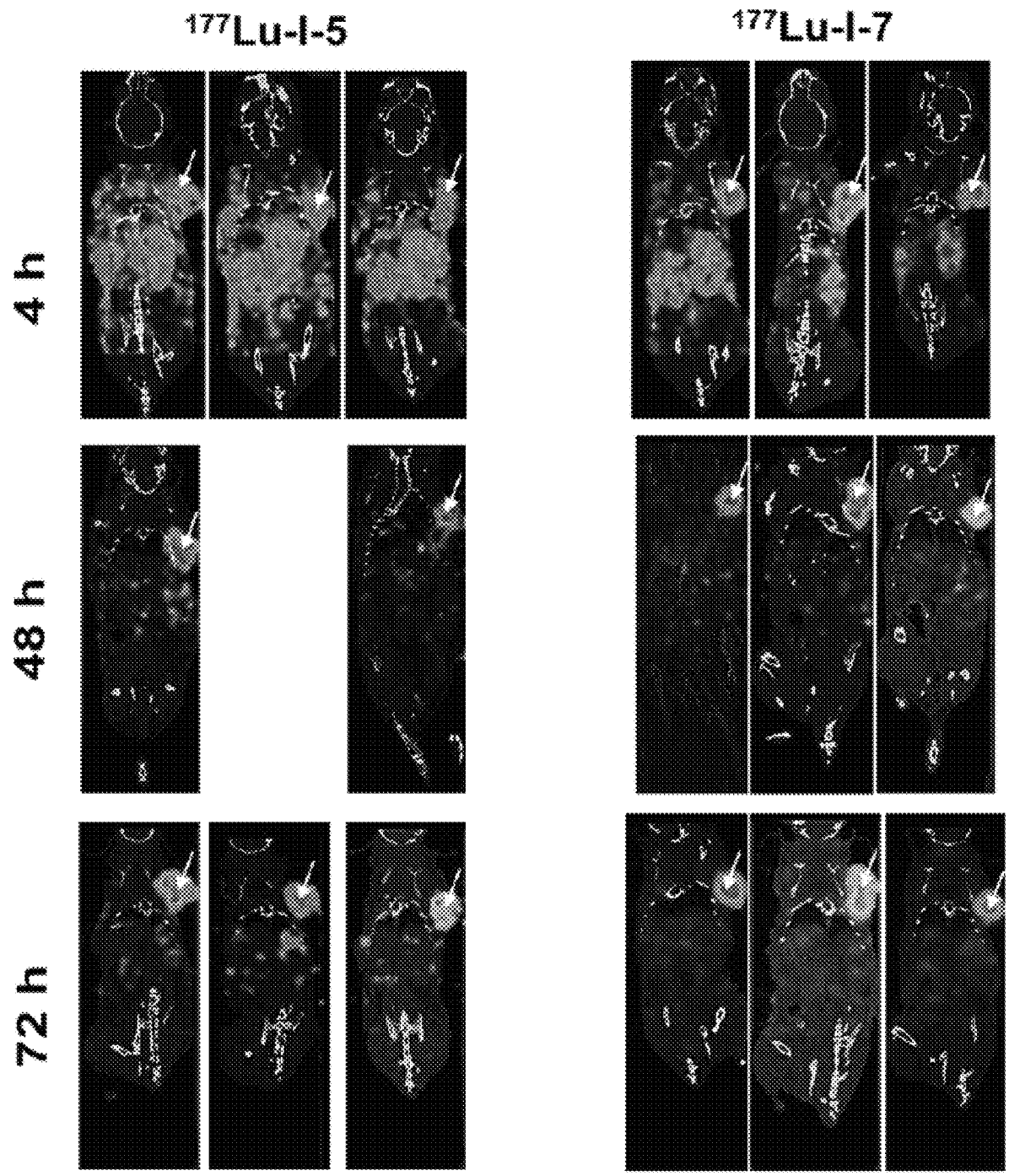
FIG. 5 illustrates mice SPECT/CT imaging results after administration of the exemplary $^{177}$Lu labeled complexes, $^{177}$Lu—I-5, and $^{177}$Lu—I-7, of the present application over 72 hours.

As shown in FIG. 5, $^{177}$Lu-labeled complexes of the present application $^{177}$Lu—I-5 and $^{177}$Lu—I-7 displayed sustained retention in tumors (as shown in white arrows in FIG. 5) and rapid clearance from other organs or tissues over 72 hours.

Example 27 PEC/CT Imaging Study of $^{68}$Ga-Labeled Complexes

ASPC-1 tumor-bearing mice were IV-injected with 150 μCi of $^{68}$Ga-labeled compounds, anesthetized under 2% isoflurane/oxygen gas and placed on the scanner. PET images were acquired in one bed position for 10 min using an animal PET/SPECT/CT (Inliview-3000B). Whole-body PET images were acquired at 30, 60, 120 and 180 minutes after injection of the radiotracers.

As shown in FIG. 6, $^{68}$Ga-labeled complex $^{68}$Ga—I-6 displayed stronger tumor uptake/retention as compared to $^{68}$Ga—C-5 (as shown in white arrows in FIG. 6) and better tumor to normal contrast over 180 minutes (such as tumor to liver, as annotated by white triangles in FIG. 6).

Example 28 Efficacy Study of $^{177}$Lu and $^{225}$Ac Labeled Complexes

In vivo efficacy of the $^{177}$Lu labeled complexes and $^{225}$Ac labeled complexes of the present application was evaluated in ASPC-1 tumor-bearing mice. For $^{177}$Lu therapy study, animals in each group were dosed with vehicle or 0.6 mCi activity of the radiolabeled complexes at Day 1 and Day 5, respectively. For $^{225}$Ac therapy studies, animals in each group were administered with a single dose of vehicle, 18, 37 or 74 KBq activity of the radiolabeled complexes, respectively.

The tumor volume (V) was determined according to the equation (V=(π+6)×L×W×H) at different time points, where L is the longest axis and W is the perpendicular axis to L, and H is the perpendicular axis to L and W plane. Endpoint (sacrifice) criteria were defined as either when the tumor volume exceeded 1.5 cm$^3$, or 20% body weight loss.

As shown in FIG. 7A, administration of the $^{177}$Lu labeled complexes of the present application significantly inhibited growth of the tumor as compared to the vehicle group, indicating the in vivo efficacy of the $^{177}$Lu therapy. Administration of the $^{177}$Lu therapy did not significantly affect body weight of the animals, as shown in FIG. 7B.

FIGS. 8A and 8C illustrate the anti-tumor efficacy of the representative $^{225}$Ac labeled complexes at different doses. From FIGS. 8A and 8C, it can be seen that all the three doses including 18, 37 or 74 KBq displayed significant tumor inhibition as compared to the vehicle group, in which the 37 and 74 KBq groups of $^{225}$Ac—I-5 or the 37 and 74 KBq groups of $^{225}$Ac—I-7 showed similar trends, indicating the 37 KBq of $^{225}$A-I-5 or $^{225}$Ac—I-7 is sufficient to achieve the maximal effect in the animals. Administration of the $^{225}$Ac therapy did not significantly affect body weight of the animals, as shown in FIGS. 8B and 8D.

While the present application has been described with reference to examples, it is to be understood that the scope of the claims should not be limited by the embodiments set forth in the examples, but should be given the broadest interpretation consistent with the description as a whole.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the application described and claimed herein.

FULL CITATIONS FOR DOCUMENTS REFERRED TO IN THE SPECIFICATION

A number of publications are cited herein. Full citations for these references are provided below. Each of these references is incorporated herein by reference in its entirety into the present disclosure, to the same extent as if each individual reference was specifically and individually indicated to be incorporated by reference 1. Vincent, J. P., Neurotensin receptors: binding properties, transduction pathways, and structure. Cell Mol Neurobiol 1995; 15:501-12.
2. Sarret, P. and Kitabgi, P., Neurotensin and receptors. Encycl Neurosci 2010:1021-34.

3. Gui, et al., Increased neurotensin receptor-1 expression during progression of colonic adenocarcinoma. Peptides 2008; 29:1609-15. http://dx.doi.org/10.1016/j.peptides.2008.04.014.
4. Souzan et al., Expression of neurotensin and NT1 receptor in human breast cancer: a potential role in tumor progression. Cancer Res 2006; 66:6243-9. http://dx.doi.org/10.1158/0008-5472.CAN-06-0450.
5. Ehlers, R. A., et al., Gut peptide receptor expression in human pancreatic cancers. Ann Surg 2000:231:838-48.
6. Dupouy, S. et al., The neurotensin receptor-1 pathway contributes to human ductal breast cancer progression. PLoS One. 2009; 4(1):e4223. doi: 10.1371/journal.pone.0004223. Epub 2009 Jan. 19. PMID: 19156213; PMCID: PMC2626627.
7. Gully D. et al, Biochemical and pharmacological activities of SR 142948A, a new potent neurotensin receptor antagonist, J. Pharmacol Exp Ther. 1997 February; 280 (2):802-12. PMID: 9023294.
8. Shultz J. et al., Comparative Evaluation of the Biodistribution Profiles of a Series of Nonpeptidic Neurotensin Receptor-1 Antagonists Reveals a Promising Candidate for Theranostic Applications. J Nucl Med. 2016 July; 57(7):1120-3. doi: 10.2967/jnumed.115.170530. Epub 2016 Mar. 3. PMID: 26940767.
9. Schulz J, et al., Proof of Therapeutic Efficacy of a $^{177}$Lu-Labeled Neurotensin Receptor 1 Antagonist in a Colon Carcinoma Xenograft Model. J Nucl Med. 2017 June; 58(6):936-941. doi: 10.2967/jnumed.116.185140. Epub 2017 Mar. 2. PMID: 28254866.
10. Baum R P, et al., $^{177}$Lu-3BP-227 for Neurotensin Receptor 1-Targeted Therapy of Metastatic Pancreatic Adenocarcinoma: First Clinical Results. J Nucl Med. 2018 May; 59(5):809-814. doi: 10.2967/jnumed.117.193847. Epub 2017 Oct. 12. PMID: 29025990.

The invention claimed is:
1. A compound of Formula I or a pharmaceutically acceptable salt or solvate thereof

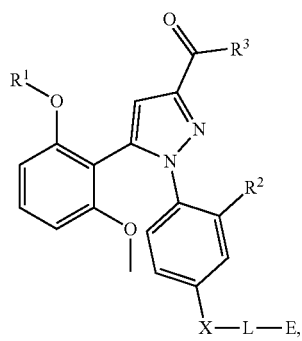

(I)

wherein $R^1$ is selected from H, $C_{1-6}$alkyl, $C_{3-6}$cycloalkyl and $C_{1-3}$alkylene$C_{3-6}$cycloalkyl, the latter three groups being optionally substituted with one or more halo;

$R^2$ is selected from H, halo, $NO_2$, $C_{1-6}$alkyl, $C_{3-8}$cycloalkyl and $C_{1-3}$alkylene$C_{3-8}$cycloalkyl, the latter three groups being optionally substituted with one or more halo;

$R^3$ is selected from 2-amino-2-adamantane carboxylic acid, cyclohexylglycine and 9-amino-bicyclo[3.3.1]nonane-9-carboxylic acid;

X is O;

L consists of 1 to 10 groups independently selected from $C_{1-6}$alkyleneO, $C_{1-6}$alkyleneNR$^7$, C(O)$C_{1-6}$alkyleneO and C(O)$C_{1-6}$alkyleneNR$^7$, wherein R$^7$ is H or $C_{1-4}$alkyl;

E is selected from the group selected from the group consisting of 1,4,7-triazacyclononane (TACN): 1,4,7-triazacyclononane-triacetic acid (NOTA); 1,4,7-triazacyclononane-N-succinic acid-N,N''-diacetic acid (NOTASA); 1,4,7-triazacyclononane-N-glutamic acid-N,N''-diacetic acid (NODAGA); 1,4,7-triazacyclononane-N,N',N''-tris(methylenephosphonic) acid (NOTP); 1,4,7,10-tetraazacyclododecane ([12]aneN4) (cyclen); 1,4,7,10-tetraazacyclotridecane ([13]aneN4); 1.4.7.11-tetraazacyclotetradecane (iso-cyclam); 1,4,7,10-tetraazacyclododecane-1,4,7,10-tetraacetic acid (DOTA); 2-(1,4,7,10-tetraazacyclododecan-1-yl)acetate (DO1A); 2.2'-(1.4.7.10-tetraazacyclododecane-1,7-diyl) diacetic acid (DO2A); 2,2',2''-(1,4,7,10-tetraazacyclododecane-1,4,7-triyl) triacetic acid (DO3A); 1,4,7,10-tetraazacyclododecane-1,4,7,10-tetra(methanepnosphonic acid) (DOTP); 1,4,7,10-tetraazacyclododecane-1,7-di(methanephosphoriic acid) (DO2P); 1,4,7,10-tetraazacyclododecane-1,4,7-tri(methanephosphonic acid) (DO3P); 1,4,7,10-tetraazacyclo-decane-1-qlutamic acid-4,7,10-triacetic acid (DOTAGA); 1,4,7,10-tetraazacyclodecane-1-succinic acid-4,7,10-triacetic acid (DOTASA); 1,4,8,11-tetraazacyclotetradecane ([14]aneN4) (cyclam); 1,4,8,12-tetraazacyclopentadecane ([15]aneN4); 1,5,9,13-tetraazacyclohexadecane ([16]aneN4); 1,4-ethano-1,4,8,11-tetraazacyclo-tetradecane (et-cyclam); 1,4,8,11-tetraazacyclotetradecane-1,4,8,11-tetraacetic acid (TETA); 2-(1,4,8,11-tetraazacyclotetradecane-1-yl) acetic acid (TE1A); 2,2'-(1,4,8,11-tetraazacyclotetradecane-1,8-diyl) diacetic acid (TE2A); 4,11-bis(carboxy methyl)-1,4,8,11-tetraazabicyclo[6.6.2]-hexadecane (CB-TE2A); 3,6,10,13,16,19-hexaazabicyclo[6.6.6]icosane (Sar); 1,4,7,10-tetra-(2-carbamoyl-methyl)-cyclododecane (TCMC); N,N'-bis[(6-carboxy-2-pyridil)methyl]-4,13-diaza-18-crown-6 (macropa), phthalocyanines, and porphyrins.

2. The compound of claim 1, or a pharmaceutically acceptable salt or solvate thereof, wherein $R^1$ is selected from H, $C_{1-4}$alkyl, $C_{3-6}$cycloalkyl and $C_{1-3}$alkylene$C_{3-6}$cycloalkyl, the latter three groups being optionally substituted with one or more halo.

3. The compound of claim 1, or a pharmaceutically acceptable salt or solvate thereof, wherein $R^1$ is $CH_3$.

4. The compound of claim 1, or a pharmaceutically acceptable salt or solvate thereof, wherein $R^2$ is selected from $CH_3$, $CH_2CH_3$, $CH_2CH_2CH_3$, $CH(CH_3)_2$, each of which is optionally substituted with one to three fluoro.

5. The compound of claim 1, or a pharmaceutically acceptable salt or solvate thereof, wherein $R^2$ is $CH(CH_3)_2$.

6. The compound of claim 1, or a pharmaceutically acceptable salt or solvate thereof, wherein $R^3$ is a group having the following formula

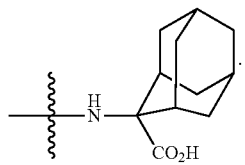

7. The compound of claim 1, or a pharmaceutically acceptable salt or solvate thereof, wherein L consists of 2 to 4 $C_3$alkyleneNR$^7$ groups and each $C_3$alkyleneNR$^7$ group is the same or different.

8. The compound of claim 1, or a pharmaceutically acceptable salt or solvate thereof, wherein L consists of 2 to 6 $C_{1-6}$alkyleneO groups and each $C_{1-6}$alkyleneO group is the same or different and 1 or 2 $C_{1-6}$alkyleneNR$^7$ groups and each $C_{1-6}$alkyleneNR$^7$ group is the same or different.

9. The compound of claim 1, or a pharmaceutically acceptable salt or solvate thereof, wherein the compound of Formula I

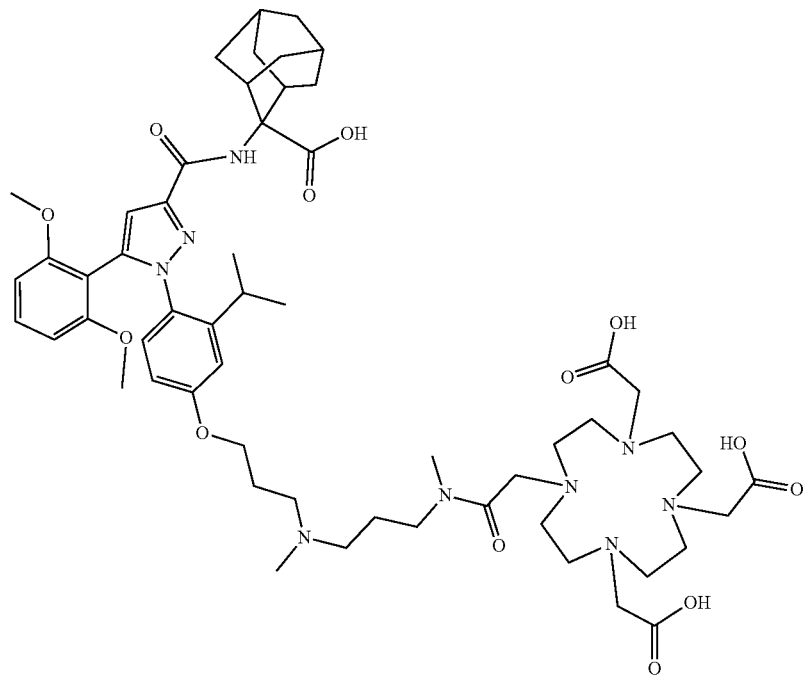

or a pharmaceutically acceptable salt or solvate thereof.

10. A compound of Formula I or a pharmaceutically acceptable salt or solvate thereof

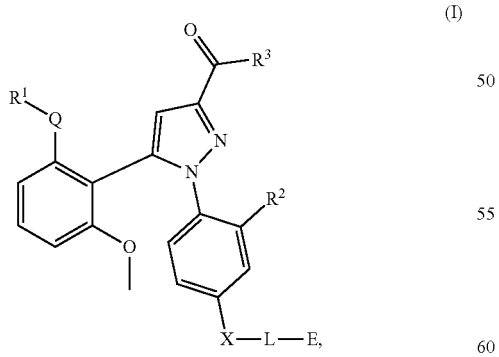

wherein

R$^1$ is selected from H, $C_{1-6}$alkyl, $C_{3-6}$cycloalkyl and $C_{1-3}$alkylene$C_{3-6}$cycloalkyl, the latter three groups being optionally substituted with one or more halo;

R$^2$ is selected from H, halo, $NO_2$, $C_{1-6}$alkyl, $C_{3-8}$cycloalkyl and $C_{1-3}$alkylene$C_{3-8}$cycloalkyl, the latter three groups being optionally substituted with one or more halo;

R$^3$ is selected from 2-amino-2-adamantane carboxylic acid, cyclohexylglycine and 9-amino-bicyclo [3.3.1] nonane-9-carboxylic acid;

X is NR$^4$, or NR$^4$C (O);

L consists of 1 to 10 groups independently selected from $C_{1-6}$alkyleneO, $C_{1-6}$alkyleneNR$^7$, C (O) $C_{1-6}$alkyleneO and C (O) $C_{1-6}$alkyleneNR$^7$, wherein R$^7$ is H or $C_{1-4}$alkyl;

E is selected from the group consisting of 1,4,7-triazacyclononane (TACN); 1,4,7-triazacyclononane-triacetic acid (NOTA); 1,4,7-triazacyclononane-N-succinic acid-N',N"-diacetic acid (NOTASA); 1,4,7-triazacyclononane-N-glutamic acid-N', N"-diacetic acid (NODAGA); 1,4,7-triazacyclononane-N,N', N"-tris (methylenephosphonic) acid (NOTP); 1,4,7,10-tetraazacyclododecane ([12]aneN4) (cyclen); 1,4,7,10-tetraazacyclotridecane ([13]aneN4); 1,4,7,11-tetraazacyclotetradecane (iso-cyclam); 1,4,7, 10-tetraazacyclododecane-1,4,7,10-tetraacetic acid (DOTA); 2-(1,4,7,10-tetraazacyclododecan-1-yl) acetate (DO1A); 2,2'-(1,4,7,10-tetraazacyclododecane-1,7-diyl) diacetic acid (DO2A); 2,2',2"-(1,4,7,10-tetraazacyclododecane-1,4,7-triyl) triacetic acid (DO3A); 1,4,7,10-tetraazacyclododecane-1,4,7,10-tetra(methanepnosphonic acid) (DOTP); 1,4,7, 10-tetraazacyclododecane-1,7-di(methanephosphoriic acid) (DO2P); 1,4,7,10-tetraazacyclododecane-1,4,7-tri(methanephosphonic acid) (DO3P); 1,4,7,10-tetraazacyclo-decane-1-glutamic acid-4,7,10-triacetic acid (DOTAGA); 1,4, 7,10-tetraazacyclodecane-1-succinic acid-4,7,10-triacetic acid (DOTASA); 1,4,8,11-tetraazacyclotetradecane ([14]aneN4) (cyclam); 1,4,8, 12-tetraazacyclopentadecane ([15]aneN4); 1,5,9,13- tetraazacyclohexadecane ([16]aneN4); 1,4-ethano-1,4,8,11-tetraazacyclo-tetradecane (et-cyclam); 1,4,8,11-tetraazacyclotetradecane-1,4,8,11-tetraacetic acid (TETA); 2-(1,4,8,11-tetraazacyclotetradecane-1-yl) acetic acid (TE1A); 2,2'-(1,4,8,11-tetraazacyclotetradecane-1,8-diyl) diacetic acid (TE2A); 4,11-bis (carboxymethyl)-1,4,8, 11-tetraazabicyclo [6.6.2]-hexadecane (CB-TE2A); 3,6,10,13,16,19-hexaazabicyclo [6.6.6] icosane (Sar); 1,4,7,10-tetra-(2-carbamoyl-methyl)-cyclododecane (TCMC); N, N'-bis [(6-carboxy-2-pyridil) methyl]-4, 13-diaza-18-crown-6 (macropa), phthalocyanines, and porphyrins;

$R^4$ is selected from H, $C_{1-6}$alkyl, $C_{1-6}$alkenyl, $C_{1-6}$alkynyl, C (O) $C_{1-6}$alkyl, $C_{1-10}$alkyleneNR$^5$R$^6$, $C_{1-10}$alkenyleneNR$^5$R$^6$, and $C_{1-10}$alkynyleneNR$^5$R$^6$; and $R^5$ and $R^6$ are independently selected from H and $C_{1-6}$alkyl.

11. The compound of claim 10, or a pharmaceutically acceptable salt or solvate thereof, wherein the compound of Formula I is selected from the group consisting of:

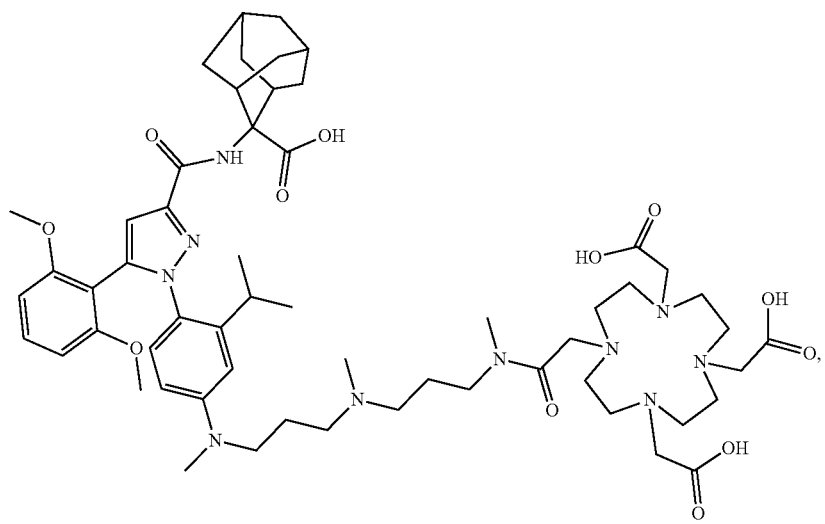

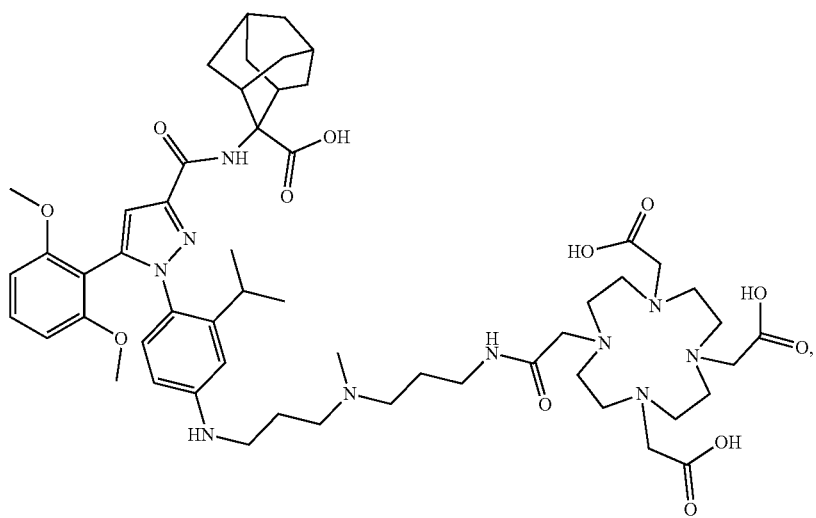

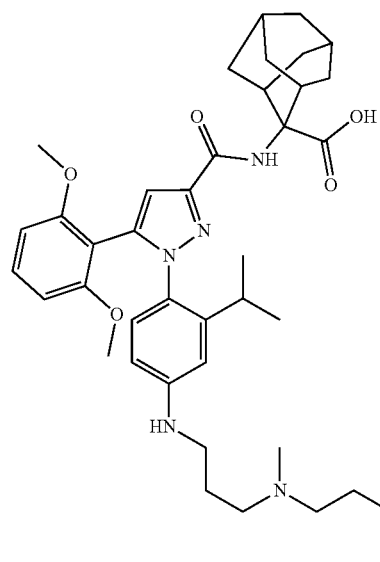
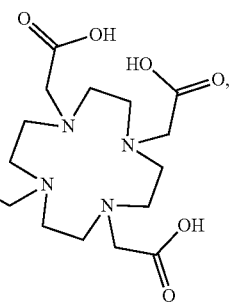
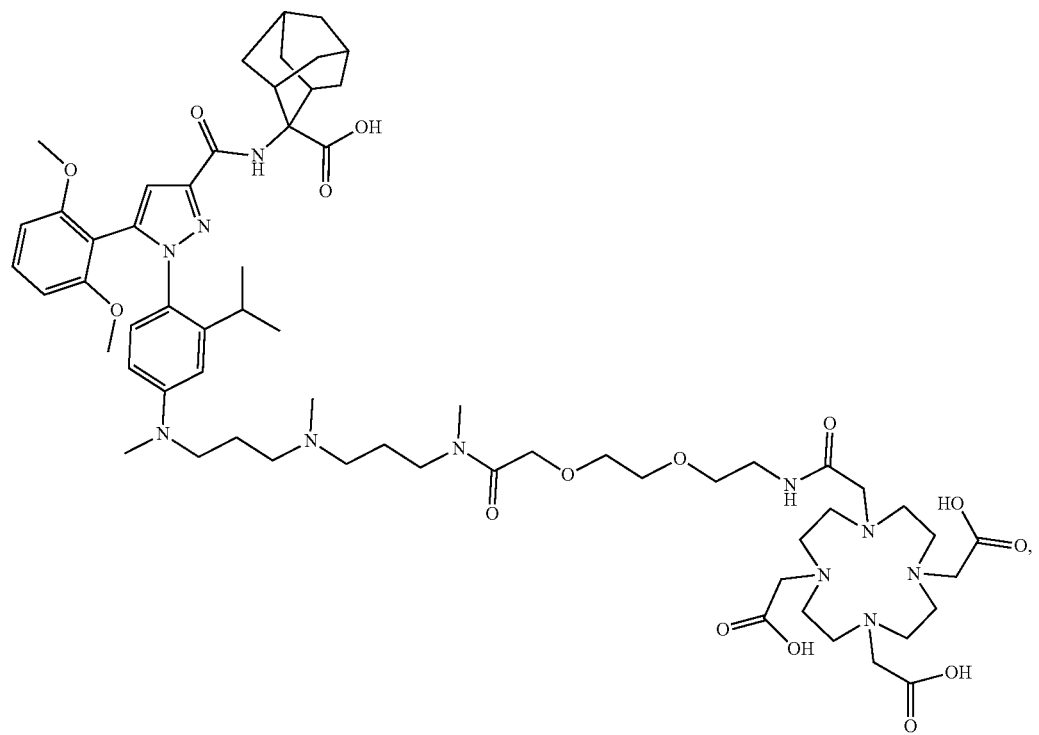

-continued
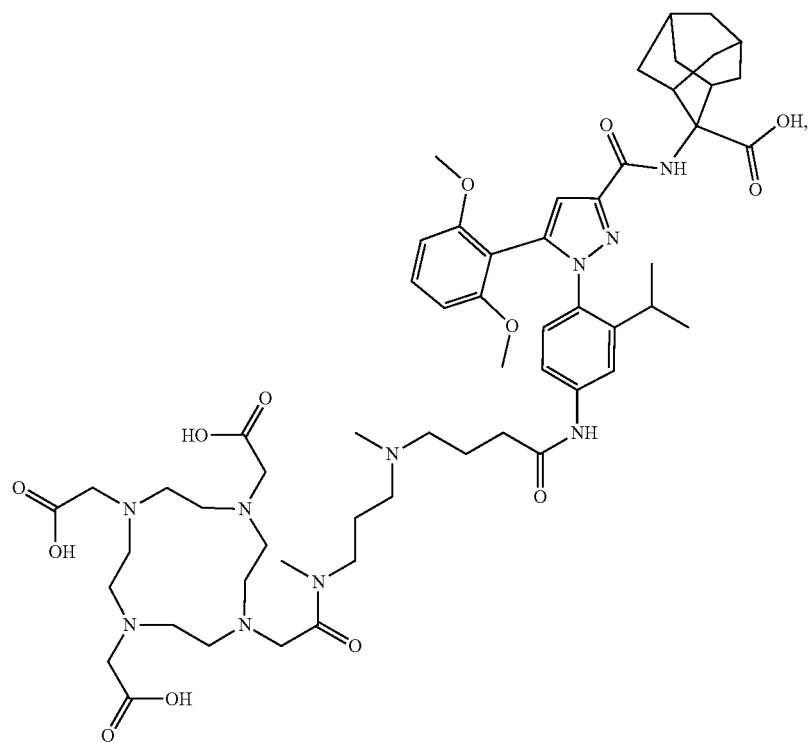
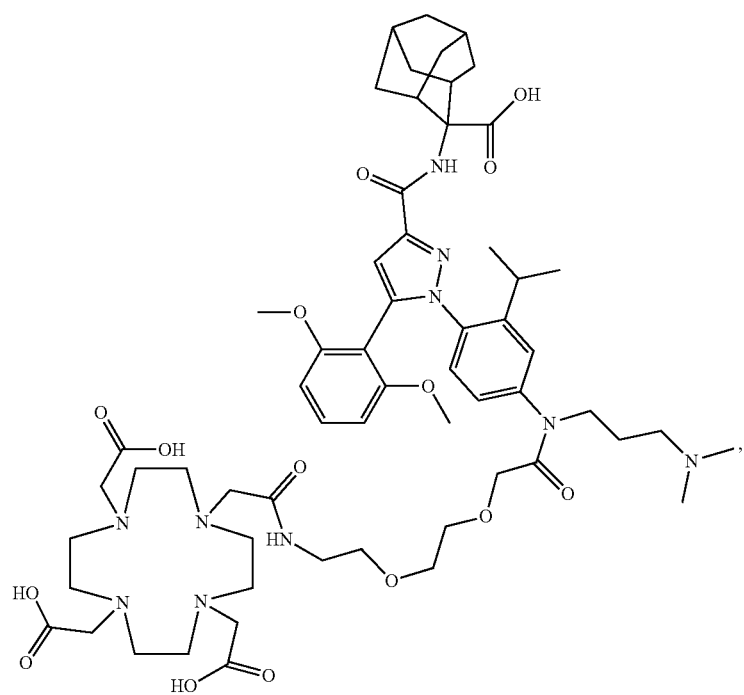

-continued
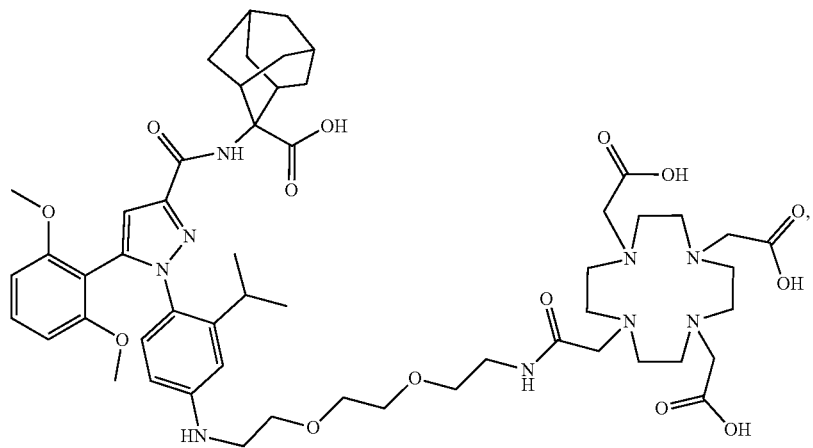
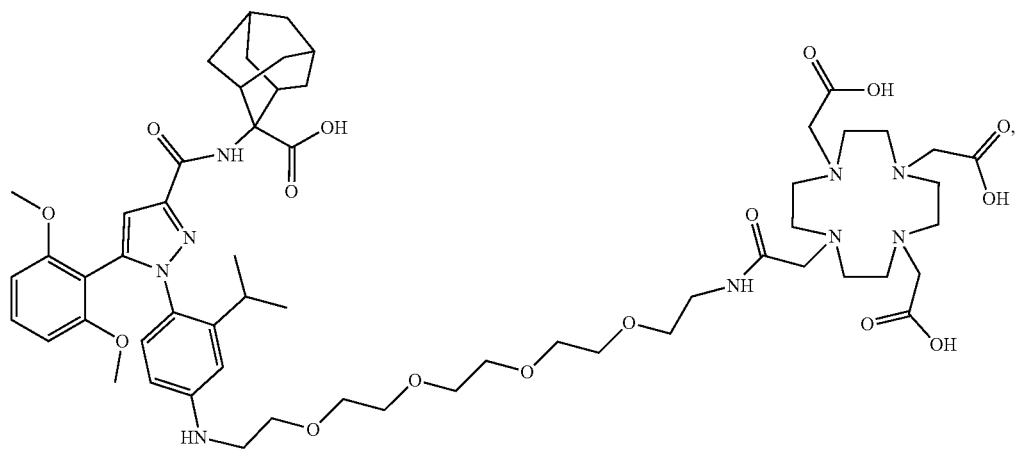
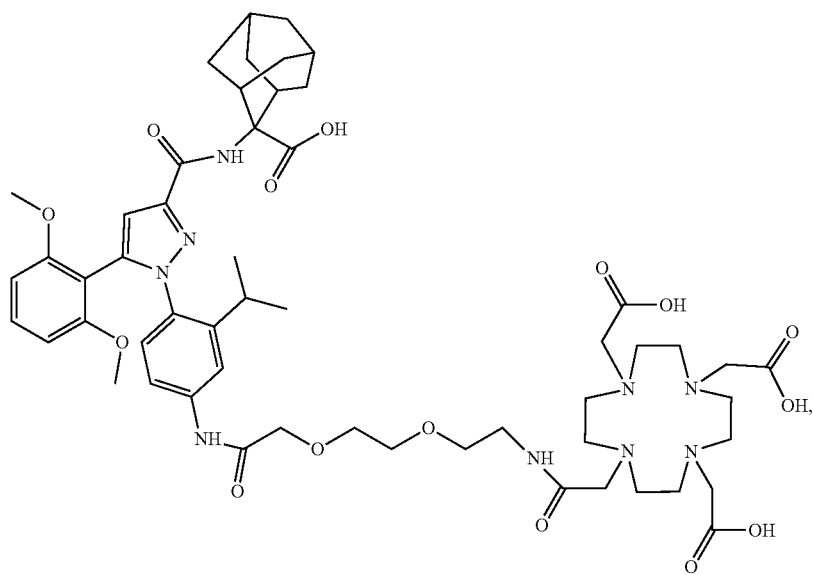

-continued

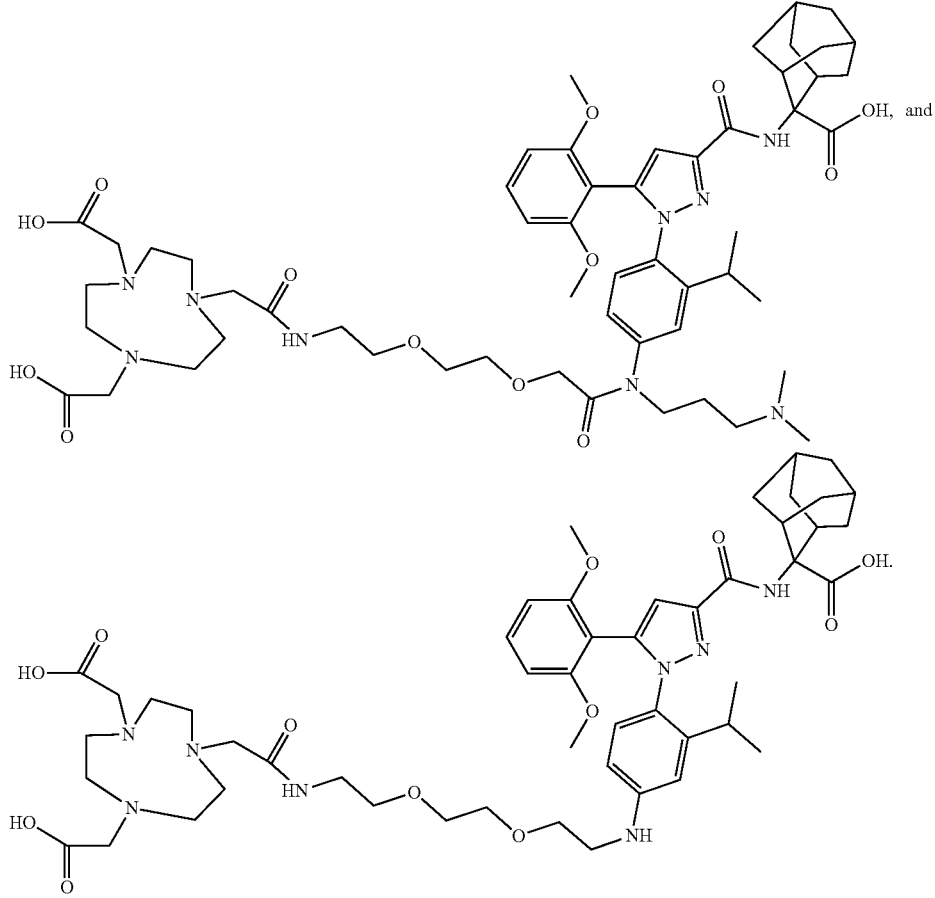

12. The compound of claim 10, or a pharmaceutically acceptable salt or solvate thereof, wherein $R^1$ is selected from H, $C_{1-4}$alkyl, $C_{3-6}$cycloalkyl and $C_1$-salkylene$C_{3-6}$cycloalkyl, the latter three groups being optionally substituted with one or more halo.

13. The compound of claim 10, or a pharmaceutically acceptable salt or solvate thereof, wherein $R^1$ is $CH_3$.

14. The compound of claim 10, or a pharmaceutically acceptable salt or solvate thereof, wherein $R^2$ is selected from $CH_3$, $CH_2CH_3$, $CH_2CH_2CH_3$, CH $(CH_3)_2$, each of which is optionally substituted with one to three fluoro.

15. The compound of claim 10, or a pharmaceutically acceptable salt or solvate thereof, wherein $R^2$ is CH $(CH_3)_2$.

16. The compound of claim 10, or a pharmaceutically acceptable salt or solvate thereof, wherein $R^3$ is a group having the following formula

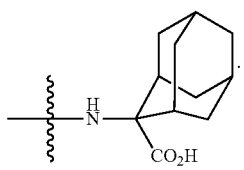 [SMILES: *NC1(C(=O)O)C2CC3CC(C2)CC1C3]

17. The compound of claim 10, or a pharmaceutically acceptable salt or solvate thereof, wherein L consists of 2 to 4 Csalkylene$NR^7$ groups and each CsalkyleneNR$^7$ group is the same or different.

18. The compound of claim 10, or a pharmaceutically acceptable salt or solvate thereof, wherein L consists of 2 to 6 $C_{1-6}$alkyleneO groups and each $C_{1-6}$salkyleneO group is the same or different and 1 or 2 $C_{1-6}$alkyleneNR$^7$ groups and each $C_{1-6}$alkyleneNR$^7$ group is the same or different.

19. A compound of Formula I or a pharmaceutically acceptable salt or solvate thereof

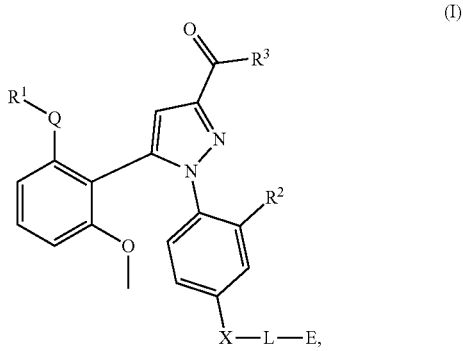

wherein $R^1$ is selected from H, $C_{1-6}$alkyl, $C_{3-6}$cycloalkyl and $C_{1-3}$alkylene$C_{3-6}$cycloalkyl, the latter three groups being optionally substituted with one or more halo;

$R^2$ is selected from H, halo, $NO_2$, $C_{1-6}$alkyl, $C_{3-8}$cycloalkyl and $C_{1-3}$alkylene$C_{3-8}$cycloalkyl, the latter three groups being optionally substituted with one or more halo;

$R^3$ is selected from 2-amino-2-adamantane carboxylic acid, cyclohexylglycine and 9-amino-bicyclo [3.3.1] nonane-9-carboxylic acid;

X is $NR^4$, or $NR^4C$ (O);

L consists of 1 to 10 groups independently selected from $C_{1-6}$alkyleneO, $C_{1-6}$alkyleneNR$^7$, C (O) $C_{1-6}$alkyleneO and C (O) $C_{1-6}$alkyleneNR$^7$, wherein $R^7$ is H or $C_{1-4}$alkyl;

E is selected from the group consisting of 1,4,7-triazacyclononane (TACN); 1,4,7-triazacyclononane-triacetic acid (NOTA); 1,4,7-triazacyclononane-N-succinic acid-N',N"-diacetic acid (NOTASA); 1,4,7-triazacyclononane-N-glutamic acid-N', N"-diacetic acid (NODAGA); 1,4,7-triazacyclononane-N,N', N"-tris (methylenephosphonic) acid (NOTP); 1,4,7,10-tetraazacyclododecane ([12]aneN4) (cyclen); 1,4,7,10-tetraazacyclotridecane ([13]aneN4); 1,4,7,11-tetraazacyclotetradecane (iso-cyclam); 1,4,7,10-tetraazacyclododecane-1,4,7,10-tetraacetic acid (DOTA); 2-(1,4,7,10-tetraazacyclododecan-1-yl) acetate (DO1A); 2,2'-(1,4,7,10-tetraazacyclododecane-1,7-diyl) diacetic acid (DO2A); 2,2',2''-(1,4,7,10-tetraazacyclododecane-1,4,7-triyl) triacetic acid (DO3A); 1,4,7,10-tetraazacyclododecane-1,4,7,10-tetra(methanepnosphonic acid) (DOTP); 1,4,7, 10-tetraazacyclododecane-1,7-di(methanephosphoriic acid) (DO2P); 1,4,7,10-tetraazacyclododecane-1,4,7-tri(methanephosphonic acid) (DO3P); 1,4,7,10-tetraazacyclo-decane-1-glutamic acid-4,7,10-triacetic acid (DOTAGA); 1,4, 7,10-tetraazacyclodecane-1-succinic acid-4,7,10-triacetic acid (DOTASA); 1,4,8,11-tetraazacyclotetradecane ([14]aneN4) (cyclam); 1,4,8, 12-tetraazacyclopentadecane ([15]aneN4); 1,5,9,13-tetraazacyclohexadecane ([16]aneN4); 1,4-ethano-1,4, 8,11-tetraazacyclo-tetradecane (et-cyclam); 1,4,8,11-tetraazacyclotetradecane-1,4,8,11-tetraacetic acid (TETA); 2-(1,4,8,11-tetraazacyclotetradecane-1-yl) acetic acid (TE1A); 2,2'-(1,4,8,11-tetraazacyclotetradecane-1,8-diyl) diacetic acid (TE2A); 4,11-bis (carboxymethyl)-1,4,8, 11-tetraazabicyclo [6.6.2]-hexadecane (CB-TE2A); 3,6,10,13,16,19-hexaazabicyclo [6.6.6] icosane (Sar); 1,4,7,10-tetra-(2-carbamoyl-methyl)-cyclododecane (TCMC); N, N'-bis [(6-carboxy-2-pyridil) methyl]-4, 13-diaza-18-crown-6 (macropa), phthalocyanines, and porphyrins;

$R^4$ is selected from H, $C_{1-6}$alkyl, $C_{1-6}$alkenyl, $C_{1-6}$alkynyl, C (O) $C_{1-6}$alkyl, $C_{1-10}$alkyleneNR$^5$R$^6$, $C_{1-10}$alkenyleneNR$^5$R$^6$, and $C_{1-10}$alkynyleneNR$^5$R$^6$; and $R^5$ and $R^6$ are independently selected from H and $C_{1-6}$alkyl.

20. The compound of claim 19, or a pharmaceutically acceptable salt or solvate thereof, wherein the compound of Formula I is selected from the group consisting of:

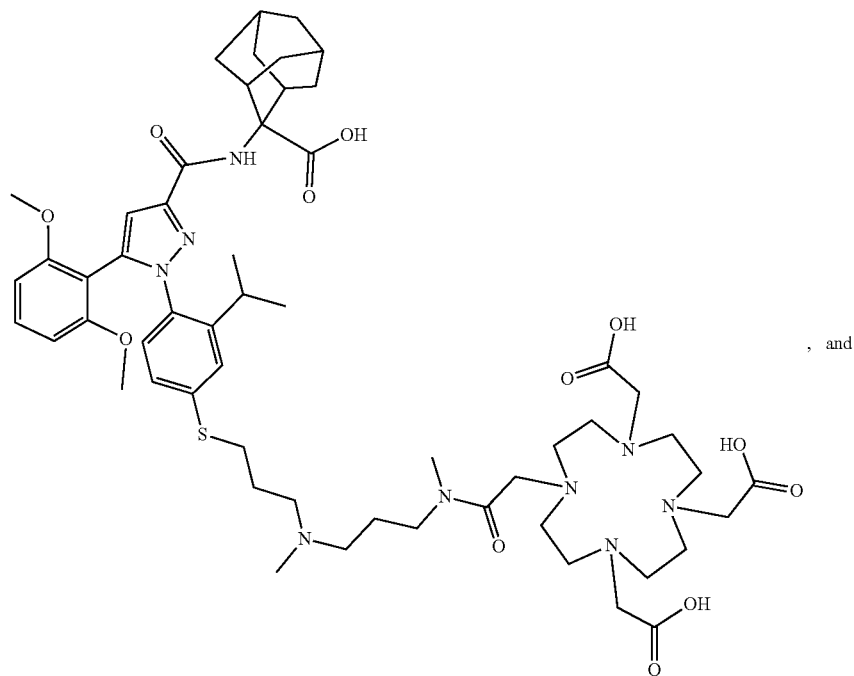

, and

-continued

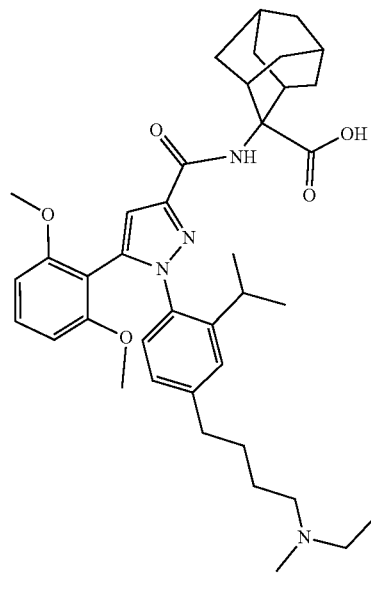

21. The compound of claim 19, or a pharmaceutically acceptable salt or solvate thereof, wherein $R^1$ is selected from H, $C_{1-4}$alkyl, $C_{3-6}$cycloalkyl and $C_{1-3}$salkylene$C_{3-6}$cycloalkyl, the latter three groups being optionally substituted with one or more halo.

22. The compound of claim 19, or a pharmaceutically acceptable salt or solvate thereof, wherein $R^1$ is $CH_3$.

23. The compound of claim 19, or a pharmaceutically acceptable salt or solvate thereof, wherein $R^2$ is selected from $CH_3$, $CH_2CH_3$, $CH_2CH_2CH_3$, CH $(CH3)_2$, each of which is optionally substituted with one to three fluoro.

24. The compound of claim 19, or a pharmaceutically acceptable salt or solvate thereof, wherein $R^2$ is CH $(CH_3)_2$.

25. The compound of claim 19, or a pharmaceutically acceptable salt or solvate thereof, wherein $R^3$ is a group having the following formula

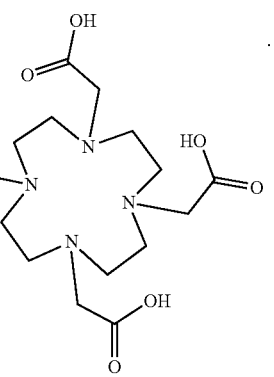

26. The compound of claim 19, or a pharmaceutically acceptable salt or solvate thereof, wherein L consists of 2 to 4 CsalkyleneNR$^7$ groups and each CsalkyleneNR$^7$ group is the same or different.

27. The compound of claim 19, or a pharmaceutically acceptable salt or solvate thereof, wherein L consists of 2 to 6 $C_{1-6}$alkyleneO groups and each $C_{1-6}$salkyleneO group is the same or different and 1 or 2 $C_{1-6}$alkyleneNR$^7$ groups and each $C_{1-6}$alkyleneNR$^7$ group is the same or different.

* * * * *